United States Patent
Jia et al.

(10) Patent No.: US 12,162,919 B2
(45) Date of Patent: Dec. 10, 2024

(54) ONCOLYTIC HERPES SIMPLEX VIRUS VECTORS EXPRESSING IMMUNE SYSTEM-STIMULATORY MOLECULES

(71) Applicant: VIROGIN BIOTECH CANADA LTD, Vancouver (CA)

(72) Inventors: William Jia, Burnaby (CA); Guoyu Liu, Richmond (CA); Erica Lee, Burnaby (CA); Dmitry Chouljenko, Vancouver (CA); Jun Ding, Vancouver (CA)

(73) Assignee: Virogin Biotech Canada Ltd (CA)

( * ) Notice: Subject to any disclaimer, the term of this patent is extended or adjusted under 35 U.S.C. 154(b) by 1715 days.

(21) Appl. No.: 16/322,903

(22) PCT Filed: Aug. 1, 2017

(86) PCT No.: PCT/US2017/044993
§ 371 (c)(1),
(2) Date: Feb. 1, 2019

(87) PCT Pub. No.: WO2018/026872
PCT Pub. Date: Feb. 8, 2018

(65) Prior Publication Data
US 2019/0169253 A1 Jun. 6, 2019

Related U.S. Application Data

(60) Provisional application No. 62/396,646, filed on Aug. 1, 2016.

(51) Int. Cl.
| | | |
|---|---|---|
| C07K 14/00 | (2006.01) | |
| A61K 35/763 | (2015.01) | |
| A61P 35/00 | (2006.01) | |
| C07K 14/035 | (2006.01) | |
| C07K 14/54 | (2006.01) | |
| C07K 14/715 | (2006.01) | |
| C12N 15/00 | (2006.01) | |
| C12N 15/62 | (2006.01) | |
| C12N 15/85 | (2006.01) | |
| A61K 38/00 | (2006.01) | |
| C12N 15/869 | (2006.01) | |

(52) U.S. Cl.
CPC ........ *C07K 14/5443* (2013.01); *A61K 35/763* (2013.01); *A61P 35/00* (2018.01); *C07K 14/035* (2013.01); *C07K 14/5434* (2013.01); *C07K 14/7155* (2013.01); *C12N 15/00* (2013.01); *C12N 15/625* (2013.01); *C12N 15/85* (2013.01); *A61K 38/00* (2013.01); *C12N 15/8695* (2013.01); *C12N 2710/16632* (2013.01); *C12N 2710/16643* (2013.01)

(58) Field of Classification Search
CPC .............. C07K 14/5443; C07K 14/035; C07K 14/5434; C07K 14/7155; A61K 35/763; A61K 38/00; A61P 35/00; C12N 15/00; C12N 15/625; C12N 15/85; C12N 15/8695

See application file for complete search history.

(56) References Cited

U.S. PATENT DOCUMENTS

| | | |
|---|---|---|
| 2007/0116690 A1 | 5/2007 | Yang et al. |
| 2011/0081311 A1 | 4/2011 | Pavlakis et al. |
| 2013/0195800 A1 | 8/2013 | Roeth et al. |
| 2015/0291966 A1 | 10/2015 | Zhang et al. |

FOREIGN PATENT DOCUMENTS

| | | |
|---|---|---|
| WO | 99/07394 A1 | 2/1999 |
| WO | 00/75292 A1 | 12/2000 |
| WO | 2005/014642 A2 | 2/2005 |
| WO | 2015018529 A1 | 2/2015 |

OTHER PUBLICATIONS

Lorenzo et al. (2015). Cancer Gene Therapy (2015) 22, 542-551).*
Anderson et al. (1995). Functional characterization of the human interleukin-15 receptor alpha chain and close linkage of IL15RA and IL2RA genes.J Biol Chem Dec. 1995;270(50)29862-29869.*
Roth, Justin C. et al., "Evaluation of the Safety and Biodistribution of M032, an Attenuated Herpes Simplex Virus Type 1 Expressing hIL-12, After Intracerebral Administration to Aotus Nonhuman Primates", Human Gene Therapy Clinical Development; vol. 25, Mar. 2014, pp. 16-27.
Zhang, Wei et al., "Combination of Oncolytic Herpes Simplex Viruses Armed with Angiostatin and IL-12 Enhances Antitumor Efficacy in Human Glioblastoma Models", Neoplasia, vol. 15, No. 6, Jun. 2013, pp. 591-599.
Saha, Diponghkor et al., "Immunovirotherapy Combined with Immune Checkpoint Inhibitors for Treating Glioblastoma", Molecular Therapy, vol. 23, Supplement 1, No. 624, May 2015, p. S248.
Gaston, David S. et al., "Production of Bioactive Soluble Interleukin-15 in Complex with Interleukin-15 Receptor Alpha from a Conditionally-Replicating Oncolytic HSV-1", PLOS One, vol. 8, issue 11, e81768, Nov. 2013, pp. 1-131.
International Search Report and Written Opinion dated Dec. 8, 2017, for International Application No. PCT/US2017/044993.
Satoh, T. et al., "In Situ Gene Therapy for Prostate Cancer", Current Gene Therapy, Feb. 2005, vol. 5, No. 1, pp. 111-119.
Tosic, V. et al., "Myxoma Virus Expressing a Fusion Protein of Interleukin-15 (IL15) and IL15Receptor Alpha has Enhanced Anti-tumor Activity", PLoS One, Oct. 16, 2014, vol. 9, No. 10, pp. 1-12.

* cited by examiner

*Primary Examiner* — Jeanette M Lieb
(74) *Attorney, Agent, or Firm* — Kurious LLC

(57) ABSTRACT

An HSV vector comprising an expression cassette for one or more of IL12, IL15, and hIL15Receptor alpha subunit is provided.

18 Claims, 87 Drawing Sheets
Specification includes a Sequence Listing.

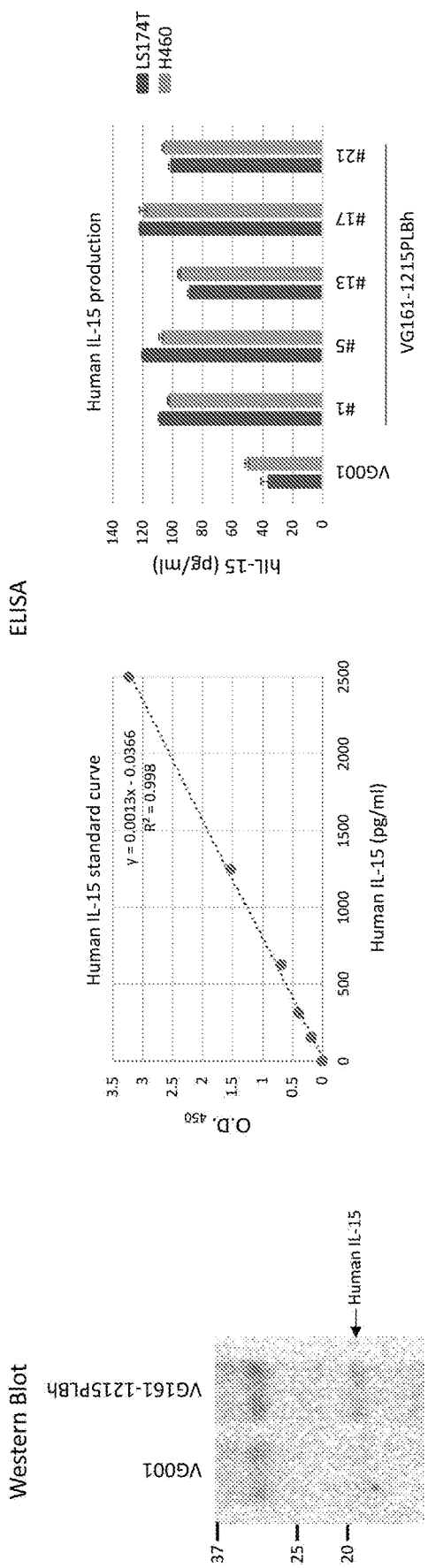
*FIG. 7A*  *FIG. 7B*  *FIG. 7C*

FIG. 9A

FIG. 10A pBI-CMV_IL15_RA4

| IL15RA4 | BI-CMV | IL15 |

FIG. 12D pEF1α-IL15-IRES-sushi

| EF1a Promoter | IL15 | IRES | sushi |

ACGAAGACCTGGAGAACTGCTCACATCATCTGTAAGAT 3'
                                        3938
TGCTTCTGGACCTCTTGACGAGTGTAGTAGACATTCTA-(P) 5'

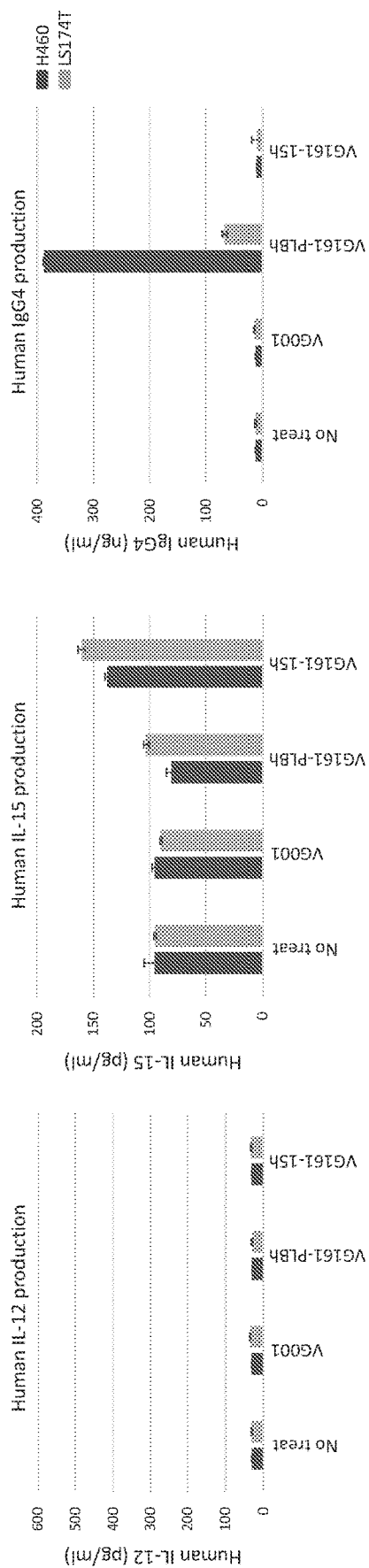
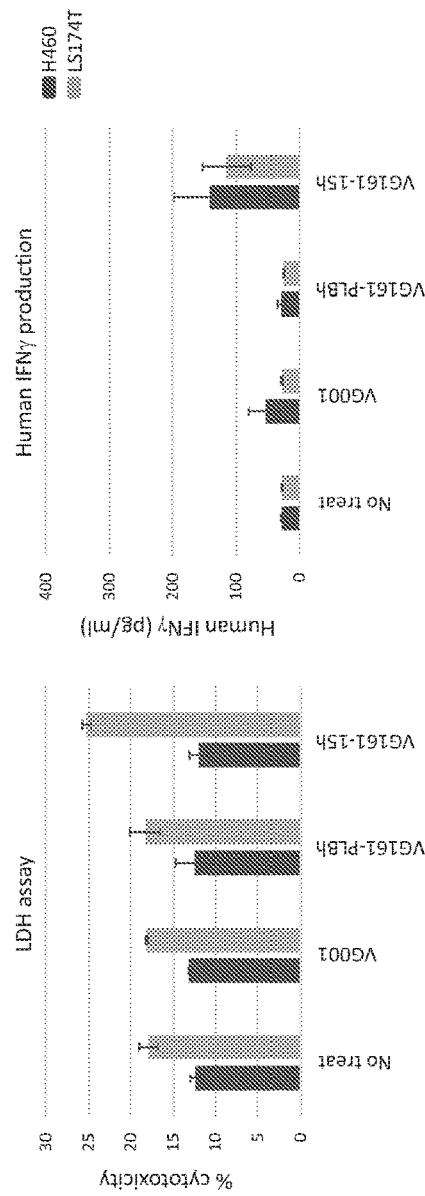
FIG. 25A  FIG. 25B  FIG. 25C  FIG. 25D  FIG. 25E

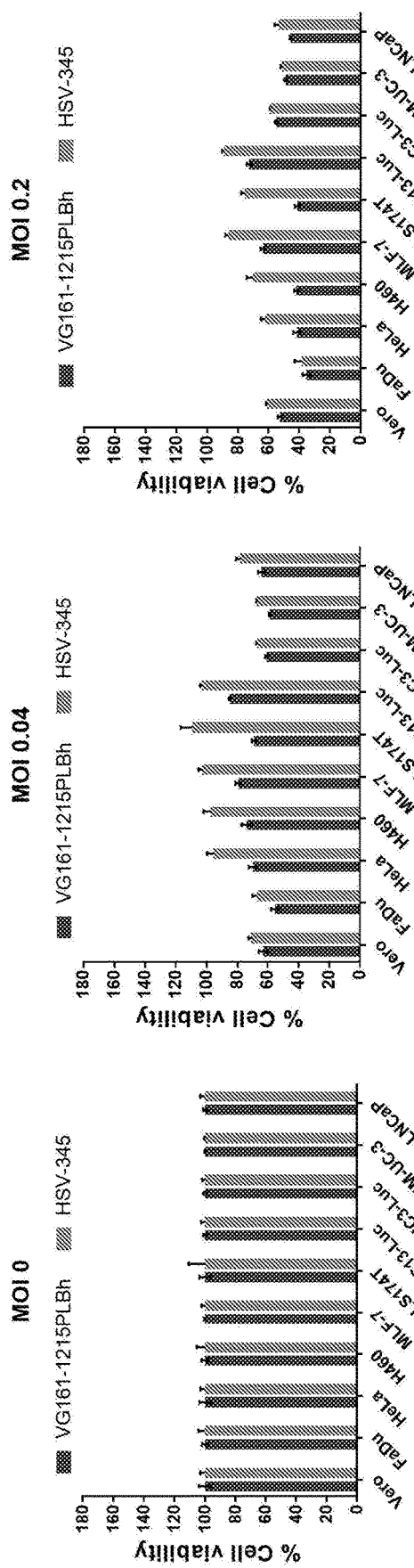
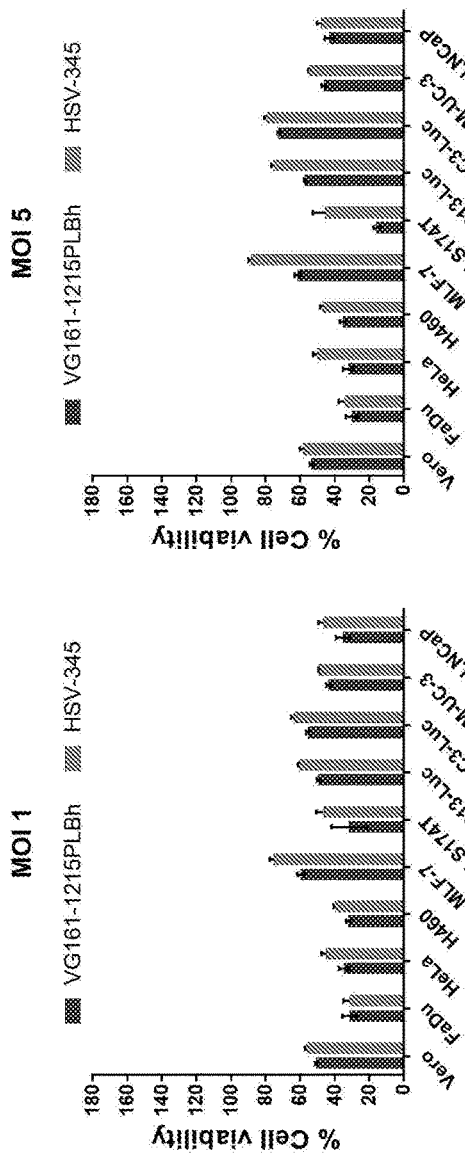
FIG. 27A  FIG. 27B  FIG. 27C  FIG. 27D  FIG. 27E

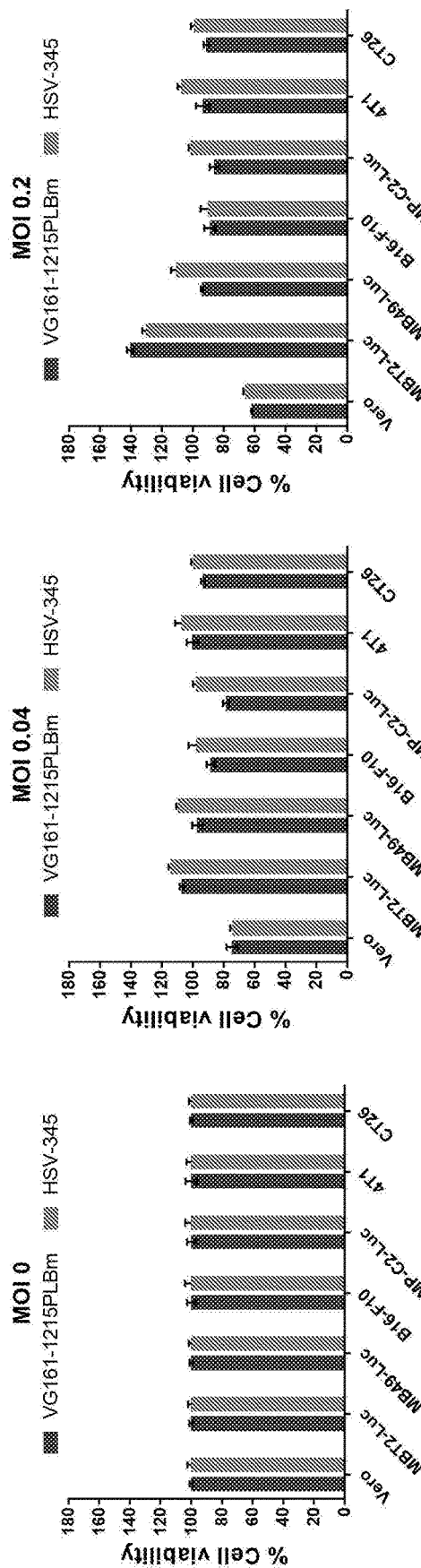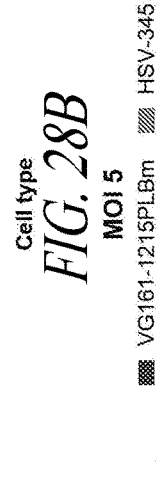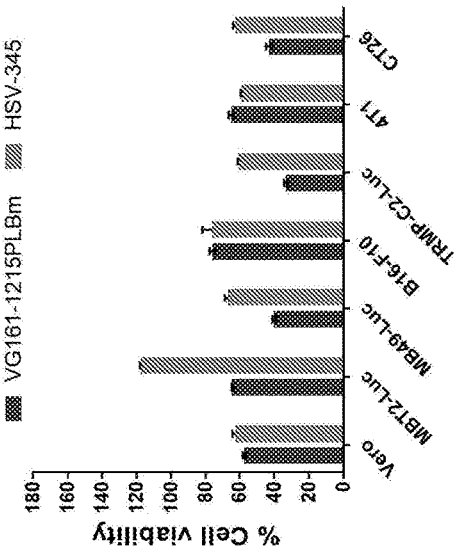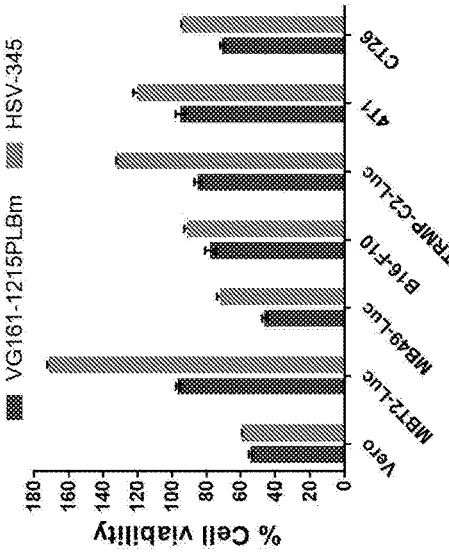
FIG. 28A FIG. 28B FIG. 28C FIG. 28D FIG. 28E

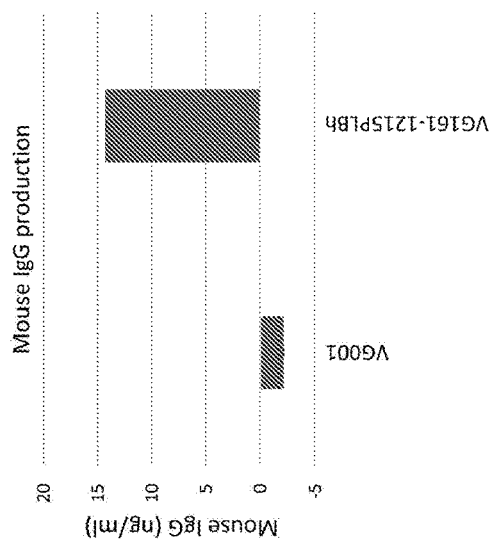
FIG. 28H
FIG. 28G
FIG. 28J
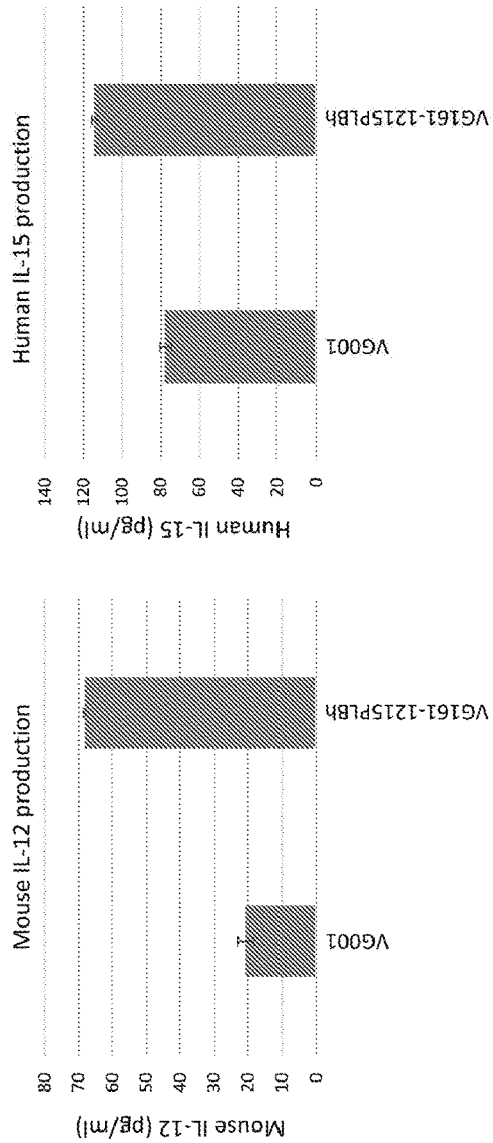
FIG. 28F
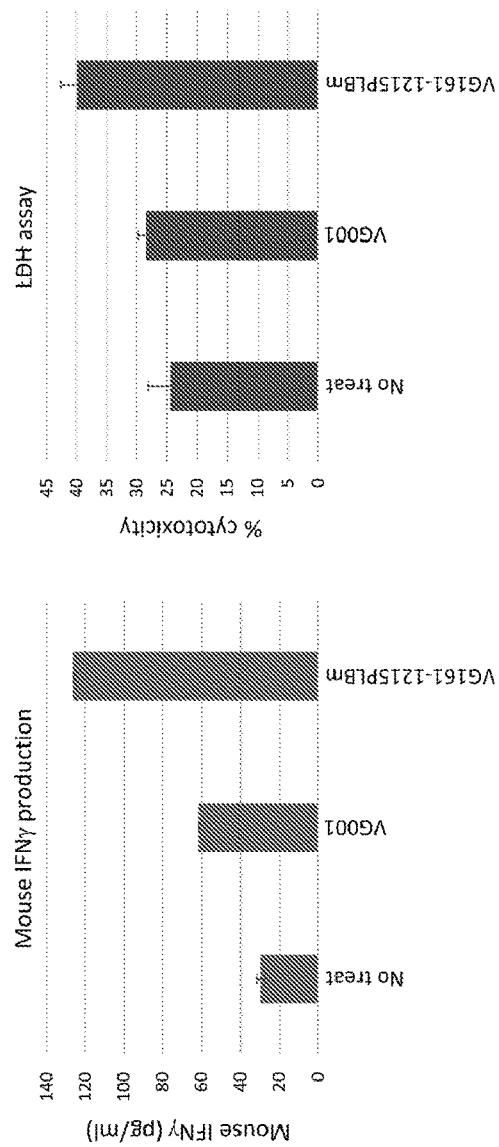
FIG. 28I

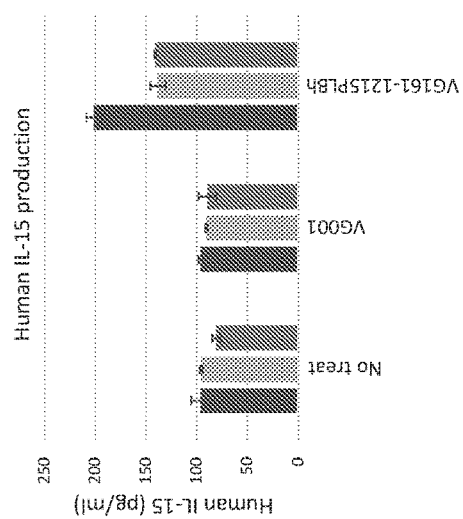
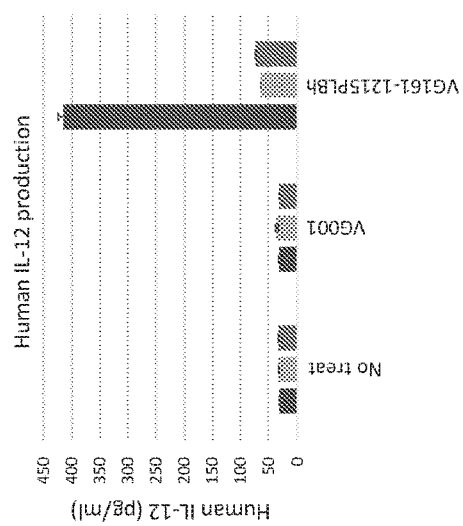
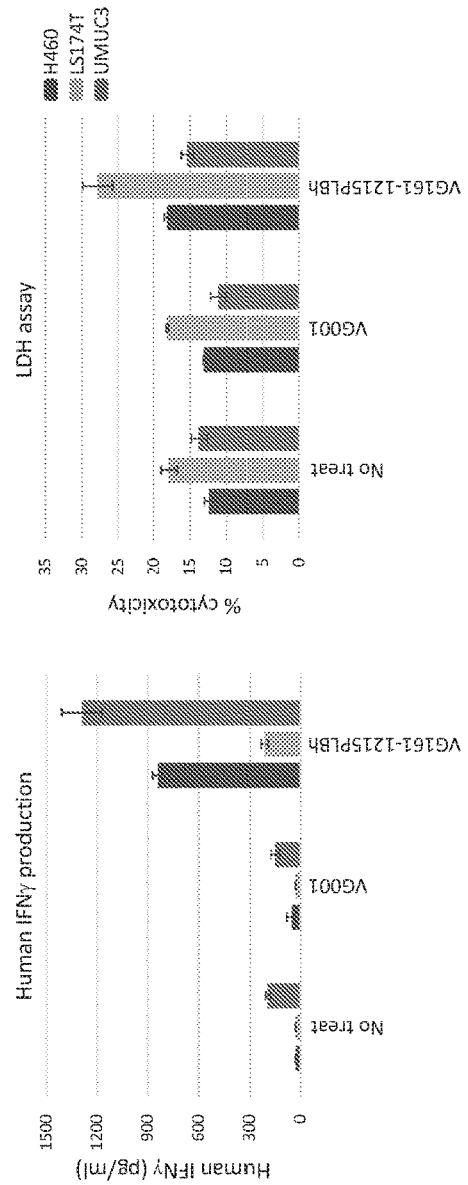
FIG. 29A, FIG. 29B, FIG. 29C, FIG. 29D, FIG. 29E

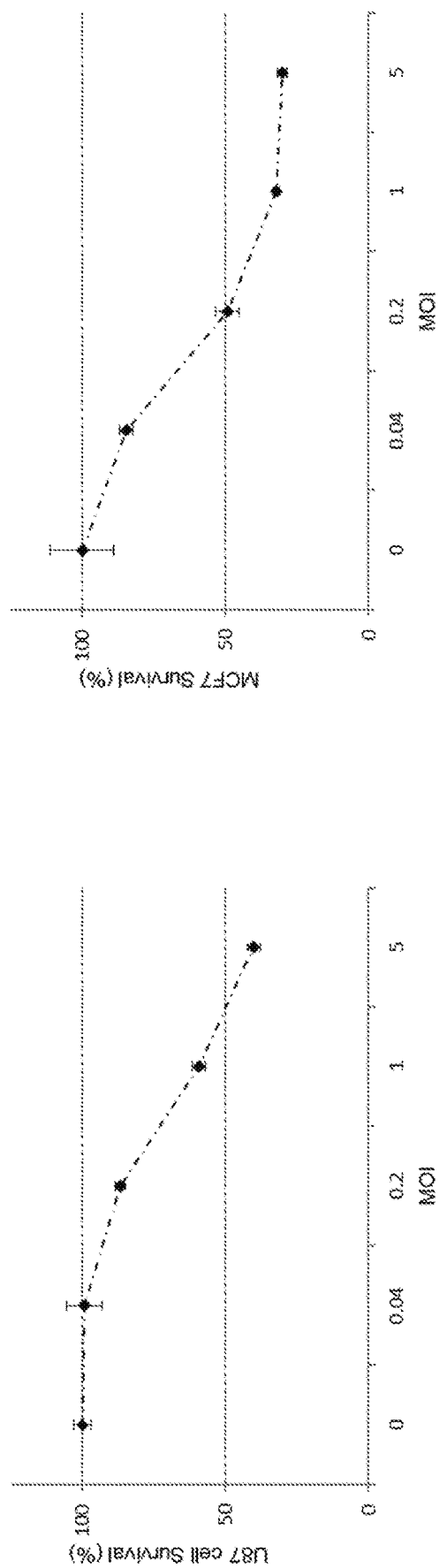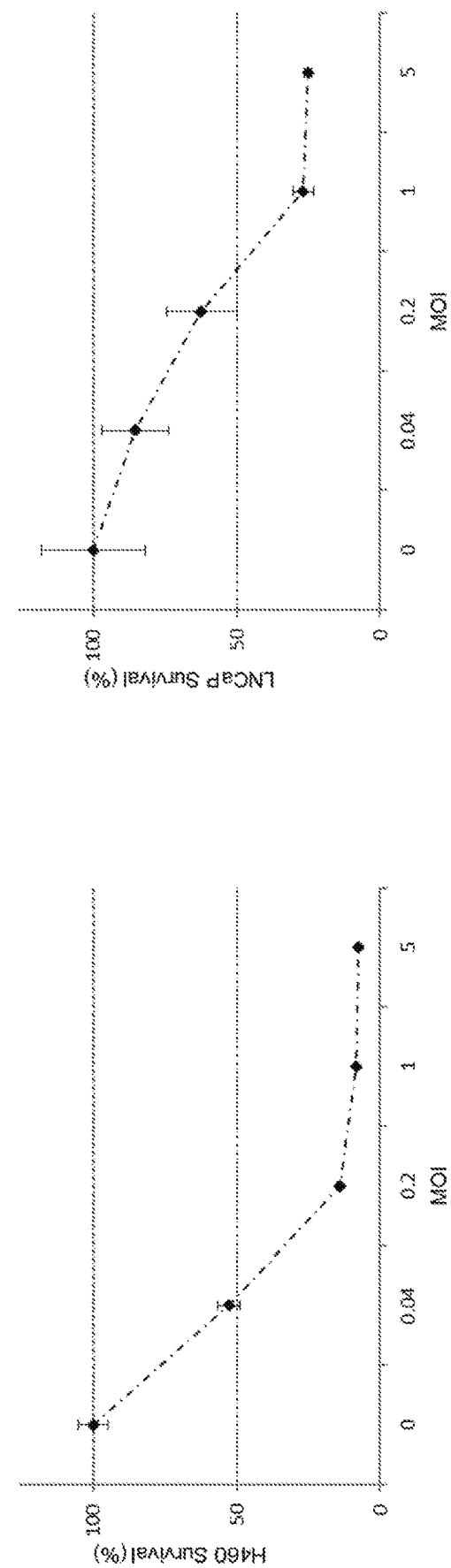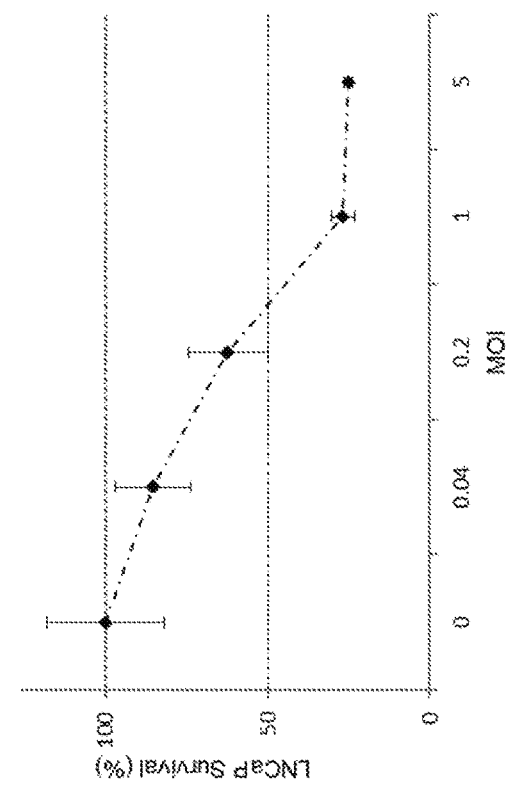

SEQUENCE LISTING

<160> NUMBER OF SEQ ID NOS: 575

<210> SEQ ID NO 1
<211> LENGTH: 335
<212> TYPE: PRT
<213> ORGANISM: Mus musculus

<400> SEQUENCE: 1

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser
                325                 330                 335

<210> SEQ ID NO 2
<211> LENGTH: 162
<212> TYPE: PRT
<213> ORGANISM: Homo sapiens

```
<400> SEQUENCE: 2

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 3
<211> LENGTH: 267
<212> TYPE: PRT
<213> ORGANISM: Homo sapiens

<400> SEQUENCE: 3

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
```

```
              195                 200                 205
Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265
```

<210> SEQ ID NO 4
<211> LENGTH: 234
<212> TYPE: PRT
<213> ORGANISM: Homo sapiens

<400> SEQUENCE: 4

```
Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
                20                  25                  30

Cys Pro Pro Pro Met Ser Val Glu His Ala Asp Ile Trp Val Lys Ser
            35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Lys Pro
                85                  90                  95

Ala Ala Ser Ser Pro Ser Ser Asn Asn Thr Ala Ala Thr Thr Ala Ala
            100                 105                 110

Ile Val Pro Gly Ser Gln Leu Met Pro Ser Lys Ser Pro Ser Thr Gly
        115                 120                 125

Thr Thr Glu Ile Ser Ser His Glu Ser Ser His Gly Thr Pro Ser Gln
130                 135                 140

Thr Thr Ala Lys Asn Trp Glu Leu Thr Ala Ser Ala Ser His Gln Pro
145                 150                 155                 160

Pro Gly Val Tyr Pro Gln Gly His Ser Asp Thr Thr Val Ala Ile Ser
                165                 170                 175

Thr Ser Thr Val Leu Leu Cys Gly Leu Ser Ala Val Ser Leu Leu Ala
            180                 185                 190

Cys Tyr Leu Lys Ser Arg Gln Thr Pro Pro Leu Ala Ser Val Glu Met
        195                 200                 205

Glu Ala Met Glu Ala Leu Pro Val Thr Trp Gly Thr Ser Ser Arg Asp
    210                 215                 220

Glu Asp Leu Glu Asn Cys Ser His His Leu
225                 230
```

<210> SEQ ID NO 5
<211> LENGTH: 231
<212> TYPE: PRT
<213> ORGANISM: Homo sapiens

<400> SEQUENCE: 5

```
Met Ser Val Glu His Ala Asp Ile Trp Val Lys Ser Tyr Ser Leu Tyr
1               5                   10                  15

Ser Arg Glu Arg Tyr Ile Cys Asn Ser Gly Phe Lys Arg Lys Ala Gly
```

-continued

```
                20                  25                  30
Thr Ser Ser Leu Thr Glu Cys Val Leu Asn Lys Ala Thr Asn Val Ala
            35                  40                  45
His Trp Thr Thr Pro Ser Leu Lys Cys Ile Arg Asp Pro Ala Leu Val
 50                  55                  60
His Gln Arg Pro Ala Pro Pro Ser Thr Val Thr Thr Ala Gly Val Thr
 65                  70                  75                  80
Pro Gln Pro Glu Ser Leu Ser Pro Ser Gly Lys Glu Pro Ala Ala Ser
                85                  90                  95
Ser Pro Ser Ser Asn Asn Thr Ala Ala Thr Ala Ala Ile Val Pro
            100                 105                 110
Gly Ser Gln Leu Met Pro Ser Lys Ser Pro Ser Thr Gly Thr Thr Glu
            115                 120                 125
Ile Ser Ser His Glu Ser His Gly Thr Pro Ser Gln Thr Thr Ala
            130                 135                 140
Lys Asn Trp Glu Leu Thr Ala Ser Ala Ser His Gln Pro Pro Gly Val
145                 150                 155                 160
Tyr Pro Gln Gly His Ser Asp Thr Thr Val Ala Ile Ser Thr Ser Thr
                165                 170                 175
Val Leu Leu Cys Gly Leu Ser Ala Val Ser Leu Ala Cys Tyr Leu
            180                 185                 190
Lys Ser Arg Gln Thr Pro Pro Leu Ala Ser Val Glu Met Glu Ala Met
            195                 200                 205
Glu Ala Leu Pro Val Thr Trp Gly Thr Ser Ser Arg Asp Glu Asp Leu
 210                 215                 220
Glu Asn Cys Ser His His Leu
 225                 230

<210> SEQ ID NO 6
<211> LENGTH: 353
<212> TYPE: PRT
<213> ORGANISM: Homo sapiens

<400> SEQUENCE: 6

Met Arg Leu Ala Gly Arg Gln Val Pro Glu Gln Arg Ser Pro Pro Pro
 1                   5                  10                  15
Pro Gly Leu Gly Ser Ala Arg Pro Gly Ser Pro Ala Val Ser Cys Gly
                20                  25                  30
Ala Ala Ala Met Ala Pro Arg Arg Ala Arg Gly Cys Arg Thr Leu Gly
            35                  40                  45
Leu Pro Ala Leu Leu Leu Leu Leu Leu Arg Pro Pro Ala Thr Arg
 50                  55                  60
Asp Ala Arg Asp Arg Leu Ala Val Leu Ala Gly Arg Ser Arg Ile Ser
 65                  70                  75                  80
Glu Ser Phe Asn His Glu Val Gln Thr His Glu Ala Cys Val Arg Leu
                85                  90                  95
Arg Thr Met Glu Asn Cys Pro Gln Cys His His Arg Thr Ser Arg
            100                 105                 110
Gln Gln Ala Gly Ile Thr Cys Pro Pro Pro Met Ser Val Glu His Ala
            115                 120                 125
Asp Ile Trp Val Lys Ser Tyr Ser Leu Tyr Ser Arg Glu Arg Tyr Ile
 130                 135                 140
Cys Asn Ser Gly Phe Lys Arg Lys Ala Gly Thr Ser Ser Leu Thr Glu
 145                 150                 155                 160
```

```
Cys Val Leu Asn Lys Ala Thr Asn Val Ala His Trp Thr Thr Pro Ser
                165                 170                 175

Leu Lys Cys Ile Arg Asp Pro Ala Leu Val His Gln Arg Pro Ala Pro
            180                 185                 190

Pro Ser Thr Val Thr Thr Ala Gly Val Thr Pro Gln Pro Glu Ser Leu
        195                 200                 205

Ser Pro Ser Gly Lys Glu Pro Ala Ala Ser Ser Pro Ser Ser Asn Asn
    210                 215                 220

Thr Ala Ala Thr Thr Ala Ala Ile Val Pro Gly Ser Gln Leu Met Pro
225                 230                 235                 240

Ser Lys Ser Pro Ser Thr Gly Thr Thr Glu Ile Ser Ser His Glu Ser
                245                 250                 255

Ser His Gly Thr Pro Ser Gln Thr Thr Ala Lys Asn Trp Glu Leu Thr
            260                 265                 270

Ala Ser Ala Ser His Gln Pro Pro Gly Val Tyr Pro Gln Gly His Ser
        275                 280                 285

Asp Thr Thr Val Ala Ile Ser Thr Ser Thr Val Leu Leu Cys Gly Leu
    290                 295                 300

Ser Ala Val Ser Leu Leu Ala Cys Tyr Leu Lys Ser Arg Gln Thr Pro
305                 310                 315                 320

Pro Leu Ala Ser Val Glu Met Glu Ala Met Glu Ala Leu Pro Val Thr
                325                 330                 335

Trp Gly Thr Ser Ser Arg Asp Glu Asp Leu Glu Asn Cys Ser His His
            340                 345                 350

Leu

<210> SEQ ID NO 7
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<223> OTHER INFORMATION: Synthetic sequence

<400> SEQUENCE: 7

Lys Val Ser Ala Leu Lys Glu
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic sequence

<400> SEQUENCE: 8

Glu Val Ser Ala Leu Glu Lys
1               5

<210> SEQ ID NO 9
<211> LENGTH: 35
<212> TYPE: PRT
<213> ORGANISM: Artificial Sequence
<220> FEATURE:
<223> OTHER INFORMATION: Synthetic sequence

<400> SEQUENCE: 9

Lys Val Ser Ala Leu Lys Glu Lys Val Ser Ala Leu Lys Glu Lys Val
1               5                   10                  15
```

-continued

Ser Ala Leu Lys Glu Lys Val Ser Ala Leu Lys Glu Lys Val Ser Ala
            20                  25                  30

Leu Lys Glu
        35

<210> SEQ ID NO 10
<211> LENGTH: 35
<212> TYPE: PRT
<213> ORGANISM: Artificial Sequence
<220> FEATURE:
<223> OTHER INFORMATION: Synthetic sequence

<400> SEQUENCE: 10

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys Glu Val Ser Ala
            20                  25                  30

Leu Glu Lys
        35

<210> SEQ ID NO 11
<211> LENGTH: 96
<212> TYPE: PRT
<213> ORGANISM: Homo sapiens

<400> SEQUENCE: 11

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

<210> SEQ ID NO 12
<211> LENGTH: 146
<212> TYPE: PRT
<213> ORGANISM: Homo sapiens

<400> SEQUENCE: 12

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Gly Gly Gly Gly Ser Gly Gly Gly Gly Ser Gly Gly Gly Gly Ser Glu

```
                100             105             110
Val Ser Ala Leu Glu Lys Glu Val Ser Ala Leu Glu Lys Glu Val Ser
                115             120             125
Ala Leu Glu Lys Glu Val Ser Ala Leu Glu Lys Glu Val Ser Ala Leu
                130             135             140
Glu Lys
145

<210> SEQ ID NO 13
<211> LENGTH: 403
<212> TYPE: PRT
<213> ORGANISM: Homo sapiens

<400> SEQUENCE: 13

Met Arg Leu Ala Gly Arg Gln Val Pro Glu Gln Arg Ser Pro Pro
1               5               10              15
Pro Gly Leu Gly Ser Ala Arg Pro Gly Ser Pro Ala Val Ser Cys Gly
                20              25              30
Ala Ala Ala Met Ala Pro Arg Ala Arg Gly Cys Arg Thr Leu Gly
                35              40              45
Leu Pro Ala Leu Leu Leu Leu Leu Leu Arg Pro Pro Ala Thr Arg
50              55              60
Asp Ala Arg Asp Arg Leu Ala Val Leu Ala Gly Arg Ser Arg Ile Ser
65              70              75              80
Glu Ser Phe Asn His Glu Val Gln Thr His Glu Ala Cys Val Arg Leu
                85              90              95
Arg Thr Met Glu Asn Cys Pro Gln Cys His His His Arg Thr Ser Arg
                100             105             110
Gln Gln Ala Gly Ile Thr Cys Pro Pro Met Ser Val Glu His Ala
                115             120             125
Asp Ile Trp Val Lys Ser Tyr Ser Leu Tyr Ser Arg Glu Arg Tyr Ile
    130             135             140
Cys Asn Ser Gly Phe Lys Arg Lys Ala Gly Thr Ser Ser Leu Thr Glu
145             150             155             160
Cys Val Leu Asn Lys Ala Thr Asn Val Ala His Trp Thr Thr Pro Ser
                165             170             175
Leu Lys Cys Ile Arg Asp Pro Ala Leu Val His Gln Arg Pro Ala Pro
                180             185             190
Pro Ser Thr Val Thr Thr Ala Gly Val Thr Pro Gln Pro Glu Ser Leu
                195             200             205
Ser Pro Ser Gly Lys Glu Pro Ala Ala Ser Ser Pro Ser Ser Asn Asn
    210             215             220
Thr Ala Thr Thr Ala Ala Ile Val Pro Gly Ser Gln Leu Met Pro
225             230             235             240
Ser Lys Ser Pro Ser Thr Gly Thr Thr Glu Ile Ser Ser His Glu Ser
                245             250             255
Ser His Gly Thr Pro Ser Gln Thr Thr Ala Lys Asn Trp Glu Leu Thr
                260             265             270
Ala Ser Ala Ser His Gln Pro Pro Gly Val Tyr Pro Gln Gly His Ser
                275             280             285
Asp Thr Thr Val Ala Ile Ser Thr Ser Thr Val Leu Leu Cys Gly Leu
    290             295             300
Ser Ala Val Ser Leu Leu Ala Cys Tyr Leu Lys Ser Arg Gln Thr Pro
305             310             315             320
```

```
Pro Leu Ala Ser Val Glu Met Glu Ala Met Glu Ala Leu Pro Val Thr
                325                 330                 335

Trp Gly Thr Ser Ser Arg Asp Glu Asp Leu Glu Asn Cys Ser His His
            340                 345                 350

Leu Gly Gly Gly Ser Gly Gly Gly Ser Gly Gly Gly Ser
        355                 360                 365

Glu Val Ser Ala Leu Glu Lys Glu Val Ser Ala Leu Glu Lys Glu Val
    370                 375                 380

Ser Ala Leu Glu Lys Glu Val Ser Ala Leu Glu Lys Glu Val Ser Ala
385                 390                 395                 400

Leu Glu Lys

<210> SEQ ID NO 14
<211> LENGTH: 317
<212> TYPE: PRT
<213> ORGANISM: Homo sapiens

<400> SEQUENCE: 14

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu Gly Gly Gly Gly Ser
            260                 265                 270

Gly Gly Gly Gly Ser Gly Gly Gly Ser Glu Val Ser Ala Leu Glu
        275                 280                 285
```

```
Lys Glu Val Ser Ala Leu Glu Lys Glu Val Ser Ala Leu Glu Lys Glu
    290                 295                 300
Val Ser Ala Leu Glu Lys Glu Val Ser Ala Leu Glu Lys
305                 310                 315
```

<210> SEQ ID NO 15
<211> LENGTH: 215
<212> TYPE: PRT
<213> ORGANISM: Homo sapiens

<400> SEQUENCE: 15

```
Met Arg Ile Ser Lys Pro His Leu Arg Ser Ile Ser Ile Gln Cys Tyr
1               5                   10                  15
Leu Cys Leu Leu Leu Asn Ser His Phe Leu Thr Glu Ala Gly Ile His
                20                  25                  30
Val Phe Ile Leu Gly Cys Phe Ser Ala Gly Leu Pro Lys Thr Glu Ala
            35                  40                  45
Asn Trp Val Asn Val Ile Ser Asp Leu Lys Lys Ile Glu Asp Leu Ile
        50                  55                  60
Gln Ser Met His Ile Asp Ala Thr Leu Tyr Thr Glu Ser Asp Val His
65                  70                  75                  80
Pro Ser Cys Lys Val Thr Ala Met Lys Cys Phe Leu Leu Glu Leu Gln
                85                  90                  95
Val Ile Ser Leu Glu Ser Gly Asp Ala Ser Ile His Asp Thr Val Glu
            100                 105                 110
Asn Leu Ile Ile Leu Ala Asn Asn Ser Leu Ser Ser Asn Gly Asn Val
        115                 120                 125
Thr Glu Ser Gly Cys Lys Glu Cys Glu Glu Leu Glu Glu Lys Asn Ile
130                 135                 140
Lys Glu Phe Leu Gln Ser Phe Val His Ile Val Gln Met Phe Ile Asn
145                 150                 155                 160
Thr Ser Gly Gly Gly Ser Gly Gly Gly Ser Gly Gly Gly Gly
                165                 170                 175
Ser Cys Gly Gly Lys Val Ser Ala Leu Lys Glu Lys Val Ser Ala Leu
            180                 185                 190
Lys Glu Lys Val Ser Ala Leu Lys Glu Lys Val Ser Ala Leu Lys Glu
        195                 200                 205
Lys Val Ser Ala Leu Lys Glu
    210                 215
```

<210> SEQ ID NO 16
<211> LENGTH: 14
<212> TYPE: PRT
<213> ORGANISM: Homo sapiens

<400> SEQUENCE: 16

```
Thr Ala His Pro Ser Pro Ser Pro Arg Ser Ala Gly Gln Phe
1               5                   10
```

<210> SEQ ID NO 17
<211> LENGTH: 10
<212> TYPE: PRT
<213> ORGANISM: Homo sapiens

<400> SEQUENCE: 17

```
Glu Tyr Arg Met Ser Pro Ser Asn Gln Thr
1               5                   10
```

```
<210> SEQ ID NO 18
<211> LENGTH: 10
<212> TYPE: PRT
<213> ORGANISM: Homo sapiens

<400> SEQUENCE: 18

Tyr Tyr Arg Met Ser Pro Ser Asn Gln Thr
1               5                   10

<210> SEQ ID NO 19
<211> LENGTH: 14
<212> TYPE: PRT
<213> ORGANISM: Mus musculus

<400> SEQUENCE: 19

Thr Arg Tyr Pro Ser Pro Ser Pro Lys Pro Glu Gly Arg Phe
1               5                   10

<210> SEQ ID NO 20
<211> LENGTH: 10
<212> TYPE: PRT
<213> ORGANISM: Homo sapiens

<400> SEQUENCE: 20

Trp Asn Arg Leu Ser Pro Ser Asn Gln Thr
1               5                   10

<210> SEQ ID NO 21
<211> LENGTH: 14
<212> TYPE: PRT
<213> ORGANISM: Homo sapiens

<400> SEQUENCE: 21

Thr Ala His Pro Ser Pro Ser Pro Arg Ser Ala Gly Gln Ala
1               5                   10

<210> SEQ ID NO 22
<211> LENGTH: 14
<212> TYPE: PRT
<213> ORGANISM: Homo sapiens

<400> SEQUENCE: 22

Thr Ala His Pro Ser Pro Ser Pro Arg Ser Ala Gly Gln Arg
1               5                   10

<210> SEQ ID NO 23
<211> LENGTH: 14
<212> TYPE: PRT
<213> ORGANISM: Homo sapiens

<400> SEQUENCE: 23

Thr Ala His Pro Ser Pro Ser Pro Arg Ser Ala Gly Gln Asn
1               5                   10

<210> SEQ ID NO 24
<211> LENGTH: 14
<212> TYPE: PRT
<213> ORGANISM: Homo sapiens

<400> SEQUENCE: 24

Thr Ala His Pro Ser Pro Ser Pro Arg Ser Ala Gly Gln Asp
1               5                   10

<210> SEQ ID NO 25
<211> LENGTH: 14
```

```
<212> TYPE: PRT
<213> ORGANISM: Homo sapiens

<400> SEQUENCE: 25

Thr Ala His Pro Ser Pro Ser Pro Arg Ser Ala Gly Gln Cys
1               5                   10

<210> SEQ ID NO 26
<211> LENGTH: 14
<212> TYPE: PRT
<213> ORGANISM: Homo sapiens

<400> SEQUENCE: 26

Thr Ala His Pro Ser Pro Ser Pro Arg Ser Ala Gly Gln Gln
1               5                   10

<210> SEQ ID NO 27
<211> LENGTH: 14
<212> TYPE: PRT
<213> ORGANISM: Homo sapiens

<400> SEQUENCE: 27

Thr Ala His Pro Ser Pro Ser Pro Arg Ser Ala Gly Gln Glu
1               5                   10

<210> SEQ ID NO 28
<211> LENGTH: 14
<212> TYPE: PRT
<213> ORGANISM: Homo sapiens

<400> SEQUENCE: 28

Thr Ala His Pro Ser Pro Ser Pro Arg Ser Ala Gly Gln Gly
1               5                   10

<210> SEQ ID NO 29
<211> LENGTH: 14
<212> TYPE: PRT
<213> ORGANISM: Homo sapiens

<400> SEQUENCE: 29

Thr Ala His Pro Ser Pro Ser Pro Arg Ser Ala Gly Gln His
1               5                   10

<210> SEQ ID NO 30
<211> LENGTH: 14
<212> TYPE: PRT
<213> ORGANISM: Homo sapiens

<400> SEQUENCE: 30

Thr Ala His Pro Ser Pro Ser Pro Arg Ser Ala Gly Gln Ile
1               5                   10

<210> SEQ ID NO 31
<211> LENGTH: 14
<212> TYPE: PRT
<213> ORGANISM: Homo sapiens

<400> SEQUENCE: 31

Thr Ala His Pro Ser Pro Ser Pro Arg Ser Ala Gly Gln Leu
1               5                   10

<210> SEQ ID NO 32
<211> LENGTH: 14
<212> TYPE: PRT
<213> ORGANISM: Homo sapiens
```

<400> SEQUENCE: 32

Thr Ala His Pro Ser Pro Ser Pro Arg Ser Ala Gly Gln Lys
1               5                   10

<210> SEQ ID NO 33
<211> LENGTH: 14
<212> TYPE: PRT
<213> ORGANISM: Homo sapiens

<400> SEQUENCE: 33

Thr Ala His Pro Ser Pro Ser Pro Arg Ser Ala Gly Gln Met
1               5                   10

<210> SEQ ID NO 34
<211> LENGTH: 14
<212> TYPE: PRT
<213> ORGANISM: Homo sapiens

<400> SEQUENCE: 34

Thr Ala His Pro Ser Pro Ser Pro Arg Ser Ala Gly Gln Phe
1               5                   10

<210> SEQ ID NO 35
<211> LENGTH: 14
<212> TYPE: PRT
<213> ORGANISM: Homo sapiens

<400> SEQUENCE: 35

Thr Ala His Pro Ser Pro Ser Pro Arg Ser Ala Gly Gln Pro
1               5                   10

<210> SEQ ID NO 36
<211> LENGTH: 14
<212> TYPE: PRT
<213> ORGANISM: Homo sapiens

<400> SEQUENCE: 36

Thr Ala His Pro Ser Pro Ser Pro Arg Ser Ala Gly Gln Ser
1               5                   10

<210> SEQ ID NO 37
<211> LENGTH: 14
<212> TYPE: PRT
<213> ORGANISM: Homo sapiens

<400> SEQUENCE: 37

Thr Ala His Pro Ser Pro Ser Pro Arg Ser Ala Gly Gln Thr
1               5                   10

<210> SEQ ID NO 38
<211> LENGTH: 14
<212> TYPE: PRT
<213> ORGANISM: Homo sapiens

<400> SEQUENCE: 38

Thr Ala His Pro Ser Pro Ser Pro Arg Ser Ala Gly Gln Trp
1               5                   10

<210> SEQ ID NO 39
<211> LENGTH: 14
<212> TYPE: PRT
<213> ORGANISM: Homo sapiens

<400> SEQUENCE: 39

Thr Ala His Pro Ser Pro Ser Pro Arg Ser Ala Gly Gln Tyr
1               5                   10

<210> SEQ ID NO 40
<211> LENGTH: 14
<212> TYPE: PRT
<213> ORGANISM: Homo sapiens

<400> SEQUENCE: 40

Thr Ala His Pro Ser Pro Ser Pro Arg Ser Ala Gly Gln Val
1               5                   10

<210> SEQ ID NO 41
<211> LENGTH: 14
<212> TYPE: PRT
<213> ORGANISM: Homo sapiens

<400> SEQUENCE: 41

Thr Ala His Pro Ser Pro Ser Pro Arg Ser Ala Gly Ala Phe
1               5                   10

<210> SEQ ID NO 42
<211> LENGTH: 14
<212> TYPE: PRT
<213> ORGANISM: Homo sapiens

<400> SEQUENCE: 42

Thr Ala His Pro Ser Pro Ser Pro Arg Ser Ala Gly Arg Phe
1               5                   10

<210> SEQ ID NO 43
<211> LENGTH: 14
<212> TYPE: PRT
<213> ORGANISM: Homo sapiens

<400> SEQUENCE: 43

Thr Ala His Pro Ser Pro Ser Pro Arg Ser Ala Gly Asn Phe
1               5                   10

<210> SEQ ID NO 44
<211> LENGTH: 14
<212> TYPE: PRT
<213> ORGANISM: Homo sapiens

<400> SEQUENCE: 44

Thr Ala His Pro Ser Pro Ser Pro Arg Ser Ala Gly Asp Phe
1               5                   10

<210> SEQ ID NO 45
<211> LENGTH: 14
<212> TYPE: PRT
<213> ORGANISM: Homo sapiens

<400> SEQUENCE: 45

Thr Ala His Pro Ser Pro Ser Pro Arg Ser Ala Gly Cys Phe
1               5                   10

<210> SEQ ID NO 46
<211> LENGTH: 14
<212> TYPE: PRT
<213> ORGANISM: Homo sapiens

<400> SEQUENCE: 46

Thr Ala His Pro Ser Pro Ser Pro Arg Ser Ala Gly Gln Phe

```
1               5                   10
```

<210> SEQ ID NO 47
<211> LENGTH: 14
<212> TYPE: PRT
<213> ORGANISM: Homo sapiens

<400> SEQUENCE: 47

```
Thr Ala His Pro Ser Pro Ser Pro Arg Ser Ala Gly Glu Phe
1               5                   10
```

<210> SEQ ID NO 48
<211> LENGTH: 14
<212> TYPE: PRT
<213> ORGANISM: Homo sapiens

<400> SEQUENCE: 48

```
Thr Ala His Pro Ser Pro Ser Pro Arg Ser Ala Gly Gly Phe
1               5                   10
```

<210> SEQ ID NO 49
<211> LENGTH: 14
<212> TYPE: PRT
<213> ORGANISM: Homo sapiens

<400> SEQUENCE: 49

```
Thr Ala His Pro Ser Pro Ser Pro Arg Ser Ala Gly His Phe
1               5                   10
```

<210> SEQ ID NO 50
<211> LENGTH: 14
<212> TYPE: PRT
<213> ORGANISM: Homo sapiens

<400> SEQUENCE: 50

```
Thr Ala His Pro Ser Pro Ser Pro Arg Ser Ala Gly Ile Phe
1               5                   10
```

<210> SEQ ID NO 51
<211> LENGTH: 14
<212> TYPE: PRT
<213> ORGANISM: Homo sapiens

<400> SEQUENCE: 51

```
Thr Ala His Pro Ser Pro Ser Pro Arg Ser Ala Gly Leu Phe
1               5                   10
```

<210> SEQ ID NO 52
<211> LENGTH: 14
<212> TYPE: PRT
<213> ORGANISM: Homo sapiens

<400> SEQUENCE: 52

```
Thr Ala His Pro Ser Pro Ser Pro Arg Ser Ala Gly Lys Phe
1               5                   10
```

<210> SEQ ID NO 53
<211> LENGTH: 14
<212> TYPE: PRT
<213> ORGANISM: Homo sapiens

<400> SEQUENCE: 53

```
Thr Ala His Pro Ser Pro Ser Pro Arg Ser Ala Gly Met Phe
1               5                   10
```

<210> SEQ ID NO 54
<211> LENGTH: 14
<212> TYPE: PRT
<213> ORGANISM: Homo sapiens

<400> SEQUENCE: 54

Thr Ala His Pro Ser Pro Ser Pro Arg Ser Ala Gly Phe Phe
1               5                   10

<210> SEQ ID NO 55
<211> LENGTH: 14
<212> TYPE: PRT
<213> ORGANISM: Homo sapiens

<400> SEQUENCE: 55

Thr Ala His Pro Ser Pro Ser Pro Arg Ser Ala Gly Pro Phe
1               5                   10

<210> SEQ ID NO 56
<211> LENGTH: 14
<212> TYPE: PRT
<213> ORGANISM: Homo sapiens

<400> SEQUENCE: 56

Thr Ala His Pro Ser Pro Ser Pro Arg Ser Ala Gly Ser Phe
1               5                   10

<210> SEQ ID NO 57
<211> LENGTH: 14
<212> TYPE: PRT
<213> ORGANISM: Homo sapiens

<400> SEQUENCE: 57

Thr Ala His Pro Ser Pro Ser Pro Arg Ser Ala Gly Thr Phe
1               5                   10

<210> SEQ ID NO 58
<211> LENGTH: 14
<212> TYPE: PRT
<213> ORGANISM: Homo sapiens

<400> SEQUENCE: 58

Thr Ala His Pro Ser Pro Ser Pro Arg Ser Ala Gly Trp Phe
1               5                   10

<210> SEQ ID NO 59
<211> LENGTH: 14
<212> TYPE: PRT
<213> ORGANISM: Homo sapiens

<400> SEQUENCE: 59

Thr Ala His Pro Ser Pro Ser Pro Arg Ser Ala Gly Tyr Phe
1               5                   10

<210> SEQ ID NO 60
<211> LENGTH: 14
<212> TYPE: PRT
<213> ORGANISM: Homo sapiens

<400> SEQUENCE: 60

Thr Ala His Pro Ser Pro Ser Pro Arg Ser Ala Gly Val Phe
1               5                   10

<210> SEQ ID NO 61

```
<211> LENGTH: 14
<212> TYPE: PRT
<213> ORGANISM: Homo sapiens

<400> SEQUENCE: 61

Thr Ala His Pro Ser Pro Ser Pro Arg Ser Ala Ala Gln Phe
1               5                   10

<210> SEQ ID NO 62
<211> LENGTH: 14
<212> TYPE: PRT
<213> ORGANISM: Homo sapiens

<400> SEQUENCE: 62

Thr Ala His Pro Ser Pro Ser Pro Arg Ser Ala Arg Gln Phe
1               5                   10

<210> SEQ ID NO 63
<211> LENGTH: 14
<212> TYPE: PRT
<213> ORGANISM: Homo sapiens

<400> SEQUENCE: 63

Thr Ala His Pro Ser Pro Ser Pro Arg Ser Ala Asn Gln Phe
1               5                   10

<210> SEQ ID NO 64
<211> LENGTH: 14
<212> TYPE: PRT
<213> ORGANISM: Homo sapiens

<400> SEQUENCE: 64

Thr Ala His Pro Ser Pro Ser Pro Arg Ser Ala Asp Gln Phe
1               5                   10

<210> SEQ ID NO 65
<211> LENGTH: 14
<212> TYPE: PRT
<213> ORGANISM: Homo sapiens

<400> SEQUENCE: 65

Thr Ala His Pro Ser Pro Ser Pro Arg Ser Ala Cys Gln Phe
1               5                   10

<210> SEQ ID NO 66
<211> LENGTH: 14
<212> TYPE: PRT
<213> ORGANISM: Homo sapiens

<400> SEQUENCE: 66

Thr Ala His Pro Ser Pro Ser Pro Arg Ser Ala Gln Gln Phe
1               5                   10

<210> SEQ ID NO 67
<211> LENGTH: 14
<212> TYPE: PRT
<213> ORGANISM: Homo sapiens

<400> SEQUENCE: 67

Thr Ala His Pro Ser Pro Ser Pro Arg Ser Ala Glu Gln Phe
1               5                   10

<210> SEQ ID NO 68
<211> LENGTH: 14
<212> TYPE: PRT
```

<213> ORGANISM: Homo sapiens

<400> SEQUENCE: 68

Thr Ala His Pro Ser Pro Ser Pro Arg Ser Ala Gly Gln Phe
1               5                   10

<210> SEQ ID NO 69
<211> LENGTH: 14
<212> TYPE: PRT
<213> ORGANISM: Homo sapiens

<400> SEQUENCE: 69

Thr Ala His Pro Ser Pro Ser Pro Arg Ser Ala His Gln Phe
1               5                   10

<210> SEQ ID NO 70
<211> LENGTH: 14
<212> TYPE: PRT
<213> ORGANISM: Homo sapiens

<400> SEQUENCE: 70

Thr Ala His Pro Ser Pro Ser Pro Arg Ser Ala Ile Gln Phe
1               5                   10

<210> SEQ ID NO 71
<211> LENGTH: 14
<212> TYPE: PRT
<213> ORGANISM: Homo sapiens

<400> SEQUENCE: 71

Thr Ala His Pro Ser Pro Ser Pro Arg Ser Ala Leu Gln Phe
1               5                   10

<210> SEQ ID NO 72
<211> LENGTH: 14
<212> TYPE: PRT
<213> ORGANISM: Homo sapiens

<400> SEQUENCE: 72

Thr Ala His Pro Ser Pro Ser Pro Arg Ser Ala Lys Gln Phe
1               5                   10

<210> SEQ ID NO 73
<211> LENGTH: 14
<212> TYPE: PRT
<213> ORGANISM: Homo sapiens

<400> SEQUENCE: 73

Thr Ala His Pro Ser Pro Ser Pro Arg Ser Ala Met Gln Phe
1               5                   10

<210> SEQ ID NO 74
<211> LENGTH: 14
<212> TYPE: PRT
<213> ORGANISM: Homo sapiens

<400> SEQUENCE: 74

Thr Ala His Pro Ser Pro Ser Pro Arg Ser Ala Phe Gln Phe
1               5                   10

<210> SEQ ID NO 75
<211> LENGTH: 14
<212> TYPE: PRT
<213> ORGANISM: Homo sapiens

```
<400> SEQUENCE: 75

Thr Ala His Pro Ser Pro Ser Pro Arg Ser Ala Pro Gln Phe
1               5                   10

<210> SEQ ID NO 76
<211> LENGTH: 14
<212> TYPE: PRT
<213> ORGANISM: Homo sapiens

<400> SEQUENCE: 76

Thr Ala His Pro Ser Pro Ser Pro Arg Ser Ala Ser Gln Phe
1               5                   10

<210> SEQ ID NO 77
<211> LENGTH: 14
<212> TYPE: PRT
<213> ORGANISM: Homo sapiens

<400> SEQUENCE: 77

Thr Ala His Pro Ser Pro Ser Pro Arg Ser Ala Thr Gln Phe
1               5                   10

<210> SEQ ID NO 78
<211> LENGTH: 14
<212> TYPE: PRT
<213> ORGANISM: Homo sapiens

<400> SEQUENCE: 78

Thr Ala His Pro Ser Pro Ser Pro Arg Ser Ala Trp Gln Phe
1               5                   10

<210> SEQ ID NO 79
<211> LENGTH: 14
<212> TYPE: PRT
<213> ORGANISM: Homo sapiens

<400> SEQUENCE: 79

Thr Ala His Pro Ser Pro Ser Pro Arg Ser Ala Tyr Gln Phe
1               5                   10

<210> SEQ ID NO 80
<211> LENGTH: 14
<212> TYPE: PRT
<213> ORGANISM: Homo sapiens

<400> SEQUENCE: 80

Thr Ala His Pro Ser Pro Ser Pro Arg Ser Ala Val Gln Phe
1               5                   10

<210> SEQ ID NO 81
<211> LENGTH: 14
<212> TYPE: PRT
<213> ORGANISM: Homo sapiens

<400> SEQUENCE: 81

Thr Ala His Pro Ser Pro Ser Pro Arg Ser Ala Gly Gln Phe
1               5                   10

<210> SEQ ID NO 82
<211> LENGTH: 14
<212> TYPE: PRT
<213> ORGANISM: Homo sapiens

<400> SEQUENCE: 82
```

Thr Ala His Pro Ser Pro Ser Pro Arg Ser Arg Gly Gln Phe
1               5                   10

<210> SEQ ID NO 83
<211> LENGTH: 14
<212> TYPE: PRT
<213> ORGANISM: Homo sapiens

<400> SEQUENCE: 83

Thr Ala His Pro Ser Pro Ser Pro Arg Ser Asn Gly Gln Phe
1               5                   10

<210> SEQ ID NO 84
<211> LENGTH: 14
<212> TYPE: PRT
<213> ORGANISM: Homo sapiens

<400> SEQUENCE: 84

Thr Ala His Pro Ser Pro Ser Pro Arg Ser Asp Gly Gln Phe
1               5                   10

<210> SEQ ID NO 85
<211> LENGTH: 14
<212> TYPE: PRT
<213> ORGANISM: Homo sapiens

<400> SEQUENCE: 85

Thr Ala His Pro Ser Pro Ser Pro Arg Ser Cys Gly Gln Phe
1               5                   10

<210> SEQ ID NO 86
<211> LENGTH: 14
<212> TYPE: PRT
<213> ORGANISM: Homo sapiens

<400> SEQUENCE: 86

Thr Ala His Pro Ser Pro Ser Pro Arg Ser Gln Gly Gln Phe
1               5                   10

<210> SEQ ID NO 87
<211> LENGTH: 14
<212> TYPE: PRT
<213> ORGANISM: Homo sapiens

<400> SEQUENCE: 87

Thr Ala His Pro Ser Pro Ser Pro Arg Ser Glu Gly Gln Phe
1               5                   10

<210> SEQ ID NO 88
<211> LENGTH: 14
<212> TYPE: PRT
<213> ORGANISM: Homo sapiens

<400> SEQUENCE: 88

Thr Ala His Pro Ser Pro Ser Pro Arg Ser Gly Gly Gln Phe
1               5                   10

<210> SEQ ID NO 89
<211> LENGTH: 14
<212> TYPE: PRT
<213> ORGANISM: Homo sapiens

<400> SEQUENCE: 89

Thr Ala His Pro Ser Pro Ser Pro Arg Ser His Gly Gln Phe
1               5                   10

```
<210> SEQ ID NO 90
<211> LENGTH: 14
<212> TYPE: PRT
<213> ORGANISM: Homo sapiens

<400> SEQUENCE: 90

Thr Ala His Pro Ser Pro Ser Pro Arg Ser Ile Gly Gln Phe
1               5                   10

<210> SEQ ID NO 91
<211> LENGTH: 14
<212> TYPE: PRT
<213> ORGANISM: Homo sapiens

<400> SEQUENCE: 91

Thr Ala His Pro Ser Pro Ser Pro Arg Ser Leu Gly Gln Phe
1               5                   10

<210> SEQ ID NO 92
<211> LENGTH: 14
<212> TYPE: PRT
<213> ORGANISM: Homo sapiens

<400> SEQUENCE: 92

Thr Ala His Pro Ser Pro Ser Pro Arg Ser Lys Gly Gln Phe
1               5                   10

<210> SEQ ID NO 93
<211> LENGTH: 14
<212> TYPE: PRT
<213> ORGANISM: Homo sapiens

<400> SEQUENCE: 93

Thr Ala His Pro Ser Pro Ser Pro Arg Ser Met Gly Gln Phe
1               5                   10

<210> SEQ ID NO 94
<211> LENGTH: 14
<212> TYPE: PRT
<213> ORGANISM: Homo sapiens

<400> SEQUENCE: 94

Thr Ala His Pro Ser Pro Ser Pro Arg Ser Phe Gly Gln Phe
1               5                   10

<210> SEQ ID NO 95
<211> LENGTH: 14
<212> TYPE: PRT
<213> ORGANISM: Homo sapiens

<400> SEQUENCE: 95

Thr Ala His Pro Ser Pro Ser Pro Arg Ser Pro Gly Gln Phe
1               5                   10

<210> SEQ ID NO 96
<211> LENGTH: 14
<212> TYPE: PRT
<213> ORGANISM: Homo sapiens

<400> SEQUENCE: 96

Thr Ala His Pro Ser Pro Ser Pro Arg Ser Ser Gly Gln Phe
1               5                   10
```

```
<210> SEQ ID NO 97
<211> LENGTH: 14
<212> TYPE: PRT
<213> ORGANISM: Homo sapiens

<400> SEQUENCE: 97

Thr Ala His Pro Ser Pro Ser Pro Arg Ser Thr Gly Gln Phe
1               5                   10

<210> SEQ ID NO 98
<211> LENGTH: 14
<212> TYPE: PRT
<213> ORGANISM: Homo sapiens

<400> SEQUENCE: 98

Thr Ala His Pro Ser Pro Ser Pro Arg Ser Trp Gly Gln Phe
1               5                   10

<210> SEQ ID NO 99
<211> LENGTH: 14
<212> TYPE: PRT
<213> ORGANISM: Homo sapiens

<400> SEQUENCE: 99

Thr Ala His Pro Ser Pro Ser Pro Arg Ser Tyr Gly Gln Phe
1               5                   10

<210> SEQ ID NO 100
<211> LENGTH: 14
<212> TYPE: PRT
<213> ORGANISM: Homo sapiens

<400> SEQUENCE: 100

Thr Ala His Pro Ser Pro Ser Pro Arg Ser Val Gly Gln Phe
1               5                   10

<210> SEQ ID NO 101
<211> LENGTH: 14
<212> TYPE: PRT
<213> ORGANISM: Homo sapiens

<400> SEQUENCE: 101

Thr Ala His Pro Ser Pro Ser Pro Arg Ala Ala Gly Gln Phe
1               5                   10

<210> SEQ ID NO 102
<211> LENGTH: 14
<212> TYPE: PRT
<213> ORGANISM: Homo sapiens

<400> SEQUENCE: 102

Thr Ala His Pro Ser Pro Ser Pro Arg Arg Ala Gly Gln Phe
1               5                   10

<210> SEQ ID NO 103
<211> LENGTH: 14
<212> TYPE: PRT
<213> ORGANISM: Homo sapiens

<400> SEQUENCE: 103

Thr Ala His Pro Ser Pro Ser Pro Arg Asn Ala Gly Gln Phe
1               5                   10

<210> SEQ ID NO 104
<211> LENGTH: 14
```

<212> TYPE: PRT
<213> ORGANISM: Homo sapiens

<400> SEQUENCE: 104

Thr Ala His Pro Ser Pro Ser Pro Arg Asp Ala Gly Gln Phe
1               5                   10

<210> SEQ ID NO 105
<211> LENGTH: 14
<212> TYPE: PRT
<213> ORGANISM: Homo sapiens

<400> SEQUENCE: 105

Thr Ala His Pro Ser Pro Ser Pro Arg Cys Ala Gly Gln Phe
1               5                   10

<210> SEQ ID NO 106
<211> LENGTH: 14
<212> TYPE: PRT
<213> ORGANISM: Homo sapiens

<400> SEQUENCE: 106

Thr Ala His Pro Ser Pro Ser Pro Arg Gln Ala Gly Gln Phe
1               5                   10

<210> SEQ ID NO 107
<211> LENGTH: 14
<212> TYPE: PRT
<213> ORGANISM: Homo sapiens

<400> SEQUENCE: 107

Thr Ala His Pro Ser Pro Ser Pro Arg Glu Ala Gly Gln Phe
1               5                   10

<210> SEQ ID NO 108
<211> LENGTH: 14
<212> TYPE: PRT
<213> ORGANISM: Homo sapiens

<400> SEQUENCE: 108

Thr Ala His Pro Ser Pro Ser Pro Arg Gly Ala Gly Gln Phe
1               5                   10

<210> SEQ ID NO 109
<211> LENGTH: 14
<212> TYPE: PRT
<213> ORGANISM: Homo sapiens

<400> SEQUENCE: 109

Thr Ala His Pro Ser Pro Ser Pro Arg His Ala Gly Gln Phe
1               5                   10

<210> SEQ ID NO 110
<211> LENGTH: 14
<212> TYPE: PRT
<213> ORGANISM: Homo sapiens

<400> SEQUENCE: 110

Thr Ala His Pro Ser Pro Ser Pro Arg Ile Ala Gly Gln Phe
1               5                   10

<210> SEQ ID NO 111
<211> LENGTH: 14
<212> TYPE: PRT
<213> ORGANISM: Homo sapiens

<400> SEQUENCE: 111

Thr Ala His Pro Ser Pro Ser Pro Arg Leu Ala Gly Gln Phe
1               5                   10

<210> SEQ ID NO 112
<211> LENGTH: 14
<212> TYPE: PRT
<213> ORGANISM: Homo sapiens

<400> SEQUENCE: 112

Thr Ala His Pro Ser Pro Ser Pro Arg Lys Ala Gly Gln Phe
1               5                   10

<210> SEQ ID NO 113
<211> LENGTH: 14
<212> TYPE: PRT
<213> ORGANISM: Homo sapiens

<400> SEQUENCE: 113

Thr Ala His Pro Ser Pro Ser Pro Arg Met Ala Gly Gln Phe
1               5                   10

<210> SEQ ID NO 114
<211> LENGTH: 14
<212> TYPE: PRT
<213> ORGANISM: Homo sapiens

<400> SEQUENCE: 114

Thr Ala His Pro Ser Pro Ser Pro Arg Phe Ala Gly Gln Phe
1               5                   10

<210> SEQ ID NO 115
<211> LENGTH: 14
<212> TYPE: PRT
<213> ORGANISM: Homo sapiens

<400> SEQUENCE: 115

Thr Ala His Pro Ser Pro Ser Pro Arg Pro Ala Gly Gln Phe
1               5                   10

<210> SEQ ID NO 116
<211> LENGTH: 14
<212> TYPE: PRT
<213> ORGANISM: Homo sapiens

<400> SEQUENCE: 116

Thr Ala His Pro Ser Pro Ser Pro Arg Ser Ala Gly Gln Phe
1               5                   10

<210> SEQ ID NO 117
<211> LENGTH: 14
<212> TYPE: PRT
<213> ORGANISM: Homo sapiens

<400> SEQUENCE: 117

Thr Ala His Pro Ser Pro Ser Pro Arg Thr Ala Gly Gln Phe
1               5                   10

<210> SEQ ID NO 118
<211> LENGTH: 14
<212> TYPE: PRT
<213> ORGANISM: Homo sapiens

<400> SEQUENCE: 118

Thr Ala His Pro Ser Pro Ser Pro Arg Trp Ala Gly Gln Phe
1               5                   10

<210> SEQ ID NO 119
<211> LENGTH: 14
<212> TYPE: PRT
<213> ORGANISM: Homo sapiens

<400> SEQUENCE: 119

Thr Ala His Pro Ser Pro Ser Pro Arg Tyr Ala Gly Gln Phe
1               5                   10

<210> SEQ ID NO 120
<211> LENGTH: 14
<212> TYPE: PRT
<213> ORGANISM: Homo sapiens

<400> SEQUENCE: 120

Thr Ala His Pro Ser Pro Ser Pro Arg Val Ala Gly Gln Phe
1               5                   10

<210> SEQ ID NO 121
<211> LENGTH: 14
<212> TYPE: PRT
<213> ORGANISM: Homo sapiens

<400> SEQUENCE: 121

Thr Ala His Pro Ser Pro Ser Pro Ala Ser Ala Gly Gln Phe
1               5                   10

<210> SEQ ID NO 122
<211> LENGTH: 14
<212> TYPE: PRT
<213> ORGANISM: Homo sapiens

<400> SEQUENCE: 122

Thr Ala His Pro Ser Pro Ser Pro Arg Ser Ala Gly Gln Phe
1               5                   10

<210> SEQ ID NO 123
<211> LENGTH: 14
<212> TYPE: PRT
<213> ORGANISM: Homo sapiens

<400> SEQUENCE: 123

Thr Ala His Pro Ser Pro Ser Pro Asn Ser Ala Gly Gln Phe
1               5                   10

<210> SEQ ID NO 124
<211> LENGTH: 14
<212> TYPE: PRT
<213> ORGANISM: Homo sapiens

<400> SEQUENCE: 124

Thr Ala His Pro Ser Pro Ser Pro Asp Ser Ala Gly Gln Phe
1               5                   10

<210> SEQ ID NO 125
<211> LENGTH: 14
<212> TYPE: PRT
<213> ORGANISM: Homo sapiens

<400> SEQUENCE: 125

Thr Ala His Pro Ser Pro Ser Pro Cys Ser Ala Gly Gln Phe

```
1               5                   10
```

<210> SEQ ID NO 126
<211> LENGTH: 14
<212> TYPE: PRT
<213> ORGANISM: Homo sapiens

<400> SEQUENCE: 126

```
Thr Ala His Pro Ser Pro Ser Pro Gln Ser Ala Gly Gln Phe
1               5                   10
```

<210> SEQ ID NO 127
<211> LENGTH: 14
<212> TYPE: PRT
<213> ORGANISM: Homo sapiens

<400> SEQUENCE: 127

```
Thr Ala His Pro Ser Pro Ser Pro Glu Ser Ala Gly Gln Phe
1               5                   10
```

<210> SEQ ID NO 128
<211> LENGTH: 14
<212> TYPE: PRT
<213> ORGANISM: Homo sapiens

<400> SEQUENCE: 128

```
Thr Ala His Pro Ser Pro Ser Pro Gly Ser Ala Gly Gln Phe
1               5                   10
```

<210> SEQ ID NO 129
<211> LENGTH: 14
<212> TYPE: PRT
<213> ORGANISM: Homo sapiens

<400> SEQUENCE: 129

```
Thr Ala His Pro Ser Pro Ser Pro His Ser Ala Gly Gln Phe
1               5                   10
```

<210> SEQ ID NO 130
<211> LENGTH: 14
<212> TYPE: PRT
<213> ORGANISM: Homo sapiens

<400> SEQUENCE: 130

```
Thr Ala His Pro Ser Pro Ser Pro Ile Ser Ala Gly Gln Phe
1               5                   10
```

<210> SEQ ID NO 131
<211> LENGTH: 14
<212> TYPE: PRT
<213> ORGANISM: Homo sapiens

<400> SEQUENCE: 131

```
Thr Ala His Pro Ser Pro Ser Pro Leu Ser Ala Gly Gln Phe
1               5                   10
```

<210> SEQ ID NO 132
<211> LENGTH: 14
<212> TYPE: PRT
<213> ORGANISM: Homo sapiens

<400> SEQUENCE: 132

```
Thr Ala His Pro Ser Pro Ser Pro Lys Ser Ala Gly Gln Phe
1               5                   10
```

-continued

<210> SEQ ID NO 133
<211> LENGTH: 14
<212> TYPE: PRT
<213> ORGANISM: Homo sapiens

<400> SEQUENCE: 133

Thr Ala His Pro Ser Pro Ser Pro Met Ser Ala Gly Gln Phe
1               5                   10

<210> SEQ ID NO 134
<211> LENGTH: 14
<212> TYPE: PRT
<213> ORGANISM: Homo sapiens

<400> SEQUENCE: 134

Thr Ala His Pro Ser Pro Ser Pro Phe Ser Ala Gly Gln Phe
1               5                   10

<210> SEQ ID NO 135
<211> LENGTH: 14
<212> TYPE: PRT
<213> ORGANISM: Homo sapiens

<400> SEQUENCE: 135

Thr Ala His Pro Ser Pro Ser Pro Pro Ser Ala Gly Gln Phe
1               5                   10

<210> SEQ ID NO 136
<211> LENGTH: 14
<212> TYPE: PRT
<213> ORGANISM: Homo sapiens

<400> SEQUENCE: 136

Thr Ala His Pro Ser Pro Ser Pro Ser Ser Ala Gly Gln Phe
1               5                   10

<210> SEQ ID NO 137
<211> LENGTH: 14
<212> TYPE: PRT
<213> ORGANISM: Homo sapiens

<400> SEQUENCE: 137

Thr Ala His Pro Ser Pro Ser Pro Thr Ser Ala Gly Gln Phe
1               5                   10

<210> SEQ ID NO 138
<211> LENGTH: 14
<212> TYPE: PRT
<213> ORGANISM: Homo sapiens

<400> SEQUENCE: 138

Thr Ala His Pro Ser Pro Ser Pro Trp Ser Ala Gly Gln Phe
1               5                   10

<210> SEQ ID NO 139
<211> LENGTH: 14
<212> TYPE: PRT
<213> ORGANISM: Homo sapiens

<400> SEQUENCE: 139

Thr Ala His Pro Ser Pro Ser Pro Tyr Ser Ala Gly Gln Phe
1               5                   10

<210> SEQ ID NO 140

```
<211> LENGTH: 14
<212> TYPE: PRT
<213> ORGANISM: Homo sapiens

<400> SEQUENCE: 140

Thr Ala His Pro Ser Pro Ser Pro Val Ser Ala Gly Gln Phe
1               5                   10

<210> SEQ ID NO 141
<211> LENGTH: 14
<212> TYPE: PRT
<213> ORGANISM: Homo sapiens

<400> SEQUENCE: 141

Thr Ala His Pro Ser Pro Ser Ala Arg Ser Ala Gly Gln Phe
1               5                   10

<210> SEQ ID NO 142
<211> LENGTH: 14
<212> TYPE: PRT
<213> ORGANISM: Homo sapiens

<400> SEQUENCE: 142

Thr Ala His Pro Ser Pro Ser Arg Arg Ser Ala Gly Gln Phe
1               5                   10

<210> SEQ ID NO 143
<211> LENGTH: 14
<212> TYPE: PRT
<213> ORGANISM: Homo sapiens

<400> SEQUENCE: 143

Thr Ala His Pro Ser Pro Ser Asn Arg Ser Ala Gly Gln Phe
1               5                   10

<210> SEQ ID NO 144
<211> LENGTH: 14
<212> TYPE: PRT
<213> ORGANISM: Homo sapiens

<400> SEQUENCE: 144

Thr Ala His Pro Ser Pro Ser Asp Arg Ser Ala Gly Gln Phe
1               5                   10

<210> SEQ ID NO 145
<211> LENGTH: 14
<212> TYPE: PRT
<213> ORGANISM: Homo sapiens

<400> SEQUENCE: 145

Thr Ala His Pro Ser Pro Ser Cys Arg Ser Ala Gly Gln Phe
1               5                   10

<210> SEQ ID NO 146
<211> LENGTH: 14
<212> TYPE: PRT
<213> ORGANISM: Homo sapiens

<400> SEQUENCE: 146

Thr Ala His Pro Ser Pro Ser Gln Arg Ser Ala Gly Gln Phe
1               5                   10

<210> SEQ ID NO 147
<211> LENGTH: 14
<212> TYPE: PRT
```

<213> ORGANISM: Homo sapiens

<400> SEQUENCE: 147

Thr Ala His Pro Ser Pro Ser Glu Arg Ser Ala Gly Gln Phe
1               5                   10

<210> SEQ ID NO 148
<211> LENGTH: 14
<212> TYPE: PRT
<213> ORGANISM: Homo sapiens

<400> SEQUENCE: 148

Thr Ala His Pro Ser Pro Ser Gly Arg Ser Ala Gly Gln Phe
1               5                   10

<210> SEQ ID NO 149
<211> LENGTH: 14
<212> TYPE: PRT
<213> ORGANISM: Homo sapiens

<400> SEQUENCE: 149

Thr Ala His Pro Ser Pro Ser His Arg Ser Ala Gly Gln Phe
1               5                   10

<210> SEQ ID NO 150
<211> LENGTH: 14
<212> TYPE: PRT
<213> ORGANISM: Homo sapiens

<400> SEQUENCE: 150

Thr Ala His Pro Ser Pro Ser Ile Arg Ser Ala Gly Gln Phe
1               5                   10

<210> SEQ ID NO 151
<211> LENGTH: 14
<212> TYPE: PRT
<213> ORGANISM: Homo sapiens

<400> SEQUENCE: 151

Thr Ala His Pro Ser Pro Ser Leu Arg Ser Ala Gly Gln Phe
1               5                   10

<210> SEQ ID NO 152
<211> LENGTH: 14
<212> TYPE: PRT
<213> ORGANISM: Homo sapiens

<400> SEQUENCE: 152

Thr Ala His Pro Ser Pro Ser Lys Arg Ser Ala Gly Gln Phe
1               5                   10

<210> SEQ ID NO 153
<211> LENGTH: 14
<212> TYPE: PRT
<213> ORGANISM: Homo sapiens

<400> SEQUENCE: 153

Thr Ala His Pro Ser Pro Ser Met Arg Ser Ala Gly Gln Phe
1               5                   10

<210> SEQ ID NO 154
<211> LENGTH: 14
<212> TYPE: PRT
<213> ORGANISM: Homo sapiens

<400> SEQUENCE: 154

Thr Ala His Pro Ser Pro Ser Phe Arg Ser Ala Gly Gln Phe
1               5                   10

<210> SEQ ID NO 155
<211> LENGTH: 14
<212> TYPE: PRT
<213> ORGANISM: Homo sapiens

<400> SEQUENCE: 155

Thr Ala His Pro Ser Pro Ser Pro Arg Ser Ala Gly Gln Phe
1               5                   10

<210> SEQ ID NO 156
<211> LENGTH: 14
<212> TYPE: PRT
<213> ORGANISM: Homo sapiens

<400> SEQUENCE: 156

Thr Ala His Pro Ser Pro Ser Ser Arg Ser Ala Gly Gln Phe
1               5                   10

<210> SEQ ID NO 157
<211> LENGTH: 14
<212> TYPE: PRT
<213> ORGANISM: Homo sapiens

<400> SEQUENCE: 157

Thr Ala His Pro Ser Pro Ser Thr Arg Ser Ala Gly Gln Phe
1               5                   10

<210> SEQ ID NO 158
<211> LENGTH: 14
<212> TYPE: PRT
<213> ORGANISM: Homo sapiens

<400> SEQUENCE: 158

Thr Ala His Pro Ser Pro Ser Trp Arg Ser Ala Gly Gln Phe
1               5                   10

<210> SEQ ID NO 159
<211> LENGTH: 14
<212> TYPE: PRT
<213> ORGANISM: Homo sapiens

<400> SEQUENCE: 159

Thr Ala His Pro Ser Pro Ser Tyr Arg Ser Ala Gly Gln Phe
1               5                   10

<210> SEQ ID NO 160
<211> LENGTH: 14
<212> TYPE: PRT
<213> ORGANISM: Homo sapiens

<400> SEQUENCE: 160

Thr Ala His Pro Ser Pro Ser Val Arg Ser Ala Gly Gln Phe
1               5                   10

<210> SEQ ID NO 161
<211> LENGTH: 14
<212> TYPE: PRT
<213> ORGANISM: Homo sapiens

<400> SEQUENCE: 161

Thr Ala His Pro Ser Pro Ala Pro Arg Ser Ala Gly Gln Phe
1               5                   10

<210> SEQ ID NO 162
<211> LENGTH: 14
<212> TYPE: PRT
<213> ORGANISM: Homo sapiens

<400> SEQUENCE: 162

Thr Ala His Pro Ser Pro Arg Pro Arg Ser Ala Gly Gln Phe
1               5                   10

<210> SEQ ID NO 163
<211> LENGTH: 14
<212> TYPE: PRT
<213> ORGANISM: Homo sapiens

<400> SEQUENCE: 163

Thr Ala His Pro Ser Pro Asn Pro Arg Ser Ala Gly Gln Phe
1               5                   10

<210> SEQ ID NO 164
<211> LENGTH: 14
<212> TYPE: PRT
<213> ORGANISM: Homo sapiens

<400> SEQUENCE: 164

Thr Ala His Pro Ser Pro Asp Pro Arg Ser Ala Gly Gln Phe
1               5                   10

<210> SEQ ID NO 165
<211> LENGTH: 14
<212> TYPE: PRT
<213> ORGANISM: Homo sapiens

<400> SEQUENCE: 165

Thr Ala His Pro Ser Pro Cys Pro Arg Ser Ala Gly Gln Phe
1               5                   10

<210> SEQ ID NO 166
<211> LENGTH: 14
<212> TYPE: PRT
<213> ORGANISM: Homo sapiens

<400> SEQUENCE: 166

Thr Ala His Pro Ser Pro Glu Pro Arg Ser Ala Gly Gln Phe
1               5                   10

<210> SEQ ID NO 167
<211> LENGTH: 14
<212> TYPE: PRT
<213> ORGANISM: Homo sapiens

<400> SEQUENCE: 167

Thr Ala His Pro Ser Pro Gln Pro Arg Ser Ala Gly Gln Phe
1               5                   10

<210> SEQ ID NO 168
<211> LENGTH: 14
<212> TYPE: PRT
<213> ORGANISM: Homo sapiens

<400> SEQUENCE: 168

Thr Ala His Pro Ser Pro Gly Pro Arg Ser Ala Gly Gln Phe
1               5                   10

<210> SEQ ID NO 169
<211> LENGTH: 14
<212> TYPE: PRT
<213> ORGANISM: Homo sapiens

<400> SEQUENCE: 169

Thr Ala His Pro Ser Pro His Pro Arg Ser Ala Gly Gln Phe
1               5                   10

<210> SEQ ID NO 170
<211> LENGTH: 14
<212> TYPE: PRT
<213> ORGANISM: Homo sapiens

<400> SEQUENCE: 170

Thr Ala His Pro Ser Pro Ile Pro Arg Ser Ala Gly Gln Phe
1               5                   10

<210> SEQ ID NO 171
<211> LENGTH: 14
<212> TYPE: PRT
<213> ORGANISM: Homo sapiens

<400> SEQUENCE: 171

Thr Ala His Pro Ser Pro Leu Pro Arg Ser Ala Gly Gln Phe
1               5                   10

<210> SEQ ID NO 172
<211> LENGTH: 14
<212> TYPE: PRT
<213> ORGANISM: Homo sapiens

<400> SEQUENCE: 172

Thr Ala His Pro Ser Pro Lys Pro Arg Ser Ala Gly Gln Phe
1               5                   10

<210> SEQ ID NO 173
<211> LENGTH: 14
<212> TYPE: PRT
<213> ORGANISM: Homo sapiens

<400> SEQUENCE: 173

Thr Ala His Pro Ser Pro Met Pro Arg Ser Ala Gly Gln Phe
1               5                   10

<210> SEQ ID NO 174
<211> LENGTH: 14
<212> TYPE: PRT
<213> ORGANISM: Homo sapiens

<400> SEQUENCE: 174

Thr Ala His Pro Ser Pro Phe Pro Arg Ser Ala Gly Gln Phe
1               5                   10

<210> SEQ ID NO 175
<211> LENGTH: 14
<212> TYPE: PRT
<213> ORGANISM: Homo sapiens

<400> SEQUENCE: 175

Thr Ala His Pro Ser Pro Pro Pro Arg Ser Ala Gly Gln Phe
1               5                   10

```
<210> SEQ ID NO 176
<211> LENGTH: 14
<212> TYPE: PRT
<213> ORGANISM: Homo sapiens

<400> SEQUENCE: 176

Thr Ala His Pro Ser Pro Ser Pro Arg Ser Ala Gly Gln Phe
1               5                   10

<210> SEQ ID NO 177
<211> LENGTH: 14
<212> TYPE: PRT
<213> ORGANISM: Homo sapiens

<400> SEQUENCE: 177

Thr Ala His Pro Ser Pro Thr Pro Arg Ser Ala Gly Gln Phe
1               5                   10

<210> SEQ ID NO 178
<211> LENGTH: 14
<212> TYPE: PRT
<213> ORGANISM: Homo sapiens

<400> SEQUENCE: 178

Thr Ala His Pro Ser Pro Trp Pro Arg Ser Ala Gly Gln Phe
1               5                   10

<210> SEQ ID NO 179
<211> LENGTH: 14
<212> TYPE: PRT
<213> ORGANISM: Homo sapiens

<400> SEQUENCE: 179

Thr Ala His Pro Ser Pro Tyr Pro Arg Ser Ala Gly Gln Phe
1               5                   10

<210> SEQ ID NO 180
<211> LENGTH: 14
<212> TYPE: PRT
<213> ORGANISM: Homo sapiens

<400> SEQUENCE: 180

Thr Ala His Pro Ser Pro Val Pro Arg Ser Ala Gly Gln Phe
1               5                   10

<210> SEQ ID NO 181
<211> LENGTH: 14
<212> TYPE: PRT
<213> ORGANISM: Homo sapiens

<400> SEQUENCE: 181

Thr Ala His Pro Ser Ala Ser Pro Arg Ser Ala Gly Gln Phe
1               5                   10

<210> SEQ ID NO 182
<211> LENGTH: 14
<212> TYPE: PRT
<213> ORGANISM: Homo sapiens

<400> SEQUENCE: 182

Thr Ala His Pro Ser Arg Ser Pro Arg Ser Ala Gly Gln Phe
1               5                   10

<210> SEQ ID NO 183
<211> LENGTH: 14
```

<210> SEQ ID NO 183
<211> LENGTH: 14
<212> TYPE: PRT
<213> ORGANISM: Homo sapiens

<400> SEQUENCE: 183

Thr Ala His Pro Ser Asn Ser Pro Arg Ser Ala Gly Gln Phe
1               5                   10

<210> SEQ ID NO 184
<211> LENGTH: 14
<212> TYPE: PRT
<213> ORGANISM: Homo sapiens

<400> SEQUENCE: 184

Thr Ala His Pro Ser Asp Ser Pro Arg Ser Ala Gly Gln Phe
1               5                   10

<210> SEQ ID NO 185
<211> LENGTH: 14
<212> TYPE: PRT
<213> ORGANISM: Homo sapiens

<400> SEQUENCE: 185

Thr Ala His Pro Ser Cys Ser Pro Arg Ser Ala Gly Gln Phe
1               5                   10

<210> SEQ ID NO 186
<211> LENGTH: 14
<212> TYPE: PRT
<213> ORGANISM: Homo sapiens

<400> SEQUENCE: 186

Thr Ala His Pro Ser Gln Ser Pro Arg Ser Ala Gly Gln Phe
1               5                   10

<210> SEQ ID NO 187
<211> LENGTH: 14
<212> TYPE: PRT
<213> ORGANISM: Homo sapiens

<400> SEQUENCE: 187

Thr Ala His Pro Ser Glu Ser Pro Arg Ser Ala Gly Gln Phe
1               5                   10

<210> SEQ ID NO 188
<211> LENGTH: 14
<212> TYPE: PRT
<213> ORGANISM: Homo sapiens

<400> SEQUENCE: 188

Thr Ala His Pro Ser Gly Ser Pro Arg Ser Ala Gly Gln Phe
1               5                   10

<210> SEQ ID NO 189
<211> LENGTH: 14
<212> TYPE: PRT
<213> ORGANISM: Homo sapiens

<400> SEQUENCE: 189

Thr Ala His Pro Ser His Ser Pro Arg Ser Ala Gly Gln Phe
1               5                   10

<210> SEQ ID NO 190
<211> LENGTH: 14
<212> TYPE: PRT
<213> ORGANISM: Homo sapiens

<400> SEQUENCE: 190

Thr Ala His Pro Ser Ile Ser Pro Arg Ser Ala Gly Gln Phe
1               5                   10

<210> SEQ ID NO 191
<211> LENGTH: 14
<212> TYPE: PRT
<213> ORGANISM: Homo sapiens

<400> SEQUENCE: 191

Thr Ala His Pro Ser Leu Ser Pro Arg Ser Ala Gly Gln Phe
1               5                   10

<210> SEQ ID NO 192
<211> LENGTH: 14
<212> TYPE: PRT
<213> ORGANISM: Homo sapiens

<400> SEQUENCE: 192

Thr Ala His Pro Ser Lys Ser Pro Arg Ser Ala Gly Gln Phe
1               5                   10

<210> SEQ ID NO 193
<211> LENGTH: 14
<212> TYPE: PRT
<213> ORGANISM: Homo sapiens

<400> SEQUENCE: 193

Thr Ala His Pro Ser Met Ser Pro Arg Ser Ala Gly Gln Phe
1               5                   10

<210> SEQ ID NO 194
<211> LENGTH: 14
<212> TYPE: PRT
<213> ORGANISM: Homo sapiens

<400> SEQUENCE: 194

Thr Ala His Pro Ser Phe Ser Pro Arg Ser Ala Gly Gln Phe
1               5                   10

<210> SEQ ID NO 195
<211> LENGTH: 14
<212> TYPE: PRT
<213> ORGANISM: Homo sapiens

<400> SEQUENCE: 195

Thr Ala His Pro Ser Pro Ser Pro Arg Ser Ala Gly Gln Phe
1               5                   10

<210> SEQ ID NO 196
<211> LENGTH: 14
<212> TYPE: PRT
<213> ORGANISM: Homo sapiens

<400> SEQUENCE: 196

Thr Ala His Pro Ser Ser Ser Pro Arg Ser Ala Gly Gln Phe
1               5                   10

<210> SEQ ID NO 197
<211> LENGTH: 14
<212> TYPE: PRT
<213> ORGANISM: Homo sapiens

<400> SEQUENCE: 197

Thr Ala His Pro Ser Thr Ser Pro Arg Ser Ala Gly Gln Phe
1               5                   10

<210> SEQ ID NO 198
<211> LENGTH: 14
<212> TYPE: PRT
<213> ORGANISM: Homo sapiens

<400> SEQUENCE: 198

Thr Ala His Pro Ser Trp Ser Pro Arg Ser Ala Gly Gln Phe
1               5                   10

<210> SEQ ID NO 199
<211> LENGTH: 14
<212> TYPE: PRT
<213> ORGANISM: Homo sapiens

<400> SEQUENCE: 199

Thr Ala His Pro Ser Tyr Ser Pro Arg Ser Ala Gly Gln Phe
1               5                   10

<210> SEQ ID NO 200
<211> LENGTH: 14
<212> TYPE: PRT
<213> ORGANISM: Homo sapiens

<400> SEQUENCE: 200

Thr Ala His Pro Ser Val Ser Pro Arg Ser Ala Gly Gln Phe
1               5                   10

<210> SEQ ID NO 201
<211> LENGTH: 14
<212> TYPE: PRT
<213> ORGANISM: Homo sapiens

<400> SEQUENCE: 201

Thr Ala His Pro Ala Pro Ser Pro Arg Ser Ala Gly Gln Phe
1               5                   10

<210> SEQ ID NO 202
<211> LENGTH: 14
<212> TYPE: PRT
<213> ORGANISM: Homo sapiens

<400> SEQUENCE: 202

Thr Ala His Pro Arg Pro Ser Pro Arg Ser Ala Gly Gln Phe
1               5                   10

<210> SEQ ID NO 203
<211> LENGTH: 14
<212> TYPE: PRT
<213> ORGANISM: Homo sapiens

<400> SEQUENCE: 203

Thr Ala His Pro Asn Pro Ser Pro Arg Ser Ala Gly Gln Phe
1               5                   10

<210> SEQ ID NO 204
<211> LENGTH: 14
<212> TYPE: PRT
<213> ORGANISM: Homo sapiens

<400> SEQUENCE: 204

Thr Ala His Pro Asp Pro Ser Pro Arg Ser Ala Gly Gln Phe

-continued

```
1               5                   10

<210> SEQ ID NO 205
<211> LENGTH: 14
<212> TYPE: PRT
<213> ORGANISM: Homo sapiens

<400> SEQUENCE: 205

Thr Ala His Pro Cys Pro Ser Pro Arg Ser Ala Gly Gln Phe
1               5                   10

<210> SEQ ID NO 206
<211> LENGTH: 14
<212> TYPE: PRT
<213> ORGANISM: Homo sapiens

<400> SEQUENCE: 206

Thr Ala His Pro Gln Pro Ser Pro Arg Ser Ala Gly Gln Phe
1               5                   10

<210> SEQ ID NO 207
<211> LENGTH: 14
<212> TYPE: PRT
<213> ORGANISM: Homo sapiens

<400> SEQUENCE: 207

Thr Ala His Pro Glu Pro Ser Pro Arg Ser Ala Gly Gln Phe
1               5                   10

<210> SEQ ID NO 208
<211> LENGTH: 14
<212> TYPE: PRT
<213> ORGANISM: Homo sapiens

<400> SEQUENCE: 208

Thr Ala His Pro Gly Pro Ser Pro Arg Ser Ala Gly Gln Phe
1               5                   10

<210> SEQ ID NO 209
<211> LENGTH: 14
<212> TYPE: PRT
<213> ORGANISM: Homo sapiens

<400> SEQUENCE: 209

Thr Ala His Pro His Pro Ser Pro Arg Ser Ala Gly Gln Phe
1               5                   10

<210> SEQ ID NO 210
<211> LENGTH: 14
<212> TYPE: PRT
<213> ORGANISM: Homo sapiens

<400> SEQUENCE: 210

Thr Ala His Pro Ile Pro Ser Pro Arg Ser Ala Gly Gln Phe
1               5                   10

<210> SEQ ID NO 211
<211> LENGTH: 14
<212> TYPE: PRT
<213> ORGANISM: Homo sapiens

<400> SEQUENCE: 211

Thr Ala His Pro Leu Pro Ser Pro Arg Ser Ala Gly Gln Phe
1               5                   10
```

```
<210> SEQ ID NO 212
<211> LENGTH: 14
<212> TYPE: PRT
<213> ORGANISM: Homo sapiens

<400> SEQUENCE: 212

Thr Ala His Pro Lys Pro Ser Pro Arg Ser Ala Gly Gln Phe
1               5                   10

<210> SEQ ID NO 213
<211> LENGTH: 14
<212> TYPE: PRT
<213> ORGANISM: Homo sapiens

<400> SEQUENCE: 213

Thr Ala His Pro Met Pro Ser Pro Arg Ser Ala Gly Gln Phe
1               5                   10

<210> SEQ ID NO 214
<211> LENGTH: 14
<212> TYPE: PRT
<213> ORGANISM: Homo sapiens

<400> SEQUENCE: 214

Thr Ala His Pro Phe Pro Ser Pro Arg Ser Ala Gly Gln Phe
1               5                   10

<210> SEQ ID NO 215
<211> LENGTH: 14
<212> TYPE: PRT
<213> ORGANISM: Homo sapiens

<400> SEQUENCE: 215

Thr Ala His Pro Pro Pro Ser Pro Arg Ser Ala Gly Gln Phe
1               5                   10

<210> SEQ ID NO 216
<211> LENGTH: 14
<212> TYPE: PRT
<213> ORGANISM: Homo sapiens

<400> SEQUENCE: 216

Thr Ala His Pro Ser Pro Ser Pro Arg Ser Ala Gly Gln Phe
1               5                   10

<210> SEQ ID NO 217
<211> LENGTH: 14
<212> TYPE: PRT
<213> ORGANISM: Homo sapiens

<400> SEQUENCE: 217

Thr Ala His Pro Thr Pro Ser Pro Arg Ser Ala Gly Gln Phe
1               5                   10

<210> SEQ ID NO 218
<211> LENGTH: 14
<212> TYPE: PRT
<213> ORGANISM: Homo sapiens

<400> SEQUENCE: 218

Thr Ala His Pro Trp Pro Ser Pro Arg Ser Ala Gly Gln Phe
1               5                   10

<210> SEQ ID NO 219
```

```
<210> SEQ ID NO 219
<211> LENGTH: 14
<212> TYPE: PRT
<213> ORGANISM: Homo sapiens

<400> SEQUENCE: 219

Thr Ala His Pro Tyr Pro Ser Pro Arg Ser Ala Gly Gln Phe
1               5                   10

<210> SEQ ID NO 220
<211> LENGTH: 14
<212> TYPE: PRT
<213> ORGANISM: Homo sapiens

<400> SEQUENCE: 220

Thr Ala His Pro Val Pro Ser Pro Arg Ser Ala Gly Gln Phe
1               5                   10

<210> SEQ ID NO 221
<211> LENGTH: 14
<212> TYPE: PRT
<213> ORGANISM: Homo sapiens

<400> SEQUENCE: 221

Thr Ala His Ala Ser Pro Ser Pro Arg Ser Ala Gly Gln Phe
1               5                   10

<210> SEQ ID NO 222
<211> LENGTH: 14
<212> TYPE: PRT
<213> ORGANISM: Homo sapiens

<400> SEQUENCE: 222

Thr Ala His Arg Ser Pro Ser Pro Arg Ser Ala Gly Gln Phe
1               5                   10

<210> SEQ ID NO 223
<211> LENGTH: 14
<212> TYPE: PRT
<213> ORGANISM: Homo sapiens

<400> SEQUENCE: 223

Thr Ala His Asn Ser Pro Ser Pro Arg Ser Ala Gly Gln Phe
1               5                   10

<210> SEQ ID NO 224
<211> LENGTH: 14
<212> TYPE: PRT
<213> ORGANISM: Homo sapiens

<400> SEQUENCE: 224

Thr Ala His Asp Ser Pro Ser Pro Arg Ser Ala Gly Gln Phe
1               5                   10

<210> SEQ ID NO 225
<211> LENGTH: 14
<212> TYPE: PRT
<213> ORGANISM: Homo sapiens

<400> SEQUENCE: 225

Thr Ala His Cys Ser Pro Ser Pro Arg Ser Ala Gly Gln Phe
1               5                   10

<210> SEQ ID NO 226
<211> LENGTH: 14
<212> TYPE: PRT
```

<213> ORGANISM: Homo sapiens

<400> SEQUENCE: 226

Thr Ala His Gln Ser Pro Ser Pro Arg Ser Ala Gly Gln Phe
1               5                   10

<210> SEQ ID NO 227
<211> LENGTH: 14
<212> TYPE: PRT
<213> ORGANISM: Homo sapiens

<400> SEQUENCE: 227

Thr Ala His Glu Ser Pro Ser Pro Arg Ser Ala Gly Gln Phe
1               5                   10

<210> SEQ ID NO 228
<211> LENGTH: 14
<212> TYPE: PRT
<213> ORGANISM: Homo sapiens

<400> SEQUENCE: 228

Thr Ala His Gly Ser Pro Ser Pro Arg Ser Ala Gly Gln Phe
1               5                   10

<210> SEQ ID NO 229
<211> LENGTH: 14
<212> TYPE: PRT
<213> ORGANISM: Homo sapiens

<400> SEQUENCE: 229

Thr Ala His His Ser Pro Ser Pro Arg Ser Ala Gly Gln Phe
1               5                   10

<210> SEQ ID NO 230
<211> LENGTH: 14
<212> TYPE: PRT
<213> ORGANISM: Homo sapiens

<400> SEQUENCE: 230

Thr Ala His Ile Ser Pro Ser Pro Arg Ser Ala Gly Gln Phe
1               5                   10

<210> SEQ ID NO 231
<211> LENGTH: 14
<212> TYPE: PRT
<213> ORGANISM: Homo sapiens

<400> SEQUENCE: 231

Thr Ala His Leu Ser Pro Ser Pro Arg Ser Ala Gly Gln Phe
1               5                   10

<210> SEQ ID NO 232
<211> LENGTH: 14
<212> TYPE: PRT
<213> ORGANISM: Homo sapiens

<400> SEQUENCE: 232

Thr Ala His Lys Ser Pro Ser Pro Arg Ser Ala Gly Gln Phe
1               5                   10

<210> SEQ ID NO 233
<211> LENGTH: 14
<212> TYPE: PRT
<213> ORGANISM: Homo sapiens

<400> SEQUENCE: 233

Thr Ala His Met Ser Pro Ser Pro Arg Ser Ala Gly Gln Phe
1               5                   10

<210> SEQ ID NO 234
<211> LENGTH: 14
<212> TYPE: PRT
<213> ORGANISM: Homo sapiens

<400> SEQUENCE: 234

Thr Ala His Phe Ser Pro Ser Pro Arg Ser Ala Gly Gln Phe
1               5                   10

<210> SEQ ID NO 235
<211> LENGTH: 14
<212> TYPE: PRT
<213> ORGANISM: Homo sapiens

<400> SEQUENCE: 235

Thr Ala His Pro Ser Pro Ser Pro Arg Ser Ala Gly Gln Phe
1               5                   10

<210> SEQ ID NO 236
<211> LENGTH: 14
<212> TYPE: PRT
<213> ORGANISM: Homo sapiens

<400> SEQUENCE: 236

Thr Ala His Ser Ser Pro Ser Pro Arg Ser Ala Gly Gln Phe
1               5                   10

<210> SEQ ID NO 237
<211> LENGTH: 14
<212> TYPE: PRT
<213> ORGANISM: Homo sapiens

<400> SEQUENCE: 237

Thr Ala His Thr Ser Pro Ser Pro Arg Ser Ala Gly Gln Phe
1               5                   10

<210> SEQ ID NO 238
<211> LENGTH: 14
<212> TYPE: PRT
<213> ORGANISM: Homo sapiens

<400> SEQUENCE: 238

Thr Ala His Trp Ser Pro Ser Pro Arg Ser Ala Gly Gln Phe
1               5                   10

<210> SEQ ID NO 239
<211> LENGTH: 14
<212> TYPE: PRT
<213> ORGANISM: Homo sapiens

<400> SEQUENCE: 239

Thr Ala His Tyr Ser Pro Ser Pro Arg Ser Ala Gly Gln Phe
1               5                   10

<210> SEQ ID NO 240
<211> LENGTH: 14
<212> TYPE: PRT
<213> ORGANISM: Homo sapiens

<400> SEQUENCE: 240

Thr Ala His Val Ser Pro Ser Pro Arg Ser Ala Gly Gln Phe
1               5                   10

<210> SEQ ID NO 241
<211> LENGTH: 14
<212> TYPE: PRT
<213> ORGANISM: Homo sapiens

<400> SEQUENCE: 241

Thr Ala Ala Pro Ser Pro Ser Pro Arg Ser Ala Gly Gln Phe
1               5                   10

<210> SEQ ID NO 242
<211> LENGTH: 14
<212> TYPE: PRT
<213> ORGANISM: Homo sapiens

<400> SEQUENCE: 242

Thr Ala Arg Pro Ser Pro Ser Pro Arg Ser Ala Gly Gln Phe
1               5                   10

<210> SEQ ID NO 243
<211> LENGTH: 14
<212> TYPE: PRT
<213> ORGANISM: Homo sapiens

<400> SEQUENCE: 243

Thr Ala Asn Pro Ser Pro Ser Pro Arg Ser Ala Gly Gln Phe
1               5                   10

<210> SEQ ID NO 244
<211> LENGTH: 14
<212> TYPE: PRT
<213> ORGANISM: Homo sapiens

<400> SEQUENCE: 244

Thr Ala Asp Pro Ser Pro Ser Pro Arg Ser Ala Gly Gln Phe
1               5                   10

<210> SEQ ID NO 245
<211> LENGTH: 14
<212> TYPE: PRT
<213> ORGANISM: Homo sapiens

<400> SEQUENCE: 245

Thr Ala Cys Pro Ser Pro Ser Pro Arg Ser Ala Gly Gln Phe
1               5                   10

<210> SEQ ID NO 246
<211> LENGTH: 14
<212> TYPE: PRT
<213> ORGANISM: Homo sapiens

<400> SEQUENCE: 246

Thr Ala Gln Pro Ser Pro Ser Pro Arg Ser Ala Gly Gln Phe
1               5                   10

<210> SEQ ID NO 247
<211> LENGTH: 14
<212> TYPE: PRT
<213> ORGANISM: Homo sapiens

<400> SEQUENCE: 247

Thr Ala Glu Pro Ser Pro Ser Pro Arg Ser Ala Gly Gln Phe
1               5                   10

<210> SEQ ID NO 248
<211> LENGTH: 14
<212> TYPE: PRT
<213> ORGANISM: Homo sapiens

<400> SEQUENCE: 248

Thr Ala Gly Pro Ser Pro Ser Pro Arg Ser Ala Gly Gln Phe
1               5                   10

<210> SEQ ID NO 249
<211> LENGTH: 14
<212> TYPE: PRT
<213> ORGANISM: Homo sapiens

<400> SEQUENCE: 249

Thr Ala His Pro Ser Pro Ser Pro Arg Ser Ala Gly Gln Phe
1               5                   10

<210> SEQ ID NO 250
<211> LENGTH: 14
<212> TYPE: PRT
<213> ORGANISM: Homo sapiens

<400> SEQUENCE: 250

Thr Ala Ile Pro Ser Pro Ser Pro Arg Ser Ala Gly Gln Phe
1               5                   10

<210> SEQ ID NO 251
<211> LENGTH: 14
<212> TYPE: PRT
<213> ORGANISM: Homo sapiens

<400> SEQUENCE: 251

Thr Ala Leu Pro Ser Pro Ser Pro Arg Ser Ala Gly Gln Phe
1               5                   10

<210> SEQ ID NO 252
<211> LENGTH: 14
<212> TYPE: PRT
<213> ORGANISM: Homo sapiens

<400> SEQUENCE: 252

Thr Ala Lys Pro Ser Pro Ser Pro Arg Ser Ala Gly Gln Phe
1               5                   10

<210> SEQ ID NO 253
<211> LENGTH: 14
<212> TYPE: PRT
<213> ORGANISM: Homo sapiens

<400> SEQUENCE: 253

Thr Ala Met Pro Ser Pro Ser Pro Arg Ser Ala Gly Gln Phe
1               5                   10

<210> SEQ ID NO 254
<211> LENGTH: 14
<212> TYPE: PRT
<213> ORGANISM: Homo sapiens

<400> SEQUENCE: 254

Thr Ala Phe Pro Ser Pro Ser Pro Arg Ser Ala Gly Gln Phe
1               5                   10

-continued

```
<210> SEQ ID NO 255
<211> LENGTH: 14
<212> TYPE: PRT
<213> ORGANISM: Homo sapiens

<400> SEQUENCE: 255

Thr Ala Pro Pro Ser Pro Ser Pro Arg Ser Ala Gly Gln Phe
1               5                   10

<210> SEQ ID NO 256
<211> LENGTH: 14
<212> TYPE: PRT
<213> ORGANISM: Homo sapiens

<400> SEQUENCE: 256

Thr Ala Ser Pro Ser Pro Ser Pro Arg Ser Ala Gly Gln Phe
1               5                   10

<210> SEQ ID NO 257
<211> LENGTH: 14
<212> TYPE: PRT
<213> ORGANISM: Homo sapiens

<400> SEQUENCE: 257

Thr Ala Thr Pro Ser Pro Ser Pro Arg Ser Ala Gly Gln Phe
1               5                   10

<210> SEQ ID NO 258
<211> LENGTH: 14
<212> TYPE: PRT
<213> ORGANISM: Homo sapiens

<400> SEQUENCE: 258

Thr Ala Trp Pro Ser Pro Ser Pro Arg Ser Ala Gly Gln Phe
1               5                   10

<210> SEQ ID NO 259
<211> LENGTH: 14
<212> TYPE: PRT
<213> ORGANISM: Homo sapiens

<400> SEQUENCE: 259

Thr Ala Tyr Pro Ser Pro Ser Pro Arg Ser Ala Gly Gln Phe
1               5                   10

<210> SEQ ID NO 260
<211> LENGTH: 14
<212> TYPE: PRT
<213> ORGANISM: Homo sapiens

<400> SEQUENCE: 260

Thr Ala Val Pro Ser Pro Ser Pro Arg Ser Ala Gly Gln Phe
1               5                   10

<210> SEQ ID NO 261
<211> LENGTH: 14
<212> TYPE: PRT
<213> ORGANISM: Homo sapiens

<400> SEQUENCE: 261

Thr Ala His Pro Ser Pro Ser Pro Arg Ser Ala Gly Gln Phe
1               5                   10

<210> SEQ ID NO 262
<211> LENGTH: 14
```

<210> SEQ ID NO 262
<211> LENGTH: 14
<212> TYPE: PRT
<213> ORGANISM: Homo sapiens

<400> SEQUENCE: 262

Thr Arg His Pro Ser Pro Ser Pro Arg Ser Ala Gly Gln Phe
1               5                   10

<210> SEQ ID NO 263
<211> LENGTH: 14
<212> TYPE: PRT
<213> ORGANISM: Homo sapiens

<400> SEQUENCE: 263

Thr Asn His Pro Ser Pro Ser Pro Arg Ser Ala Gly Gln Phe
1               5                   10

<210> SEQ ID NO 264
<211> LENGTH: 14
<212> TYPE: PRT
<213> ORGANISM: Homo sapiens

<400> SEQUENCE: 264

Thr Asp His Pro Ser Pro Ser Pro Arg Ser Ala Gly Gln Phe
1               5                   10

<210> SEQ ID NO 265
<211> LENGTH: 14
<212> TYPE: PRT
<213> ORGANISM: Homo sapiens

<400> SEQUENCE: 265

Thr Cys His Pro Ser Pro Ser Pro Arg Ser Ala Gly Gln Phe
1               5                   10

<210> SEQ ID NO 266
<211> LENGTH: 14
<212> TYPE: PRT
<213> ORGANISM: Homo sapiens

<400> SEQUENCE: 266

Thr Gln His Pro Ser Pro Ser Pro Arg Ser Ala Gly Gln Phe
1               5                   10

<210> SEQ ID NO 267
<211> LENGTH: 14
<212> TYPE: PRT
<213> ORGANISM: Homo sapiens

<400> SEQUENCE: 267

Thr Glu His Pro Ser Pro Ser Pro Arg Ser Ala Gly Gln Phe
1               5                   10

<210> SEQ ID NO 268
<211> LENGTH: 14
<212> TYPE: PRT
<213> ORGANISM: Homo sapiens

<400> SEQUENCE: 268

Thr Gly His Pro Ser Pro Ser Pro Arg Ser Ala Gly Gln Phe
1               5                   10

<210> SEQ ID NO 269
<211> LENGTH: 14
<212> TYPE: PRT
<213> ORGANISM: Homo sapiens

<400> SEQUENCE: 269

Thr His His Pro Ser Pro Ser Pro Arg Ser Ala Gly Gln Phe
1               5                   10

<210> SEQ ID NO 270
<211> LENGTH: 14
<212> TYPE: PRT
<213> ORGANISM: Homo sapiens

<400> SEQUENCE: 270

Thr Ile His Pro Ser Pro Ser Pro Arg Ser Ala Gly Gln Phe
1               5                   10

<210> SEQ ID NO 271
<211> LENGTH: 14
<212> TYPE: PRT
<213> ORGANISM: Homo sapiens

<400> SEQUENCE: 271

Thr Leu His Pro Ser Pro Ser Pro Arg Ser Ala Gly Gln Phe
1               5                   10

<210> SEQ ID NO 272
<211> LENGTH: 14
<212> TYPE: PRT
<213> ORGANISM: Homo sapiens

<400> SEQUENCE: 272

Thr Lys His Pro Ser Pro Ser Pro Arg Ser Ala Gly Gln Phe
1               5                   10

<210> SEQ ID NO 273
<211> LENGTH: 14
<212> TYPE: PRT
<213> ORGANISM: Homo sapiens

<400> SEQUENCE: 273

Thr Met His Pro Ser Pro Ser Pro Arg Ser Ala Gly Gln Phe
1               5                   10

<210> SEQ ID NO 274
<211> LENGTH: 14
<212> TYPE: PRT
<213> ORGANISM: Homo sapiens

<400> SEQUENCE: 274

Thr Phe His Pro Ser Pro Ser Pro Arg Ser Ala Gly Gln Phe
1               5                   10

<210> SEQ ID NO 275
<211> LENGTH: 14
<212> TYPE: PRT
<213> ORGANISM: Homo sapiens

<400> SEQUENCE: 275

Thr Pro His Pro Ser Pro Ser Pro Arg Ser Ala Gly Gln Phe
1               5                   10

<210> SEQ ID NO 276
<211> LENGTH: 14
<212> TYPE: PRT
<213> ORGANISM: Homo sapiens

<400> SEQUENCE: 276

Thr Ser His Pro Ser Pro Ser Pro Arg Ser Ala Gly Gln Phe
1               5                   10

<210> SEQ ID NO 277
<211> LENGTH: 14
<212> TYPE: PRT
<213> ORGANISM: Homo sapiens

<400> SEQUENCE: 277

Thr Thr His Pro Ser Pro Ser Pro Arg Ser Ala Gly Gln Phe
1               5                   10

<210> SEQ ID NO 278
<211> LENGTH: 14
<212> TYPE: PRT
<213> ORGANISM: Homo sapiens

<400> SEQUENCE: 278

Thr Trp His Pro Ser Pro Ser Pro Arg Ser Ala Gly Gln Phe
1               5                   10

<210> SEQ ID NO 279
<211> LENGTH: 14
<212> TYPE: PRT
<213> ORGANISM: Homo sapiens

<400> SEQUENCE: 279

Thr Tyr His Pro Ser Pro Ser Pro Arg Ser Ala Gly Gln Phe
1               5                   10

<210> SEQ ID NO 280
<211> LENGTH: 14
<212> TYPE: PRT
<213> ORGANISM: Homo sapiens

<400> SEQUENCE: 280

Thr Val His Pro Ser Pro Ser Pro Arg Ser Ala Gly Gln Phe
1               5                   10

<210> SEQ ID NO 281
<211> LENGTH: 14
<212> TYPE: PRT
<213> ORGANISM: Homo sapiens

<400> SEQUENCE: 281

Ala Ala His Pro Ser Pro Ser Pro Arg Ser Ala Gly Gln Phe
1               5                   10

<210> SEQ ID NO 282
<211> LENGTH: 14
<212> TYPE: PRT
<213> ORGANISM: Homo sapiens

<400> SEQUENCE: 282

Arg Ala His Pro Ser Pro Ser Pro Arg Ser Ala Gly Gln Phe
1               5                   10

<210> SEQ ID NO 283
<211> LENGTH: 14
<212> TYPE: PRT
<213> ORGANISM: Homo sapiens

<400> SEQUENCE: 283

Asn Ala His Pro Ser Pro Ser Pro Arg Ser Ala Gly Gln Phe

```
1               5                   10
```

<210> SEQ ID NO 284
<211> LENGTH: 14
<212> TYPE: PRT
<213> ORGANISM: Homo sapiens

<400> SEQUENCE: 284

```
Asp Ala His Pro Ser Pro Ser Pro Arg Ser Ala Gly Gln Phe
1               5                   10
```

<210> SEQ ID NO 285
<211> LENGTH: 14
<212> TYPE: PRT
<213> ORGANISM: Homo sapiens

<400> SEQUENCE: 285

```
Cys Ala His Pro Ser Pro Ser Pro Arg Ser Ala Gly Gln Phe
1               5                   10
```

<210> SEQ ID NO 286
<211> LENGTH: 14
<212> TYPE: PRT
<213> ORGANISM: Homo sapiens

<400> SEQUENCE: 286

```
Gln Ala His Pro Ser Pro Ser Pro Arg Ser Ala Gly Gln Phe
1               5                   10
```

<210> SEQ ID NO 287
<211> LENGTH: 14
<212> TYPE: PRT
<213> ORGANISM: Homo sapiens

<400> SEQUENCE: 287

```
Glu Ala His Pro Ser Pro Ser Pro Arg Ser Ala Gly Gln Phe
1               5                   10
```

<210> SEQ ID NO 288
<211> LENGTH: 14
<212> TYPE: PRT
<213> ORGANISM: Homo sapiens

<400> SEQUENCE: 288

```
Gly Ala His Pro Ser Pro Ser Pro Arg Ser Ala Gly Gln Phe
1               5                   10
```

<210> SEQ ID NO 289
<211> LENGTH: 14
<212> TYPE: PRT
<213> ORGANISM: Homo sapiens

<400> SEQUENCE: 289

```
His Ala His Pro Ser Pro Ser Pro Arg Ser Ala Gly Gln Phe
1               5                   10
```

<210> SEQ ID NO 290
<211> LENGTH: 14
<212> TYPE: PRT
<213> ORGANISM: Homo sapiens

<400> SEQUENCE: 290

```
Ile Ala His Pro Ser Pro Ser Pro Arg Ser Ala Gly Gln Phe
1               5                   10
```

<210> SEQ ID NO 291
<211> LENGTH: 14
<212> TYPE: PRT
<213> ORGANISM: Homo sapiens

<400> SEQUENCE: 291

Leu Ala His Pro Ser Pro Ser Pro Arg Ser Ala Gly Gln Phe
1               5                   10

<210> SEQ ID NO 292
<211> LENGTH: 14
<212> TYPE: PRT
<213> ORGANISM: Homo sapiens

<400> SEQUENCE: 292

Lys Ala His Pro Ser Pro Ser Pro Arg Ser Ala Gly Gln Phe
1               5                   10

<210> SEQ ID NO 293
<211> LENGTH: 14
<212> TYPE: PRT
<213> ORGANISM: Homo sapiens

<400> SEQUENCE: 293

Met Ala His Pro Ser Pro Ser Pro Arg Ser Ala Gly Gln Phe
1               5                   10

<210> SEQ ID NO 294
<211> LENGTH: 14
<212> TYPE: PRT
<213> ORGANISM: Homo sapiens

<400> SEQUENCE: 294

Phe Ala His Pro Ser Pro Ser Pro Arg Ser Ala Gly Gln Phe
1               5                   10

<210> SEQ ID NO 295
<211> LENGTH: 14
<212> TYPE: PRT
<213> ORGANISM: Homo sapiens

<400> SEQUENCE: 295

Pro Ala His Pro Ser Pro Ser Pro Arg Ser Ala Gly Gln Phe
1               5                   10

<210> SEQ ID NO 296
<211> LENGTH: 14
<212> TYPE: PRT
<213> ORGANISM: Homo sapiens

<400> SEQUENCE: 296

Ser Ala His Pro Ser Pro Ser Pro Arg Ser Ala Gly Gln Phe
1               5                   10

<210> SEQ ID NO 297
<211> LENGTH: 14
<212> TYPE: PRT
<213> ORGANISM: Homo sapiens

<400> SEQUENCE: 297

Thr Ala His Pro Ser Pro Ser Pro Arg Ser Ala Gly Gln Phe
1               5                   10

<210> SEQ ID NO 298

```
<211> LENGTH: 14
<212> TYPE: PRT
<213> ORGANISM: Homo sapiens

<400> SEQUENCE: 298

Trp Ala His Pro Ser Pro Ser Pro Arg Ser Ala Gly Gln Phe
1               5                   10

<210> SEQ ID NO 299
<211> LENGTH: 14
<212> TYPE: PRT
<213> ORGANISM: Homo sapiens

<400> SEQUENCE: 299

Tyr Ala His Pro Ser Pro Ser Pro Arg Ser Ala Gly Gln Phe
1               5                   10

<210> SEQ ID NO 300
<211> LENGTH: 14
<212> TYPE: PRT
<213> ORGANISM: Homo sapiens

<400> SEQUENCE: 300

Val Ala His Pro Ser Pro Ser Pro Arg Ser Ala Gly Gln Phe
1               5                   10

<210> SEQ ID NO 301
<211> LENGTH: 10
<212> TYPE: PRT
<213> ORGANISM: Homo sapiens

<400> SEQUENCE: 301

Trp Tyr Arg Met Ser Pro Ser Asn Gln Ala
1               5                   10

<210> SEQ ID NO 302
<211> LENGTH: 10
<212> TYPE: PRT
<213> ORGANISM: Homo sapiens

<400> SEQUENCE: 302

Trp Tyr Arg Met Ser Pro Ser Asn Gln Arg
1               5                   10

<210> SEQ ID NO 303
<211> LENGTH: 10
<212> TYPE: PRT
<213> ORGANISM: Homo sapiens

<400> SEQUENCE: 303

Trp Tyr Arg Met Ser Pro Ser Asn Gln Asn
1               5                   10

<210> SEQ ID NO 304
<211> LENGTH: 10
<212> TYPE: PRT
<213> ORGANISM: Homo sapiens

<400> SEQUENCE: 304

Trp Tyr Arg Met Ser Pro Ser Asn Gln Asp
1               5                   10

<210> SEQ ID NO 305
<211> LENGTH: 10
<212> TYPE: PRT
```

<213> ORGANISM: Homo sapiens

<400> SEQUENCE: 305

Trp Tyr Arg Met Ser Pro Ser Asn Gln Cys
1               5                   10

<210> SEQ ID NO 306
<211> LENGTH: 10
<212> TYPE: PRT
<213> ORGANISM: Homo sapiens

<400> SEQUENCE: 306

Trp Tyr Arg Met Ser Pro Ser Asn Gln Gln
1               5                   10

<210> SEQ ID NO 307
<211> LENGTH: 10
<212> TYPE: PRT
<213> ORGANISM: Homo sapiens

<400> SEQUENCE: 307

Trp Tyr Arg Met Ser Pro Ser Asn Gln Glu
1               5                   10

<210> SEQ ID NO 308
<211> LENGTH: 10
<212> TYPE: PRT
<213> ORGANISM: Homo sapiens

<400> SEQUENCE: 308

Trp Tyr Arg Met Ser Pro Ser Asn Gln Gly
1               5                   10

<210> SEQ ID NO 309
<211> LENGTH: 10
<212> TYPE: PRT
<213> ORGANISM: Homo sapiens

<400> SEQUENCE: 309

Trp Tyr Arg Met Ser Pro Ser Asn Gln His
1               5                   10

<210> SEQ ID NO 310
<211> LENGTH: 10
<212> TYPE: PRT
<213> ORGANISM: Homo sapiens

<400> SEQUENCE: 310

Trp Tyr Arg Met Ser Pro Ser Asn Gln Ile
1               5                   10

<210> SEQ ID NO 311
<211> LENGTH: 10
<212> TYPE: PRT
<213> ORGANISM: Homo sapiens

<400> SEQUENCE: 311

Trp Tyr Arg Met Ser Pro Ser Asn Gln Leu
1               5                   10

<210> SEQ ID NO 312
<211> LENGTH: 10
<212> TYPE: PRT
<213> ORGANISM: Homo sapiens

<400> SEQUENCE: 312

Trp Tyr Arg Met Ser Pro Ser Asn Gln Lys
1               5                   10

<210> SEQ ID NO 313
<211> LENGTH: 10
<212> TYPE: PRT
<213> ORGANISM: Homo sapiens

<400> SEQUENCE: 313

Trp Tyr Arg Met Ser Pro Ser Asn Gln Met
1               5                   10

<210> SEQ ID NO 314
<211> LENGTH: 10
<212> TYPE: PRT
<213> ORGANISM: Homo sapiens

<400> SEQUENCE: 314

Trp Tyr Arg Met Ser Pro Ser Asn Gln Phe
1               5                   10

<210> SEQ ID NO 315
<211> LENGTH: 10
<212> TYPE: PRT
<213> ORGANISM: Homo sapiens

<400> SEQUENCE: 315

Trp Tyr Arg Met Ser Pro Ser Asn Gln Pro
1               5                   10

<210> SEQ ID NO 316
<211> LENGTH: 10
<212> TYPE: PRT
<213> ORGANISM: Homo sapiens

<400> SEQUENCE: 316

Trp Tyr Arg Met Ser Pro Ser Asn Gln Ser
1               5                   10

<210> SEQ ID NO 317
<211> LENGTH: 10
<212> TYPE: PRT
<213> ORGANISM: Homo sapiens

<400> SEQUENCE: 317

Trp Tyr Arg Met Ser Pro Ser Asn Gln Thr
1               5                   10

<210> SEQ ID NO 318
<211> LENGTH: 10
<212> TYPE: PRT
<213> ORGANISM: Homo sapiens

<400> SEQUENCE: 318

Trp Tyr Arg Met Ser Pro Ser Asn Gln Trp
1               5                   10

<210> SEQ ID NO 319
<211> LENGTH: 10
<212> TYPE: PRT
<213> ORGANISM: Homo sapiens

<400> SEQUENCE: 319

Trp Tyr Arg Met Ser Pro Ser Asn Gln Tyr
1               5                   10

<210> SEQ ID NO 320
<211> LENGTH: 10
<212> TYPE: PRT
<213> ORGANISM: Homo sapiens

<400> SEQUENCE: 320

Trp Tyr Arg Met Ser Pro Ser Asn Gln Val
1               5                   10

<210> SEQ ID NO 321
<211> LENGTH: 10
<212> TYPE: PRT
<213> ORGANISM: Homo sapiens

<400> SEQUENCE: 321

Trp Tyr Arg Met Ser Pro Ser Asn Ala Thr
1               5                   10

<210> SEQ ID NO 322
<211> LENGTH: 10
<212> TYPE: PRT
<213> ORGANISM: Homo sapiens

<400> SEQUENCE: 322

Trp Tyr Arg Met Ser Pro Ser Asn Arg Thr
1               5                   10

<210> SEQ ID NO 323
<211> LENGTH: 10
<212> TYPE: PRT
<213> ORGANISM: Homo sapiens

<400> SEQUENCE: 323

Trp Tyr Arg Met Ser Pro Ser Asn Asn Thr
1               5                   10

<210> SEQ ID NO 324
<211> LENGTH: 10
<212> TYPE: PRT
<213> ORGANISM: Homo sapiens

<400> SEQUENCE: 324

Trp Tyr Arg Met Ser Pro Ser Asn Asp Thr
1               5                   10

<210> SEQ ID NO 325
<211> LENGTH: 10
<212> TYPE: PRT
<213> ORGANISM: Homo sapiens

<400> SEQUENCE: 325

Trp Tyr Arg Met Ser Pro Ser Asn Cys Thr
1               5                   10

<210> SEQ ID NO 326
<211> LENGTH: 10
<212> TYPE: PRT
<213> ORGANISM: Homo sapiens

<400> SEQUENCE: 326

Trp Tyr Arg Met Ser Pro Ser Asn Gln Thr
1               5                   10

```
<210> SEQ ID NO 327
<211> LENGTH: 10
<212> TYPE: PRT
<213> ORGANISM: Homo sapiens

<400> SEQUENCE: 327

Trp Tyr Arg Met Ser Pro Ser Asn Glu Thr
1               5                   10

<210> SEQ ID NO 328
<211> LENGTH: 10
<212> TYPE: PRT
<213> ORGANISM: Homo sapiens

<400> SEQUENCE: 328

Trp Tyr Arg Met Ser Pro Ser Asn Gly Thr
1               5                   10

<210> SEQ ID NO 329
<211> LENGTH: 10
<212> TYPE: PRT
<213> ORGANISM: Homo sapiens

<400> SEQUENCE: 329

Trp Tyr Arg Met Ser Pro Ser Asn His Thr
1               5                   10

<210> SEQ ID NO 330
<211> LENGTH: 10
<212> TYPE: PRT
<213> ORGANISM: Homo sapiens

<400> SEQUENCE: 330

Trp Tyr Arg Met Ser Pro Ser Asn Ile Thr
1               5                   10

<210> SEQ ID NO 331
<211> LENGTH: 10
<212> TYPE: PRT
<213> ORGANISM: Homo sapiens

<400> SEQUENCE: 331

Trp Tyr Arg Met Ser Pro Ser Asn Leu Thr
1               5                   10

<210> SEQ ID NO 332
<211> LENGTH: 10
<212> TYPE: PRT
<213> ORGANISM: Homo sapiens

<400> SEQUENCE: 332

Trp Tyr Arg Met Ser Pro Ser Asn Lys Thr
1               5                   10

<210> SEQ ID NO 333
<211> LENGTH: 10
<212> TYPE: PRT
<213> ORGANISM: Homo sapiens

<400> SEQUENCE: 333

Trp Tyr Arg Met Ser Pro Ser Asn Met Thr
1               5                   10
```

```
<210> SEQ ID NO 334
<211> LENGTH: 10
<212> TYPE: PRT
<213> ORGANISM: Homo sapiens

<400> SEQUENCE: 334

Trp Tyr Arg Met Ser Pro Ser Asn Phe Thr
1               5                   10

<210> SEQ ID NO 335
<211> LENGTH: 10
<212> TYPE: PRT
<213> ORGANISM: Homo sapiens

<400> SEQUENCE: 335

Trp Tyr Arg Met Ser Pro Ser Asn Pro Thr
1               5                   10

<210> SEQ ID NO 336
<211> LENGTH: 10
<212> TYPE: PRT
<213> ORGANISM: Homo sapiens

<400> SEQUENCE: 336

Trp Tyr Arg Met Ser Pro Ser Asn Ser Thr
1               5                   10

<210> SEQ ID NO 337
<211> LENGTH: 10
<212> TYPE: PRT
<213> ORGANISM: Homo sapiens

<400> SEQUENCE: 337

Trp Tyr Arg Met Ser Pro Ser Asn Thr Thr
1               5                   10

<210> SEQ ID NO 338
<211> LENGTH: 10
<212> TYPE: PRT
<213> ORGANISM: Homo sapiens

<400> SEQUENCE: 338

Trp Tyr Arg Met Ser Pro Ser Asn Trp Thr
1               5                   10

<210> SEQ ID NO 339
<211> LENGTH: 10
<212> TYPE: PRT
<213> ORGANISM: Homo sapiens

<400> SEQUENCE: 339

Trp Tyr Arg Met Ser Pro Ser Asn Tyr Thr
1               5                   10

<210> SEQ ID NO 340
<211> LENGTH: 10
<212> TYPE: PRT
<213> ORGANISM: Homo sapiens

<400> SEQUENCE: 340

Trp Tyr Arg Met Ser Pro Ser Asn Val Thr
1               5                   10

<210> SEQ ID NO 341
<211> LENGTH: 10
```

```
<212> TYPE: PRT
<213> ORGANISM: Homo sapiens

<400> SEQUENCE: 341

Trp Tyr Arg Met Ser Pro Ser Ala Gln Thr
1               5                   10

<210> SEQ ID NO 342
<211> LENGTH: 10
<212> TYPE: PRT
<213> ORGANISM: Homo sapiens

<400> SEQUENCE: 342

Trp Tyr Arg Met Ser Pro Ser Arg Gln Thr
1               5                   10

<210> SEQ ID NO 343
<211> LENGTH: 10
<212> TYPE: PRT
<213> ORGANISM: Homo sapiens

<400> SEQUENCE: 343

Trp Tyr Arg Met Ser Pro Ser Asn Gln Thr
1               5                   10

<210> SEQ ID NO 344
<211> LENGTH: 10
<212> TYPE: PRT
<213> ORGANISM: Homo sapiens

<400> SEQUENCE: 344

Trp Tyr Arg Met Ser Pro Ser Asp Gln Thr
1               5                   10

<210> SEQ ID NO 345
<211> LENGTH: 10
<212> TYPE: PRT
<213> ORGANISM: Homo sapiens

<400> SEQUENCE: 345

Trp Tyr Arg Met Ser Pro Ser Cys Gln Thr
1               5                   10

<210> SEQ ID NO 346
<211> LENGTH: 10
<212> TYPE: PRT
<213> ORGANISM: Homo sapiens

<400> SEQUENCE: 346

Trp Tyr Arg Met Ser Pro Ser Gln Gln Thr
1               5                   10

<210> SEQ ID NO 347
<211> LENGTH: 10
<212> TYPE: PRT
<213> ORGANISM: Homo sapiens

<400> SEQUENCE: 347

Trp Tyr Arg Met Ser Pro Ser Glu Gln Thr
1               5                   10

<210> SEQ ID NO 348
<211> LENGTH: 10
<212> TYPE: PRT
<213> ORGANISM: Homo sapiens
```

<400> SEQUENCE: 348

Trp Tyr Arg Met Ser Pro Ser Gly Gln Thr
1               5                   10

<210> SEQ ID NO 349
<211> LENGTH: 10
<212> TYPE: PRT
<213> ORGANISM: Homo sapiens

<400> SEQUENCE: 349

Trp Tyr Arg Met Ser Pro Ser His Gln Thr
1               5                   10

<210> SEQ ID NO 350
<211> LENGTH: 10
<212> TYPE: PRT
<213> ORGANISM: Homo sapiens

<400> SEQUENCE: 350

Trp Tyr Arg Met Ser Pro Ser Ile Gln Thr
1               5                   10

<210> SEQ ID NO 351
<211> LENGTH: 10
<212> TYPE: PRT
<213> ORGANISM: Homo sapiens

<400> SEQUENCE: 351

Trp Tyr Arg Met Ser Pro Ser Leu Gln Thr
1               5                   10

<210> SEQ ID NO 352
<211> LENGTH: 10
<212> TYPE: PRT
<213> ORGANISM: Homo sapiens

<400> SEQUENCE: 352

Trp Tyr Arg Met Ser Pro Ser Lys Gln Thr
1               5                   10

<210> SEQ ID NO 353
<211> LENGTH: 10
<212> TYPE: PRT
<213> ORGANISM: Homo sapiens

<400> SEQUENCE: 353

Trp Tyr Arg Met Ser Pro Ser Met Gln Thr
1               5                   10

<210> SEQ ID NO 354
<211> LENGTH: 10
<212> TYPE: PRT
<213> ORGANISM: Homo sapiens

<400> SEQUENCE: 354

Trp Tyr Arg Met Ser Pro Ser Phe Gln Thr
1               5                   10

<210> SEQ ID NO 355
<211> LENGTH: 10
<212> TYPE: PRT
<213> ORGANISM: Homo sapiens

<400> SEQUENCE: 355

Trp Tyr Arg Met Ser Pro Ser Pro Gln Thr
1               5                   10

<210> SEQ ID NO 356
<211> LENGTH: 10
<212> TYPE: PRT
<213> ORGANISM: Homo sapiens

<400> SEQUENCE: 356

Trp Tyr Arg Met Ser Pro Ser Ser Gln Thr
1               5                   10

<210> SEQ ID NO 357
<211> LENGTH: 10
<212> TYPE: PRT
<213> ORGANISM: Homo sapiens

<400> SEQUENCE: 357

Trp Tyr Arg Met Ser Pro Ser Thr Gln Thr
1               5                   10

<210> SEQ ID NO 358
<211> LENGTH: 10
<212> TYPE: PRT
<213> ORGANISM: Homo sapiens

<400> SEQUENCE: 358

Trp Tyr Arg Met Ser Pro Ser Trp Gln Thr
1               5                   10

<210> SEQ ID NO 359
<211> LENGTH: 10
<212> TYPE: PRT
<213> ORGANISM: Homo sapiens

<400> SEQUENCE: 359

Trp Tyr Arg Met Ser Pro Ser Tyr Gln Thr
1               5                   10

<210> SEQ ID NO 360
<211> LENGTH: 10
<212> TYPE: PRT
<213> ORGANISM: Homo sapiens

<400> SEQUENCE: 360

Trp Tyr Arg Met Ser Pro Ser Val Gln Thr
1               5                   10

<210> SEQ ID NO 361
<211> LENGTH: 10
<212> TYPE: PRT
<213> ORGANISM: Homo sapiens

<400> SEQUENCE: 361

Trp Tyr Arg Met Ser Pro Ala Asn Gln Thr
1               5                   10

<210> SEQ ID NO 362
<211> LENGTH: 10
<212> TYPE: PRT
<213> ORGANISM: Homo sapiens

<400> SEQUENCE: 362

Trp Tyr Arg Met Ser Pro Arg Asn Gln Thr

```
1               5                   10

<210> SEQ ID NO 363
<211> LENGTH: 10
<212> TYPE: PRT
<213> ORGANISM: Homo sapiens

<400> SEQUENCE: 363

Trp Tyr Arg Met Ser Pro Asn Asn Gln Thr
1               5                   10

<210> SEQ ID NO 364
<211> LENGTH: 10
<212> TYPE: PRT
<213> ORGANISM: Homo sapiens

<400> SEQUENCE: 364

Trp Tyr Arg Met Ser Pro Asp Asn Gln Thr
1               5                   10

<210> SEQ ID NO 365
<211> LENGTH: 10
<212> TYPE: PRT
<213> ORGANISM: Homo sapiens

<400> SEQUENCE: 365

Trp Tyr Arg Met Ser Pro Cys Asn Gln Thr
1               5                   10

<210> SEQ ID NO 366
<211> LENGTH: 10
<212> TYPE: PRT
<213> ORGANISM: Homo sapiens

<400> SEQUENCE: 366

Trp Tyr Arg Met Ser Pro Gln Asn Gln Thr
1               5                   10

<210> SEQ ID NO 367
<211> LENGTH: 10
<212> TYPE: PRT
<213> ORGANISM: Homo sapiens

<400> SEQUENCE: 367

Trp Tyr Arg Met Ser Pro Glu Asn Gln Thr
1               5                   10

<210> SEQ ID NO 368
<211> LENGTH: 10
<212> TYPE: PRT
<213> ORGANISM: Homo sapiens

<400> SEQUENCE: 368

Trp Tyr Arg Met Ser Pro Gly Asn Gln Thr
1               5                   10

<210> SEQ ID NO 369
<211> LENGTH: 10
<212> TYPE: PRT
<213> ORGANISM: Homo sapiens

<400> SEQUENCE: 369

Trp Tyr Arg Met Ser Pro His Asn Gln Thr
1               5                   10
```

<210> SEQ ID NO 370
<211> LENGTH: 10
<212> TYPE: PRT
<213> ORGANISM: Homo sapiens

<400> SEQUENCE: 370

Trp Tyr Arg Met Ser Pro Ile Asn Gln Thr
1               5                   10

<210> SEQ ID NO 371
<211> LENGTH: 10
<212> TYPE: PRT
<213> ORGANISM: Homo sapiens

<400> SEQUENCE: 371

Trp Tyr Arg Met Ser Pro Leu Asn Gln Thr
1               5                   10

<210> SEQ ID NO 372
<211> LENGTH: 10
<212> TYPE: PRT
<213> ORGANISM: Homo sapiens

<400> SEQUENCE: 372

Trp Tyr Arg Met Ser Pro Lys Asn Gln Thr
1               5                   10

<210> SEQ ID NO 373
<211> LENGTH: 10
<212> TYPE: PRT
<213> ORGANISM: Homo sapiens

<400> SEQUENCE: 373

Trp Tyr Arg Met Ser Pro Met Asn Gln Thr
1               5                   10

<210> SEQ ID NO 374
<211> LENGTH: 10
<212> TYPE: PRT
<213> ORGANISM: Homo sapiens

<400> SEQUENCE: 374

Trp Tyr Arg Met Ser Pro Phe Asn Gln Thr
1               5                   10

<210> SEQ ID NO 375
<211> LENGTH: 10
<212> TYPE: PRT
<213> ORGANISM: Homo sapiens

<400> SEQUENCE: 375

Trp Tyr Arg Met Ser Pro Pro Asn Gln Thr
1               5                   10

<210> SEQ ID NO 376
<211> LENGTH: 10
<212> TYPE: PRT
<213> ORGANISM: Homo sapiens

<400> SEQUENCE: 376

Trp Tyr Arg Met Ser Pro Ser Asn Gln Thr
1               5                   10

<210> SEQ ID NO 377

```
<210> SEQ ID NO 377
<211> LENGTH: 10
<212> TYPE: PRT
<213> ORGANISM: Homo sapiens

<400> SEQUENCE: 377

Trp Tyr Arg Met Ser Pro Thr Asn Gln Thr
1               5                   10

<210> SEQ ID NO 378
<211> LENGTH: 10
<212> TYPE: PRT
<213> ORGANISM: Homo sapiens

<400> SEQUENCE: 378

Trp Tyr Arg Met Ser Pro Trp Asn Gln Thr
1               5                   10

<210> SEQ ID NO 379
<211> LENGTH: 10
<212> TYPE: PRT
<213> ORGANISM: Homo sapiens

<400> SEQUENCE: 379

Trp Tyr Arg Met Ser Pro Tyr Asn Gln Thr
1               5                   10

<210> SEQ ID NO 380
<211> LENGTH: 10
<212> TYPE: PRT
<213> ORGANISM: Homo sapiens

<400> SEQUENCE: 380

Trp Tyr Arg Met Ser Pro Val Asn Gln Thr
1               5                   10

<210> SEQ ID NO 381
<211> LENGTH: 10
<212> TYPE: PRT
<213> ORGANISM: Homo sapiens

<400> SEQUENCE: 381

Trp Tyr Arg Met Ser Ala Ser Asn Gln Thr
1               5                   10

<210> SEQ ID NO 382
<211> LENGTH: 10
<212> TYPE: PRT
<213> ORGANISM: Homo sapiens

<400> SEQUENCE: 382

Trp Tyr Arg Met Ser Arg Ser Asn Gln Thr
1               5                   10

<210> SEQ ID NO 383
<211> LENGTH: 10
<212> TYPE: PRT
<213> ORGANISM: Homo sapiens

<400> SEQUENCE: 383

Trp Tyr Arg Met Ser Asn Ser Asn Gln Thr
1               5                   10

<210> SEQ ID NO 384
<211> LENGTH: 10
<212> TYPE: PRT
```

<213> ORGANISM: Homo sapiens

<400> SEQUENCE: 384

Trp Tyr Arg Met Ser Asp Ser Asn Gln Thr
1               5                   10

<210> SEQ ID NO 385
<211> LENGTH: 10
<212> TYPE: PRT
<213> ORGANISM: Homo sapiens

<400> SEQUENCE: 385

Trp Tyr Arg Met Ser Cys Ser Asn Gln Thr
1               5                   10

<210> SEQ ID NO 386
<211> LENGTH: 10
<212> TYPE: PRT
<213> ORGANISM: Homo sapiens

<400> SEQUENCE: 386

Trp Tyr Arg Met Ser Gln Ser Asn Gln Thr
1               5                   10

<210> SEQ ID NO 387
<211> LENGTH: 10
<212> TYPE: PRT
<213> ORGANISM: Homo sapiens

<400> SEQUENCE: 387

Trp Tyr Arg Met Ser Glu Ser Asn Gln Thr
1               5                   10

<210> SEQ ID NO 388
<211> LENGTH: 10
<212> TYPE: PRT
<213> ORGANISM: Homo sapiens

<400> SEQUENCE: 388

Trp Tyr Arg Met Ser Gly Ser Asn Gln Thr
1               5                   10

<210> SEQ ID NO 389
<211> LENGTH: 10
<212> TYPE: PRT
<213> ORGANISM: Homo sapiens

<400> SEQUENCE: 389

Trp Tyr Arg Met Ser His Ser Asn Gln Thr
1               5                   10

<210> SEQ ID NO 390
<211> LENGTH: 10
<212> TYPE: PRT
<213> ORGANISM: Homo sapiens

<400> SEQUENCE: 390

Trp Tyr Arg Met Ser Ile Ser Asn Gln Thr
1               5                   10

<210> SEQ ID NO 391
<211> LENGTH: 10
<212> TYPE: PRT
<213> ORGANISM: Homo sapiens

```
<400> SEQUENCE: 391

Trp Tyr Arg Met Ser Leu Ser Asn Gln Thr
1               5                   10

<210> SEQ ID NO 392
<211> LENGTH: 10
<212> TYPE: PRT
<213> ORGANISM: Homo sapiens

<400> SEQUENCE: 392

Trp Tyr Arg Met Ser Lys Ser Asn Gln Thr
1               5                   10

<210> SEQ ID NO 393
<211> LENGTH: 10
<212> TYPE: PRT
<213> ORGANISM: Homo sapiens

<400> SEQUENCE: 393

Trp Tyr Arg Met Ser Met Ser Asn Gln Thr
1               5                   10

<210> SEQ ID NO 394
<211> LENGTH: 10
<212> TYPE: PRT
<213> ORGANISM: Homo sapiens

<400> SEQUENCE: 394

Trp Tyr Arg Met Ser Phe Ser Asn Gln Thr
1               5                   10

<210> SEQ ID NO 395
<211> LENGTH: 10
<212> TYPE: PRT
<213> ORGANISM: Homo sapiens

<400> SEQUENCE: 395

Trp Tyr Arg Met Ser Pro Ser Asn Gln Thr
1               5                   10

<210> SEQ ID NO 396
<211> LENGTH: 10
<212> TYPE: PRT
<213> ORGANISM: Homo sapiens

<400> SEQUENCE: 396

Trp Tyr Arg Met Ser Ser Ser Asn Gln Thr
1               5                   10

<210> SEQ ID NO 397
<211> LENGTH: 10
<212> TYPE: PRT
<213> ORGANISM: Homo sapiens

<400> SEQUENCE: 397

Trp Tyr Arg Met Ser Thr Ser Asn Gln Thr
1               5                   10

<210> SEQ ID NO 398
<211> LENGTH: 10
<212> TYPE: PRT
<213> ORGANISM: Homo sapiens

<400> SEQUENCE: 398
```

Trp Tyr Arg Met Ser Trp Ser Asn Gln Thr
1               5                   10

<210> SEQ ID NO 399
<211> LENGTH: 10
<212> TYPE: PRT
<213> ORGANISM: Homo sapiens

<400> SEQUENCE: 399

Trp Tyr Arg Met Ser Tyr Ser Asn Gln Thr
1               5                   10

<210> SEQ ID NO 400
<211> LENGTH: 10
<212> TYPE: PRT
<213> ORGANISM: Homo sapiens

<400> SEQUENCE: 400

Trp Tyr Arg Met Ser Val Ser Asn Gln Thr
1               5                   10

<210> SEQ ID NO 401
<211> LENGTH: 10
<212> TYPE: PRT
<213> ORGANISM: Homo sapiens

<400> SEQUENCE: 401

Trp Tyr Arg Met Ala Pro Ser Asn Gln Thr
1               5                   10

<210> SEQ ID NO 402
<211> LENGTH: 10
<212> TYPE: PRT
<213> ORGANISM: Homo sapiens

<400> SEQUENCE: 402

Trp Tyr Arg Met Arg Pro Ser Asn Gln Thr
1               5                   10

<210> SEQ ID NO 403
<211> LENGTH: 10
<212> TYPE: PRT
<213> ORGANISM: Homo sapiens

<400> SEQUENCE: 403

Trp Tyr Arg Met Asn Pro Ser Asn Gln Thr
1               5                   10

<210> SEQ ID NO 404
<211> LENGTH: 10
<212> TYPE: PRT
<213> ORGANISM: Homo sapiens

<400> SEQUENCE: 404

Trp Tyr Arg Met Asp Pro Ser Asn Gln Thr
1               5                   10

<210> SEQ ID NO 405
<211> LENGTH: 10
<212> TYPE: PRT
<213> ORGANISM: Homo sapiens

<400> SEQUENCE: 405

Trp Tyr Arg Met Cys Pro Ser Asn Gln Thr
1               5                   10

<210> SEQ ID NO 406
<211> LENGTH: 10
<212> TYPE: PRT
<213> ORGANISM: Homo sapiens

<400> SEQUENCE: 406

Trp Tyr Arg Met Gln Pro Ser Asn Gln Thr
1               5                   10

<210> SEQ ID NO 407
<211> LENGTH: 10
<212> TYPE: PRT
<213> ORGANISM: Homo sapiens

<400> SEQUENCE: 407

Trp Tyr Arg Met Glu Pro Ser Asn Gln Thr
1               5                   10

<210> SEQ ID NO 408
<211> LENGTH: 10
<212> TYPE: PRT
<213> ORGANISM: Homo sapiens

<400> SEQUENCE: 408

Trp Tyr Arg Met Gly Pro Ser Asn Gln Thr
1               5                   10

<210> SEQ ID NO 409
<211> LENGTH: 10
<212> TYPE: PRT
<213> ORGANISM: Homo sapiens

<400> SEQUENCE: 409

Trp Tyr Arg Met His Pro Ser Asn Gln Thr
1               5                   10

<210> SEQ ID NO 410
<211> LENGTH: 10
<212> TYPE: PRT
<213> ORGANISM: Homo sapiens

<400> SEQUENCE: 410

Trp Tyr Arg Met Ile Pro Ser Asn Gln Thr
1               5                   10

<210> SEQ ID NO 411
<211> LENGTH: 10
<212> TYPE: PRT
<213> ORGANISM: Homo sapiens

<400> SEQUENCE: 411

Trp Tyr Arg Met Leu Pro Ser Asn Gln Thr
1               5                   10

<210> SEQ ID NO 412
<211> LENGTH: 10
<212> TYPE: PRT
<213> ORGANISM: Homo sapiens

<400> SEQUENCE: 412

Trp Tyr Arg Met Lys Pro Ser Asn Gln Thr
1               5                   10

```
<210> SEQ ID NO 413
<211> LENGTH: 10
<212> TYPE: PRT
<213> ORGANISM: Homo sapiens

<400> SEQUENCE: 413

Trp Tyr Arg Met Met Pro Ser Asn Gln Thr
1               5                   10

<210> SEQ ID NO 414
<211> LENGTH: 10
<212> TYPE: PRT
<213> ORGANISM: Homo sapiens

<400> SEQUENCE: 414

Trp Tyr Arg Met Phe Pro Ser Asn Gln Thr
1               5                   10

<210> SEQ ID NO 415
<211> LENGTH: 10
<212> TYPE: PRT
<213> ORGANISM: Homo sapiens

<400> SEQUENCE: 415

Trp Tyr Arg Met Pro Pro Ser Asn Gln Thr
1               5                   10

<210> SEQ ID NO 416
<211> LENGTH: 10
<212> TYPE: PRT
<213> ORGANISM: Homo sapiens

<400> SEQUENCE: 416

Trp Tyr Arg Met Ser Pro Ser Asn Gln Thr
1               5                   10

<210> SEQ ID NO 417
<211> LENGTH: 10
<212> TYPE: PRT
<213> ORGANISM: Homo sapiens

<400> SEQUENCE: 417

Trp Tyr Arg Met Thr Pro Ser Asn Gln Thr
1               5                   10

<210> SEQ ID NO 418
<211> LENGTH: 10
<212> TYPE: PRT
<213> ORGANISM: Homo sapiens

<400> SEQUENCE: 418

Trp Tyr Arg Met Trp Pro Ser Asn Gln Thr
1               5                   10

<210> SEQ ID NO 419
<211> LENGTH: 10
<212> TYPE: PRT
<213> ORGANISM: Homo sapiens

<400> SEQUENCE: 419

Trp Tyr Arg Met Tyr Pro Ser Asn Gln Thr
1               5                   10

<210> SEQ ID NO 420
<211> LENGTH: 10
```

```
<212> TYPE: PRT
<213> ORGANISM: Homo sapiens

<400> SEQUENCE: 420

Trp Tyr Arg Met Val Pro Ser Asn Gln Thr
1               5                   10

<210> SEQ ID NO 421
<211> LENGTH: 10
<212> TYPE: PRT
<213> ORGANISM: Homo sapiens

<400> SEQUENCE: 421

Trp Tyr Arg Ala Ser Pro Ser Asn Gln Thr
1               5                   10

<210> SEQ ID NO 422
<211> LENGTH: 10
<212> TYPE: PRT
<213> ORGANISM: Homo sapiens

<400> SEQUENCE: 422

Trp Tyr Arg Arg Ser Pro Ser Asn Gln Thr
1               5                   10

<210> SEQ ID NO 423
<211> LENGTH: 10
<212> TYPE: PRT
<213> ORGANISM: Homo sapiens

<400> SEQUENCE: 423

Trp Tyr Arg Asn Ser Pro Ser Asn Gln Thr
1               5                   10

<210> SEQ ID NO 424
<211> LENGTH: 10
<212> TYPE: PRT
<213> ORGANISM: Homo sapiens

<400> SEQUENCE: 424

Trp Tyr Arg Asp Ser Pro Ser Asn Gln Thr
1               5                   10

<210> SEQ ID NO 425
<211> LENGTH: 10
<212> TYPE: PRT
<213> ORGANISM: Homo sapiens

<400> SEQUENCE: 425

Trp Tyr Arg Cys Ser Pro Ser Asn Gln Thr
1               5                   10

<210> SEQ ID NO 426
<211> LENGTH: 10
<212> TYPE: PRT
<213> ORGANISM: Homo sapiens

<400> SEQUENCE: 426

Trp Tyr Arg Gln Ser Pro Ser Asn Gln Thr
1               5                   10

<210> SEQ ID NO 427
<211> LENGTH: 10
<212> TYPE: PRT
<213> ORGANISM: Homo sapiens
```

<400> SEQUENCE: 427

Trp Tyr Arg Glu Ser Pro Ser Asn Gln Thr
1               5                   10

<210> SEQ ID NO 428
<211> LENGTH: 10
<212> TYPE: PRT
<213> ORGANISM: Homo sapiens

<400> SEQUENCE: 428

Trp Tyr Arg Gly Ser Pro Ser Asn Gln Thr
1               5                   10

<210> SEQ ID NO 429
<211> LENGTH: 10
<212> TYPE: PRT
<213> ORGANISM: Homo sapiens

<400> SEQUENCE: 429

Trp Tyr Arg His Ser Pro Ser Asn Gln Thr
1               5                   10

<210> SEQ ID NO 430
<211> LENGTH: 10
<212> TYPE: PRT
<213> ORGANISM: Homo sapiens

<400> SEQUENCE: 430

Trp Tyr Arg Ile Ser Pro Ser Asn Gln Thr
1               5                   10

<210> SEQ ID NO 431
<211> LENGTH: 10
<212> TYPE: PRT
<213> ORGANISM: Homo sapiens

<400> SEQUENCE: 431

Trp Tyr Arg Leu Ser Pro Ser Asn Gln Thr
1               5                   10

<210> SEQ ID NO 432
<211> LENGTH: 10
<212> TYPE: PRT
<213> ORGANISM: Homo sapiens

<400> SEQUENCE: 432

Trp Tyr Arg Lys Ser Pro Ser Asn Gln Thr
1               5                   10

<210> SEQ ID NO 433
<211> LENGTH: 10
<212> TYPE: PRT
<213> ORGANISM: Homo sapiens

<400> SEQUENCE: 433

Trp Tyr Arg Met Ser Pro Ser Asn Gln Thr
1               5                   10

<210> SEQ ID NO 434
<211> LENGTH: 10
<212> TYPE: PRT
<213> ORGANISM: Homo sapiens

<400> SEQUENCE: 434

Trp Tyr Arg Phe Ser Pro Ser Asn Gln Thr
1               5                   10

<210> SEQ ID NO 435
<211> LENGTH: 10
<212> TYPE: PRT
<213> ORGANISM: Homo sapiens

<400> SEQUENCE: 435

Trp Tyr Arg Pro Ser Pro Ser Asn Gln Thr
1               5                   10

<210> SEQ ID NO 436
<211> LENGTH: 10
<212> TYPE: PRT
<213> ORGANISM: Homo sapiens

<400> SEQUENCE: 436

Trp Tyr Arg Ser Ser Pro Ser Asn Gln Thr
1               5                   10

<210> SEQ ID NO 437
<211> LENGTH: 10
<212> TYPE: PRT
<213> ORGANISM: Homo sapiens

<400> SEQUENCE: 437

Trp Tyr Arg Thr Ser Pro Ser Asn Gln Thr
1               5                   10

<210> SEQ ID NO 438
<211> LENGTH: 10
<212> TYPE: PRT
<213> ORGANISM: Homo sapiens

<400> SEQUENCE: 438

Trp Tyr Arg Trp Ser Pro Ser Asn Gln Thr
1               5                   10

<210> SEQ ID NO 439
<211> LENGTH: 10
<212> TYPE: PRT
<213> ORGANISM: Homo sapiens

<400> SEQUENCE: 439

Trp Tyr Arg Tyr Ser Pro Ser Asn Gln Thr
1               5                   10

<210> SEQ ID NO 440
<211> LENGTH: 10
<212> TYPE: PRT
<213> ORGANISM: Homo sapiens

<400> SEQUENCE: 440

Trp Tyr Arg Val Ser Pro Ser Asn Gln Thr
1               5                   10

<210> SEQ ID NO 441
<211> LENGTH: 10
<212> TYPE: PRT
<213> ORGANISM: Homo sapiens

<400> SEQUENCE: 441

Trp Tyr Ala Met Ser Pro Ser Asn Gln Thr

```
1               5                  10
```

<210> SEQ ID NO 442
<211> LENGTH: 10
<212> TYPE: PRT
<213> ORGANISM: Homo sapiens

<400> SEQUENCE: 442

```
Trp Tyr Arg Met Ser Pro Ser Asn Gln Thr
1               5                  10
```

<210> SEQ ID NO 443
<211> LENGTH: 10
<212> TYPE: PRT
<213> ORGANISM: Homo sapiens

<400> SEQUENCE: 443

```
Trp Tyr Asn Met Ser Pro Ser Asn Gln Thr
1               5                  10
```

<210> SEQ ID NO 444
<211> LENGTH: 10
<212> TYPE: PRT
<213> ORGANISM: Homo sapiens

<400> SEQUENCE: 444

```
Trp Tyr Asp Met Ser Pro Ser Asn Gln Thr
1               5                  10
```

<210> SEQ ID NO 445
<211> LENGTH: 10
<212> TYPE: PRT
<213> ORGANISM: Homo sapiens

<400> SEQUENCE: 445

```
Trp Tyr Cys Met Ser Pro Ser Asn Gln Thr
1               5                  10
```

<210> SEQ ID NO 446
<211> LENGTH: 10
<212> TYPE: PRT
<213> ORGANISM: Homo sapiens

<400> SEQUENCE: 446

```
Trp Tyr Gln Met Ser Pro Ser Asn Gln Thr
1               5                  10
```

<210> SEQ ID NO 447
<211> LENGTH: 10
<212> TYPE: PRT
<213> ORGANISM: Homo sapiens

<400> SEQUENCE: 447

```
Trp Tyr Glu Met Ser Pro Ser Asn Gln Thr
1               5                  10
```

<210> SEQ ID NO 448
<211> LENGTH: 10
<212> TYPE: PRT
<213> ORGANISM: Homo sapiens

<400> SEQUENCE: 448

```
Trp Tyr Gly Met Ser Pro Ser Asn Gln Thr
1               5                  10
```

<210> SEQ ID NO 449
<211> LENGTH: 10
<212> TYPE: PRT
<213> ORGANISM: Homo sapiens

<400> SEQUENCE: 449

Trp Tyr His Met Ser Pro Ser Asn Gln Thr
1               5                   10

<210> SEQ ID NO 450
<211> LENGTH: 10
<212> TYPE: PRT
<213> ORGANISM: Homo sapiens

<400> SEQUENCE: 450

Trp Tyr Ile Met Ser Pro Ser Asn Gln Thr
1               5                   10

<210> SEQ ID NO 451
<211> LENGTH: 10
<212> TYPE: PRT
<213> ORGANISM: Homo sapiens

<400> SEQUENCE: 451

Trp Tyr Leu Met Ser Pro Ser Asn Gln Thr
1               5                   10

<210> SEQ ID NO 452
<211> LENGTH: 10
<212> TYPE: PRT
<213> ORGANISM: Homo sapiens

<400> SEQUENCE: 452

Trp Tyr Lys Met Ser Pro Ser Asn Gln Thr
1               5                   10

<210> SEQ ID NO 453
<211> LENGTH: 10
<212> TYPE: PRT
<213> ORGANISM: Homo sapiens

<400> SEQUENCE: 453

Trp Tyr Met Met Ser Pro Ser Asn Gln Thr
1               5                   10

<210> SEQ ID NO 454
<211> LENGTH: 10
<212> TYPE: PRT
<213> ORGANISM: Homo sapiens

<400> SEQUENCE: 454

Trp Tyr Phe Met Ser Pro Ser Asn Gln Thr
1               5                   10

<210> SEQ ID NO 455
<211> LENGTH: 10
<212> TYPE: PRT
<213> ORGANISM: Homo sapiens

<400> SEQUENCE: 455

Trp Tyr Pro Met Ser Pro Ser Asn Gln Thr
1               5                   10

<210> SEQ ID NO 456

```
<211> LENGTH: 10
<212> TYPE: PRT
<213> ORGANISM: Homo sapiens

<400> SEQUENCE: 456

Trp Tyr Ser Met Ser Pro Ser Asn Gln Thr
1               5                   10

<210> SEQ ID NO 457
<211> LENGTH: 10
<212> TYPE: PRT
<213> ORGANISM: Homo sapiens

<400> SEQUENCE: 457

Trp Tyr Thr Met Ser Pro Ser Asn Gln Thr
1               5                   10

<210> SEQ ID NO 458
<211> LENGTH: 10
<212> TYPE: PRT
<213> ORGANISM: Homo sapiens

<400> SEQUENCE: 458

Trp Tyr Trp Met Ser Pro Ser Asn Gln Thr
1               5                   10

<210> SEQ ID NO 459
<211> LENGTH: 10
<212> TYPE: PRT
<213> ORGANISM: Homo sapiens

<400> SEQUENCE: 459

Trp Tyr Tyr Met Ser Pro Ser Asn Gln Thr
1               5                   10

<210> SEQ ID NO 460
<211> LENGTH: 10
<212> TYPE: PRT
<213> ORGANISM: Homo sapiens

<400> SEQUENCE: 460

Trp Tyr Val Met Ser Pro Ser Asn Gln Thr
1               5                   10

<210> SEQ ID NO 461
<211> LENGTH: 10
<212> TYPE: PRT
<213> ORGANISM: Homo sapiens

<400> SEQUENCE: 461

Trp Ala Arg Met Ser Pro Ser Asn Gln Thr
1               5                   10

<210> SEQ ID NO 462
<211> LENGTH: 10
<212> TYPE: PRT
<213> ORGANISM: Homo sapiens

<400> SEQUENCE: 462

Trp Arg Arg Met Ser Pro Ser Asn Gln Thr
1               5                   10

<210> SEQ ID NO 463
<211> LENGTH: 10
<212> TYPE: PRT
```

```
<213> ORGANISM: Homo sapiens

<400> SEQUENCE: 463

Trp Asn Arg Met Ser Pro Ser Asn Gln Thr
1               5                   10

<210> SEQ ID NO 464
<211> LENGTH: 10
<212> TYPE: PRT
<213> ORGANISM: Homo sapiens

<400> SEQUENCE: 464

Trp Asp Arg Met Ser Pro Ser Asn Gln Thr
1               5                   10

<210> SEQ ID NO 465
<211> LENGTH: 10
<212> TYPE: PRT
<213> ORGANISM: Homo sapiens

<400> SEQUENCE: 465

Trp Cys Arg Met Ser Pro Ser Asn Gln Thr
1               5                   10

<210> SEQ ID NO 466
<211> LENGTH: 10
<212> TYPE: PRT
<213> ORGANISM: Homo sapiens

<400> SEQUENCE: 466

Trp Gln Arg Met Ser Pro Ser Asn Gln Thr
1               5                   10

<210> SEQ ID NO 467
<211> LENGTH: 10
<212> TYPE: PRT
<213> ORGANISM: Homo sapiens

<400> SEQUENCE: 467

Trp Glu Arg Met Ser Pro Ser Asn Gln Thr
1               5                   10

<210> SEQ ID NO 468
<211> LENGTH: 10
<212> TYPE: PRT
<213> ORGANISM: Homo sapiens

<400> SEQUENCE: 468

Trp Gly Arg Met Ser Pro Ser Asn Gln Thr
1               5                   10

<210> SEQ ID NO 469
<211> LENGTH: 10
<212> TYPE: PRT
<213> ORGANISM: Homo sapiens

<400> SEQUENCE: 469

Trp His Arg Met Ser Pro Ser Asn Gln Thr
1               5                   10

<210> SEQ ID NO 470
<211> LENGTH: 10
<212> TYPE: PRT
<213> ORGANISM: Homo sapiens
```

<400> SEQUENCE: 470

Trp Ile Arg Met Ser Pro Ser Asn Gln Thr
1               5                   10

<210> SEQ ID NO 471
<211> LENGTH: 10
<212> TYPE: PRT
<213> ORGANISM: Homo sapiens

<400> SEQUENCE: 471

Trp Leu Arg Met Ser Pro Ser Asn Gln Thr
1               5                   10

<210> SEQ ID NO 472
<211> LENGTH: 10
<212> TYPE: PRT
<213> ORGANISM: Homo sapiens

<400> SEQUENCE: 472

Trp Lys Arg Met Ser Pro Ser Asn Gln Thr
1               5                   10

<210> SEQ ID NO 473
<211> LENGTH: 10
<212> TYPE: PRT
<213> ORGANISM: Homo sapiens

<400> SEQUENCE: 473

Trp Met Arg Met Ser Pro Ser Asn Gln Thr
1               5                   10

<210> SEQ ID NO 474
<211> LENGTH: 10
<212> TYPE: PRT
<213> ORGANISM: Homo sapiens

<400> SEQUENCE: 474

Trp Phe Arg Met Ser Pro Ser Asn Gln Thr
1               5                   10

<210> SEQ ID NO 475
<211> LENGTH: 10
<212> TYPE: PRT
<213> ORGANISM: Homo sapiens

<400> SEQUENCE: 475

Trp Pro Arg Met Ser Pro Ser Asn Gln Thr
1               5                   10

<210> SEQ ID NO 476
<211> LENGTH: 10
<212> TYPE: PRT
<213> ORGANISM: Homo sapiens

<400> SEQUENCE: 476

Trp Ser Arg Met Ser Pro Ser Asn Gln Thr
1               5                   10

<210> SEQ ID NO 477
<211> LENGTH: 10
<212> TYPE: PRT
<213> ORGANISM: Homo sapiens

<400> SEQUENCE: 477

Trp Thr Arg Met Ser Pro Ser Asn Gln Thr
1               5                   10

<210> SEQ ID NO 478
<211> LENGTH: 10
<212> TYPE: PRT
<213> ORGANISM: Homo sapiens

<400> SEQUENCE: 478

Trp Trp Arg Met Ser Pro Ser Asn Gln Thr
1               5                   10

<210> SEQ ID NO 479
<211> LENGTH: 10
<212> TYPE: PRT
<213> ORGANISM: Homo sapiens

<400> SEQUENCE: 479

Trp Tyr Arg Met Ser Pro Ser Asn Gln Thr
1               5                   10

<210> SEQ ID NO 480
<211> LENGTH: 10
<212> TYPE: PRT
<213> ORGANISM: Homo sapiens

<400> SEQUENCE: 480

Trp Val Arg Met Ser Pro Ser Asn Gln Thr
1               5                   10

<210> SEQ ID NO 481
<211> LENGTH: 10
<212> TYPE: PRT
<213> ORGANISM: Homo sapiens

<400> SEQUENCE: 481

Ala Tyr Arg Met Ser Pro Ser Asn Gln Thr
1               5                   10

<210> SEQ ID NO 482
<211> LENGTH: 10
<212> TYPE: PRT
<213> ORGANISM: Homo sapiens

<400> SEQUENCE: 482

Arg Tyr Arg Met Ser Pro Ser Asn Gln Thr
1               5                   10

<210> SEQ ID NO 483
<211> LENGTH: 10
<212> TYPE: PRT
<213> ORGANISM: Homo sapiens

<400> SEQUENCE: 483

Asn Tyr Arg Met Ser Pro Ser Asn Gln Thr
1               5                   10

<210> SEQ ID NO 484
<211> LENGTH: 10
<212> TYPE: PRT
<213> ORGANISM: Homo sapiens

<400> SEQUENCE: 484

Asp Tyr Arg Met Ser Pro Ser Asn Gln Thr
1               5                   10

```
<210> SEQ ID NO 485
<211> LENGTH: 10
<212> TYPE: PRT
<213> ORGANISM: Homo sapiens

<400> SEQUENCE: 485

Cys Tyr Arg Met Ser Pro Ser Asn Gln Thr
1               5                   10

<210> SEQ ID NO 486
<211> LENGTH: 10
<212> TYPE: PRT
<213> ORGANISM: Homo sapiens

<400> SEQUENCE: 486

Gln Tyr Arg Met Ser Pro Ser Asn Gln Thr
1               5                   10

<210> SEQ ID NO 487
<211> LENGTH: 10
<212> TYPE: PRT
<213> ORGANISM: Homo sapiens

<400> SEQUENCE: 487

Glu Tyr Arg Met Ser Pro Ser Asn Gln Thr
1               5                   10

<210> SEQ ID NO 488
<211> LENGTH: 10
<212> TYPE: PRT
<213> ORGANISM: Homo sapiens

<400> SEQUENCE: 488

Gly Tyr Arg Met Ser Pro Ser Asn Gln Thr
1               5                   10

<210> SEQ ID NO 489
<211> LENGTH: 10
<212> TYPE: PRT
<213> ORGANISM: Homo sapiens

<400> SEQUENCE: 489

His Tyr Arg Met Ser Pro Ser Asn Gln Thr
1               5                   10

<210> SEQ ID NO 490
<211> LENGTH: 10
<212> TYPE: PRT
<213> ORGANISM: Homo sapiens

<400> SEQUENCE: 490

Ile Tyr Arg Met Ser Pro Ser Asn Gln Thr
1               5                   10

<210> SEQ ID NO 491
<211> LENGTH: 10
<212> TYPE: PRT
<213> ORGANISM: Homo sapiens

<400> SEQUENCE: 491

Leu Tyr Arg Met Ser Pro Ser Asn Gln Thr
1               5                   10
```

```
<210> SEQ ID NO 492
<211> LENGTH: 10
<212> TYPE: PRT
<213> ORGANISM: Homo sapiens

<400> SEQUENCE: 492

Lys Tyr Arg Met Ser Pro Ser Asn Gln Thr
1               5                   10

<210> SEQ ID NO 493
<211> LENGTH: 10
<212> TYPE: PRT
<213> ORGANISM: Homo sapiens

<400> SEQUENCE: 493

Met Tyr Arg Met Ser Pro Ser Asn Gln Thr
1               5                   10

<210> SEQ ID NO 494
<211> LENGTH: 10
<212> TYPE: PRT
<213> ORGANISM: Homo sapiens

<400> SEQUENCE: 494

Phe Tyr Arg Met Ser Pro Ser Asn Gln Thr
1               5                   10

<210> SEQ ID NO 495
<211> LENGTH: 10
<212> TYPE: PRT
<213> ORGANISM: Homo sapiens

<400> SEQUENCE: 495

Pro Tyr Arg Met Ser Pro Ser Asn Gln Thr
1               5                   10

<210> SEQ ID NO 496
<211> LENGTH: 10
<212> TYPE: PRT
<213> ORGANISM: Homo sapiens

<400> SEQUENCE: 496

Ser Tyr Arg Met Ser Pro Ser Asn Gln Thr
1               5                   10

<210> SEQ ID NO 497
<211> LENGTH: 10
<212> TYPE: PRT
<213> ORGANISM: Homo sapiens

<400> SEQUENCE: 497

Thr Tyr Arg Met Ser Pro Ser Asn Gln Thr
1               5                   10

<210> SEQ ID NO 498
<211> LENGTH: 10
<212> TYPE: PRT
<213> ORGANISM: Homo sapiens

<400> SEQUENCE: 498

Trp Tyr Arg Met Ser Pro Ser Asn Gln Thr
1               5                   10

<210> SEQ ID NO 499
<211> LENGTH: 10
```

```
<212> TYPE: PRT
<213> ORGANISM: Homo sapiens

<400> SEQUENCE: 499

Tyr Tyr Arg Met Ser Pro Ser Asn Gln Thr
1               5                   10

<210> SEQ ID NO 500
<211> LENGTH: 10
<212> TYPE: PRT
<213> ORGANISM: Homo sapiens

<400> SEQUENCE: 500

Val Tyr Arg Met Ser Pro Ser Asn Gln Thr
1               5                   10

<210> SEQ ID NO 501
<211> LENGTH: 20
<212> TYPE: PRT
<213> ORGANISM: Homo sapiens

<400> SEQUENCE: 501

Met Glu Thr Asp Thr Leu Leu Leu Trp Val Leu Leu Leu Trp Val Pro
1               5                   10                  15

Gly Ser Thr Gly
            20

<210> SEQ ID NO 502
<211> LENGTH: 20
<212> TYPE: PRT
<213> ORGANISM: Homo sapiens

<400> SEQUENCE: 502

Met Tyr Arg Met Gln Leu Leu Ser Cys Ile Ala Leu Ser Leu Ala Leu
1               5                   10                  15

Val Thr Asn Ser
            20

<210> SEQ ID NO 503
<211> LENGTH: 15
<212> TYPE: PRT
<213> ORGANISM: Artificial Sequence
<220> FEATURE:
<223> OTHER INFORMATION: Synthetic sequence

<400> SEQUENCE: 503

Gly Gly Gly Gly Ser Gly Gly Gly Ser Gly Gly Gly Gly Ser
1               5                   10                  15

<210> SEQ ID NO 504
<211> LENGTH: 16
<212> TYPE: PRT
<213> ORGANISM: Artificial Sequence
<220> FEATURE:
<223> OTHER INFORMATION: Synthetic sequence

<400> SEQUENCE: 504

Gly Gly Gly Gly Ser Leu Val Pro Arg Gly Ser Gly Gly Gly Ser
1               5                   10                  15

<210> SEQ ID NO 505
<211> LENGTH: 6
<212> TYPE: PRT
<213> ORGANISM: Artificial Sequence
<220> FEATURE:
```

```
<223> OTHER INFORMATION: Synthetic sequence

<400> SEQUENCE: 505

Gly Ser Gly Ser Gly Ser
1               5

<210> SEQ ID NO 506
<211> LENGTH: 8
<212> TYPE: PRT
<213> ORGANISM: Artificial Sequence
<220> FEATURE:
<223> OTHER INFORMATION: Synthetic sequence

<400> SEQUENCE: 506

Gly Ser Gly Ser Gly Ser Gly Ser
1               5

<210> SEQ ID NO 507
<211> LENGTH: 14
<212> TYPE: PRT
<213> ORGANISM: Artificial Sequence
<220> FEATURE:
<223> OTHER INFORMATION: Synthetic sequence

<400> SEQUENCE: 507

Gly Gly Gly Gly Ser Leu Val Pro Arg Gly Ser Gly Gly Gly
1               5                   10

<210> SEQ ID NO 508
<211> LENGTH: 10
<212> TYPE: PRT
<213> ORGANISM: Artificial Sequence
<220> FEATURE:
<223> OTHER INFORMATION: Synthetic sequence

<400> SEQUENCE: 508

Gly Ser Gly Gly His Met Gly Ser Gly Gly
1               5                   10

<210> SEQ ID NO 509
<211> LENGTH: 11
<212> TYPE: PRT
<213> ORGANISM: Artificial Sequence
<220> FEATURE:
<223> OTHER INFORMATION: Synthetic sequence

<400> SEQUENCE: 509

Gly Gly Ser Gly Gly Ser Gly Gly Ser Gly Gly
1               5                   10

<210> SEQ ID NO 510
<211> LENGTH: 5
<212> TYPE: PRT
<213> ORGANISM: Artificial Sequence
<220> FEATURE:
<223> OTHER INFORMATION: Synthetic sequence

<400> SEQUENCE: 510

Gly Gly Ser Gly Gly
1               5

<210> SEQ ID NO 511
<211> LENGTH: 8
<212> TYPE: PRT
<213> ORGANISM: Artificial Sequence
<220> FEATURE:
<223> OTHER INFORMATION: Synthetic sequence
```

<400> SEQUENCE: 511

Gly Gly Ser Gly Gly Gly Gly
1               5

<210> SEQ ID NO 512
<211> LENGTH: 18
<212> TYPE: PRT
<213> ORGANISM: Artificial Sequence
<220> FEATURE:
<223> OTHER INFORMATION: Synthetic sequence

<400> SEQUENCE: 512

Gly Gly Gly Ser Glu Gly Gly Gly Ser Glu Gly Gly Gly Ser Glu Gly
1               5                   10                  15

Gly Gly

<210> SEQ ID NO 513
<211> LENGTH: 8
<212> TYPE: PRT
<213> ORGANISM: Artificial Sequence
<220> FEATURE:
<223> OTHER INFORMATION: Synthetic sequence

<400> SEQUENCE: 513

Ala Ala Gly Ala Ala Thr Ala Ala
1               5

<210> SEQ ID NO 514
<211> LENGTH: 5
<212> TYPE: PRT
<213> ORGANISM: Artificial Sequence
<220> FEATURE:
<223> OTHER INFORMATION: Synthetic sequence

<400> SEQUENCE: 514

Gly Gly Gly Gly Gly
1               5

<210> SEQ ID NO 515
<211> LENGTH: 5
<212> TYPE: PRT
<213> ORGANISM: Artificial Sequence
<220> FEATURE:
<223> OTHER INFORMATION: Synthetic sequence

<400> SEQUENCE: 515

Gly Gly Ser Ser Gly
1               5

<210> SEQ ID NO 516
<211> LENGTH: 11
<212> TYPE: PRT
<213> ORGANISM: Artificial Sequence
<220> FEATURE:
<223> OTHER INFORMATION: Synthetic sequence

<400> SEQUENCE: 516

Gly Ser Gly Gly Gly Thr Gly Gly Gly Ser Gly
1               5                   10

<210> SEQ ID NO 517
<211> LENGTH: 2
<212> TYPE: PRT
<213> ORGANISM: Artificial Sequence
<220> FEATURE:

```
<223> OTHER INFORMATION: Synthetic sequence

<400> SEQUENCE: 517

Gly Thr
1

<210> SEQ ID NO 518
<211> LENGTH: 26
<212> TYPE: PRT
<213> ORGANISM: Artificial Sequence
<220> FEATURE:
<223> OTHER INFORMATION: Synthetic sequence

<400> SEQUENCE: 518

Gly Ser Gly Ser Gly Ser Gly Ser Gly Gly Ser Gly Gly Ser Gly Gly
1               5                   10                  15

Ser Gly Gly Ser Gly Gly Ser Gly Gly Ser
            20                  25

<210> SEQ ID NO 519
<211> LENGTH: 14
<212> TYPE: PRT
<213> ORGANISM: Artificial Sequence
<220> FEATURE:
<223> OTHER INFORMATION: Synthetic sequence

<400> SEQUENCE: 519

Gly Ser Gly Gly Ser Gly Ser Gly Gly Ser Gly Gly Ser Gly
1               5                   10

<210> SEQ ID NO 520
<211> LENGTH: 22
<212> TYPE: PRT
<213> ORGANISM: Artificial Sequence
<220> FEATURE:
<223> OTHER INFORMATION: Synthetic sequence

<400> SEQUENCE: 520

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 521
<211> LENGTH: 20
<212> TYPE: PRT
<213> ORGANISM: Artificial Sequence
<220> FEATURE:
<223> OTHER INFORMATION: Synthetic sequence

<400> SEQUENCE: 521

Gln Cys Thr Asn Tyr Ala Leu Leu Lys Leu Ala Gly Asp Val Glu Ser
1               5                   10                  15

Asn Pro Gly Pro
            20

<210> SEQ ID NO 522
<211> LENGTH: 19
<212> TYPE: PRT
<213> ORGANISM: Artificial Sequence
<220> FEATURE:
<223> OTHER INFORMATION: Synthetic sequence

<400> SEQUENCE: 522

Ala Thr Asn Phe Ser Leu Leu Lys Gln Ala Gly Asp Val Glu Glu Asn
```

```
                1               5                   10                  15

Pro Gly Pro

<210> SEQ ID NO 523
<211> LENGTH: 20
<212> TYPE: PRT
<213> ORGANISM: Artificial Sequence
<220> FEATURE:
<223> OTHER INFORMATION: Synthetic sequence

<400> SEQUENCE: 523

His Tyr Ala Gly Tyr Phe Ala Asp Leu Leu Ile His Asp Ile Glu Thr
1               5                   10                  15

Asn Pro Gly Pro
            20

<210> SEQ ID NO 524
<211> LENGTH: 25
<212> TYPE: PRT
<213> ORGANISM: Artificial Sequence
<220> FEATURE:
<223> OTHER INFORMATION: Synthetic sequence

<400> SEQUENCE: 524

Gly Ile Phe Asn Ala His Tyr Ala Gly Tyr Phe Ala Asp Leu Leu Ile
1               5                   10                  15

His Asp Ile Glu Thr Asn Pro Gly Pro
            20                  25

<210> SEQ ID NO 525
<211> LENGTH: 25
<212> TYPE: PRT
<213> ORGANISM: Artificial Sequence
<220> FEATURE:
<223> OTHER INFORMATION: Synthetic sequence

<400> SEQUENCE: 525

Lys Ala Val Arg Gly Tyr His Ala Asp Tyr Tyr Lys Gln Arg Leu Ile
1               5                   10                  15

His Asp Val Glu Met Asn Pro Gly Pro
            20                  25

<210> SEQ ID NO 526
<211> LENGTH: 20
<212> TYPE: PRT
<213> ORGANISM: Artificial Sequence
<220> FEATURE:
<223> OTHER INFORMATION: Synthetic sequence

<400> SEQUENCE: 526

Gly Ala Thr Asn Phe Ser Leu Leu Lys Leu Ala Gly Asp Val Glu Leu
1               5                   10                  15

Asn Pro Gly Pro
            20

<210> SEQ ID NO 527
<211> LENGTH: 18
<212> TYPE: PRT
<213> ORGANISM: Artificial Sequence
<220> FEATURE:
<223> OTHER INFORMATION: Synthetic sequence

<400> SEQUENCE: 527

Glu Gly Arg Gly Ser Leu Leu Thr Cys Gly Asp Val Glu Glu Asn Pro
```

```
1               5                   10                  15

Gly Pro

<210> SEQ ID NO 528
<211> LENGTH: 19
<212> TYPE: PRT
<213> ORGANISM: Artificial Sequence
<220> FEATURE:
<223> OTHER INFORMATION: Synthetic sequence

<400> SEQUENCE: 528

Ala Ala Arg Gln Met Leu Leu Leu Leu Ser Gly Asp Val Glu Thr Asn
1               5                   10                  15

Pro Gly Pro

<210> SEQ ID NO 529
<211> LENGTH: 20
<212> TYPE: PRT
<213> ORGANISM: Artificial Sequence
<220> FEATURE:
<223> OTHER INFORMATION: Synthetic sequence

<400> SEQUENCE: 529

Phe Leu Arg Lys Arg Thr Gln Leu Leu Met Ser Gly Asp Val Glu Ser
1               5                   10                  15

Asn Pro Gly Pro
            20

<210> SEQ ID NO 530
<211> LENGTH: 20
<212> TYPE: PRT
<213> ORGANISM: Artificial Sequence
<220> FEATURE:
<223> OTHER INFORMATION: Synthetic sequence

<400> SEQUENCE: 530

Gly Ser Trp Thr Asp Ile Leu Leu Leu Ser Gly Asp Val Glu Thr
1               5                   10                  15

Asn Pro Gly Pro
            20

<210> SEQ ID NO 531
<211> LENGTH: 19
<212> TYPE: PRT
<213> ORGANISM: Artificial Sequence
<220> FEATURE:
<223> OTHER INFORMATION: Synthetic sequence

<400> SEQUENCE: 531

Thr Arg Ala Glu Glu Asp Glu Leu Ile Arg Ala Gly Ile Glu Ser Asn
1               5                   10                  15

Pro Gly Pro

<210> SEQ ID NO 532
<211> LENGTH: 20
<212> TYPE: PRT
<213> ORGANISM: Artificial Sequence
<220> FEATURE:
<223> OTHER INFORMATION: Synthetic sequence

<400> SEQUENCE: 532

Ala Lys Phe Gln Ile Asp Lys Ile Leu Ile Ser Gly Asp Val Glu Leu
1               5                   10                  15
```

Asn Pro Gly Pro
        20

<210> SEQ ID NO 533
<211> LENGTH: 20
<212> TYPE: PRT
<213> ORGANISM: Artificial Sequence
<220> FEATURE:
<223> OTHER INFORMATION: Synthetic sequence

<400> SEQUENCE: 533

Ser Lys Phe Gln Ile Asp Lys Ile Leu Ile Ser Gly Asp Ile Glu Leu
1               5                   10                  15

Asn Pro Gly Pro
        20

<210> SEQ ID NO 534
<211> LENGTH: 20
<212> TYPE: PRT
<213> ORGANISM: Artificial Sequence
<220> FEATURE:
<223> OTHER INFORMATION: Synthetic sequence

<400> SEQUENCE: 534

Ser Ser Ile Ile Arg Thr Lys Met Leu Val Ser Gly Asp Val Glu Glu
1               5                   10                  15

Asn Pro Gly Pro
        20

<210> SEQ ID NO 535
<211> LENGTH: 20
<212> TYPE: PRT
<213> ORGANISM: Artificial Sequence
<220> FEATURE:
<223> OTHER INFORMATION: Synthetic sequence

<400> SEQUENCE: 535

Cys Asp Ala Gln Arg Gln Lys Leu Leu Leu Ser Gly Asp Ile Glu Gln
1               5                   10                  15

Asn Pro Gly Pro
        20

<210> SEQ ID NO 536
<211> LENGTH: 668
<212> TYPE: DNA
<213> ORGANISM: Artificial Sequence
<220> FEATURE:
<223> OTHER INFORMATION: Synthetic sequence

<400> SEQUENCE: 536
gcgatctgac ggttcactaa acgagctctg cttatatagg cctcccaccg tacacgccac      60
ctcgacatac tcgagtagtt attaatagta atcaattacg ggtcattag ttcatagccc      120 atatatggag ttccgcgtta cataacttac ggtaaatggc ccgcctggct gaccgcccaa     180
cgacccccgc ccattgacgt caataatgac gtatgttccc atagtaacgc caatagggac     240
tttccattga cgtcaatggg tggagtattt acggtaaact gcccacttgg cagtacatca     300
agtgtatcat atgccaagta cgccccctat tgacgtcaat gacggtaaat ggcccgcctg     360
gcattatgcc cagtacatga ccttatggga ctttcctact ggcagtaca tctacgtatt      420 agtcatcgct attaccatgg tgatgcggtt ttggcagtac atcaatgggc gtggatagcg     480
gtttgactca cggggatttc caagtctcca ccccattgac gtcaatggga gtttgttttg     540

```
gcaccaaaat caacgggact ttccaaaatg tcgtaacaac tccgccccat tgacgcaaat    600
gggcggtagg cgtgtacggt gggaggtcta tataagcaga gctggtttag tgaaccgtca    660
gatccgct                                                             668
```

<210> SEQ ID NO 537
<211> LENGTH: 34
<212> TYPE: PRT
<213> ORGANISM: Artificial Sequence
<220> FEATURE:
<223> OTHER INFORMATION: Synthetic sequence

<400> SEQUENCE: 537

```
Met Glu Thr Asp Thr Leu Leu Leu Trp Val Leu Leu Trp Val Pro
1               5                   10                  15

Gly Ser Thr Gly Thr Ala His Pro Ser Pro Ser Pro Arg Ser Ala Gly
            20                  25                  30

Gln Phe
```

<210> SEQ ID NO 538
<211> LENGTH: 59
<212> TYPE: PRT
<213> ORGANISM: Artificial Sequence
<220> FEATURE:
<223> OTHER INFORMATION: Synthetic sequence

<400> SEQUENCE: 538

```
Met Glu Thr Asp Thr Leu Leu Leu Trp Val Leu Leu Trp Val Pro
1               5                   10                  15

Gly Ser Thr Gly Glu Tyr Arg Met Ser Pro Ser Asn Gln Thr Gly Gly
            20                  25                  30

Gly Gly Ser Gly Gly Gly Gly Ser Gly Gly Gly Gly Ser Thr Ala His
        35                  40                  45

Pro Ser Pro Ser Pro Arg Ser Ala Gly Gln Phe
    50                  55
```

<210> SEQ ID NO 539
<211> LENGTH: 59
<212> TYPE: PRT
<213> ORGANISM: Artificial Sequence
<220> FEATURE:
<223> OTHER INFORMATION: Synthetic sequence

<400> SEQUENCE: 539

```
Met Glu Thr Asp Thr Leu Leu Leu Trp Val Leu Leu Trp Val Pro
1               5                   10                  15

Gly Ser Thr Gly Tyr Tyr Arg Met Ser Pro Ser Asn Gln Thr Gly Gly
            20                  25                  30

Gly Gly Ser Gly Gly Gly Gly Ser Gly Gly Gly Gly Ser Thr Ala His
        35                  40                  45

Pro Ser Pro Ser Pro Arg Ser Ala Gly Gln Phe
    50                  55
```

<210> SEQ ID NO 540
<211> LENGTH: 34
<212> TYPE: PRT
<213> ORGANISM: Artificial Sequence
<220> FEATURE:
<223> OTHER INFORMATION: Synthetic sequence

<400> SEQUENCE: 540

```
Met Glu Thr Asp Thr Leu Leu Leu Trp Val Leu Leu Trp Val Pro
```

```
                1               5                  10                 15
Gly Ser Thr Gly Thr Arg Tyr Pro Ser Pro Ser Pro Lys Pro Glu Gly
                20                 25                 30

Arg Phe

<210> SEQ ID NO 541
<211> LENGTH: 59
<212> TYPE: PRT
<213> ORGANISM: Artificial Sequence
<220> FEATURE:
<223> OTHER INFORMATION: Synthetic sequence

<400> SEQUENCE: 541

Met Glu Thr Asp Thr Leu Leu Leu Trp Val Leu Leu Leu Trp Val Pro
1               5                   10                  15

Gly Ser Thr Gly Trp Asn Arg Leu Ser Pro Ser Asn Gln Thr Gly Gly
                20                  25                  30

Gly Gly Ser Gly Gly Gly Gly Ser Gly Gly Gly Ser Thr Arg Tyr
            35                  40                  45

Pro Ser Pro Ser Pro Lys Pro Glu Gly Arg Phe
    50                  55

<210> SEQ ID NO 542
<211> LENGTH: 107
<212> TYPE: PRT
<213> ORGANISM: Artificial Sequence
<220> FEATURE:
<223> OTHER INFORMATION: Synthetic sequence

<400> SEQUENCE: 542

Met Glu Thr Asp Thr Leu Leu Leu Trp Val Leu Leu Leu Trp Val Pro
1               5                   10                  15

Gly Ser Thr Gly Thr Ala His Pro Ser Pro Ser Pro Arg Ser Ala Gly
                20                  25                  30

Gln Phe Thr Ala His Pro Ser Pro Ser Pro Arg Ser Ala Gly Gln Phe
            35                  40                  45

Thr Ala His Pro Ser Pro Ser Pro Arg Ser Ala Gly Gln Phe Gly Gly
        50                  55                  60

Gly Gly Ser Gly Gly Gly Gly Ser Gly Gly Gly Ser Glu Tyr Arg
65                  70                  75                  80

Met Ser Pro Ser Asn Gln Thr Glu Tyr Arg Met Ser Pro Ser Asn Gln
                85                  90                  95

Thr Glu Tyr Arg Met Ser Pro Ser Asn Gln Thr
            100                 105

<210> SEQ ID NO 543
<211> LENGTH: 107
<212> TYPE: PRT
<213> ORGANISM: Artificial Sequence
<220> FEATURE:
<223> OTHER INFORMATION: Synthetic sequence

<400> SEQUENCE: 543

Met Glu Thr Asp Thr Leu Leu Leu Trp Val Leu Leu Leu Trp Val Pro
1               5                   10                  15

Gly Ser Thr Gly Glu Tyr Arg Met Ser Pro Ser Asn Gln Thr Glu Tyr
                20                  25                  30

Arg Met Ser Pro Ser Asn Gln Thr Glu Tyr Arg Met Ser Pro Ser Asn
            35                  40                  45
```

```
Gln Thr Gly Gly Gly Ser Gly Gly Gly Ser Gly Gly Gly
        50                  55                  60

Ser Thr Ala His Pro Ser Pro Ser Pro Arg Ser Ala Gly Gln Phe Thr
 65                  70                  75                  80

Ala His Pro Ser Pro Ser Pro Arg Ser Ala Gly Gln Phe Thr Ala His
                 85                  90                  95

Pro Ser Pro Ser Pro Arg Ser Ala Gly Gln Phe
                100                 105
```

<210> SEQ ID NO 544
<211> LENGTH: 231
<212> TYPE: PRT
<213> ORGANISM: Homo sapiens

<400> SEQUENCE: 544

```
Ile Ser Ala Met Val Arg Ser Pro Pro Cys Pro Ser Cys Pro Ala Pro
 1               5                  10                  15

Glu Phe Leu Gly Gly Pro Ser Val Phe Leu Phe Pro Pro Lys Pro Lys
                20                  25                  30

Asp Thr Leu Met Ile Ser Arg Thr Pro Glu Val Thr Cys Val Val Val
                35                  40                  45

Asp Val Ser Gln Glu Asp Pro Glu Val Gln Phe Asn Trp Tyr Val Asp
 50                  55                  60

Gly Val Glu Val His Asn Ala Lys Thr Lys Pro Arg Glu Glu Gln Phe
 65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Gly Leu
                100                 105                 110

Pro Ser Ser Ile Glu Lys Thr Ile Ser Lys Ala Lys Gly Gln Pro Arg
                115                 120                 125

Glu Pro Gln Val Tyr Thr Leu Pro Pro Ser Gln Glu Glu Met Thr Lys
                130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Arg Leu Thr Val Asp Lys Ser Arg Trp Gln Glu Gly Asn Val Phe Ser
                195                 200                 205

Cys Ser Val Met His Glu Ala Leu His Asn His Tyr Thr Gln Lys Ser
                210                 215                 220

Leu Ser Leu Ser Pro Gly Lys
225                 230
```

<210> SEQ ID NO 545
<211> LENGTH: 229
<212> TYPE: PRT
<213> ORGANISM: Mus musculus

<400> SEQUENCE: 545

```
Ile Ser Ala Met Val Arg Ser Gly Cys Lys Pro Cys Ile Cys Thr Val
 1               5                  10                  15

Pro Glu Val Ser Ser Val Phe Ile Phe Pro Pro Lys Pro Lys Asp Val
                20                  25                  30
```

```
Leu Thr Ile Thr Leu Thr Pro Lys Val Thr Cys Val Val Asp Ile
         35                  40                  45

Ser Lys Asp Asp Pro Glu Val Gln Phe Ser Trp Phe Val Asp Val
 50                  55                  60

Glu Val His Thr Ala Gln Thr Gln Pro Arg Glu Glu Gln Phe Asn Ser
 65                  70                  75                  80

Thr Phe Arg Ser Val Ser Glu Leu Pro Ile Met His Gln Asp Trp Leu
                 85                  90                  95

Asn Gly Lys Glu Phe Lys Cys Arg Val Asn Ser Ala Ala Phe Pro Ala
             100                 105                 110

Pro Ile Glu Lys Thr Ile Ser Lys Thr Lys Gly Arg Pro Lys Ala Pro
         115                 120                 125

Gln Val Tyr Thr Ile Pro Pro Pro Lys Glu Gln Met Ala Lys Asp Lys
     130                 135                 140

Val Ser Leu Thr Cys Met Ile Thr Asp Phe Phe Pro Glu Asp Ile Thr
145                 150                 155                 160

Val Glu Trp Gln Trp Asn Gly Gln Pro Ala Glu Asn Tyr Lys Asn Thr
                 165                 170                 175

Gln Pro Ile Met Asp Thr Asp Gly Ser Tyr Phe Val Tyr Ser Lys Leu
             180                 185                 190

Asn Val Gln Lys Ser Asn Trp Glu Ala Gly Asn Thr Phe Thr Cys Ser
         195                 200                 205

Val Leu His Glu Gly Leu His Asn His His Thr Glu Lys Ser Leu Ser
     210                 215                 220

His Ser Pro Gly Lys
225

<210> SEQ ID NO 546
<211> LENGTH: 265
<212> TYPE: PRT
<213> ORGANISM: Artificial Sequence
<220> FEATURE:
<223> OTHER INFORMATION: Synthetic sequence

<400> SEQUENCE: 546

Met Tyr Arg Met Gln Leu Leu Ser Cys Ile Ala Leu Ser Leu Ala Leu
 1               5                  10                  15

Val Thr Asn Ser Thr Ala His Pro Ser Pro Ser Pro Arg Ser Ala Gly
             20                  25                  30

Gln Phe Ile Ser Ala Met Val Arg Ser Pro Pro Cys Pro Ser Cys Pro
         35                  40                  45

Ala Pro Glu Phe Leu Gly Gly Pro Ser Val Phe Leu Phe Pro Pro Lys
 50                  55                  60

Pro Lys Asp Thr Leu Met Ile Ser Arg Thr Pro Glu Val Thr Cys Val
 65                  70                  75                  80

Val Val Asp Val Ser Gln Glu Asp Pro Glu Val Gln Phe Asn Trp Tyr
                 85                  90                  95

Val Asp Gly Val Glu Val His Asn Ala Lys Thr Lys Pro Arg Glu Glu
             100                 105                 110

Gln Phe Asn Ser Thr Tyr Arg Val Val Ser Val Leu Thr Val Leu His
         115                 120                 125

Gln Asp Trp Leu Asn Gly Lys Glu Tyr Lys Cys Lys Val Ser Asn Lys
     130                 135                 140

Gly Leu Pro Ser Ser Ile Glu Lys Thr Ile Ser Lys Ala Lys Gly Gln
145                 150                 155                 160
```

```
Pro Arg Glu Pro Gln Val Tyr Thr Leu Pro Pro Ser Gln Glu Glu Met
            165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
            195                 200                 205

Tyr Lys Thr Thr Pro Pro Val Leu Asp Ser Asp Gly Ser Phe Phe Leu
            210                 215                 220

Tyr Ser Arg Leu Thr Val Asp Lys Ser Arg Trp Gln Glu Gly Asn Val
225                 230                 235                 240

Phe Ser Cys Ser Val Met His Glu Ala Leu His Asn His Tyr Thr Gln
            245                 250                 255

Lys Ser Leu Ser Leu Ser Pro Gly Lys
            260                 265

<210> SEQ ID NO 547
<211> LENGTH: 290
<212> TYPE: PRT
<213> ORGANISM: Artificial Sequence
<220> FEATURE:
<223> OTHER INFORMATION: Synthetic sequence

<400> SEQUENCE: 547

Met Tyr Arg Met Gln Leu Leu Ser Cys Ile Ala Leu Ser Leu Ala Leu
1               5                   10                  15

Val Thr Asn Ser Glu Tyr Arg Met Ser Pro Ser Asn Gln Thr Gly Gly
            20                  25                  30

Gly Gly Ser Gly Gly Gly Gly Ser Gly Gly Gly Gly Ser Thr Ala His
            35                  40                  45

Pro Ser Pro Ser Pro Arg Ser Ala Gly Gln Phe Ile Ser Ala Met Val
            50                  55                  60

Arg Ser Pro Pro Cys Pro Ser Cys Pro Ala Pro Glu Phe Leu Gly Gly
65                  70                  75                  80

Pro Ser Val Phe Leu Phe Pro Pro Lys Pro Lys Asp Thr Leu Met Ile
            85                  90                  95

Ser Arg Thr Pro Glu Val Thr Cys Val Val Asp Val Ser Gln Glu
            100                 105                 110

Asp Pro Glu Val Gln Phe Asn Trp Tyr Val Asp Gly Val Glu Val His
            115                 120                 125

Asn Ala Lys Thr Lys Pro Arg Glu Glu Gln Phe Asn Ser Thr Tyr Arg
130                 135                 140

Val Val Ser Val Leu Thr Val Leu His Gln Asp Trp Leu Asn Gly Lys
145                 150                 155                 160

Glu Tyr Lys Cys Lys Val Ser Asn Lys Gly Leu Pro Ser Ser Ile Glu
            165                 170                 175

Lys Thr Ile Ser Lys Ala Lys Gly Gln Pro Arg Glu Pro Gln Val Tyr
            180                 185                 190

Thr Leu Pro Pro Ser Gln Glu Glu Met Thr Lys Asn Gln Val Ser Leu
            195                 200                 205

Thr Cys Leu Val Lys Gly Phe Tyr Pro Ser Asp Ile Ala Val Glu Trp
            210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Arg Leu Thr Val Asp
            245                 250                 255
```

Lys Ser Arg Trp Gln Glu Gly Asn Val Phe Ser Cys Ser Val Met His
        260                 265                 270

Glu Ala Leu His Asn His Tyr Thr Gln Lys Ser Leu Ser Leu Ser Pro
        275                 280                 285

Gly Lys
    290

<210> SEQ ID NO 548
<211> LENGTH: 290
<212> TYPE: PRT
<213> ORGANISM: Artificial Sequence
<220> FEATURE:
<223> OTHER INFORMATION: Synthetic sequence

<400> SEQUENCE: 548

Met Tyr Arg Met Gln Leu Leu Ser Cys Ile Ala Leu Ser Leu Ala Leu
1               5                   10                  15

Val Thr Asn Ser Tyr Tyr Arg Met Ser Pro Ser Asn Gln Thr Gly Gly
            20                  25                  30

Gly Gly Ser Gly Gly Gly Gly Ser Gly Gly Gly Gly Ser Thr Ala His
        35                  40                  45

Pro Ser Pro Ser Pro Arg Ser Ala Gly Gln Phe Ile Ser Ala Met Val
    50                  55                  60

Arg Ser Pro Pro Cys Pro Ser Cys Pro Ala Pro Glu Phe Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Asp Val Ser Gln Glu
            100                 105                 110

Asp Pro Glu Val Gln Phe Asn Trp Tyr Val Asp Gly Val Glu Val His
            115                 120                 125

Asn Ala Lys Thr Lys Pro Arg Glu Glu Gln Phe Asn Ser Thr Tyr Arg
    130                 135                 140

Val Val Ser Val Leu Thr Val Leu His Gln Asp Trp Leu Asn Gly Lys
145                 150                 155                 160

Glu Tyr Lys Cys Lys Val Ser Asn Lys Gly Leu Pro Ser Ser Ile Glu
                165                 170                 175

Lys Thr Ile Ser Lys Ala Lys Gly Gln Pro Arg Glu Pro Gln Val Tyr
            180                 185                 190

Thr Leu Pro Pro Ser Gln Glu Glu Met Thr Lys Asn Gln Val Ser Leu
        195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Arg Leu Thr Val Asp
                245                 250                 255

Lys Ser Arg Trp Gln Glu Gly Asn Val Phe Ser Cys Ser Val Met His
            260                 265                 270

Glu Ala Leu His Asn His Tyr Thr Gln Lys Ser Leu Ser Leu Ser Pro
        275                 280                 285

Gly Lys
    290

<210> SEQ ID NO 549
<211> LENGTH: 263

```
<212> TYPE: PRT
<213> ORGANISM: Artificial Sequence
<220> FEATURE:
<223> OTHER INFORMATION: Synthetic sequence

<400> SEQUENCE: 549

Met Tyr Arg Met Gln Leu Leu Ser Cys Ile Ala Leu Ser Leu Ala Leu
1               5                   10                  15

Val Thr Asn Ser Thr Arg Tyr Pro Ser Pro Ser Pro Lys Pro Glu Gly
            20                  25                  30

Arg Phe Ile Ser Ala Met Val Arg Ser Gly Cys Lys Pro Cys Ile Cys
        35                  40                  45

Thr Val Pro Glu Val Ser Val Phe Ile Phe Pro Pro Lys Pro Lys
    50                  55                  60

Asp Val Leu Thr Ile Thr Leu Thr Pro Lys Val Thr Cys Val Val Val
65                  70                  75                  80

Asp Ile Ser Lys Asp Asp Pro Glu Val Gln Phe Ser Trp Phe Val Asp
                85                  90                  95

Asp Val Glu Val His Thr Ala Gln Thr Gln Pro Arg Glu Glu Gln Phe
            100                 105                 110

Asn Ser Thr Phe Arg Ser Val Ser Glu Leu Pro Ile Met His Gln Asp
        115                 120                 125

Trp Leu Asn Gly Lys Glu Phe Lys Cys Arg Val Asn Ser Ala Ala Phe
130                 135                 140

Pro Ala Pro Ile Glu Lys Thr Ile Ser Lys Thr Lys Gly Arg Pro Lys
145                 150                 155                 160

Ala Pro Gln Val Tyr Thr Ile Pro Pro Lys Glu Gln Met Ala Lys
                165                 170                 175

Asp Lys Val Ser Leu Thr Cys Met Ile Thr Asp Phe Phe Pro Glu Asp
            180                 185                 190

Ile Thr Val Glu Trp Gln Trp Asn Gly Gln Pro Ala Glu Asn Tyr Lys
        195                 200                 205

Asn Thr Gln Pro Ile Met Asp Thr Asp Gly Ser Tyr Phe Val Tyr Ser
    210                 215                 220

Lys Leu Asn Val Gln Lys Ser Asn Trp Glu Ala Gly Asn Thr Phe Thr
225                 230                 235                 240

Cys Ser Val Leu His Glu Gly Leu His Asn His His Thr Glu Lys Ser
                245                 250                 255

Leu Ser His Ser Pro Gly Lys
                260

<210> SEQ ID NO 550
<211> LENGTH: 288
<212> TYPE: PRT
<213> ORGANISM: Artificial Sequence
<220> FEATURE:
<223> OTHER INFORMATION: Synthetic sequence

<400> SEQUENCE: 550

Met Tyr Arg Met Gln Leu Leu Ser Cys Ile Ala Leu Ser Leu Ala Leu
1               5                   10                  15

Val Thr Asn Ser Trp Asn Arg Leu Ser Pro Ser Asn Gln Thr Gly Gly
            20                  25                  30

Gly Gly Ser Gly Gly Gly Ser Gly Gly Gly Ser Thr Arg Tyr
        35                  40                  45

Pro Ser Pro Ser Pro Lys Pro Glu Gly Arg Phe Ile Ser Ala Met Val
    50                  55                  60
```

```
Arg Ser Gly Cys Lys Pro Cys Ile Cys Thr Val Pro Glu Val Ser Ser
 65                  70                  75                  80

Val Phe Ile Phe Pro Lys Pro Lys Asp Val Leu Thr Ile Thr Leu
             85                  90                  95

Thr Pro Lys Val Thr Cys Val Val Asp Ile Ser Lys Asp Asp Pro
            100                 105                 110

Glu Val Gln Phe Ser Trp Phe Val Asp Asp Val Glu Val His Thr Ala
            115                 120                 125

Gln Thr Gln Pro Arg Glu Glu Gln Phe Asn Ser Thr Phe Arg Ser Val
            130                 135                 140

Ser Glu Leu Pro Ile Met His Gln Asp Trp Leu Asn Gly Lys Glu Phe
145                 150                 155                 160

Lys Cys Arg Val Asn Ser Ala Ala Phe Pro Ala Pro Ile Glu Lys Thr
                165                 170                 175

Ile Ser Lys Thr Lys Gly Arg Pro Lys Ala Pro Gln Val Tyr Thr Ile
            180                 185                 190

Pro Pro Pro Lys Glu Gln Met Ala Lys Asp Lys Val Ser Leu Thr Cys
            195                 200                 205

Met Ile Thr Asp Phe Phe Pro Glu Asp Ile Thr Val Glu Trp Gln Trp
210                 215                 220

Asn Gly Gln Pro Ala Glu Asn Tyr Lys Asn Thr Gln Pro Ile Met Asp
225                 230                 235                 240

Thr Asp Gly Ser Tyr Phe Val Tyr Ser Lys Leu Asn Val Gln Lys Ser
                245                 250                 255

Asn Trp Glu Ala Gly Asn Thr Phe Thr Cys Ser Val Leu His Glu Gly
            260                 265                 270

Leu His Asn His His Thr Glu Lys Ser Leu Ser His Ser Pro Gly Lys
            275                 280                 285

<210> SEQ ID NO 551
<211> LENGTH: 1335
<212> TYPE: DNA
<213> ORGANISM: Homo sapiens

<400> SEQUENCE: 551
gagtaattca tacaaaagga ctcgcccctg ccttggggaa tcccagggac cgtcgttaaa      60
ctcccactaa cgtagaaccc agagatcgct gcgttcccgc cccctcaccc gcccgctctc     120
gtcatcactg aggtggagaa gagcatgcgt gaggctccgg tgcccgtcag tgggcagagc     180
gcacatcgcc cacagtcccc gagaagttgg ggggaggggt cggcaattga accggtgcct     240
agagaaggtg gcgcggggta aactgggaaa gtgatgtcgt gtactggctc cgccttttc     300
ccgagggtgg gggagaaccg tatataagtg cagtagtcgc cgtgaacgtt cttttcgca     360
acgggtttgc cgccagaaca caggtaagtg ccgtgtgtgg ttcccgcggg cctggcctct     420
ttacgggtta tggcccttgc gtgccttgaa ttacttccac gccctggct gcagtacgtg     480
attcttgatc ccgagcttcg ggttggaagt gggtgggaga gttcgaggcc ttgcgcttaa     540
ggagccccctt cgcctcgtgc ttgagttgag gcctggcttg ggcgctgggg ccgccgcgtg    600
cgaatctggt ggcaccttcg cgcctgtctc gctgctttcg ataagtctct agccatttaa    660
aattttgat gacctgctgc gacgcttttt ttctggcaag atagtcttgt aaatgcgggc     720
caagatctgc acactggtat ttcggttttt gggccgcgg gcggcgacgg ggcccgtgcg     780
tcccagcgca catgttcggc gaggcggggc ctgcgagcgc ggccaccgag aatcggacgg     840
```

```
gggtagtctc aagctggccg gcctgctctg gtgcctggcc tcgcgccgcc gtgtatcgcc      900
ccgccctggg cggcaaggct ggcccggtcg gcaccagttg cgtgagcgga agatggccg       960 cttcccggcc ctgctgcagg gagctcaaaa tggaggacgc ggcgctcggg agagcgggcg     1020
ggtgagtcac ccacacaaag gaaaagggcc tttccgtcct cagccgtcgc ttcatgtgac     1080
tccacggagt accgggcgcc gtccaggcac ctcgattagt tctcgagctt ttggagtacg     1140
tcgtctttag gttgggggga ggggttttat gcgatggagt ttccccacac tgagtgggtg     1200
gagactgaag ttaggccagc ttggcacttg atgtaattct ccttggaatt tgcccttttt     1260
gagtttggat cttggttcat tctcaagcct cagacagtgg ttcaaagttt ttttcttcca     1320
tttcaggtgt cgtga                                                      1335
```

<210> SEQ ID NO 552
<211> LENGTH: 601
<212> TYPE: DNA
<213> ORGANISM: Artificial Sequence
<220> FEATURE:
<223> OTHER INFORMATION: Synthetic sequence

<400> SEQUENCE: 552

```
cctctccccc ccccccctct ccctcccccc ccctaacgt tactggccga agccgcttgg       60
aataaggccg gtgtgcgttt gtctatatgt tatttccac catattgccg tcttttggca      120
atgtgagggc ccggaaacct ggccctgtct tcttgacgag cattcctagg ggtctttccc      180
ctctcgccaa aggaatgcaa ggtctgttga atgtcgtgaa ggaagcagtt cctctggaag      240
cttcttgaag acaaacaacg tctgtagcga cccctttgcag gcagcggaac cccccacctg     300
gcgacaggtg cctctgcggc caaaagccac gtgtataaga tacacctgca aaggcggcac      360
aaccccagtg ccacgttgtg agttggatag ttgtggaaag agtcaaatgg ctctcctcaa      420
gcgtattcaa caaggggctg aaggatgccc agaaggtacc ccattgtatg ggatctgatc      480
tggggcctcg gtgcacatgc tttacatgtg tttagtcgag gttaaaaaaa cgtcctaggcc     540 ccccgaacca cggggacgtg gttttccttt gaaaaacacg atgataagct tgccacaacc     600
c                                                                    601
```

<210> SEQ ID NO 553
<211> LENGTH: 536
<212> TYPE: DNA
<213> ORGANISM: Human cytomegalovirus

<400> SEQUENCE: 553

```
ccgcgttaca taacttacgg taaatggccc gcctggctga ccgcccaacg accccgccc       60 attgacgtca ataatgacgt atgttcccat agtaacgcca atagggactt tccattgacg     120
tcaatgggtg gagtatttac ggtaaactgc ccacttggca gtacatcaag tgtatcatat     180
gccaagtacg ccccctattg acgtcaatga cggtaaatgg cccgcctggc attatgccca     240
gtacatgacc ttatgggact ttcctacttg gcagtacatc tacgtattag tcatcgctat     300
taccatggtg atgcggtttt ggcagtacat caatgggcgt ggatagcggt ttgactcacg     360
gggatttcca gtctccacc ccattgacgt caatgggagt ttgttttggc accaaaatca      420
acgggacttt ccaaaatgtc gtaacaactc cgccccattg acgcaaatgg gcggtaggcg     480
tgtacggtgg gaggtctata taagcagagc tggtttagtg aaccgtcaga tccgct         536
```

<210> SEQ ID NO 554
<211> LENGTH: 22

<212> TYPE: PRT
<213> ORGANISM: Artificial Sequence
<220> FEATURE:
<223> OTHER INFORMATION: Synthetic sequence

<400> SEQUENCE: 554

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 555
<211> LENGTH: 1433
<212> TYPE: DNA
<213> ORGANISM: Artificial Sequence
<220> FEATURE:
<223> OTHER INFORMATION: Synthetic sequence

<400> SEQUENCE: 555

```
atgtcgggcg tcgggggaga gggagttccc tctgcgcttg cgattctagc ctcgtggggc      60
tggacgttcg acacgccaaa ccacgagtcg gggatatcgc cagatacgac tcccgcagat     120
tccattcggg gtgccgctgt ggcctcacct gaccaacctt tacacggggg cccggaacgg     180
gaggccacag cgccgtcttt ctccccaacg cgcgcggatg acggcccgcc ctgtaccgac     240
gggccctacg tgacgtttga taccctgttt atggtgtcgt cgatcgacga attagggcgt     300
cgccagctca cggacaccat ccgcaaggac ctgcggttgt cgctggccaa gtttagcatt     360
gcgtgcacca agacctcctc gttttcggga acgccccgc gccaccacag acgcggggcg      420
ttccagcgcg gcacgcgggc gccgcgcagc aacaaaagcc tccagatgtt tgtgttgtgc     480
aaacgcgccc acgccgctcg agtgcgagag cagcttcggg tcgttattca gtcccgcaag     540
ccgcgcaagt attacacgcg atcttcggac gggcggctct gccccgccgt ccccgtgttc     600
gtccacgagt tcgtctcgtc cgagccaatg cgcctccacc gagataacgt catgctggcc     660
tcgggggccg agtaaccgcc cccccccat gccaccctca ctgcccgtcg cgcgtgtttg      720
atgttaataa ataacacata aatttggctg gttgtttgtt gtctttaatg gaccgcccgc     780
aagggggggg gggcatttca gtgtcgggtg acgagcgcga tccggccggg atcctaggac     840
cccaaaagtt tgtctgcgta ttccagggcg gggctcagtt gaatctcccg cagcacctct     900
accagcaggt ccgcggtggg ctggagaaac tcggccgtcc cggggcaggc ggttgtcggg     960
ggtggaggcg cggcgccac ccccgtgtgcc gcgcctggcg tctcctctgg gggcgacccg     1020
taaatggttg cagtgatgta aatggtgtcc gcggtccaga ccacggtcaa atgccggcc     1080
gtggcgctcc gggcgctttc gccgcgcgag gagctgaccc aggagtcgaa cggatacgcg     1140
tacatatggg cgtccccacc gcgttcgagc ttctggttgc tgtcccggcc tataaagcgg     1200
taggcacaaa attcggcgcg acagtcgata tcaccaaca gcccaatggg ggtgtgctgg     1260
ataacaacgc ctccgcgcgg caggcggtcc tggcgctccc ggccccgtac catgatcgcg     1320
cgggtgccgt actcaaaaac atgcaccacc tgcgcggcgt cgggcagtgc gctggtcagc     1380
gaggccctgg cgtggcatag gctatacgcg atggtcgtct gtggattgga cat            1433
```

<210> SEQ ID NO 556
<211> LENGTH: 1533
<212> TYPE: DNA
<213> ORGANISM: Artificial Sequence
<220> FEATURE:
<223> OTHER INFORMATION: Synthetic sequence

<400> SEQUENCE: 556

```
ggccctcaat ccctaataca tttcagtgat ggggtagtcc agtgagccac atttgttgcc      60
ttgttcagca cgcactctgt cagggagctg gtgccggcct tccgcttgaa gccagagttg     120
cagatgtatc tctcccggga atacaggctg taagacttca cccagatgtc tgcgtgctcc     180
acgctcattg gaggtgggca ggtgatgccc cttgtagcgg ggggtctcag cagcagcagc     240
agcagcaggg caggcagtcc cagggtccga catcctctag cgcggcgtgg agccatggtg     300
gcgaattctc caggcgatct gacggttcac taaacgagct ctgcttatat aggcctccca     360
ccgtacacgc cacctcgaca tactcgagta gttattaata gtaatcaatt acggggtcat     420
tagttcatag cccatatatg gagttccgcg ttacataact tacggtaaat ggcccgcctg     480
gctgaccgcc caacgacccc cgcccattga cgtcaataat gacgtatgtt cccatagtaa     540
cgccaatagg gactttccat tgacgtcaat gggtggagta tttacggtaa actgcccact     600
tggcagtaca tcaagtgtat catatgccaa gtacgccccc tattgacgtc aatgacggta     660
aatggcccgc ctggcattat gcccagtaca tgaccttatg gactttcct acttggcagt     720
acatctacgt attagtcatc gctattacca tggtgatgcg gttttggcag tacatcaatg     780
ggcgtggata gcggtttgac tcacggggat ttccaagtct ccaccccatt gacgtcaatg     840
ggagtttgtt ttggcaccaa aatcaacggg actttccaaa atgtcgtaac aactccgccc     900
cattgacgca aatgggcggt aggcgtgtac ggtgggaggt ctatataagc agagctggtt     960
tagtgaaccg tcagatccgc tagggatcct ctagtcagct gacgcgtgct agcgcggccg    1020
catcgataag cttgccacca tgcggatttc caagccccat ctgcgctcca tttccatcca    1080
gtgttacctg tgcctgctgc tgaatagcca ttttctgacc gaagccggca tccacgtgtt    1140
catcctgggc tgcttttccg ccggcctgcc aaagaccgag gcaaactggg tgaatgtgat    1200
ctctgacctg aagaagatcg aggatctgat ccagagcatg cacatcgacg ccaccctgta    1260
cacagagtcc gatgtgcacc cttcttgcaa ggtgacagcc atgaagtgtt tcctgctgga    1320
gctgcaggtc atctctctgg agagcggcga cgcctctatc cacgataccg tggagaacct    1380
gatcatcctg gccaacaata gcctgagctc aacggcaat gtgacagagt ccggctgcaa    1440
ggagtgtgag gagctggagg agaagaatat caaagagttc ctgcagagtt tcgtccatat    1500
cgtccagatg tttatcaata cttcctaagt cga                                 1533
```

<210> SEQ ID NO 557
<211> LENGTH: 2304
<212> TYPE: DNA
<213> ORGANISM: Artificial Sequence
<220> FEATURE:
<223> OTHER INFORMATION: Synthetic sequence

<400> SEQUENCE: 557

```
ggcccttaca gatggtgact acagttttcc aggtcctcgt ctcttgatga agttccccag      60
gtgacgggca gggcctccat ggcctccatc tccacagagg ccagagggg ggtctgtctg     120
gacttcagat aacaggccag cagggacacg gcgctcaggc cgcacagcag cactgtagag     180
gtggagatgg ccactgtggt gtcggagtgg ccctgtgggt acacgcctgg aggctggtgg     240
ctggcagatg ctgtcagctc ccaattcttg gctgtggtct gagaaggggt gccgtggcta     300
gactcgtggg agctgatctc tgtggtgcct gtggatgggc tcttagaagg catcagctgg     360
gagccaggca cgattgctgc tgtggttgct gcggtattgt tagaggatgg gctagatgct     420
gcaggctcct tgccggatgg gctcagagac tctggctgtg gtgtcacgcc ggctgtggtc     480
```

```
acggtgctgg gtggtgcggg ccgctggtgc accagggcgg gatcccggat gcacttcaga    540
gagggtgtgg tccagtgggc cacattggtg gccttgttca gcacgcactc tgtcagggag    600
ctggtgccgg ccttcctctt aaagccgctg ttgcagatgt atctctcccg agaatacagg    660
gagtagctct tcacccagat gtcggcgtgc tccacggaca taggggtgg acatgtgatg     720 cctgcctgct gtctgctggt ccggtggtgg tgacactggg ggcaattctc cattgtcctc    780
agcctcacgc atgcctcgtg ggtctgcacc tcgtggttga aagactcgga gattctgctc    840
cggcctgcca gcacggccag gcgatccctt gcgtcgcgtg ttgcaggggg cctcagcagc    900
agcagtaata acagggcggg caggcccagg gtgcgacagc ccctggctct ccttggtgcc    960
attgctgctg ctccgcagga cacggcgggt gagccgggtc ttgcgctgcc cagtccgggt    1020
ggtggagggg atctctgttc ggggacctgt cttcctgcca gtctcatggt ggcgaattct    1080
ccaggcgatc tgacggttca ctaaacgagc tctgcttata taggcctccc accgtacacg    1140
ccacctcgac atactcgagt agttattaat agtaatcaat tacggggtca ttagttcata    1200
gcccatatat ggagttccgc gttacataac ttacggtaaa tggcccgcct ggctgaccgc    1260
ccaacgaccc ccgcccattg acgtcaataa tgacgtatgt tcccatagta acgccaatag    1320
ggactttcca ttgacgtcaa tgggtggagt atttacggta aactgcccac ttggcagtac    1380
atcaagtgta tcatatgcca agtacgcccc ctattgacgt caatgacggt aaatggcccg    1440
cctggcatta tgcccagtac atgaccttat gggactttcc tacttggcag tacatctacg    1500
tattagtcat cgctattacc atggtgatgc ggttttggca gtacatcaat gggcgtggat    1560
agcggtttga ctcacgggga tttccaagtc tccacccat tgacgtcaat gggagtttgt     1620
tttggcacca aaatcaacgg gactttccaa aatgtcgtaa caactccgcc ccattgacgc    1680
aaatgggcgg taggcgtgta cggtgggagg tctatataag cagagctggt ttagtgaacc    1740
gtcagatccg ctagggatcc tctagtcagc tgacgcgtgc tagcgcggcc gcatcgataa    1800
gcttgccacc atgcggattt ccaagcccca tctgcgctcc atttccatcc agtgttacct    1860
gtgcctgctg ctgaatagcc attttctgac cgaagccggc atccacgtgt tcatcctggg    1920
ctgcttttcc gccggcctgc caaagaccga ggcaaactgg gtgaatgtga tctctgacct    1980
gaagaagatc gaggatctga tccagagcat gcacatcgac gccaccctgt acacagagtc    2040
cgatgtgcac ccttccttgca aggtgacagc catgaagtgt tcctgctgg agctgcaggt    2100 catctctctg gagagcggcg acgcctctat ccacgatacc gtggagaacc tgatcatcct    2160
ggccaacaat agcctgagct ccaacggcaa tgtgacagag tccggctgca aggagtgtga    2220
ggagctggag gagaagaata tcaaagagtt cctgcagagt ttcgtccata tcgtccagat    2280
gtttatcaat acttcctaag tcga                                           2304
```

<210> SEQ ID NO 558
<211> LENGTH: 1842
<212> TYPE: DNA
<213> ORGANISM: Artificial Sequence
<220> FEATURE:
<223> OTHER INFORMATION: Synthetic sequence

<400> SEQUENCE: 558

```
ggcccttatt tttccagtgc ggacacctct tttttccaggg ctgacacctc cttttccagg    60
gctgagactt cttttttccag ggcagacacc tccttctcca gggcagacac ctcggagccg    120
ccgccgccgg atcctcctcc tccgcttcct cctcctccat cccggataca cttcagggag    180
```

| | |
|---|---|
| ggtgtggtcc agtgggccac atttgtggcc ttgttcagca cgcactctgt cagggagctg | 240 |
| gtgccggcct tcctcttgaa gccgctgttg cagatgtatc tctcccgaga atacaggctg | 300 |
| taagacttca cccagatgtc tgcgtgctcc acgctcattg gaggtgggca ggtgatgccc | 360 |
| cttgtagcag gtggtctcag cagcagcagc agcagcaggg caggcagtcc cagtgtgcga | 420 |
| catcctcggg ctcttctagg ggccatggtg gcgaattctc caggcgatct gacggttcac | 480 |
| taaacgagct ctgcttatat aggcctccca ccgtacacgc cacctcgaca tactcgagta | 540 |
| gttattaata gtaatcaatt acgggtcat tagttcatag cccatatatg gagttccgcg | 600 |
| ttacataact tacggtaaat ggcccgcctg gctgaccgcc caacgacccc cgcccattga | 660 |
| cgtcaataat gacgtatgtt cccatagtaa cgccaatagg gactttccat tgacgtcaat | 720 |
| gggtggagta tttacggtaa actgcccact tggcagtaca tcaagtgtat catatgccaa | 780 |
| gtacgccccc tattgacgtc aatgacggta atggcccgc ctggcattat gcccagtaca | 840 |
| tgaccttatg ggactttcct acttggcagt acatctacgt attagtcatc gctattacca | 900 |
| tggtgatgcg gttttggcag tacatcaatg ggcgtggata gcggtttgac tcacggggat | 960 |
| ttccaagtct ccaccccatt gacgtcaatg ggagtttgtt ttggcaccaa aatcaacggg | 1020 |
| actttccaaa atgtcgtaac aactccgccc cattgacgca aatgggcggt aggcgtgtac | 1080 |
| ggtgggaggt ctatataagc agagctggtt tagtgaaccg tcagatccgc tagggatcct | 1140 |
| ctagtcagct gacgcgtgct agcgcggccg catcgataag cttgccacca tgcggatttc | 1200 |
| caaacctcac ctgcgatcta tctccatcca gtgctatctg tgcctgctgc tgaactctca | 1260 |
| tttcctgacc gaagccggca tccacgtgtt catcctgggc tgctttagcg ccggcctgcc | 1320 |
| aaagaccgag gcaaactggg tgaatgtgat ctctgacctg aagaagatcg aggatctgat | 1380 |
| ccagagcatg cacatcgacg ccaccctgta cacagagtcc gatgtgcacc cttcttgcaa | 1440 |
| ggtgacagcc atgaagtgtt tcctgctgga gctgcaggtc atctctctgg agagcggcga | 1500 |
| cgcctccatc cacgataccg tggagaacct gatcatcctg ccaacaata gcctgagctc | 1560 |
| caacggcaat gtgacagagt ccggctgcaa ggagtgtgag gagctggagg agaagaacat | 1620 |
| caaggagttc ctgcagtctt ttgtgcacat cgtgcagatg tttatcaata ccagcggagg | 1680 |
| aggaggatcc ggcggaggag gctctggcgg cggcggcagc tgtgcggca aggtgtccgc | 1740 |
| cctgaaggag aaggtgtctg ccctgaagga aaaagtgtcc gctctgaagg aaaaggtgtc | 1800 |
| cgcactgaaa gaaaaggtct ccgccctgaa ggaataagtc ga | 1842 |

<210> SEQ ID NO 559
<211> LENGTH: 2613
<212> TYPE: DNA
<213> ORGANISM: Artificial Sequence
<220> FEATURE:
<223> OTHER INFORMATION: Synthetic sequence

<400> SEQUENCE: 559

| | |
|---|---|
| ggcccttatt tttccagtgc ggacacctct ttttccagtg ctgacacctc cttctccagg | 60 |
| gctgacactt cttttttccag ggcgctcacc tcttttttcca gggcagacac ctcggagccg | 120 |
| ccgccgccgg agcctcctcc tccgcttcct cctcctccca ggtggtggga acaattctcc | 180 |
| agatcctcgt cgcgagagga tgtgccccag gtcactggca gggcctccat tgcctccatc | 240 |
| tccacagatg ccagaggtgg ggtctgcctg gacttcagat aacaggccag caggctcacg | 300 |
| gcagacaggc cgcacagcag cactgtggag gtgctgatgg ccactgtggt gtcggagtgg | 360 |
| ccctgtgggt acacgcctgg aggctggtga gaggcggatg ctgtcagctc ccagttcttg | 420 |

```
gctgtggtct gagaaggggt gccgtggcta gactcgtggg agctgatctc tgtggtgccg    480
gtgcttggag acttggaagg catcagctgg gagccaggca cgattgctgc tgtggttgct    540
gcggtattgt tagaggatgg gctagatgct gcaggctcct tgccgcttgg agacagggac    600
tctggctgtg gtgtcactcc tgctgtggtc acggtgctgg gtggtgcggg ccgctggtgc    660
accagggcgg gatcccggat gcacttcaga gagggtgtgg tccagtgggc cacattggtg    720
gccttgttca gcacgcactc tgtcaggag ctggtgccgg ccttccgctt aaagccgctg    780
ttgcagatgt atctctcccg agaatacagg ctgtaagact tcacccagat gtcggcgtgc    840
tccacggaca tagggggtgg acatgtgatg cctgcctgct gtctgctggt ccggtggtgg    900
tgacactggg ggcaattctc cattgtcctc agcctcacgc atgcctcgtg gtctgcacc    960 tcgtggttga aggactcgct gattctgctc cggcctgcca gcacggccag gcgatccctt   1020
gcgtcgcgtg ttgcaggggg cctcagcagc agcagtaata acagggcggg caggcccagg   1080
gtgcgacagc ccctggctct ccttggtgcc attgctgctg ctccgcagga cacagcggga   1140
ctgccgggtc ttgcactgcc cagcccagga ggaggagggg atctctgctc ggggacctgc   1200
cttccagcca gccgcatggt ggcgaattct ccaggcgatc tgacggttca ctaaacgagc   1260
tctgcttata taggcctccc accgtacacg ccacctcgac atactcgagt agttattaat   1320
agtaatcaat tacggggtca ttagttcata gcccatatat ggagttccgc gttacataac   1380
ttacggtaaa tggcccgcct ggctgaccgc ccaacgaccc ccgcccattg acgtcaataa   1440
tgacgtatgt tcccatagta acgccaatag ggactttcca ttgacgtcaa tgggtggagt   1500
atttacggta aactgcccac ttggcagtac atcaagtgta tcatatgcca agtacgcccc   1560
ctattgacgt caatgacggt aaatggcccg cctggcatta tgcccagtac atgaccttat   1620
gggactttcc tacttggcag tacatctacg tattagtcat cgctattacc atggtgatgc   1680
ggttttggca gtacatcaat gggcgtggat agcggtttga ctcacgggga tttccaagtc   1740 tccacccat tgacgtcaat gggagtttgt tttggcacca aaatcaacgg gactttccaa   1800
aatgtcgtaa caactccgcc ccattgacgc aaatgggcgg taggcgtgta cggtgggagg   1860
tctatataag cagagctggt ttagtgaacc gtcagatccg ctagggatcc tctagtcagc   1920
tgacgcgtgc tagcgcggcc gcatcgataa gcttgccacc atgcggattt ccaaacctca   1980
cctgcgatct atctccatcc agtgctatct gtgcctgctg ctgaactctc atttcctgac   2040
cgaagccggc atccacgtgt tcatcctggg ctgctttagc gccggcctgc aaagaccga   2100 ggcaaactgg gtgaatgtga tctctgacct gaagaagatc gaggatctga tccagagcat   2160
gcacatcgac gccaccctgt acacagagtc cgatgtgcac ccttcttgca aggtgacagc   2220
catgaagtgt ttcctgctgg agctgcaggt catctctctg gagagcggcg acgcctccat   2280
ccacgatacc gtggagaacc tgatcatcct ggccaacaat agcctgagct ccaacggcaa   2340
tgtgacagag tccggctgca aggagtgtga ggagctggag gagaagaaca tcaaggagtt   2400
cctgcagtct tttgtgcaca tcgtgcagat gtttatcaat accagcggag gaggaggatc   2460
cggcggagga ggctctggcg gcggcggcag ctgtggcggc aaggtgtccg ccctgaagga   2520
gaaggtgtct gccctgaagg aaaaagtgtc cgctctgaag gaaaaggtgt ccgcactgaa   2580
agaaaaggtc tccgccctga aggaataagt cga                                 2613

<210> SEQ ID NO 560
<211> LENGTH: 3135
<212> TYPE: DNA
```

<213> ORGANISM: Artificial Sequence
<220> FEATURE:
<223> OTHER INFORMATION: Synthetic sequence

<400> SEQUENCE: 560

| | | | | | |
|---|---|---|---|---|---|
| gagtaattca | tacaaaagga | ctcgcccctg | ccttggggaa | tcccagggac | cgtcgttaaa | 60 |
| ctcccactaa | cgtagaaccc | agagatcgct | gcgttcccgc | ccctcaccc | gcccgctctc | 120 |
| gtcatcactg | aggtggagaa | gagcatgcgt | gaggctccgg | tgcccgtcag | tgggcagagc | 180 |
| gcacatcgcc | cacagtcccc | gagaagttgg | ggggaggggt | cggcaattga | accggtgcct | 240 |
| agagaaggtg | gcgcggggta | aactgggaaa | gtgatgtcgt | gtactggctc | cgccttttc | 300 |
| ccgagggtgg | gggagaaccg | tatataagtg | cagtagtcgc | cgtgaacgtt | cttttcgca | 360 |
| acgggtttgc | cgccagaaca | caggtaagtg | ccgtgtgtgg | ttcccgcggg | cctggcctct | 420 |
| ttacgggtta | tggcccttgc | gtgccttgaa | ttacttccac | gccctggct | gcagtacgtg | 480 |
| attcttgatc | ccgagcttcg | ggttggaagt | gggtgggaga | gttcgaggcc | ttgcgcttaa | 540 |
| ggagcccctt | cgcctcgtgc | ttgagttgag | gcctggcttg | ggcgctgggg | ccgccgcgtg | 600 |
| cgaatctggt | ggcaccttcg | cgcctgtctc | gctgctttcg | ataagtctct | agccatttaa | 660 |
| aattttgat | gacctgctgc | gacgcttttt | ttctggcaag | atagtcttgt | aaatgcgggc | 720 |
| caagatctgc | acactggtat | ttcggttttt | ggggccgcgg | gcggcgacgg | ggcccgtgcg | 780 |
| tcccagcgca | catgttcggc | gaggcggggc | ctgcgagcgc | ggccaccgag | aatcggacgg | 840 |
| gggtagtctc | aagctggccg | gcctgctctg | gtgcctggcc | tcgcgccgcc | gtgtatcgcc | 900 |
| ccgcccgggg | cggcaaggct | ggcccggtcg | gcaccagttg | cgtgagcgga | agatggccg | 960 |
| cttcccggcc | ctgctgcagg | gagctcaaaa | tggaggacgc | ggcgctcggg | agagcgggcg | 1020 |
| ggtgagtcac | ccacacaaag | gaaaagggcc | tttccgtcct | cagccgtcgc | ttcatgtgac | 1080 |
| tccacggagt | accgggcgcc | gtccaggcac | ctcgattagt | tctcgagctt | ttggagtacg | 1140 |
| tcgtctttag | gttgggggga | ggggttttat | gcgatggagt | ttccccacac | tgagtgggtg | 1200 |
| gagactgaag | ttaggccagc | ttggcacttg | atgtaattct | ccttggaatt | tgcccttttt | 1260 |
| gagtttggat | cttggttcat | tctcaagcct | cagacagtgg | ttcaaagttt | ttttcttcca | 1320 |
| tttcaggtgt | cgtgaactag | aagctttatt | gcggtagttt | atcacagtta | aattgctaac | 1380 |
| gcagtcagtg | cttctgacac | aacagtctcg | aacttaagct | gcagtgactc | tcttaaggta | 1440 |
| gccttgcaga | agttggtcgt | gaggcactgg | gcaggtaagt | atcaaggtta | caagacaggt | 1500 |
| ttaaggagac | caatagaaac | tgggcttgtc | gagacagaga | agactcttgc | gtttctgata | 1560 |
| ggcacctatt | ggtcttactg | acatccactt | tgcctttctc | tccacaggtg | tccactccca | 1620 |
| gttcaattac | agctcttaag | gctagagtac | ttaatacgac | tcactatagg | ctagcgccac | 1680 |
| catgcggatt | tccaagcccc | atctgcgctc | catttccatc | cagtgttacc | tgtgcctgct | 1740 |
| gctgaatagc | cattttctga | ccgaagccgg | catccacgtg | ttcatcctgg | gctgcttttc | 1800 |
| cgccggcctg | ccaaagaccg | aggcaaactg | ggtgaatgtg | atctctgacc | tgaagaagat | 1860 |
| cgaggatctg | atccagagca | tgcacatcga | cgccaccctg | tacacagagt | ccgatgtgca | 1920 |
| cccttcttgc | aaggtgacag | ccatgaagtg | tttcctgctg | gagctgcagg | tcatctctct | 1980 |
| ggagagcggc | gacgcctcta | ccacgatac | cgtggagaac | ctgatcatcc | tggccaacaa | 2040 |
| tagcctgagc | tccaacggca | atgtgacaga | gtccggctgc | aaggagtgtg | aggagctgga | 2100 |
| ggagaagaat | atcaaagagt | tcctgcagag | tttcgtccat | atcgtccaga | tgtttatcaa | 2160 |
| tacttcctaa | gaattcacgc | gtcgagcatg | catctagggc | ggccaattcc | gcccctctcc | 2220 |

| | | | |
|---|---|---|---|
| cccccccccc | tctccctccc | cccccccctaa | cgttactggc cgaagccgct tggaataagg | 2280 |
| ccggtgtgcg | tttgtctata | tgttattttc | caccatattg ccgtcttttg gcaatgtgag | 2340 |
| ggcccggaaa | cctggccctg | tcttcttgac | gagcattcct aggggtcttt ccctctcgc | 2400 |
| caaaggaatg | caaggtctgt | tgaatgtcgt | gaaggaagca gttcctctgg aagcttcttg | 2460 |
| aagacaaaca | acgtctgtag | cgacccttg | caggcagcgg aaccccccac ctggcgacag | 2520 |
| gtgcctctgc | ggccaaaagc | cacgtgtata | agatacacct gcaaaggcgg cacaacccca | 2580 |
| gtgccacgtt | gtgagttgga | tagttgtgga | aagagtcaaa tggctctcct caagcgtatt | 2640 |
| caacaagggg | ctgaaggatg | cccagaaggt | accccattgt atgggatctg atctggggcc | 2700 |
| tcggtgcaca | tgctttacat | gtgtttagtc | gaggttaaaa aaacgtctag gccccccgaa | 2760 |
| ccacggggac | gtggttttcc | tttgaaaaac | acgatgataa gcttgccaca acccgggatc | 2820 |
| ctctagagtc | gacgccacca | tggctccacg | ccgcgctaga ggatgtcgga ccctgggact | 2880 |
| gcctgcctg | ctgctgctgc | tgctgctgag | accccccgct acaaggggca tcacctgccc | 2940 |
| acctccaatg | agcgtggagc | acgcagacat | ctgggtgaag tcttacagcc tgtattcccg | 3000 |
| ggagagatac | atctgcaact | ctggcttcaa | gcggaaggcc ggcaccagct ccctgacaga | 3060 |
| gtgcgtgctg | aacaaggcaa | caaatgtggc | tcactggact accccatcac tgaaatgtat | 3120 |
| tagggattga | gtcga | | | 3135 |

<210> SEQ ID NO 561
<211> LENGTH: 3906
<212> TYPE: DNA
<213> ORGANISM: Artificial Sequence
<220> FEATURE:
<223> OTHER INFORMATION: Synthetic sequence

<400> SEQUENCE: 561

| | | | | |
|---|---|---|---|---|
| gagtaattca | tacaaaagga | ctcgcccctg | ccttggggaa tcccagggac cgtcgttaaa | 60 |
| ctcccactaa | cgtagaaccc | agagatcgct | gcgttcccgc cccctcaccc gcccgctctc | 120 |
| gtcatcactg | aggtggagaa | gagcatgcgt | gaggctccgg tgcccgtcag tgggcagagc | 180 |
| gcacatcgcc | cacagtcccc | gagaagttgg | ggggaggggt cggcaattga accggtgcct | 240 |
| agagaaggtg | gcgcggggta | aactgggaaa | gtgatgtcgt gtactggctc cgccttttc | 300 |
| ccgagggtgg | gggagaaccg | tatataagtg | cagtagtcgc cgtgaacgtt cttttcgca | 360 |
| acgggtttgc | cgccagaaca | caggtaagtg | ccgtgtgtgg ttcccgcggg cctggcctct | 420 |
| ttacgggtta | tggcccttgc | gtgccttgaa | ttacttccac gccctggct gcagtacgtg | 480 |
| attcttgatc | ccgagcttcg | ggttggaagt | gggtgggaga gttcgaggcc ttgcgcttaa | 540 |
| ggagccctt | cgcctcgtgc | ttgagttgag | gcctggcttg ggcgctgggg ccgccgcgtg | 600 |
| cgaatctggt | ggcaccttcg | cgcctgtctc | gctgctttcg ataagtctct agccatttaa | 660 |
| aattttgat | gacctgctgc | gacgcttttt | ttctggcaag atagtcttgt aaatgcgggc | 720 |
| caagatctgc | acactggtat | tccggttttt | ggggccgcgg gcggcgacgg ggcccgtgcg | 780 |
| tcccagcgca | catgttcggc | gaggcggggc | ctgcgagcgc ggccaccgag atcggacgg | 840 |
| gggtagtctc | aagctggccg | gcctgctctg | tgcctggcc tcgcgccgcc gtgtatcgcc | 900 |
| ccgccctggg | cggcaaggct | ggccggtcg | gcaccagttg cgtgagcgga agatggccg | 960 |
| cttcccggcc | ctgctgcagg | gagctcaaaa | tggaggacgc ggcgctcggg agagcgggcg | 1020 |
| ggtgagtcac | ccacacaaag | gaaagggcc | tttccgtcct cagccgtcgc ttcatgtgac | 1080 |

```
tccacggagt accgggcgcc gtccaggcac ctcgattagt tctcgagctt ttggagtacg    1140
tcgtctttag gttgggggga ggggttttat gcgatggagt ttccccacac tgagtgggtg    1200
gagactgaag ttaggccagc ttggcacttg atgtaattct ccttggaatt tgccctttt    1260 gagtttggat cttggttcat tctcaagcct cagacagtgg ttcaaagttt ttttcttcca    1320
tttcaggtgt cgtgaactag aagctttatt gcggtagttt atcacagtta aattgctaac    1380
gcagtcagtg cttctgacac aacagtctcg aacttaagct gcagtgactc tcttaaggta    1440
gccttgcaga agttggtcgt gaggcactgg gcaggtaagt atcaaggtta caagacaggt    1500
ttaaggagac caatagaaac tgggcttgtc gagacagaga agactcttgc gtttctgata    1560
ggcacctatt ggtcttactg acatccactt tgcctttctc tccacaggtg tccactccca    1620
gttcaattac agctcttaag gctagagtac ttaatacgac tcactatagg ctagcgccac    1680
catgcggatt tccaagcccc atctgcgctc catttccatc cagtgttacc tgtgcctgct    1740
gctgaatagc cattttctga ccgaagccgg catccacgtg ttcatcctgg gctgcttttc    1800
cgccggcctg ccaaagaccg aggcaaactg ggtgaatgtg atctctgacc tgaagaagat    1860
cgaggatctg atccagagca tgcacatcga cgccaccctg tacacagagt ccgatgtgca    1920
cccttcttgc aaggtgacag ccatgaagtg tttcctgctg gagctgcagg tcatctctct    1980
ggagagcggc gacgcctcta tccacgatac cgtggagaac ctgatcatcc tggccaacaa    2040
tagcctgagc tccaacggca atgtgacaga gtccggctgc aaggagtgtg aggagctgga    2100
ggagaagaat atcaaagagt tcctgcagag tttcgtccat atcgtccaga tgtttatcaa    2160
tacttcctaa gaattcacgc gtcgagcatg catctagggc ggccaattcc gccctctcc    2220 cccccccccc tctccctccc ccccccctaa cgttactggc cgaagccgct tggaataagg    2280
ccggtgtgcg tttgtctata tgttattttc caccatattg ccgtcttttg gcaatgtgag    2340
ggcccggaaa cctggccctg tcttcttgac gagcattcct aggggtcttt cccctctcgc    2400
caaaggaatg caaggtctgt tgaatgtcgt gaaggaagca gttcctctgg aagcttcttg    2460
aagacaaaca acgtctgtag cgacccttg caggcagcgg aacccccac ctggcgacag    2520 gtgcctctgc ggccaaaagc cacgtgtata agatacacct gcaaaggcgg cacaacccca    2580
gtgccacgtt gtgagttgga tagttgtgga aagagtcaaa tggctctcct caagcgtatt    2640
caacaagggg ctgaaggatg cccagaaggt accccattgt atgggatctg atctggggcc    2700
tcggtgcaca tgctttacat gtgtttagtc gaggttaaaa aaacgtctag gccccccgaa    2760
ccacggggac gtggttttcc tttgaaaaac acgatgataa gcttgccaca acccgggatc    2820
ctctagagtc gacgccacca tgagactggc aggaagacag gtccccgaac agagatcccc    2880
tccaccaccc ggactgggca gcgcaagacc cggctcaccc gccgtgtcct gcggagcagc    2940
agcaatggca ccaaggagag ccaggggctg tcgcaccctg ggcctgcccg ccctgttatt    3000
actgctgctg ctgaggcccc ctgcaacacg cgacgcaagg gatcgcctgg ccgtgctggc    3060
aggccggagc agaatctccg agtctttcaa ccacgaggtg cagacccacg aggcatgcgt    3120
gaggctgagg acaatggaga attgccccca gtgtcaccac caccggacca gcagacagca    3180
ggcaggcatc acatgtccac cccctatgtc cgtggagcac gccgacatct gggtgaagag    3240
ctactccctg tattctcggg agagatacat ctgcaacagc ggctttaaga ggaaggccgg    3300
caccagctcc ctgacagagt gcgtgctgaa caaggccacc aatgtggccc actggaccac    3360
accctctctg aagtgcatcc gggatcccgc cctggtgcac cagcggcccg caccaccag    3420 caccgtgacc acagccggcg tgacaccaca gccagagtct ctgagcccat ccggcaagga    3480
```

| | | |
|---|---|---|
| gcctgcagca tctagcccat cctctaacaa taccgcagca accacagcag caatcgtgcc | 3540 | |
| tggctcccag ctgatgcctt ctaagagccc atccacaggc accacagaga tcagctccca | 3600 | |
| cgagtctagc cacggcaccc cttctcagac cacagccaag aattgggagc tgacagcatc | 3660 | |
| tgccagccac cagcctccag gcgtgtaccc acagggccac tccgacacca cagtggccat | 3720 | |
| ctccacctct acagtgctgc tgtgcggcct gagcgccgtg tccctgctgg cctgttatct | 3780 | |
| gaagtccaga cagaccccc ctctggcctc tgtggagatg gaggccatgg aggccctgcc | 3840 | |
| cgtcacctgg ggaacttcat caagagacga ggacctggaa aactgtagtc accatctgta | 3900 | |
| agtcga | 3906 | |

<210> SEQ ID NO 562
<211> LENGTH: 3487
<212> TYPE: DNA
<213> ORGANISM: Artificial Sequence
<220> FEATURE:
<223> OTHER INFORMATION: Synthetic sequence

<400> SEQUENCE: 562

| | | |
|---|---|---|
| gagtaattca tacaaaagga ctcgcccctg ccttggggaa tcccagggac cgtcgttaaa | 60 | |
| ctcccactaa cgtagaaccc agagatcgct gcgttccgc cccctcaccc gcccgctctc | 120 | |
| gtcatcactg aggtggagaa gagcatgcgt gaggctccgg tgcccgtcag tgggcagagc | 180 | |
| gcacatcgcc cacagtcccc gagaagttgg ggggaggggt cggcaattga accggtgcct | 240 | |
| agagaaggtg gcgcggggta aactgggaaa gtgatgtcgt gtactggctc cgcctttttc | 300 | |
| ccgagggtgg gggagaaccg tatataagtg cagtagtcgc cgtgaacgtt cttttcgca | 360 | |
| acgggtttgc cgccagaaca caggtaagtg ccgtgtgtgg ttcccgcggg cctggcctct | 420 | |
| ttacgggtta tggcccttgc gtgccttgaa ttacttccac gcccctggct gcagtacgtg | 480 | |
| attcttgatc ccgagcttcg ggttggaagt gggtgggaga gttcgaggcc ttgcgcttaa | 540 | |
| ggagccccctt cgcctcgtgc ttgagttgag gcctggcttg ggcgctgggg ccgccgcgtg | 600 | |
| cgaatctggt ggcaccttcg cgcctgtctc gctgctttcg ataagtctct agccatttaa | 660 | |
| aattttttgat gacctgctgc gacgcttttt ttctggcaag atagtcttgt aaatgcgggc | 720 | |
| caagatctgc acactggtat ttcggttttt ggggccgcgg gcggcgacgg ggcccgtgcg | 780 | |
| tcccagcgca catgttcggc gaggcggggc ctgcagcgc ggccaccgag aatcggacgg | 840 | |
| gggtagtctc aagctggccg gcctgctctg gtgcctggcc tcgcgccgcc gtgtatcgcc | 900 | |
| ccgccctggg cggcaaggct ggcccggtcg caccagttg cgtgagcgga agatggccg | 960 | |
| cttcccggcc ctgctgcagg gagctcaaaa tggaggacgc ggcgctcggg agagcgggcg | 1020 | |
| ggtgagtcac ccacacaaag gaaaagggcc tttccgtcct cagccgtcgc ttcatgtgac | 1080 | |
| tccacggagt accgggcgcc gtccaggcac ctcgattagt tctcgagctt ttggagtacg | 1140 | |
| tcgtctttag gttgggggga ggggtttat gcgatggagt ttcccacac tgagtgggtg | 1200 | |
| gagactgaag ttaggccagc ttggcacttg atgtaattct ccttggaatt tgcccttttt | 1260 | |
| gagtttggat cttggttcat tctcaagcct cagacagtgg ttcaaagttt ttttcttcca | 1320 | |
| tttcaggtgt cgtgaactag aagctttatt gcggtagttt atcacagtta aattgctaac | 1380 | |
| gcagtcagtg cttctgacac aacagtctcg aacttaagct gcagtgactc tcttaaggta | 1440 | |
| gccttgcaga agttggtcgt gaggcactgg gcaggtaagt atcaaggtta caagacaggt | 1500 | |
| ttaaggagac caatagaaac tgggcttgtc gagacagaga agactcttgc gtttctgata | 1560 | |

```
ggcacctatt ggtcttactg acatccactt tgcctttctc tccacaggtg tccactccca    1620
gttcaattac agctcttaag gctagagtac ttaatacgac tcactatagg ctagcgccac    1680
catgcggatt ccaaacctc acctgcgatc tatctccatc cagtgctatc tgtgcctgct     1740
gctgaactct catttcctga ccgaagccgg catccacgtg ttcatcctgg gctgctttag    1800
cgccggcctg ccaaagaccg aggcaaactg ggtgaatgtg atctctgacc tgaagaagat    1860
cgaggatctg atccagagca tgcacatcga cgccaccctg tacacagagt ccgatgtgca    1920
cccttcttgc aaggtgacag ccatgaagtg tttcctgctg gagctgcagg tcatctctct    1980
ggagagcggc gacgcctcca tccacgatac cgtggagaac ctgatcatcc tggccaacaa    2040
tagcctgagc tccaacggca atgtgacaga gtccggctgc aaggagtgtg aggagctgga    2100
ggagaagaac atcaaggagt cctgcagtc ttttgtgcac atcgtgcaga tgtttatcaa     2160
taccagcgga ggaggaggat ccggcggagg aggctctggc ggcggcggca gctgtggcgg    2220
caaggtgtcc gccctgaagg agaaggtgtc tgccctgaag gaaaagtgt ccgctctgaa     2280
ggaaaaggtg tccgcactga agaaaaggt ctccgccctg aaggaataag aattcacgcg     2340
tcgagcatgc atctagggcg gccaattccg cccctctccc ccccccccct ctccctcccc    2400
cccccctaac gttactggcc gaagccgctt ggaataaggc cggtgtgcgt ttgtctatat    2460
gttattttcc accatattgc cgtcttttgg caatgtgagg gcccggaaac ctggccctgt    2520
cttcttgacg agcattccta ggggtctttc ccctctcgcc aaaggaatgc aaggtctgtt    2580
gaatgtcgtg aaggaagcag ttcctctgga agcttcttga agacaaacaa cgtctgtagc    2640
gaccctttgc aggcagcgga accccccacc tggcgacagg tgcctctgcg gccaaaagcc    2700
acgtgtataa gatacacctg caaaggcggc acaaccccag tgccacgttg tgagttggat    2760
agttgtggaa agagtcaaat ggctctcctc aagcgtattc aacaagggc tgaaggatgc      2820
ccagaaggta ccccattgta tgggatctga tctggggcct cggtgcacat gctttacatg    2880
tgtttagtcg aggttaaaaa aacgtctagg ccccccgaac cacggggacg tggttttcct    2940
ttgaaaaaca cgatgataag cttgccacaa cccgggatcc tctagagtcg acgccaccat    3000
ggcccctaga agagcccgag gatgtcgcac actgggactg cctgccctgc tgctgctgct    3060
gctgctgaga ccacctgcta caaggggcat cacctgccca cctccaatga gcgtggagca    3120
cgcagacatc tgggtgaagt cttcagcct gtattctcgg gagagataca tctgcaacag     3180
cggcttcaag aggaaggccg gcaccagctc cctgacagag tgcgtgctga caaggccac     3240
aaatgtggcc cactggacca cccctccct gaagtgtatc cgggatggag gaggaggaag     3300
cggaggagga ggatccggcg gcggcggctc cgaggtgtct gccctggaga aggaggtgtc    3360
tgccctggaa aaagaagtct cagccctgga aaaggaggtg tcagccctgg aaaaagaggt    3420
gtccgcactg gaaaaataag tcgaagtcgg gaccttttc tccacaggcg tgacctttt      3480
attcagc                                                              3487
```

<210> SEQ ID NO 563  
<211> LENGTH: 4215  
<212> TYPE: DNA  
<213> ORGANISM: Artificial Sequence  
<220> FEATURE:  
<223> OTHER INFORMATION: Synthetic sequence

<400> SEQUENCE: 563

```
gagtaattca tacaaaagga ctcgcccctg ccttggggaa tcccagggac cgtcgttaaa      60
ctcccactaa cgtagaaccc agagatcgct gcgttcccgc cccctcaccc gccgctctc     120
```

```
gtcatcactg aggtggagaa gagcatgcgt gaggctccgg tgcccgtcag tgggcagagc    180
gcacatcgcc cacagtcccc gagaagttgg ggggaggggg cggcaattga accggtgcct    240
agagaaggtg gcgcggggta aactgggaaa gtgatgtcgt gtactggctc cgccttttc    300 ccgagggtgg gggagaaccg tatataagtg cagtagtcgc cgtgaacgtt cttttcgca    360 acgggtttgc cgccagaaca caggtaagtg ccgtgtgtgg ttcccgcggg cctggcctct    420
ttacgggtta tggcccttgc gtgccttgaa ttacttccac gccctggct gcagtacgtg    480 attcttgatc ccgagcttcg ggttggaagt gggtgggaga gttcgaggcc ttgcgcttaa    540 ggagccccctt cgcctcgtgc ttgagttgag gcctggcttg ggcgctgggg ccgccgcgtg    600
cgaatctggt ggcaccttcg cgcctgtctc gctgctttcg ataagtctct agccatttaa    660 aattttttgat gacctgctgc gacgctttt ttctggcaag atagtcttgt aaatgcgggc    720
caagatctgc acactggtat ttcggttttt ggggccgcgg gcggcgacgg ggcccgtgcg    780
tcccagcgca catgttcggc gaggcggggc ctgcgagcgc ggccaccgag aatcggacgg    840
gggtagtctc aagctggccg gcctgctctg gtgcctggcc tcgcgccgcc gtgtatcgcc    900
ccgccctggg cggcaaggct ggcccggtcg gcaccagttg cgtgagcgga agatggccg    960 cttcccggcc ctgctgcagg gagctcaaaa tggaggacgc ggcgctcggg agagcgggcg   1020
ggtgagtcac ccacacaaag gaaaagggcc tttccgtcct cagccgtcgc ttcatgtgac   1080
tccacggagt accgggcgcc gtccaggcac ctcgattagt tctcgagctt ttggagtacg   1140
tcgtctttag gttgggggga ggggtttat gcgatggagt ttccccacac tgagtgggtg   1200
gagactgaag ttaggccagc ttggcacttg atgtaattct ccttggaatt tgccctttt   1260 gagtttggat cttggttcat tctcaagcct cagacagtgg ttcaaagttt ttttcttcca   1320
tttcaggtgt cgtgaactag aagctttatt gcggtagttt atcacagtta aattgctaac   1380
gcagtcagtg cttctgacac aacagtctcg aacttaagct gcagtgactc tcttaaggta   1440
gccttgcaga agttggtcgt gaggcactgg gcaggtaagt atcaaggtta caagacaggt   1500
ttaaggagac caatagaaac tgggcttgtc gagacagaga agactcttgc gtttctgata   1560
ggcacctatt ggtcttactg acatccactt tgcctttctc tccacaggtg tccactccca   1620
gttcaattac agctcttaag gctagagtac ttaatacgac tcactatagg ctagcgccac   1680
catgcggatt tccaaacctc acctgcgatc tatctccatc cagtgctatc tgtgcctgct   1740
gctgaactct catttcctga ccgaagccgg catccacgtg ttcatcctgg ctgctttag   1800 cgccggcctc ccaaagaccg aggcaaactg ggtgaatgtg atctctgacc tgaagaagat   1860
cgaggatctg atccagagca tgcacatcga cgccaccctg tacacagagt ccgatgtgca   1920
cccttcttgc aaggtgacag ccatgaagtg tttcctgctg gagctgcagg tcatctctct   1980
ggagagcggc gacgcctcca tccacgatac cgtggagaac ctgatcatcc tggccaacaa   2040
tagcctgagc tccaacggca atgtgacaga gtccggctgc aaggagtgtg aggagctgga   2100
ggagaagaac atcaaggagt tcctgcagtc ttttgtgcac atcgtgcaga tgtttatcaa   2160
taccagcgga ggaggaggat ccggcggagg aggctctggc ggcggcggca gctgtggcgg   2220
caaggtgtcc gccctgaagg agaaggtgtc tgccctgaag gaaaaagtgt ccgctctgaa   2280
ggaaaaggtg tccgcactga agaaaaggt ctccgccctg aaggaataag aattcacgcg   2340
tcgagcatgc atctagggcg gccaattccg cccctctccc ccccccccct ctccctcccc   2400 ccccctaac gttactggcc gaagccgctt ggaataaggc cggtgtgcgt ttgtctatat   2460
```

```
gttattttcc accatattgc cgtcttttgg caatgtgagg gcccggaaac ctggccctgt    2520
cttcttgacg agcattccta ggggtctttc ccctctcgcc aaaggaatgc aaggtctgtt    2580
gaatgtcgtg aaggaagcag ttcctctgga agcttcttga agacaaacaa cgtctgtagc    2640 gacccttgc aggcagcgga acccccacc tggcgacagg tgcctctgcg gccaaaagcc    2700
acgtgtataa gatacacctg caaaggcggc acaacccag tgccacgttg tgagttggat    2760
agttgtggaa agagtcaaat ggctctcctc aagcgtattc aacaaggggc tgaaggatgc    2820
ccagaaggta ccccattgta tgggatctga tctggggcct cggtgcacat gctttacatg    2880
tgtttagtcg aggttaaaaa aacgtctagg cccccgaac cacggggacg tggttttcct    2940
ttgaaaaaca cgatgataag cttgccacaa cccgggatcc tctagagtcg acgccaccat    3000
gcggctggct ggaaggcagg tccccgagca gagatcccct cctcctcctg ggctgggcag    3060
tgcaagaccc ggcagtcccg ctgtgtcctg cggagcagca gcaatggcac caaggagagc    3120
caggggctgt cgcaccctgg gcctgcccgc cctgttatta ctgctgctgc tgaggcccc    3180 tgcaacacgc gacgcaaggg atcgcctggc cgtgctggca ggccggagca gaatcagcga    3240
gtccttcaac cacgaggtgc agacccacga ggcatgcgtg aggctgagga caatggagaa    3300 ttgccccag tgtcaccacc accggaccag cagacagcag gcaggcatca catgtccacc    3360
ccctatgtcc gtggagcacg ccgacatctg ggtgaagtct tacagcctgt attctcggga    3420
gagatacatc tgcaacagcg gctttaagcg gaaggccggc accagctccc tgacagagtg    3480
cgtgctgaac aaggccacca atgtggccca ctggaccaca ccctctctga agtgcatccg    3540
ggatcccgcc ctggtgcacc agcggcccgc accaccagc accgtgacca cagcaggagt    3600
gacaccacag ccagagtccc tgtctccaag cggcaaggag cctgcagcat ctagcccatc    3660
ctctaacaat accgcagcaa ccacagcagc aatcgtgcct ggctcccagc tgatgccttc    3720
caagtctcca agcaccggca ccacagagat cagctcccac gagtctagcc acggcacccc    3780
ttctcagacc acagcaaga actgggagct gacagcatcc gcctctcacc agcctccagg    3840
cgtgtaccca cagggccact ccgacaccac agtggccatc agcacctcca cagtgctgct    3900
gtgcggcctg tctgccgtga gcctgctggc ctgttatctg aagtccaggc agaccccacc    3960
tctggcatct gtggagatgg aggcaatgga ggccctgcca gtgacctggg gcacatcctc    4020
tcgcgacgag gatctggaga attgttccca ccacctggga ggaggaggaa gcggaggagg    4080
aggctccggc ggcggcggct ccgaggtgtc tgccctggaa aaagaggtga gcgccctgga    4140 aaagagtg tcagccctgg agaaggaggt gtcagcactg gaaaagagg tgtccgcact    4200 ggaaaaataa gtcga                                                    4215

<210> SEQ ID NO 564
<211> LENGTH: 3425
<212> TYPE: DNA
<213> ORGANISM: Artificial Sequence
<220> FEATURE:
<223> OTHER INFORMATION: Synthetic sequence

<400> SEQUENCE: 564
acattgatta ttgactagtt attaatagta atcaattacg gggtcattag ttcatagccc      60
atatatggag ttccgcgtta cataacttac ggtaaatggc ccgcctggct gaccgcccaa     120
cgacccccgc ccattgacgt caataatgac gtatgttccc atagtaacgc caatagggac     180
tttccattga cgtcaatggg tggagtattt acggtaaact gcccacttgg cagtacatca     240
agtgtatcat atgccaagta cgccccctat tgacgtcaat gacggtaaat ggcccgcctg     300
```

```
gcattatgcc cagtacatga ccttatggga ctttcctact tggcagtaca tctacgtatt     360
agtcatcgct attaccatgg tgatgcggtt ttggcagtac atcaatgggc gtggatagcg     420
gtttgactca cggggatttc caagtctcca ccccattgac gtcaatggga gtttgttttg     480
gcaccaaaat caacgggact ttccaaaatg tcgtaacaac tccgcccat tgacgcaaat      540
gggcggtagg cgtgtacggt gggaggtcta tataagcaga gctctctggc taactagaga     600
acccactgct tactggctta tcgaaattaa tacgactcac tatagggaga cccaagctgg     660
ctagcgttta aacttaagct tggtaccgag ctcggatcca ctagtccagt gtggtggaat     720
tcgccaccat gtgccctcag aaactgacta tctcatggtt cgcaatcgtg ctgctggtct     780
caccctgat ggctatgtgg gaactggaaa aggatgtgta cgtggtggag gtggactgga    840
cacccgatgc ccctggcgag acagtgaacc tgacatgcga cacccccgag gaggacgaca    900
tcacctggac atccgatcag cggcacggcg tgatcggctc tggcaagacc ctgacaatca    960
ccgtgaagga gttcctggac gccggccagt acacatgtca aagggcggc gagacactga    1020
gccactccca cctgctgctg cacaagaagg agaacggcat ctggtccaca gagatcctga    1080
agaacttcaa gaataagacc tttctgaagt gcgaggcccc caattattct ggccggttca    1140
cctgtagctg gctggtgcag agaaacatgg acctgaagtt taatatcaag agctcctcta    1200
gctcccctga tagcagggca gtgacatgcg gaatggcatc tctgagcgcc gagaaggtga    1260
ccctggacca gagagattac gagaagtatt ccgtgtcttg ccaggaggat gtgacatgtc    1320
ccaccgccga ggagacactg cctatcgagc tggcccctgg agcaaggcag cagaacaagt    1380
acgagaatta tagcacctcc ttctttatca gagacatcat caagccagat cccctaaga    1440
acctgcagat gaagcccctg aagaacagcc aggtcgaggt gagctgggag taccctgact    1500
cttggagcac accacactct tatttcagcc tgaagttctt tgtgaggatc cagcgcaaga    1560
aggagaagat gaaggagaca gaggagggct gcaaccagaa gggcgccttt ctggtggaga    1620
agacatccac cgaggtgcag tgcaagggag gaaacgtgtg cgtgcaggca caggatagat    1680
actataattc tagctgctct aagtgggcct gcgtgccctg tagggtgcgc tccggaggcg    1740
gcggctctgg aggaggagga agcggaggag gaggaagcat gtgccagtcc aggtacctgc    1800
tgttcctggc caccctggcc ctgctgaacc acctgtccct ggcacgcgtg atcccagtgt    1860
ctggaccagc ccggtgcctg tcccagtcta gaaatctgct gaagaccaca gacgatatgg    1920
tgaagacagc cagggagaag ctgaagcact attcctgtac cgccgaggac atcgatcacg    1980
aggacatcac acgcgatcag acatccaccc tgaagacctg cctgcctctg agctgcaca    2040
agaacgagtc ttgtctggcc acacgggaga caagctctac cacaagaggc agctgcctgc    2100
cacccagaa gacatccctg atgatgaccc tgtgcctggg cagcatctac gaggacctga    2160
agatgtatca gacagagttt caggccatca tgccgcccct gcagaaccac aatcaccagc    2220
agatcatcct ggacaagggc atgctggtgg ccatcgatga gctgatgcag tccctgaacc    2280
acaatggcga gacactgagg cagaagcctc cagtgggcga ggccgatcct taccgcgtga    2340
agatgaagct gtgcatcctg ctgcacgcct tcagcacaag ggtggtgacc atcaaccgcg    2400
tgatgggcta tctgagctcc gccgaggag gaggatccgg cggaggaggc tctggcggcg    2460
gcggcagcgg ctccggcgcc accaactttt ctctgctgaa gcaggcaggc gacgtggagg    2520
agaatccagg acccatgagg atcagcaagc cacacctgcg ctctatcagc atccagtgct    2580
acctgtgcct gctgctgaat agccacttcc tgacagaggc cggcatccac gtgttcatcc    2640
```

```
tgggctgttt ttccgccggc ctgccaaaga ccgaggccaa ctgggtgaat gtgatctctg    2700
acctgaagaa gatcgaggat ctgatccaga gcatgcacat cgacgccaca ctgtataccg    2760
agagcgatgt gcacccctcc tgcaaggtga ccgccatgaa gtgttttctg ctggagctgc    2820
aggtcatcag cctggagtct ggcgacgcca gcatccacga tacagtggag aacctgatca    2880
tcctggccaa caatagcctg tctagcaacg gcaatgtgac cgagtccggc tgcaaggagt    2940
gtgaggagct ggaggagaag aacatcaagg agttcctgca gtcctttgtg cacatcgtgc    3000
agatgttcat caatacatcc ggcggcggcg gctccggcgg cggagggagc ggaggaggcg    3060
gctccggctc tggcgccacc aactttagcc tgctgaagca ggccggcgac gtggaagaaa    3120
atcctggacc aatggcacct aggagagcaa ggggatgcag aaccctgggc ctgccagccc    3180
tgttattact gctgctgctg aggcccctgt caacaagggg aatcacctgt ccaccccta    3240 tgagcgtgga gcacgccgac atctgggtga agagctactc cctgtattct cgggagagat    3300
acatctgcaa tagcggcttc aagcggaagg ccggcacatc ctctctgacc gagtgcgtgc    3360
tgaacaaagc aacaaacgtg gctcattgga caacaccatc cctgaagtgc atccgcgact    3420
aagat                                                                3425
```

```
<210> SEQ ID NO 565
<211> LENGTH: 3912
<212> TYPE: DNA
<213> ORGANISM: Artificial Sequence
<220> FEATURE:
<223> OTHER INFORMATION: Synthetic sequence

<400> SEQUENCE: 565
acattgatta ttgactagtt attaatagta atcaattacg gggtcattag ttcatagccc      60
atatatggag ttccccgcct ggctgaccgc ccaacgaccc ccgcccattg acgtcaataa     120
tgacgtatgt tcccatagta acgccaatag ggactttcca ttgacgtcaa tgggtggagt     180
atttacggta aactgcccac ttggcagtac atcaagtgta tcatatgcca agtacgcccc     240
ctattgacgt caatgacggt aaatggcccg cctggcatta tgcccagtac atgaccttat     300
gggactttcc tacttggcag tacatctacg tattagtcat cgctattacc atggtgatgc     360
ggttttggca gtacatcaat gggcgtggat agcggtttga ctcacgggga tttccaagtc     420
tccaccccat tgacgtcaat gggagtttgt tttggcacca aaatcaacgg gactttccaa     480
aatgtcgtaa caactccgcc ccattgacgc aaatgggcgg taggcgtgta cggtgggagg     540
tctatataag cagagctctc tggctaacta gagaacccac tgcttactgg cttatcgaaa     600
ttaatacgac tcactatagg gagacccaag ctggctagcg tttaaactta agcttggtac     660
cgagctcgga tccactagtc cagtgtggtg gaattcgcca ccatgtgccc tcagaagctg     720
actatctctt ggtttgctat tgtgctgctg gtctcacccc tgatggctat gtgggaactg     780
gaaaaggatg tgtacgtggt ggaggtggac tggacaccag atgcccccgg cgagacagtg     840
aacctgacat gcgacaccc cgaggaggac gacatcacct ggacatctga tcagaggcac     900
ggcgtgatcg gaagcggcaa gaccctgaca atcaccgtga aggagttcct ggacgccggc     960
cagtacacat gtcacaaggg cggcgagaca ctgtctcaca gccacctgct gctgcacaag    1020
aaggagaacg gcatctggag cacagagatc ctgaagaact tcaagaataa gaccttcctg    1080
aagtgcgagg cccaaattta ttccggcagg ttcacctgtt cttggctggt gcagcgcaac    1140
atggacctga gtttaatat caagagctcc tctagctccc ccgattccag gcagtgaca     1200 tgcggaatgg catccctgtc tgccgagaag gtgacccctg accagcgcga ttacgagaag    1260
```

```
tatagcgtgt cctgccagga ggatgtgaca tgtcctaccg ccgaggagac actgccaatc   1320
gagctggccc tggaggccag gcagcagaac aagtacgaga attattctac cagcttcttt   1380
atccgcgaca tcatcaagcc agatcccct aagaacctgc agatgaagcc cctgaagaac   1440
agccaggtcg aggtgtcttg ggagtaccca gactcctggt ctacacccca ctcttatttc   1500
agcctgaagt tctttgtgag gatccagcgc aagaaggaga agatgaagga gacagaggag   1560
ggctgcaacc agaagggcgc ctttctggtg gagaagacat ccaccgaggt gcagtgcaag   1620
ggaggaaacg tgtgcgtgca ggcacaggat agatactata attctagctg cagcaagtgg   1680
gcctgcgtgc cttgtagggt gcgcagcgga ggaggaggat ccggaggagg cggctctgga   1740
ggaggaggat ctatgtgcca gagccggtac ctgctgttcc tggccaccct ggccctgctg   1800
aaccacctga gcctggcaag agtgatcccc gtgagcggac cagcaaggtg cctgagccag   1860
tccagaaatc tgctgaagac cacagacgat atggtgaaga cagcccggga gaagctgaag   1920
cactatagct gtaccgccga ggacatcgat cacgaggaca tcacaagaga tcagacatct   1980
accctgaaga cctgcctgcc cctggagctg cacaagaacg agagctgtct ggccacacgg   2040
gagacaagct ctaccacaag aggctcttgc ctgccacccc agaagacaag cctgatgatg   2100
accctgtgcc tgggcagcat ctacgaggac ctgaagatgt atcagaccga gtttcaggcc   2160
atcaatgccg ccctgcagaa ccacaatcac cagcagatca tcctggacaa gggcatgctg   2220
gtggccatcg atgagctgat gcagagcctg aaccacaatg gcgagacact gaggcagaag   2280
cctccagtgg gagaggcaga tccatacaga gtgaagatga agctgtgcat cctgctgcac   2340
gccttctcca agggtggt gaccatcaac cgcgtgatgg gctatctgag ctccgccgga   2400
ggaggaggaa gcggcggagg aggcagcggc ggcggcggct ctggcagcgg cgccaccaac   2460
tttagcctgc tgaagcaggc aggcgacgtg gaggagaatc caggacccat gaggatctcc   2520
aagccccacc tgcgctccat ctctatccag tgctacctgt gcctgctgct gaacagccac   2580
ttcctgacag aggccggcat ccacgtgttc atcctgggct gttttttctgc cggcctgcct   2640
aagaccgagg ccaactgggt gaatgtgatc agcgacctga agaagatcga ggatctgatc   2700
cagtccatgc acatcgacgc cacactgtat accgagtctg atgtgcaccc aagctgcaag   2760
gtgaccgcca tgaagtgttt tctgctggag ctgcaggtca tcagcctgga gtctggcgac   2820
gccagcatcc acgatacagt ggagaacctg atcatcctgg ccaacaattc cctgtctagc   2880
aacggcaatg tgaccgagtc tggctgcaag gagtgtgagg agctggagga aagaacatc   2940
aaggagttcc tgcagagctt tgtgcacatc gtgcagatgt tcatcaatac aagcggaggc   3000
ggaggatctg gcggcggcgg cagtggcgga ggaggaagcg gctccggcgc caccaacttt   3060
tccctgctga gcaggccgg cgacgtgaa gaaaatcctg gaccaatggc acctaggaga   3120
gcaaggggat gcagaaccct gggcctgcca gccctgttat tactgctgct gctgaggccc   3180
cctgcaacaa gggaatcac ctgtccaccc cctatgagcg tggagcacgc cgacatctgg   3240
gtgaagtctt acagcctgta ttcccgggag agatacatct gcaactctgg cttcaagagg   3300
aaggccggca catcctctct gaccgagtgc gtgctgaaca aggccaccaa tgtggcccac   3360
tggaccacac cctctctgaa gtgcatccgg gaccccgccc tggtgcacca gcggcccgca   3420
ccacccagca cagtgaccac agcaggagtg accccacagc ctgagtccct gtctccaagc   3480
ggcaaggagc cagcagcaag ctccccttct agcaacaata cagcagcaac cacagcagca   3540
atcgtgcctg gctcccagct gatgcccctcc aagtctccta gcaccggcac cacagagatc   3600
```

| | |
|---|---|
| tcctctcacg agagctccca cggcacaccc agccagacca cagccaagaa ttgggagctg | 3660 |
| accgcatccg cctctcacca gcctccaggc gtgtaccctc agggccactc cgataccaca | 3720 |
| gtggccatca gcacatccac cgtgctgctg tgcggcctga gcgccgtgtc cctgctggcc | 3780 |
| tgttatctga agagcaggca gaccccacct ctggcatccg tggagatgga ggccatggag | 3840 |
| gccctgcccg tcacctgggg gacatcatca cgggacgaag acctggagaa ctgctcacat | 3900 |
| catctgtaag at | 3912 |

<210> SEQ ID NO 566
<211> LENGTH: 3808
<212> TYPE: DNA
<213> ORGANISM: Artificial Sequence
<220> FEATURE:
<223> OTHER INFORMATION: Synthetic sequence

<400> SEQUENCE: 566

| | |
|---|---|
| acattgatta ttgactagtt attaatagta atcaattacg gggtcattag ttcatagccc | 60 |
| atatatggag ttccgcgtta cataacttac ggtaaatggc cgtaactaat aactgatcaa | 120 |
| taattatcat tagttaatgc cccagtaatc aagtatcggg tatataccct aaggccgcct | 180 |
| ggctgaccgc ccaacgaccc ccgcccattg acgtcaataa tgacgtatgt tcccatagta | 240 |
| acgccaatag ggactttcca ttgacgtcaa tgggtggagt atttacggta aactgcccac | 300 |
| ttggcagtac atcaagtgta tcatatgcca agtacgcccc ctattgacgt caatgacggt | 360 |
| aaatggcccg cctggcatta tgcccagtac atgaccttat gggactttcc tacttggcag | 420 |
| tacatctacg tattagtcat cgctattacc atggtgatgc ggttttggca gtacatcaat | 480 |
| gggcgtggat agcggtttga ctcacgggga tttccaagtc tccaccccat tgacgtcaat | 540 |
| gggagtttgt tttggcacca aaatcaacgg gactttccaa aatgtcgtaa caactccgcc | 600 |
| ccattgacgc aaatgggcgg taggcgtgta cggtgggagg tctatataag cagagctctc | 660 |
| tggctaacta gagaacccac tgcttactgg cttatcgaaa ttaatacgac tcactatagg | 720 |
| gagacccaag ctggctagcg tttaaactta agcttggtac cgagctcgga tccactagtc | 780 |
| cagtgtggtg gaattcgcca ccatgtgccc tcagaaactg acaatctcct ggttcgctat | 840 |
| cgtcctgctg gtctctcctc tgatggctat gtgggaactg gaaaaagatg tgtacgtggt | 900 |
| ggaggtggac tggacacccg atgccctgg cgagacagtg aacctgacat gcgacacccc | 960 |
| cgaggaggac gacatcacct ggacatccga tcagaggcac ggcgtgatcg gctctggcaa | 1020 |
| gaccctgaca atcaccgtga aggagttcct ggacgccggc cagtacacat gtcacaaggg | 1080 |
| cggcgagaca ctgagccact cccacctgct gctgcacaag aaggagaacg gcatctggtc | 1140 |
| cacagagatc ctgaagaact tcaagaataa gaccttctgc aagtgcgagg cccccaatta | 1200 |
| tagcggccgg ttcacctgtt cctggctggt gcagagaaac atggacctga gtttaatat | 1260 |
| caagagctcc tctagctccc ctgatagcag ggcagtgaca tgcggaatgg catctctgag | 1320 |
| cgccgagaag gtgaccctgg accagagaga ttacgagaag tattccgtgt cttgccagga | 1380 |
| ggatgtgaca tgtcccaccg ccgaggagac actgcctatc gagctggccc tggaggcaag | 1440 |
| gcagcagaac aagtacgaga attatagcac ctccttcttt atcagagaca tcatcaagcc | 1500 |
| agatccccct aagaacctgc agatgaagcc cctgaagaac agccaggtcg aggtgtcttg | 1560 |
| ggagtaccct gactcttgga gcacaccaca ctcttatttc agcctgaagt tctttgtgag | 1620 |
| gatccagcgc aagaaggaga agatgaagga gacagaggag ggctgtaacc agaagggcgc | 1680 |
| ctttctggtg gagaagacat ccaccgaggt gcagtgcaag ggaggaaacg tgtgcgtgca | 1740 |

```
ggcacaggat cggtactata attctagctg ctctaagtgg gcctgcgtgc cctgtagggt    1800
gcgcagcgga ggaggaggat ccggaggagg cggctctgga ggaggaggat ctatgtgcca    1860
gagcaggtac ctgctgttcc tggccaccct ggccctgctg aaccacctgt ccctggcacg    1920
cgtgatccca gtgtctggac cagcccggtg cctgtcccag tctagaaatc tgctgaagac    1980
cacagacgat atggtgaaga cagccaggga gaagctgaag cactatagct gtaccgccga    2040
ggacatcgat cacgaggaca tcacgcgcga tcagacatcc accctgaaga cctgcctgcc    2100
tctggagctg cacaagaacg agtcttgtct ggccacacgg gagacaagct ctaccacaag    2160
aggcagctgc ctgccacccc agaagacatc cctgatgatg accctgtgcc tgggcagcat    2220
ctacgaggac ctgaagatgt atcagacaga gtttcaggcc atcaatgccg ccctgcagaa    2280
ccacaatcac cagcagatca tcctggacaa gggcatgctg gtggccatcg atgagctgat    2340
gcagtccctg aaccacaatg gcgagacact gaggcagaag cctccagtgg gcgaggccga    2400
tccttaccgc gtgaagatga agctgtgcat cctgctgcac gccttcagca aagggtggt     2460 gaccatcaac cgcgtgatgg gctatctgag ctccgccgga ggaggaggaa gcggcggagg    2520
aggcagcggc ggcggcggca gcggctccgg cgccaccaac ttttctctgc tgaagcaggc    2580
aggcgacgtg gaggagaatc caggacccat gaggatcagc aagccacacc tgcgctctat    2640
cagcatccag tgctacctgt gcctgctgct gaatagccac ttcctgacag aggccggcat    2700
ccacgtgttc atcctgggct gttttttccgc cggcctgcca aagaccgagg ccaactgggt    2760
gaatgtgatc tctgacctga agaagatcga ggatctgatc cagagcatgc acatcgacgc    2820
cacactgtat accgagtctg atgtgcaccc cagctgcaag gtgaccgcca tgaagtgttt    2880
tctgctggag ctgcaggtca tcagcctgga gtctggcgac gcctccatcc acgatacagt    2940
ggagaacctg atcatcctgg ccaacaatag cctgtctagc aacggcaatg tgaccgagtc    3000
cggctgcaag gagtgtgagg agctggagga gaagaacatc aaggagttcc tgcagagctt    3060
tgtgcacatc gtgcagatgt tcatcaatac ctccggcggc ggaggatctg gcggcggcgg    3120
ctccggcggg ggaggatcct gcggcggcaa ggtgtctgcc ctgaaggaga aggtgagcgc    3180
cctgaaggaa aaggtgtccg ccctgaagga aaaggtgtct gccctgaagg aaaaggtgag    3240
cgccctgaag gagggcggcg gaggatctgg gggcggcggc tccggggag gaggatccgg    3300 ctctggcgcc acaaacttct ccctgctgaa gcaggccggc gacgtggaag aaaatcctgg    3360
accaatggca cctaggagag caaggggatg cagaaccctg ggcctgccag ccctgttatt    3420
actgctgctg ctgaggcccc ctgcaacaag gggaatcacc tgtccaccc ctatgagcgt     3480 ggagcacgcc gacatctggg tgaagagcta ctccctgtat tctcgggaga gatacatctg    3540
caatagcggc tttaagcgga aggccggcac atcctctctg accgagtgcg tgctgaacaa    3600
ggccaccaat gtggcccact ggaccacacc ctccctgaag tgcatcagag atggcggcgg    3660
cggatccgga ggaggcgggt ctggcggcgg cggcagcgag gtgtccgccc tggagaagga    3720
ggtgagcgcc ctggaaaag aggtgagtgc tctggaaaag gaagtgtctg ccctggaaaa    3780
ggaagtgtct gccctggaaa aatgagat                                       3808
```

<210> SEQ ID NO 567
<211> LENGTH: 4247
<212> TYPE: DNA
<213> ORGANISM: Artificial Sequence
<220> FEATURE:
<223> OTHER INFORMATION: Synthetic sequence

<400> SEQUENCE: 567

```
acattgatta ttgactagtt attaatagta atcaattacg gggtcattag ttcatagccc      60
atatatggag ttccgcgtta cataacttac ggtaaatggc ccgcctggct gaccgcccaa     120
cgacccccgc ccattgacgt caataatgac gtatgttccc atagtaacgc caatagggac     180
tttccattga cgtcaatggg tggagtattt acggtaaact gcccacttgg cagtacatca     240
agtgtatcat atgccaagta cgccccctat tgacgtcaat gacggtaaat ggcccgcctg     300
gcattatgcc cagtacatga ccttatggga ctttcctact tggcagtaca tctacgtatt     360
agtcatcgct attaccatgg tgatgcggtt ttggcagtac atcaatgggc gtggatagcg     420
gtttgactca cggggatttc caagtctcca ccccattgac gtcaatggga gtttgttttg     480
gcaccaaaat caacgggact ttccaaaatg tcgtaacaac tccgcccat tgacgcaaat     540
gggcggtagg cgtgtacggt gggaggtcta taagcaga gctctctggc taactagaga     600
acccactgct tactggctta tcgaaattaa tacgactcac tatagggaga cccaagctgg     660
ctagcgttta aacttaagct tggtaccgag ctcggatcca ctagtccagt gtggtggaat     720
tcgccaccat gtgccccag aaactgacaa tctcttggtt cgcaatcgtg ctgctggtct     780
cacccctgat ggctatgtgg gagctggaaa aggatgtgta cgtggtggag gtggactgga     840
caccagatgc cccggcgag acagtgaacc tgacatgcga caccccgag gaggacgaca     900
tcacctggac atccgatcag cggcacggcg tgatcggctc tggcaagacc ctgacaatca     960
ccgtgaagga gttcctggac gccggccagt acacatgtca aagggcggc gagacactgt    1020
cccactctca cctgctgctg cacaagaagg agaacggcat ctggagcaca gagatcctga    1080
agaacttcaa gaataagacc tttctgaagt gcgaggcccc aaattattcc ggcaggttca    1140
cctgttcttg gctggtgcag cgcaacatgg acctgaagtt taatatcaag agctcctcta    1200
gctccccga ttccagggca gtgacatgcg gaatggcaag cctgtccgcc gagaaggtga    1260
ccctggacca gagggattac gagaagtatt ctgtgagctg ccaggaggat gtgacatgtc    1320
ctaccgccga ggagacactg ccaatcgagc tggcccctga ggccaggcag cagaacaagt    1380
acgagaatta ttccacctct ttctttatcc gcgacatcat caagccagat ccccctaaga    1440
acctgcagat gaagcccctg aagaacagcc aggtcgaggt gagctgggag tacccagaca    1500
gctggtccac accccactcc tatttctctc tgaagttctt tgtgaggatc cagcgcaaga    1560
aggagaagat gaaggagaca gaggagggct gtaaccagaa gggcgccttt ctggtggaga    1620
agacatccac cgaggtgcag tgcaaggggag gaaacgtgtg cgtgcaggca caggatagat    1680
actataattc tagctgcagc aagtgggcct gcgtgccttg taggtgcgc tccggaggcg    1740
gcggctctgg aggaggagga agcggaggag gaggaagcat gtgccagtcc cggtacctgc    1800
tgttcctggc caccctggcc ctgctgaacc acctgtctct ggccagagtg atccctgtga    1860
gcggaccagc aaggtgcctg tctcagcagca gaaatctgct gaagaccaca gacgatatgg    1920
tgaagacagc ccgggagaag ctgaagcact atagctgtac cgccgaggac atcgatcacg    1980
aggacatcac aagagatcag acatccaccc tgaagacctg cctgccctg gagctgcaca    2040
agaacgagtc ttgtctggcc acacgggaga caagctctac cacaagaggc tcctgcctgc    2100
caccccagaa gacatctctg atgatgaccc tgtgcctggg cagcatctac gaggacctga    2160
agatgtatca gaccgagttt caggccatca atgccgccct gcagaaccac aatcaccagc    2220
agatcatcct ggacaagggc atgctggtgg ccatcgatga gctgatgcag agcctgaacc    2280
acaatggcga gacactgagg cagaagcctc cagtgggaga ggcagatcca tacagagtga    2340
```

```
agatgaagct gtgcatcctg ctgcacgcct tctccacaag ggtggtgacc atcaaccgcg    2400
tgatgggcta tctgagctcc gccggaggag gaggatccgg cggaggaggc tctggcggcg    2460
gcggctccgg ctctggcgcc accaactttt ctctgctgaa gcaggcaggc gacgtggagg    2520
agaatccagg acccatgagg atcagcaagc cccacctgcg cagcatctcc atccagtgct    2580
acctgtgcct gctgctgaat agccacttcc tgacagaggc cggcatccac gtgttcatcc    2640
tgggctgttt ttccgccggc ctgcctaaga ccgaggccaa ctgggtgaat gtgatctctg    2700
acctgaagaa gatcgaggat ctgatccaga gcatgcacat cgacgccaca ctgtataccg    2760
agagcgatgt gcacccatcc tgcaaggtga ccgccatgga gtgttttctg ctggagctgc    2820
aggtcatcag cctggagtcc ggcgacgcaa gcatccacga tacagtggag aacctgatca    2880
tcctggccaa caatagcctg tctagcaacg gcaatgtgac cgagtccggc tgcaaggagt    2940
gtgaggagct ggaggagaag aacatcaagg agttcctgca gtcctttgtg cacatcgtgc    3000
agatgttcat caatacttcc ggcggcggcg gcagtggcgg aggaggaagc ggaggcggcg    3060
gctcttgcgg cggcaaggtg agcgccctga aggagaaggt gtccgccctg aaggaaaagg    3120
tgtctgccct gaaggagaag gtgagcgccc tgaaggaaaa ggtgtccgcc ctgaaggagg    3180
ggggcggcgg cagcggcgga ggagggagcg ggggaggcgg ctctggcagc ggcgccacaa    3240
acttcagcct gctgaagcag gccggcgacg tggaagaaaa tcctggacca atggcaccta    3300
ggagagcaag gggatgcaga accctgggcc tgccagccct gttattactg ctgctgctga    3360 ggcccctgc aacaagggga atcacctgtc cacccctat gagcgtggag cacgccgaca    3420
tctgggtgaa gtcctactct ctgtatagcc gggagagata catctgcaat tccggcttta    3480
agaggaaggc cggcacatcc tctctgaccg agtgcgtgct gaacaaggcc accaatgtgg    3540
cccactggac cacaccatcc ctgaagtgca tccgggaccc cgccctggtg caccagcggc    3600
ccgcaccacc atctacagtg accacagcag gagtgacccc acagcctgag agcctgtccc    3660
catctggcaa ggagccagca gcaagctccc cttctagcaa caatacagca gcaaccacag    3720
cagcaatcgt gcctggctcc cagctgatgc ccagcaagtc cccttctacc ggcaccacag    3780
agatctcctc tcacgagagc tcccacggca caccagcca gaccacagcc aagaactggg    3840
agctgaccgc aagcgcctcc caccagcctc caggcgtgta ccctcagggc cactccgata    3900
ccacagtggc catctctaca agcaccgtgc tgctgtgcgg cctgtctgcc gtgagcctgc    3960
tggcctgtta tctgaagtct aggcagaccc cacctctggc aagcgtggag atggaggcaa    4020
tggaggccct gccagtgaca tggggcacct ctagccgcga cgaggatctg gagaattgca    4080
gccaccacct gggaggagga ggatcaggcg gcggcgggtc cggcggcggc ggatccgagg    4140
tgtctgccct ggagaaggag gtgtccgccc tggaaaaaga gtgtcagcc ctggagaaag    4200 aagtgtcagc cctggaaaaa gaggtgtctg ccctggaaaa ataagat                 4247
```

<210> SEQ ID NO 568
<211> LENGTH: 897
<212> TYPE: PRT
<213> ORGANISM: Artificial Sequence
<220> FEATURE:
<223> OTHER INFORMATION: Synthetic sequence

<400> SEQUENCE: 568

```
Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
```

-continued

```
                20                  25                  30
Val Glu Val Asp Trp Thr Pro Asp Ala Pro Gly Glu Thr Val Asn Leu
            35                  40                  45
Thr Cys Asp Thr Pro Glu Glu Asp Asp Ile Thr Trp Thr Ser Asp Gln
        50                  55                  60
Arg His Gly Val Ile Gly Ser Gly Lys Thr Leu Thr Ile Thr Val Lys
65                  70                  75                  80
Glu Phe Leu Asp Ala Gly Gln Tyr Thr Cys His Lys Gly Gly Glu Thr
                85                  90                  95
Leu Ser His Ser His Leu Leu Leu His Lys Lys Glu Asn Gly Ile Trp
            100                 105                 110
Ser Thr Glu Ile Leu Lys Asn Phe Lys Asn Lys Thr Phe Leu Lys Cys
        115                 120                 125
Glu Ala Pro Asn Tyr Ser Gly Arg Phe Thr Cys Ser Trp Leu Val Gln
            130                 135                 140
Arg Asn Met Asp Leu Lys Phe Asn Ile Lys Ser Ser Ser Ser Ser Pro
145                 150                 155                 160
Asp Ser Arg Ala Val Thr Cys Gly Met Ala Ser Leu Ser Ala Glu Lys
                165                 170                 175
Val Thr Leu Asp Gln Arg Asp Tyr Glu Lys Tyr Ser Val Ser Cys Gln
            180                 185                 190
Glu Asp Val Thr Cys Pro Thr Ala Glu Thr Leu Pro Ile Glu Leu
        195                 200                 205
Ala Leu Glu Ala Arg Gln Gln Asn Lys Tyr Glu Asn Tyr Ser Thr Ser
    210                 215                 220
Phe Phe Ile Arg Asp Ile Ile Lys Pro Asp Pro Lys Asn Leu Gln
225                 230                 235                 240
Met Lys Pro Leu Lys Asn Ser Gln Val Glu Val Ser Trp Glu Tyr Pro
                245                 250                 255
Asp Ser Trp Ser Thr Pro His Ser Tyr Phe Ser Leu Lys Phe Phe Val
            260                 265                 270
Arg Ile Gln Arg Lys Lys Glu Lys Met Lys Glu Thr Glu Glu Gly Cys
        275                 280                 285
Asn Gln Lys Gly Ala Phe Leu Val Glu Lys Thr Ser Thr Glu Val Gln
    290                 295                 300
Cys Lys Gly Gly Asn Val Cys Val Gln Ala Gln Asp Arg Tyr Tyr Asn
305                 310                 315                 320
Ser Ser Cys Ser Lys Trp Ala Cys Val Pro Cys Arg Val Arg Ser Gly
                325                 330                 335
Gly Gly Gly Ser Gly Gly Gly Ser Gly Gly Gly Ser Met Cys
            340                 345                 350
Gln Ser Arg Tyr Leu Leu Phe Leu Ala Thr Leu Ala Leu Leu Asn His
        355                 360                 365
Leu Ser Leu Ala Arg Val Ile Pro Val Ser Gly Pro Ala Arg Cys Leu
    370                 375                 380
Ser Gln Ser Arg Asn Leu Leu Lys Thr Thr Asp Asp Met Val Lys Thr
385                 390                 395                 400
Ala Arg Glu Lys Leu Lys His Tyr Ser Cys Thr Ala Glu Asp Ile Asp
                405                 410                 415
His Glu Asp Ile Thr Arg Asp Gln Thr Ser Thr Leu Lys Thr Cys Leu
            420                 425                 430
Pro Leu Glu Leu His Lys Asn Glu Ser Cys Leu Ala Thr Arg Glu Thr
        435                 440                 445
```

```
Ser Ser Thr Thr Arg Gly Ser Cys Leu Pro Pro Gln Lys Thr Ser Leu
    450                 455                 460

Met Met Thr Leu Cys Leu Gly Ser Ile Tyr Glu Asp Leu Lys Met Tyr
465                 470                 475                 480

Gln Thr Glu Phe Gln Ala Ile Asn Ala Ala Leu Gln Asn His Asn His
                    485                 490                 495

Gln Gln Ile Ile Leu Asp Lys Gly Met Leu Val Ala Ile Asp Glu Leu
                500                 505                 510

Met Gln Ser Leu Asn His Asn Gly Glu Thr Leu Arg Gln Lys Pro Pro
            515                 520                 525

Val Gly Glu Ala Asp Pro Tyr Arg Val Lys Met Lys Leu Cys Ile Leu
    530                 535                 540

Leu His Ala Phe Ser Thr Arg Val Val Thr Ile Asn Arg Val Met Gly
545                 550                 555                 560

Tyr Leu Ser Ser Ala Gly Gly Gly Ser Gly Gly Gly Ser Gly
                    565                 570                 575

Gly Gly Gly Ser Gly Ser Gly Ala Thr Asn Phe Ser Leu Leu Lys Gln
                580                 585                 590

Ala Gly Asp Val Glu Glu Asn Pro Gly Pro Met Arg Ile Ser Lys Pro
                595                 600                 605

His Leu Arg Ser Ile Ser Ile Gln Cys Tyr Leu Cys Leu Leu Leu Asn
            610                 615                 620

Ser His Phe Leu Thr Glu Ala Gly Ile His Val Phe Ile Leu Gly Cys
625                 630                 635                 640

Phe Ser Ala Gly Leu Pro Lys Thr Glu Ala Asn Trp Val Asn Val Ile
                    645                 650                 655

Ser Asp Leu Lys Lys Ile Glu Asp Leu Ile Gln Ser Met His Ile Asp
                660                 665                 670

Ala Thr Leu Tyr Thr Glu Ser Asp Val His Pro Ser Cys Lys Val Thr
                675                 680                 685

Ala Met Lys Cys Phe Leu Leu Glu Leu Gln Val Ile Ser Leu Glu Ser
            690                 695                 700

Gly Asp Ala Ser Ile His Asp Thr Val Glu Asn Leu Ile Ile Leu Ala
705                 710                 715                 720

Asn Asn Ser Leu Ser Ser Asn Gly Asn Val Thr Glu Ser Gly Cys Lys
                    725                 730                 735

Glu Cys Glu Glu Leu Glu Glu Lys Asn Ile Lys Glu Phe Leu Gln Ser
                740                 745                 750

Phe Val His Ile Val Gln Met Phe Ile Asn Thr Ser Gly Gly Gly Gly
            755                 760                 765

Ser Gly Gly Gly Ser Gly Gly Gly Ser Gly Ser Gly Ala Thr
770                 775                 780

Asn Phe Ser Leu Leu Lys Gln Ala Gly Asp Val Glu Glu Asn Pro Gly
785                 790                 795                 800

Pro Met Ala Pro Arg Arg Ala Arg Gly Cys Arg Thr Leu Gly Leu Pro
                805                 810                 815

Ala Leu Leu Leu Leu Leu Leu Leu Arg Pro Pro Ala Thr Arg Gly Ile
                820                 825                 830

Thr Cys Pro Pro Pro Met Ser Val Glu His Ala Asp Ile Trp Val Lys
            835                 840                 845

Ser Tyr Ser Leu Tyr Ser Arg Glu Arg Tyr Ile Cys Asn Ser Gly Phe
850                 855                 860
```

-continued

```
Lys Arg Lys Ala Gly Thr Ser Ser Leu Thr Glu Cys Val Leu Asn Lys
865                 870                 875                 880

Ala Thr Asn Val Ala His Trp Thr Thr Pro Ser Leu Lys Cys Ile Arg
            885                 890                 895

Asp

<210> SEQ ID NO 569
<211> LENGTH: 1068
<212> TYPE: PRT
<213> ORGANISM: Artificial Sequence
<220> FEATURE:
<223> OTHER INFORMATION: Synthetic sequence

<400> SEQUENCE: 569

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
                20                  25                  30

Val Glu Val Asp Trp Thr Pro Asp Ala Pro Gly Glu Thr Val Asn Leu
            35                  40                  45

Thr Cys Asp Thr Pro Glu Glu Asp Asp Ile Thr Trp Thr Ser Asp Gln
50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser Gly
```

```
                    325                 330                 335
Gly Gly Gly Ser Gly Gly Gly Ser Gly Gly Gly Ser Met Cys
                340                 345                 350
Gln Ser Arg Tyr Leu Leu Phe Leu Ala Thr Leu Ala Leu Leu Asn His
                355                 360                 365
Leu Ser Leu Ala Arg Val Ile Pro Val Ser Gly Pro Ala Arg Cys Leu
                370                 375                 380
Ser Gln Ser Arg Asn Leu Leu Lys Thr Thr Asp Asp Met Val Lys Thr
385                 390                 395                 400
Ala Arg Glu Lys Leu Lys His Tyr Ser Cys Thr Ala Glu Asp Ile Asp
                405                 410                 415
His Glu Asp Ile Thr Arg Asp Gln Thr Ser Thr Leu Lys Thr Cys Leu
                420                 425                 430
Pro Leu Glu Leu His Lys Asn Glu Ser Cys Leu Ala Thr Arg Glu Thr
                435                 440                 445
Ser Ser Thr Thr Arg Gly Ser Cys Leu Pro Pro Gln Lys Thr Ser Leu
450                 455                 460
Met Met Thr Leu Cys Leu Gly Ser Ile Tyr Glu Asp Leu Lys Met Tyr
465                 470                 475                 480
Gln Thr Glu Phe Gln Ala Ile Asn Ala Ala Leu Gln Asn His Asn His
                485                 490                 495
Gln Gln Ile Ile Leu Asp Lys Gly Met Leu Val Ala Ile Asp Glu Leu
                500                 505                 510
Met Gln Ser Leu Asn His Asn Gly Glu Thr Leu Arg Gln Lys Pro Pro
                515                 520                 525
Val Gly Glu Ala Asp Pro Tyr Arg Val Lys Met Lys Leu Cys Ile Leu
                530                 535                 540
Leu His Ala Phe Ser Thr Arg Val Val Thr Ile Asn Arg Val Met Gly
545                 550                 555                 560
Tyr Leu Ser Ser Ala Gly Gly Gly Ser Gly Gly Gly Gly Ser Gly
                565                 570                 575
Gly Gly Gly Ser Gly Ser Gly Ala Thr Asn Phe Ser Leu Leu Lys Gln
                580                 585                 590
Ala Gly Asp Val Glu Glu Asn Pro Gly Pro Met Arg Ile Ser Lys Pro
                595                 600                 605
His Leu Arg Ser Ile Ser Ile Gln Cys Tyr Leu Cys Leu Leu Leu Asn
                610                 615                 620
Ser His Phe Leu Thr Glu Ala Gly Ile His Val Phe Ile Leu Gly Cys
625                 630                 635                 640
Phe Ser Ala Gly Leu Pro Lys Thr Glu Ala Asn Trp Val Asn Val Ile
                645                 650                 655
Ser Asp Leu Lys Lys Ile Glu Asp Leu Ile Gln Ser Met His Ile Asp
                660                 665                 670
Ala Thr Leu Tyr Thr Glu Ser Asp Val His Pro Ser Cys Lys Val Thr
                675                 680                 685
Ala Met Lys Cys Phe Leu Leu Glu Leu Gln Val Ile Ser Leu Glu Ser
                690                 695                 700
Gly Asp Ala Ser Ile His Asp Thr Val Glu Asn Leu Ile Ile Leu Ala
705                 710                 715                 720
Asn Asn Ser Leu Ser Ser Asn Gly Asn Val Thr Glu Ser Gly Cys Lys
                725                 730                 735
Glu Cys Glu Glu Leu Glu Glu Lys Asn Ile Lys Glu Phe Leu Gln Ser
                740                 745                 750
```

-continued

```
Phe Val His Ile Val Gln Met Phe Ile Asn Thr Ser Gly Gly Gly
        755                 760                 765
Ser Gly Gly Gly Ser Gly Gly Gly Ser Gly Ser Gly Ala Thr
    770                 775                 780
Asn Phe Ser Leu Leu Lys Gln Ala Gly Asp Val Glu Glu Asn Pro Gly
785                 790                 795                 800
Pro Met Ala Pro Arg Arg Ala Arg Gly Cys Arg Thr Leu Gly Leu Pro
                805                 810                 815
Ala Leu Leu Leu Leu Leu Leu Arg Pro Pro Ala Thr Arg Gly Ile
            820                 825                 830
Thr Cys Pro Pro Pro Met Ser Val Glu His Ala Asp Ile Trp Val Lys
        835                 840                 845
Ser Tyr Ser Leu Tyr Ser Arg Glu Arg Tyr Ile Cys Asn Ser Gly Phe
        850                 855                 860
Lys Arg Lys Ala Gly Thr Ser Ser Leu Thr Glu Cys Val Leu Asn Lys
865                 870                 875                 880
Ala Thr Asn Val Ala His Trp Thr Thr Pro Ser Leu Lys Cys Ile Arg
                885                 890                 895
Asp Pro Ala Leu Val His Gln Arg Pro Ala Pro Pro Ser Thr Val Thr
            900                 905                 910
Thr Ala Gly Val Thr Pro Gln Pro Glu Ser Leu Ser Pro Ser Gly Lys
        915                 920                 925
Glu Pro Ala Ala Ser Ser Pro Ser Ser Asn Asn Thr Ala Ala Thr Thr
    930                 935                 940
Ala Ala Ile Val Pro Gly Ser Gln Leu Met Pro Ser Lys Ser Pro Ser
945                 950                 955                 960
Thr Gly Thr Thr Glu Ile Ser Ser His Glu Ser Ser His Gly Thr Pro
                965                 970                 975
Ser Gln Thr Thr Ala Lys Asn Trp Glu Leu Thr Ala Ser Ala Ser His
            980                 985                 990
Gln Pro Pro Gly Val Tyr Pro Gln Gly His Ser Asp Thr Thr Val Ala
        995                 1000                1005
Ile Ser Thr Ser Thr Val Leu Leu Cys Gly Leu Ser Ala Val Ser
        1010                1015                1020
Leu Leu Ala Cys Tyr Leu Lys Ser Arg Gln Thr Pro Pro Leu Ala
        1025                1030                1035
Ser Val Glu Met Glu Ala Met Glu Ala Leu Pro Val Thr Trp Gly
        1040                1045                1050
Thr Ser Ser Arg Asp Glu Asp Leu Glu Asn Cys Ser His His Leu
        1055                1060                1065

<210> SEQ ID NO 570
<211> LENGTH: 1000
<212> TYPE: PRT
<213> ORGANISM: Artificial Sequence
<220> FEATURE:
<223> OTHER INFORMATION: Synthetic sequence

<400> SEQUENCE: 570

Met Cys Pro Gln Lys Leu Thr Ile Ser Trp Phe Ala Ile Val Leu Leu
1               5                   10                  15
Val Ser Pro Leu Met Ala Met Trp Glu Leu Glu Lys Asp Val Tyr Val
            20                  25                  30
Val Glu Val Asp Trp Thr Pro Asp Ala Pro Gly Glu Thr Val Asn Leu
        35                  40                  45
```

```
Thr Cys Asp Thr Pro Glu Glu Asp Ile Thr Trp Thr Ser Asp Gln
     50                  55                  60

Arg His Gly Val Ile Gly Ser Gly Lys Thr Leu Thr Ile Thr Val Lys
 65              70                  75                      80

Glu Phe Leu Asp Ala Gly Gln Tyr Thr Cys His Lys Gly Gly Glu Thr
                 85                  90                  95

Leu Ser His Ser His Leu Leu Leu His Lys Lys Glu Asn Gly Ile Trp
             100                 105                 110

Ser Thr Glu Ile Leu Lys Asn Phe Lys Asn Lys Thr Phe Leu Lys Cys
             115                 120                 125

Glu Ala Pro Asn Tyr Ser Gly Arg Phe Thr Cys Ser Trp Leu Val Gln
 130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                 165                 170                 175

Val Thr Leu Asp Gln Arg Asp Tyr Glu Lys Tyr Ser Val Ser Cys Gln
             180                 185                 190

Glu Asp Val Thr Cys Pro Thr Ala Glu Glu Thr Leu Pro Ile Glu Leu
             195                 200                 205

Ala Leu Glu Ala Arg Gln Gln Asn Lys Tyr Glu Asn Tyr Ser Thr Ser
210                 215                 220

Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
                 245                 250                 255

Asp Ser Trp Ser Thr Pro His Ser Tyr Phe Ser Leu Lys Phe Phe Val
             260                 265                 270

Arg Ile Gln Arg Lys Lys Glu Lys Met Lys Glu Thr Glu Glu Gly Cys
             275                 280                 285

Asn Gln Lys Gly Ala Phe Leu Val Glu Lys Thr Ser Thr Glu Val Gln
290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser Gly
                 325                 330                 335

Gly Gly Ser Gly Gly Gly Ser Gly Gly Gly Ser Met Cys
             340                 345                 350

Gln Ser Arg Tyr Leu Leu Phe Leu Ala Thr Leu Ala Leu Leu Asn His
             355                 360                 365

Leu Ser Leu Ala Arg Val Ile Pro Val Ser Gly Pro Ala Arg Cys Leu
370                 375                 380

Ser Gln Ser Arg Asn Leu Leu Lys Thr Thr Asp Asp Met Val Lys Thr
385                 390                 395                 400

Ala Arg Glu Lys Leu Lys His Tyr Ser Cys Thr Ala Glu Asp Ile Asp
                 405                 410                 415

His Glu Asp Ile Thr Arg Asp Gln Thr Ser Thr Leu Lys Thr Cys Leu
             420                 425                 430

Pro Leu Glu Leu His Lys Asn Glu Ser Cys Leu Ala Thr Arg Glu Thr
             435                 440                 445

Ser Ser Thr Thr Arg Gly Ser Cys Leu Pro Pro Gln Lys Thr Ser Leu
450                 455                 460
```

```
Met Met Thr Leu Cys Leu Gly Ser Ile Tyr Glu Asp Leu Lys Met Tyr
465                 470                 475                 480

Gln Thr Glu Phe Gln Ala Ile Asn Ala Ala Leu Gln Asn His Asn His
                485                 490                 495

Gln Gln Ile Ile Leu Asp Lys Gly Met Leu Val Ala Ile Asp Glu Leu
            500                 505                 510

Met Gln Ser Leu Asn His Asn Gly Glu Thr Leu Arg Gln Lys Pro Pro
        515                 520                 525

Val Gly Glu Ala Asp Pro Tyr Arg Val Lys Met Lys Leu Cys Ile Leu
    530                 535                 540

Leu His Ala Phe Ser Thr Arg Val Val Thr Ile Asn Arg Val Met Gly
545                 550                 555                 560

Tyr Leu Ser Ser Ala Gly Gly Gly Ser Gly Gly Gly Ser Gly
                565                 570                 575

Gly Gly Gly Ser Gly Ser Gly Ala Thr Asn Phe Ser Leu Leu Lys Gln
            580                 585                 590

Ala Gly Asp Val Glu Glu Asn Pro Gly Pro Met Arg Ile Ser Lys Pro
        595                 600                 605

His Leu Arg Ser Ile Ser Ile Gln Cys Tyr Leu Cys Leu Leu Leu Asn
        610                 615                 620

Ser His Phe Leu Thr Glu Ala Gly Ile His Val Phe Ile Leu Gly Cys
625                 630                 635                 640

Phe Ser Ala Gly Leu Pro Lys Thr Glu Ala Asn Trp Val Asn Val Ile
                645                 650                 655

Ser Asp Leu Lys Lys Ile Glu Asp Leu Ile Gln Ser Met His Ile Asp
        660                 665                 670

Ala Thr Leu Tyr Thr Glu Ser Asp Val His Pro Ser Cys Lys Val Thr
        675                 680                 685

Ala Met Lys Cys Phe Leu Leu Glu Leu Gln Val Ile Ser Leu Glu Ser
        690                 695                 700

Gly Asp Ala Ser Ile His Asp Thr Val Glu Asn Leu Ile Ile Leu Ala
705                 710                 715                 720

Asn Asn Ser Leu Ser Ser Asn Gly Asn Val Thr Glu Ser Gly Cys Lys
                725                 730                 735

Glu Cys Glu Glu Leu Glu Glu Lys Asn Ile Lys Glu Phe Leu Gln Ser
            740                 745                 750

Phe Val His Ile Val Gln Met Phe Ile Asn Thr Ser Gly Gly Gly
        755                 760                 765

Ser Gly Gly Gly Ser Gly Gly Gly Ser Cys Gly Gly Lys Val
    770                 775                 780

Ser Ala Leu Lys Glu Lys Val Ser Ala Leu Lys Glu Lys Val Ser Ala
785                 790                 795                 800

Leu Lys Glu Lys Val Ser Ala Leu Lys Glu Lys Val Ser Ala Leu Lys
                805                 810                 815

Glu Gly Gly Gly Ser Gly Gly Gly Ser Gly Gly Gly Ser
            820                 825                 830

Gly Ser Gly Ala Thr Asn Phe Ser Leu Leu Lys Gln Ala Gly Asp Val
        835                 840                 845

Glu Glu Asn Pro Gly Pro Met Ala Pro Arg Ala Arg Gly Cys Arg
        850                 855                 860

Thr Leu Gly Leu Pro Ala Leu Leu Leu Leu Leu Leu Arg Pro Pro
865                 870                 875                 880

Ala Thr Arg Gly Ile Thr Cys Pro Pro Pro Met Ser Val Glu His Ala
```

885                 890                 895
Asp Ile Trp Val Lys Ser Tyr Ser Leu Tyr Ser Arg Glu Arg Tyr Ile
                900                 905                 910

Cys Asn Ser Gly Phe Lys Arg Lys Ala Gly Thr Ser Ser Leu Thr Glu
                915                 920                 925

Cys Val Leu Asn Lys Ala Thr Asn Val Ala His Trp Thr Thr Pro Ser
                930                 935                 940

Leu Lys Cys Ile Arg Asp Gly Gly Gly Ser Gly Gly Gly Gly Ser
945                 950                 955                 960

Gly Gly Gly Gly Ser Glu Val Ser Ala Leu Glu Lys Glu Val Ser Ala
                965                 970                 975

Leu Glu Lys Glu Val Ser Ala Leu Glu Lys Glu Val Ser Ala Leu Glu
                980                 985                 990

Lys Glu Val Ser Ala Leu Glu Lys
                995                 1000

<210> SEQ ID NO 571
<211> LENGTH: 1171
<212> TYPE: PRT
<213> ORGANISM: Artificial Sequence
<220> FEATURE:
<223> OTHER INFORMATION: Synthetic sequence

<400> SEQUENCE: 571

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
                20                  25                  30

Val Glu Val Asp Trp Thr Pro Asp Ala Pro Gly Glu Thr Val Asn Leu
                35                  40                  45

Thr Cys Asp Thr Pro Glu Glu Asp Ile Thr Trp Thr Ser Asp Gln
50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
                100                 105                 110

Ser Thr Glu Ile Leu Lys Asn Phe Lys Asn Lys Thr Phe Leu Lys Cys
                115                 120                 125

Glu Ala Pro Asn Tyr Ser Gly Arg Phe Thr Cys Ser Trp Leu Val Gln
                130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
                180                 185                 190

Glu Asp Val Thr Cys Pro Thr Ala Glu Glu Thr Leu Pro Ile Glu Leu
                195                 200                 205

Ala Leu Glu Ala Arg Gln Gln Asn Lys Tyr Glu Asn Tyr Ser Thr Ser
                210                 215                 220

Phe Phe Ile Arg Asp Ile Ile Lys Pro Asp Pro Lys Asn Leu Gln
225                 230                 235                 240

Met Lys Pro Leu Lys Asn Ser Gln Val Glu Val Ser Trp Glu Tyr Pro

```
                245                 250                 255
Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
            275                 280                 285

Asn Gln Lys Gly Ala Phe Leu Val Glu Lys Thr Ser Thr Glu Val Gln
            290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser Gly
            325                 330                 335

Gly Gly Gly Ser Gly Gly Gly Ser Gly Gly Gly Ser Met Cys
            340                 345                 350

Gln Ser Arg Tyr Leu Leu Phe Leu Ala Thr Leu Ala Leu Leu Asn His
            355                 360                 365

Leu Ser Leu Ala Arg Val Ile Pro Val Ser Gly Pro Ala Arg Cys Leu
            370                 375                 380

Ser Gln Ser Arg Asn Leu Leu Lys Thr Thr Asp Asp Met Val Lys Thr
385                 390                 395                 400

Ala Arg Glu Lys Leu Lys His Tyr Ser Cys Thr Ala Glu Asp Ile Asp
            405                 410                 415

His Glu Asp Ile Thr Arg Asp Gln Thr Ser Thr Leu Lys Thr Cys Leu
            420                 425                 430

Pro Leu Glu Leu His Lys Asn Glu Ser Cys Leu Ala Thr Arg Glu Thr
            435                 440                 445

Ser Ser Thr Thr Arg Gly Ser Cys Leu Pro Pro Gln Lys Thr Ser Leu
450                 455                 460

Met Met Thr Leu Cys Leu Gly Ser Ile Tyr Glu Asp Leu Lys Met Tyr
465                 470                 475                 480

Gln Thr Glu Phe Gln Ala Ile Asn Ala Ala Leu Gln Asn His Asn His
            485                 490                 495

Gln Gln Ile Ile Leu Asp Lys Gly Met Leu Val Ala Ile Asp Glu Leu
            500                 505                 510

Met Gln Ser Leu Asn His Asn Gly Glu Thr Leu Arg Gln Lys Pro Pro
            515                 520                 525

Val Gly Glu Ala Asp Pro Tyr Arg Val Lys Met Lys Leu Cys Ile Leu
            530                 535                 540

Leu His Ala Phe Ser Thr Arg Val Val Thr Ile Asn Arg Val Met Gly
545                 550                 555                 560

Tyr Leu Ser Ser Ala Gly Gly Gly Ser Gly Gly Gly Gly Ser Gly
            565                 570                 575

Gly Gly Gly Ser Gly Ser Gly Ala Thr Asn Phe Ser Leu Leu Lys Gln
            580                 585                 590

Ala Gly Asp Val Glu Glu Asn Pro Gly Pro Met Arg Ile Ser Lys Pro
            595                 600                 605

His Leu Arg Ser Ile Ser Ile Gln Cys Tyr Leu Cys Leu Leu Leu Asn
            610                 615                 620

Ser His Phe Leu Thr Glu Ala Gly Ile His Val Phe Ile Leu Gly Cys
625                 630                 635                 640

Phe Ser Ala Gly Leu Pro Lys Thr Glu Ala Asn Trp Val Asn Val Ile
            645                 650                 655

Ser Asp Leu Lys Lys Ile Glu Asp Leu Ile Gln Ser Met His Ile Asp
            660                 665                 670
```

```
Ala Thr Leu Tyr Thr Glu Ser Asp Val His Pro Ser Cys Lys Val Thr
        675                 680                 685

Ala Met Lys Cys Phe Leu Leu Glu Leu Gln Val Ile Ser Leu Glu Ser
        690                 695                 700

Gly Asp Ala Ser Ile His Asp Thr Val Glu Asn Leu Ile Ile Leu Ala
705                 710                 715                 720

Asn Asn Ser Leu Ser Ser Asn Gly Asn Val Thr Glu Ser Gly Cys Lys
                725                 730                 735

Glu Cys Glu Glu Leu Glu Glu Lys Asn Ile Lys Glu Phe Leu Gln Ser
                740                 745                 750

Phe Val His Ile Val Gln Met Phe Ile Asn Thr Ser Gly Gly Gly Gly
                755                 760                 765

Ser Gly Gly Gly Gly Ser Gly Gly Gly Gly Ser Cys Gly Gly Lys Val
770                 775                 780

Ser Ala Leu Lys Glu Lys Val Ser Ala Leu Lys Glu Lys Val Ser Ala
785                 790                 795                 800

Leu Lys Glu Lys Val Ser Ala Leu Lys Glu Lys Val Ser Ala Leu Lys
                805                 810                 815

Glu Gly Gly Gly Gly Ser Gly Gly Gly Gly Ser Gly Gly Gly Gly Ser
                820                 825                 830

Gly Ser Gly Ala Thr Asn Phe Ser Leu Leu Lys Gln Ala Gly Asp Val
        835                 840                 845

Glu Glu Asn Pro Gly Pro Met Ala Pro Arg Arg Ala Arg Gly Cys Arg
850                 855                 860

Thr Leu Gly Leu Pro Ala Leu Leu Leu Leu Leu Leu Leu Arg Pro Pro
865                 870                 875                 880

Ala Thr Arg Gly Ile Thr Cys Pro Pro Pro Met Ser Val Glu His Ala
                885                 890                 895

Asp Ile Trp Val Lys Ser Tyr Ser Leu Tyr Ser Arg Glu Arg Tyr Ile
        900                 905                 910

Cys Asn Ser Gly Phe Lys Arg Lys Ala Gly Thr Ser Ser Leu Thr Glu
        915                 920                 925

Cys Val Leu Asn Lys Ala Thr Asn Val Ala His Trp Thr Thr Pro Ser
        930                 935                 940

Leu Lys Cys Ile Arg Asp Pro Ala Leu Val His Gln Arg Pro Ala Pro
945                 950                 955                 960

Pro Ser Thr Val Thr Thr Ala Gly Val Thr Pro Gln Pro Glu Ser Leu
                965                 970                 975

Ser Pro Ser Gly Lys Glu Pro Ala Ala Ser Ser Pro Ser Ser Asn Asn
                980                 985                 990

Thr Ala Ala Thr Thr Ala Ala Ile Val Pro Gly Ser Gln Leu Met Pro
        995                 1000                1005

Ser Lys Ser Pro Ser Thr Gly Thr Thr Glu Ile Ser Ser His Glu
        1010                1015                1020

Ser Ser His Gly Thr Pro Ser Gln Thr Thr Ala Lys Asn Trp Glu
        1025                1030                1035

Leu Thr Ala Ser Ala Ser His Gln Pro Pro Gly Val Tyr Pro Gln
        1040                1045                1050

Gly His Ser Asp Thr Thr Val Ala Ile Ser Thr Ser Thr Val Leu
        1055                1060                1065

Leu Cys Gly Leu Ser Ala Val Ser Leu Leu Ala Cys Tyr Leu Lys
        1070                1075                1080
```

```
Ser Arg Gln Thr Pro Pro Leu Ala Ser Val Glu Met Glu Ala Met
    1085            1090                1095
Glu Ala Leu Pro Val Thr Trp Gly Thr Ser Ser Arg Asp Glu Asp
    1100            1105                1110
Leu Glu Asn Cys Ser His His Leu Gly Gly Gly Ser Gly Gly
    1115            1120                1125
Gly Gly Ser Gly Gly Gly Gly Ser Glu Val Ser Ala Leu Glu Lys
    1130            1135                1140
Glu Val Ser Ala Leu Glu Lys Glu Val Ser Ala Leu Glu Lys Glu
    1145            1150                1155
Val Ser Ala Leu Glu Lys Glu Val Ser Ala Leu Glu Lys
    1160            1165                1170

<210> SEQ ID NO 572
<211> LENGTH: 1230
<212> TYPE: DNA
<213> ORGANISM: Herpes Simplex Virus

<400> SEQUENCE: 572
gtgacgattc ccccaatggc cgcgcgtccc aggggaggca ggcccaccgc ggggcggccc      60
cgtcccgggg accaacccg cgccccccaa agaatatcat tagcatgcac ggcccggccc     120
ccgatttggg ggcccaaccc ggtgtccccc aaagaacccc attagcatgc ccctcccgcc     180
gacgcaacag gggcttggcc tgcgtcggtg ccccgggggct cccgccttc ccgaagaaac     240
tcattaccat acccggaacc ccaggggacc aatgcgggtt cattgagcga cccgcgggcc     300
aatgcgcgag gggccgtgtg ttccgccaaa aaagcaatta gcataaccccg gaaccccagg     360
ggagtggtta cgcgcggcgc gggaggcggg gaataccggg gttgcccatt aagggccgcg     420
ggaattgccg gaagcgggaa gggcggccgg ggccgcccat tagttacctg ggactgtgcg     480
gttgggacgg cgcccgtggg cccgggcggc cggggggcggc ggggggccgcg atggcggcgg     540
cggcgggcca tggagacaga gagcgtgccg gggtggtaga gtttgacagg caagcatgtg     600
cgtgcagagg cgagtagtgc ttgcctgtct aactcgctag tctcggccgc ggggggcccg     660
ggctgccccgc cgccgccgct ttaaagggcc gcgcgcgacc cccggggggt gtgttttggg     720
ggggggcccgt tttcggggtc tggccgctcc tcccccccgct cctccccccg ctcctccccc     780
cgctcctccc cccgctcctc ccccgctcc tccccccgct cctcccccg ctcctccccc     840
cgctcctccc cccgctcctc ccccgctcc tccccccgct cctcccccg ctcctccccc     900
cgctcctccc cccgctcctc ccccgctcc tccccccgct cctcccccg ctcctccccc     960
cgctccgcg gccccgcccc ccacgcccgc cgcgcgcgcg cacgccgccc ggaccgccgc    1020
ccgcctttttt tgcgcgcgcg cgcgcccgcg ggggcccgg gctgccacag gtgaaaccaa    1080
cagagcacgg cgcactccgc acgtcacacg tcacgtcatc caccacacct gcccaacaac    1140
acaactcaca gcgacaactc accgcgcaac aactcctgtt cctcatccac acgtcaccgc    1200
gcacctcccg ctcctccaga cgtaccccgg                                    1230

<210> SEQ ID NO 573
<211> LENGTH: 3185
<212> TYPE: DNA
<213> ORGANISM: Herpes Simplex Virus

<400> SEQUENCE: 573
atgctcgccg tccgttccct gcagcacctc tcaaccgtcg tcttgataac ggcgtacggc      60
ctcgtgctcg tgtggtacac cgtcttcggt gccagtccgc tgcaccgatg tatttacgcg     120
```

```
gtacgccca  ccggcaccaa  caacgacacc  gccctcgtgt  ggatgaaaat  gaaccagacc      180
ctattgtttc  tgggggcccc  gacgcacccc  cccaacgggg  gctggcgcaa  ccacgcccat      240
atctgctacg  ccaatcttat  cgcgggtagg  gtcgtgccct  tccaggtccc  acctgacgcc      300
atgaatcgtc  ggatcatgaa  cgtccacgag  gcagttaact  gtctggagac  cctatggtac      360
acacgggtgc  gtctggtggt  cgtagggtgg  ttcctgtatc  tggcgttcgt  cgccctccac      420
caacgccgat  gtatgtttgg  cgtcgtgagt  cccgcccaca  agatggtggc  cccggccacc      480
tacctcttga  actacgcagg  ccgcatcgta  tcgagcgtgt  tcctgcagta  ccctacacg       540 aaaattaccc  gcctgctctg  cgagctgtcg  gtccagcggc  aaaacctggt  tcagttgttt      600
gagacggacc  cggtcacctt  cttgtaccac  cgccccgcca  tcggggtcat  cgtaggctgc      660
gagttgatgc  tacgctttgt  ggccgtgggt  ctcatcgtcg  gcaccgcttt  catatcccgg      720
ggggcatgtg  cgatcacata  cccctgtttt  ctgaccatca  ccacctggtg  ttttgtctcc      780
accatcggcc  tgacagagct  gtattgtatt  ctgcggcggg  gccggcccc  caagaacgca       840 gacaaggccg  ccgccccggg  gcgatccaag  gggctgtcgg  gcgtctgcgg  gcgctgctgt      900
tccatcatcc  tctcgggcat  cgcagtgcga  ttgtgttata  tcgccgtggt  ggccggggtg      960
gtgctcgtgg  cgcttcacta  cgagcaggag  atccagaggc  gcctgtttga  tgtatgacgt     1020
cacatccagg  ccggcggaaa  ccgtaacggc  atatgcaaat  tggaaactgt  cctgtcttgg     1080
ggcccaccca  cccgacgcgt  catatgcaaa  tgaaaatcgg  tcccccgagg  ccacgtgtag     1140
cctggatccc  aacgaccccg  cccatggggtc  ccaattggcc  gtcccgttac  caagaccaac     1200
ccagccagca  tatccacccc  cgcccgggtc  cccgcgaag  cggaacgggg  tatgtgatat      1260
gctaattaaa  tacgggaatt  tccggggact  ttccggaat  ttccggggac  tttccgggaa      1320
tttccctaca  gaggtgcata  ttaacagagc  ttttgtcctg  gagaatgcca  cgtacttatg     1380
gtgtctgatt  ggtccttgtc  tgtgccgag  gtggggcggg  ggccccgccc  ggggggcgga     1440
acgaggaggg  gtttgggaga  gccggccccg  gcaccacggg  tataaggaca  tccaccaccc     1500
ggccggtggt  ggtgtgcagc  cgtgttccaa  ccacggtcac  gcttcggtgc  ctctccccga     1560
ttcgggcccg  gtcgctcgct  accggtgcgc  caccaccaga  ggccatatcc  gacacccag      1620 ccccgacggc  agccgacagc  ccggtcatgg  cgactgacat  tgatatgcta  attgacctcg     1680
gcctggacct  ctccgacagc  gatctggacg  aggacccccc  cgagccggcg  gagagccgcc     1740
gcgacgacct  ggaatcggac  agcagcgggg  agtgttcctc  gtcggacgag  gacatggaag     1800 accccccacgg  agaggacgga  ccggagccga  tactcgacgc  cgctcgcccg  gcggtccgcc     1860
cgtctcgtcc  agaagacccc  ggcgtaccca  gcacccagac  gcctcgtccg  acggagcggc     1920
agggccccaa  cgatcctcaa  ccagcgcccc  acagtgtgtg  gtcgcgcctc  ggggccggc      1980 gaccgtcttg  ctcccccgag  cagcacgggg  gcaaggtggc  ccgcctccaa  cccccaccga     2040
ccaaagccca  gcctgcccgc  ggcggacgcc  gtgggcgtcg  caggggtcgg  ggtcgcggtg     2100
gtcccggggc  tgccgatggt  ttgtcggacc  cccgccggcg  tgcccccaga  accaatcgca     2160
accctggggg  accccgcccc  ggggcggggt  ggacggacgg  cccccggcgcc  cccatggcg      2220 aggcgtggcg  cggcagtgag  cagcccgacc  cacccggagg  ccagcggaca  cggggcgtgc     2280
gccaagcacc  ccccccgcta  atgacgctgg  cgattgcccc  ccgcccgcg  gaccccgcg       2340 ccccggcccc  ggagcgaaag  gcgcccgccg  ccgacaccat  cgacgccacc  acgcggttgg     2400
tcctgcgctc  catctccgag  cgcgcggcgg  tcgaccgcat  cagcgagagc  tttggccgca     2460
```

```
gcgcacaggt catgcacgac cccctttgggg ggcagccgtt tcccgccgcg aatagcccct    2520
gggccccggt gctggcgggc caaggagggc cctttgacgc cgagaccaga cgggtctcct    2580
gggaaacctt ggtcgcccac ggcccgagcc tctatcgcac ttttgccggc aatcctcggg    2640
ccgcatcgac cgccaaggcc atgcgcgact gcgtgctgcg ccaagaaaat ttcatcgagg    2700
cgctggcctc cgccgacgag acgctggcgt ggtgcaagat gtgcatccac cacaacctgc    2760
cgctgcgccc ccaggacccc attatcggga cggccgcggc tgtgctggat aacctcgcca    2820
cgcgcctgcg gcccttcctc cagtgctacc tgaaggcgcg aggcctgtgc ggcctggacg    2880
aactgtgttc gcggcggcgt ctggcggaca ttaaggacat tgcatccttc gtgtttgtca    2940
ttctggccag gctcgccaac cgcgtcgagc gtggcgtcgc ggagatcgac tacgcgaccc    3000
ttggtgtcgg ggtcggagag aagatgcatt tctacctccc cggggcctgc atggcgggcc    3060
tgatcgaaat cctagacacg caccgccagg agtgttcgag tcgtgtctgc gagttgacgg    3120
ccagtcacat cgtcgccccc ccgtacgtgc acggcaaata ttttattgc aactccctgt    3180 tttag                                                                3185

<210> SEQ ID NO 574
<211> LENGTH: 3670
<212> TYPE: DNA
<213> ORGANISM: Herpes Simplex Virus

<400> SEQUENCE: 574
atgtcgggcg tcgggggaga gggagttccc tctgcgcttg cgattctagc ctcgtggggc      60
tggacgttcg acacgccaaa ccacgagtcg gggatatcgc cagatacgac tcccgcagat     120
tccattcggg gtgccgctgt ggcctcacct gaccaacctt tacacggggg cccggaacgg     180
gaggccacag cgccgtcttt ctccccaacg cgcgcggatg acggcccgcc ctgtaccgac     240
gggccctacg tgacgtttga taccctgttt atggtgtcgt cgatcgacga attagggcgt     300
cgccagctca cggacaccat ccgcaaggac ctgcggttgt cgctggccaa gtttagcatt     360
gcgtgcacca agacctcctc gttttcggga aacgccccgc gccaccacag acgcggggcg     420
ttccagcgcg gcacgcgggc gccgcgcagc aacaaaagcc tccagatgtt tgtgttgtgc     480
aaacgcgccc acgccgctcg agtgcgagag cagcttcggg tcgttattca gtcccgcaag     540
ccgcgcaagt attacacgcg atcttcggac gggcggctct gccccgccgt ccccgtgttc     600
gtccacgagt tcgtctcgtc cgagccaatg cgcctccacc gagataacgt catgctggcc     660 tcggggggccg agtaaccgcc cccccgcgcc accctcactg cccgtcgcgc gtgtttgatg     720
ttaataaata acgcataaat ttggctggtt gtttgttgtc tttaatggac cgcccgcagg     780
gggggtggca tttcagtgtc gggtgacgag cgcgatccgg ccgggagagg ctccggtgcc     840
cgtcagtggg cagagcgcac atcgcccaca gtccccgaga gttgggggg aggggtcggc     900 aattgaaccg gtgcctagag aaggtggcgc ggggtaaact gggaaagtga tgtcgtgtac     960
tggctccgcc ttttttcccga gggtgggga gaaccgtata taagtgcagt agtcgccgtg    1020
aacgttcttt ttcgcaacgg gtttgccgcc agaacacagg taagtgccgt gtgtggttcc    1080
cgcgggcctg gcctctttac gggttatggc ccttgcgtgc cttgaattac ttccacgccc    1140
ctggctgcag tacgtgattc ttgatcccga gcttcgggtt ggaagtgggt gggagagttc    1200
gaggccttgc gcttaaggag ccccttcgcc tcgtgcttga gttgaggcct ggcttgggcg    1260
ctggggccgc cgcgtgcgaa tctggtgca ccttcgcgcc tgtctcgctg ctttcgataa    1320
gtctctagcc atttaaaatt tttgatgacc tgctgcgacg ctttttttct ggcaagatag    1380
```

```
tcttgtaaat gcgggccaag atctgcacac tggtatttcg gttttgggg ccgcgggcgg      1440 cgacggggcc cgtgcgtccc agcgcacatg ttcggcgagg cggggcctgc gagcgcggcc      1500
accgagaatc ggacgggggt agtctcaagc tggccggcct gctctggtgc ctggcctcgc      1560
gccgccgtgt atcgccccgc cctgggcggc aaggctggcc cggtcggcac cagttgcgtg      1620
agcggaaaga tggccgcttc ccggccctgc tgcaggagc tcaaaatgga ggacgcggcg       1680
ctcgggagag cgggcgggtg agtcacccac acaaaggaaa agggcctttc cgtcctcagc      1740
cgtcgcttca tgtgactcca cggagtaccg ggcgccgtcc aggcacctcg attagttctc      1800
gagcttttgg agtacgtcgt ctttaggttg ggggagggg ttttatgcga tggagtttcc       1860
ccacactgag tgggtggaga ctgaagttag gccagcttgg cacttgatgt aattctcctt      1920
ggaatttgcc cttttgagt ttggatcttg gttcattctc aagcctcaga cagtggttca       1980
aagttttttt cttccatttc aggtgtcgtg agctagcatg tacaggatgc aactcctgtc      2040
ttgcattgca ctaagtcttg cacttgtcac gaattcgata tcgacagccc acccctctcc     2100
tagcccaaga tccgccggcc agttcgccat ggttagatct cccccatgcc catcatgccc     2160
agcacctgag ttcctggggg gaccatcagt cttcctgttc cccccaaaac ccaaggacac     2220
tctcatgatc tcccggaccc ctgaggtcac gtgcgtggtg gtggacgtga gccaggaaga     2280
ccccgaggtc cagttcaact ggtacgtgga tggcgtggag gtgcataatg ccaagacaaa     2340
gccgcgggag gagcagttca acagcacgta ccgtgtggtc agcgtcctca ccgtcctgca     2400
ccaggactgg ctgaacggca aggagtacaa gtgcaaggtc tccaacaaag gcctcccgtc     2460
ctccatcgag aaaaccatct ccaaagccaa agggcagccc cgagagccac aggtgtacac     2520
cctgccccca tcccaggagg agatgaccaa gaaccaggtc agcctgacct gcctggtcaa     2580
aggcttctac cccagcgaca tcgccgtgga gtgggagagc aatgggcagc cggagaacaa     2640
ctacaagacc acgcctcccg tgctggactc cgacggctcc ttcttcctct acagcaggct     2700
aaccgtggac aagagcaggt ggcaggaggg gaatgtcttc tcatgctccg tgatgcatga     2760
ggctctgcac aaccactaca cacagaagag cctctccctg tctccgggta atgagtgga     2820 tccaccggat ctagataact gatcataatc agccatacca catttgtaga ggttttactt     2880
gctttaaaaa acctcccaca cctcccctg aacctgaaac ataaaatgaa tgcaattgtt      2940
gttgttaact tgtttattgc agcttataat ggttacaaat aaagcaatag catcacaaat     3000
ttcacaaata aagcatttt ttcactgcat tctagttgtg gtttgtccaa actcatcaat      3060
gtatcttatc ctaggacccc aaaagtttgt ctgcgtattc cagggcgggg ctcagttgaa     3120
tctcccgcag cacctctacc agcaggtccg cggtgggctg gagaaactcg gccgtcccgg     3180
ggcaggcggt cgtcggggt ggaggcgcgg cgcccacccc gtgtgccgcg cctggcgtct      3240
cctctggggg cgacccgtaa atggttgcag tgatgtaaat ggtgtccgcg gtccagacca     3300
cggtcaaaat gccggccgtg gcgctccggg cgctttcgcc gcgcgaggag ctgacccagg     3360
agtcgaacgg atacgcgtac atatgggcgt cccacccgcg ttcgagcttc tggttgctgt     3420
cccggcctat aaagcggtag gcacaaaatt cggcgcgaca gtcgataatc accaacagcc     3480
caatgggggt gtgctggata acaacgcctc cgcgcggcag gcggtcctgg cgctcccggc     3540
cccgtaccat gatcgcgcgg gtgccgtact caaaaacatg caccacctgc gcggcgtcgg     3600
gcagtgcgct ggtcagcgag gccctggcgt ggcataggct atacgcgatg gtcgtctgtg     3660
gattggacat                                                            3670
```

<210> SEQ ID NO 575
<211> LENGTH: 6903
<212> TYPE: DNA
<213> ORGANISM: Herpes Simplex Virus

<400> SEQUENCE: 575

| | | | | | |
|---|---|---|---|---|---|
| ttagaggcgc | cgggagtggg | gtcgtcggcg | tctgcttttt | gtggcggcgt | cccgtcgcgg | 60 |
| ggtggggtcc | gacgtggcga | tgatgggcgg | cggcgtggtg | aggggcttcg | gctgcaggcc | 120 |
| cgcttcatcg | tccggcggca | gaaccggggt | ccgtccagac | gttccgttgg | taggtcccaa | 180 |
| atcctgtcgc | cctacacagc | ggcggtgcg | cgaatagtca | aagttcacac | acccagcctt | 240 |
| cacaggtgtg | tggctggcgg | cctgcttgcg | actgtccagc | gcctggcgta | tctctttata | 300 |
| aagggccaag | cgcgtttctg | tttcctgggt | gttggcagga | aacgcggggt | aactcaagtc | 360 |
| ctccaaaaaa | cccgccacaa | ataaaagggg | gttaacccaa | tatgccttct | gggcatgcct | 420 |
| atcccacaag | accgtgtcca | atccgggaca | gtgataacgc | aaaatatac | cgtctatcaa | 480 |
| agcatagttt | atagccgagg | gggtctcgta | acgccaatca | agatcgtcag | acgggagcgg | 540 |
| cacacaaggc | acctttaata | tatccccac | ctctcgagcc | acccgactcc | gaataacata | 600 |
| ttcggttgaa | gacaagcccc | cccgcacaca | caaaacccca | acggcaataa | gcccgaccca | 660 |
| acccaaaatc | cccatagcgc | ctagggtcgg | cacccacaga | aacctacagt | ccccaagtgt | 720 |
| ttgcccagta | acacaaccac | gacgtcgtgc | cacacaagcc | ccgtatcccc | gttcccgcgc | 780 |
| ttttcgttgg | tttatataca | cattgattat | tgactagtta | ttaatagtaa | tcaattacgg | 840 |
| ggtcattagt | tcatagccca | tatatggagt | tccgcgttac | ataacttacg | gtaaatggcc | 900 |
| cgcctggctg | accgcccaac | gacccccgcc | cattgacgtc | aataatgacg | tatgttccca | 960 |
| tagtaacgcc | aatagggact | ttccattgac | gtcaatgggt | ggagtattta | cggtaaactg | 1020 |
| cccacttggc | agtacatcaa | gtgtatcata | tgccaagtac | gccccctatt | gacgtcaatg | 1080 |
| acggtaaatg | gcccgcctgg | cattatgccc | agtacatgac | cttatgggac | tttcctactt | 1140 |
| ggcagtacat | ctacgtatta | gtcatcgcta | ttaccatggt | gatgcggttt | tggcagtaca | 1200 |
| tcaatgggcg | tggatagcgg | tttgactcac | ggggatttcc | aagtctccac | cccattgacg | 1260 |
| tcaatgggag | tttgttttgg | caccaaaatc | aacgggactt | tccaaaatgt | cgtaacaact | 1320 |
| ccgccccatt | gacgcaaatg | ggcggtaggc | gtgtacggtg | ggaggtctat | ataagcagag | 1380 |
| ctctctggct | aactagagaa | cccactgctt | actggcttat | cgaaattaat | acgactcact | 1440 |
| atagggagac | ccaagctggc | tagcgtttaa | acttaagctt | ggtaccgagc | tcggatccac | 1500 |
| tagtccagtg | tggtggaatt | cgccaccatg | tgccatcagc | agctggtcat | ctcatggttc | 1560 |
| tccctggtgt | ttctggcctc | acctctggtc | gcaatctggg | aactgaaaaa | ggatgtgtac | 1620 |
| gtggtggagc | tggactggta | tcccgatgcc | cctggcgaga | tggtggtgct | gacctgcgac | 1680 |
| acacccgagg | aggatggcat | cacctggaca | ctggatcaga | gctccgaggt | gctgggaagc | 1740 |
| ggcaagaccc | tgacaatcca | ggtgaaggag | ttcggcgacg | ccggccagta | cacctgtcac | 1800 |
| aagggaggag | aggtgctgag | ccactccctg | ctgctgctgc | acaagaagga | ggatggcatc | 1860 |
| tggtccacag | acatcctgaa | ggatcagaag | gagccaaaga | acaagacctt | cctgcggtgc | 1920 |
| gaggccaaga | attatagcgg | ccggttcacc | tgttggtggc | tgaccacaat | ctccaccgat | 1980 |
| ctgacatttt | ctgtgaagtc | tagcagggga | tcctctgacc | cacagggagt | gacatgcgga | 2040 |
| gcagccaccc | tgagcgccga | gagggtgcgc | ggcgataaca | aggagtacga | gtattccgtg | 2100 |
| gagtgccagg | aggactctgc | ctgtccagca | gcagaggagt | ccctgcctat | cgaagtgatg | 2160 |

```
gtggatgccg tgcacaagct gaagtacgag aattatacca gctccttctt tatccgggac    2220
atcatcaagc ccgatccccc taagaacctg cagctgaagc ctctgaagaa tagcagacag    2280
gtggaggtgt cctgggagta ccctgacacc tggagcacac cacactccta tttctctctg    2340
accttttgcg tgcaggtgca gggcaagtcc aagcgggaga agaaggacag agtgttcacc    2400
gataagacat ctgccaccgt gatctgtaga agaacgcct ctatcagcgt gagggcccag    2460
gaccgctact attctagctc ctggtccgag tgggcctctg tgccttgcag cggcggagga    2520
ggaggaggat ctatgtgccc agcaaggagc ctgctgctgg tggccacact ggtgctgctg    2580
gatcacctgt ccctggcaag gaatctgcca gtggcaaccc ctgacccagg catgttcccc    2640
tgcctgcacc acagccagaa cctgctgagg gccgtgtcca atatgctgca gaaggcccgc    2700
cagacactgg agttttaccc ttgtaccagc gaggagatcg accacgagga catcacaaag    2760
gataagacct ccacagtgga ggcctgcctg ccactggagc tgaccaagaa cgagtcctgt    2820
ctgaacagcc gggagacaag cttcatcacc aacggctcct gcctggcctc tagaaagaca    2880
agctttatga tggccctgtg cctgtctagc atctacgagg acctgaagat gtatcaggtg    2940
gagttcaaga ccatgaacgc caagctgctg atggaccca agaggcagat ctttctggat    3000
cagaatatgt tggccgtgat cgacgagctg atgcaggccc tgaacttcaa tagcgagaca    3060
gtgcctcaga gtcctctct ggaggagcca gatttctaca gaccaagat caagctgtgc    3120 atcctgctgc acgcctttcg gatcagagcc gtgacaatcg accgcgtgat gtcctatctg    3180
aacgcctctg gaggaggagg aagcggagga ggaggatccg gcggcggcgg ctccggctct    3240
ggcgccacca acttctccct gctgaagcag gcaggcgacg tggaggagaa tccaggacct    3300
atgcggatct ctaagcctca cctgagaagc atctccatcc agtgctacct gtgcctgctg    3360
ctgaacagcc actttctgac agaggccggc atccacgtgt tcatcctggg ctgtttttagc    3420 gccggcctgc caaagaccga ggcaaactgg gtgaatgtga tctctgacct gaagaagatc    3480
gaggatctga tccagagcat gcacatcgat gccacactgt ataccgagtc tgacgtgcac    3540
cctagctgca aggtgaccgc catgaagtgt ttcctgctgg agctgcaggt catcagcctg    3600
gagtccggcg acgcaagcat ccacgataca gtggagaacc tgatcatcct ggccaacaat    3660
agcctgagct ccaacggcaa tgtgaccgag tccggctgca aggagtgtga ggagctggag    3720
gagaagaaca tcaaggagtt cctgcagagc tttgtgcaca tcgtgcagat gttcatcaat    3780
acatccggag gaggaggatc aggcggagga ggaagcggcg gcggcggctc tggcagcggc    3840
gccaccaact ttcccctgct gaagcaggcc ggcgatgtgg aagaaaatcc aggaccaatg    3900
gcaccaagga gagcaagggg atgcagaacc ctgggcctgc ctgccctgtt attactgctg    3960 ctgctgagc caccagcaac aaggggaatc acctgtcctc cacccatgag cgtggagcac    4020
gccgacatct gggtgaagtc ctactctctg tattctaggg agcggtacat ctgcaacagc    4080
ggctttaaga ggaaggccgg cacatctagc ctgaccgagt gcgtgctgaa caaggccacc    4140
aatgtggccc actggaccac accttccctg aagtgcatca gggatccagc cctggtgcac    4200
cagcgccccg cacctccaag cacagtgacc acagcaggag tgacccctca gccagagagc    4260 ctgtccccctt ctggcaagga gccagcagca tcctctccaa gctccaacaa tacagcagca    4320
```

```
accacagcag caatcgtgcc aggctcccag ctgatgccaa gcaagtcccc ctctaccggc    4380
accacagaga tctctagcca cgagtcctct cacggcacac caagccagac cacagccaag    4440
aattgggagc tgaccgcaag cgcctcccac cagccacctg gcgtgtaccc acagggacac    4500
tccgacacca cagtggccat ctctaccagc acagtgctgc tgtgcggcct gtctgccgtg    4560
agcctgctgg cctgttatct gaagtccagg cagacccc cactggcatc tgtggagatg      4620
gaggccatgg aggccctgcc cgtcacatgg ggactagta gtagagacga ggatctggaa    4680
aactgtagtc accatctgta agatatccat cacactggcg gccgctcgag catgcatcta    4740
gagggcccta ttctatagtg tcacctaaat gctagagctc gctgatcagc ctcgactgtg    4800
ccttctagtt gccagccatc tgttgtttgc cctcccccg tgccttcctt gaccctggaa     4860
ggtgccactc ccactgtcct ttcctaataa aatgaggaaa ttgcatcgca ttgtctgagt    4920
aggtgtcatt ctattctggg gggtgggtg ggcaggaca gcaaggggga ggattgggaa      4980
gacaatagca ggcatgctgg ggatgcggtg ggctctatgg ggatccacta gttctagagc    5040
ggccgccgca cataaaggcc cggcgcgacc gacgcccgca gacggcgccg ccacgaacg     5100 acgggagcgg ctgcggagca cgcggaccgg gagcgggact cgcagagggc cgtcggagcg    5160
gacggcgtcg gcatcgcgac gccccggctc gggatcggga tcgcatcgga aagggacacg    5220
cggaaagacc cacccacccc acccacgaaa cacaggggac gcaccccggg ggcctccgac    5280
gacagaaacc caccggtccg cctttgtgca cgggtaagca ccttgggtgg gcggaggagg    5340
ggggacgcgg gggcggagga gggggctcac ccgcgttcgt gccttcccgc aggaggaacg    5400
tcctcgtcga ggcgaccggc ggcgaccgtt gcgtggaccg cttcctgctc gtcgggcga     5460 ccggcggcga ccgttgcgtg gaccgcttcc tgctcgtcgg gcgggggagc atgtcgtggg    5520
ccctggaaat ggcggacacc ttcctggaca acatgcgggt tgggcccagg acgtacgccg    5580
acgtacgcga tgagatcaat aaaagggggc gtgaggaccg ggaggcggcc aaaaccgccg    5640
tgcacgaccc ggagcgtcct ctgctgcgct ccccgggct gctgcccaaa atcgccccca    5700
acgcatcctt gggtgtggca catcgaagaa ccggcgggac cgtgaccgac agtccccgta    5760
atccggtaac ccgttgagtc ccgggtacga ccatcgccca gtttctgggg cggagggtgg    5820 ttcccccgt ggctctcgag atgagccaga cccaaccccc ggccccagtt gggccgggcg     5880
acccagatgt ttacttaaaa ggcgtgccgt ccgccggcat gcaccccaga ggtgttcacg    5940
cacctcgagg acaccgcgc atgatctccg gaccccgca acgggtgat aatgatcaag        6000 cggcggggca atgtggagat tcgggtctac tacgagtcgg tgcggacact acgatctcga    6060
agccatctga agccgtccga ccgccaacaa tccccaggac accgcgtgtt ccccgggagc    6120
cccgggttcc gcgaccaccc cgagaaccta gggaacccag agtaccgcga gctcccagag    6180
accccagggt accgcgtgac cccagggatc cacgacaacc ccgggagccc cggcctcccc    6240
gggagccccg gaccccacgc accccccgcg aaccacgtac ggctcgcggg tctgtatagc    6300
ccgggcaagt atgcccccct ggcgagccca gaccccttct cccacaaga tggagcgtac     6360 gctcgggccc gcgtagggct ccacaccgcg gttcgcgtcc cgcccaccgg aagcccaacc    6420
cacacgcact gcggcatga cccgggcgat gagccaacct cggatgactc agggctctac     6480
cctctggacg cccgggcgct tgcgcacctg gtgatgttgc ccgcggacca ccgggccttc    6540
tttcgaaccg tggtcgaggt gtctcgcatg tgcgctgcaa acgtgcgcga tccccgccc    6600 ccggctacag gggccatgtt gggccgcac gcgcggctgg tccacaccca gtggctccgg    6660
gccaaccaag agacgtcgcc cctgtggccc tggcggacgg cggccattaa ctttatcacc    6720
```

```
accatggccc ccgcgtcca aacccaccga cacatgcacg acctgttgat ggcctgtgct    6780
ttctggtgct gtctgacaca cgcatcgacg tgttcgtacg cggggctgta ctcgacccac    6840
tgcctgcatc tgtttggtgc gtttgggtgt ggggacccgg ccctaacccc acccctgtgc    6900
tag                                                                  6903
```

ONCOLYTIC HERPES SIMPLEX VIRUS VECTORS EXPRESSING IMMUNE SYSTEM-STIMULATORY MOLECULES

CROSS-REFERENCE TO RELATED APPLICATION

This patent application claims the benefit under 35 U.S.C. § 119(e) of U.S. Provisional Patent Application No. 62/369,646 filed Aug. 1, 2016, which application is incorporated herein by reference in its entirety for all purposes.

FIELD OF THE INVENTION

The present invention relates generally to oncolytic herpes simplex virus (oHSV) vectors that express molecules that stimulate the immune system.

BACKGROUND OF THE INVENTION

Oncolytic viruses (OVs) have been a therapeutic arsenal to specifically destroy cancer cells through oncolysis, which is a killing mechanism characterized by cancer cell lysis through the course of virus lytic replication. In addition to the direct cell killing by the virus. Among the various OVs, herpes simplex virus type 1 ("HSV-1") based OVs are the farthest advanced, e.g., a herpes virus-based OV (T-Vec) has been approved by the U.S. FDA for the treatment of melanoma. Representative examples of HSV vectors include those described in U.S. Pat. Nos. 7,223,593, 7,537,924, 7,063,835, 7,063,851, 7,118,755, 8,277,818, and 8,680,068.

The present invention overcomes shortcomings of current commercial oncolytic viruses, and further provides additional unexpected benefits.

SUMMARY

Briefly stated, the disclosure relates to an HSV vector comprising an expression cassette for one or more of IL12, IL15 and/or an ILReceptor 15 alpha subunit. Within one embodiment, the expression cassette expresses all of IL12, IL15 and the IL Receptor 15 alpha subunit. Within preferred embodiments the expression cassette expresses murine or human IL12, murine or human IL15, and murine or human IL15Receptor alpha subunit. Within yet other embodiments the expression cassette expresses either murine or human IL12, hIL15, and murine and h15Receptor alpha subunit.

Within one embodiment, the expression cassette expresses all of IL12, IL15 and the IL Receptor 15 alpha subunit. Within one embodiment, the expression cassette comprises mIL12, hIL15, and hIL15Receptor alpha subunit. Within other embodiments, the expression cassette comprises hIL12, hIL15, and hIL15Receptor alpha subunit. In certain embodiments, the nucleic acid sequence encoding a self-cleaving 2A peptide is located in-frame between coding sequences for mIL12, hIL15, and hIL15Receptor alpha subunit. In other embodiments, the HSV vector encodes a self-cleaving 2A peptide. In other embodiments, the one or more IRES sequences is located between the coding sequences for murine or human IL12, hIL15, and hIL15Receptor alpha subunit. In embodiments, the hIL15 and hIL15Receptor alpha subunit are co-expressed using a IRES sequence, and in certain embodiments, the hIL15 and hIL15Receptor alpha subunit are expressed by a bi-directional promoter, which may be bi-CMV in some embodiments. In yet other embodiments, each of the hIL15 and hIL15Receptor alpha subunit is followed by a nucleic acid sequence encoding Lys5 or Glu5. In certain embodiments, the hIL15Receptor alpha subunit is selected from the group consisting of variant 1, variant 2, variant 3 and variant 4.

The vector may further comprise an expression cassette for one or more PD-L1 blocking peptides, may further comprise sequence encoding a peptide linker or one or more IRES sequences (or both) between multiple PD-L1 blocking peptides. In some embodiments, the HSV vector may further comprise sequence encoding an Fc domain linked to the 3'-end of the PD-L1 blocking peptide. In yet other embodiments, the PD-L1 blocking peptides is inserted in between UL3 and UL4 viral genes.

In certain embodiments, the expression cassette is inserted in the terminal repeat region of HSV genome. In embodiments, the HSV vector further comprises an NFkB and an OCT4/SOX2 enhancing element in ICP4 or ICP27 regulatory regions. The HSV vector may have a deletion of the ICP34.5 genes. In other embodiments, the ICP34.5 gene is regulated by a 3'UTR containing target sequences of miRNAs that are under-expressed in tumor cells.

The expression cassette may comprise at least one bidirectional CMV promoter. It may comprise at least one cellular promoter.

In some embodiments, the expression cassette for mIL12/hIL15/hIL15Receptor alpha subunit is inserted in the terminal repeat region where the original viral sequence is replaced by the cassette.

The HSV vector may be either HSV-1 or HSV-2.

This Brief Summary has been provided to introduce certain concepts in a simplified form that are further described in detail below in the Detailed Description. Except where otherwise expressly stated, this brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the drawings, and the claims.

BRIEF DESCRIPTION OF THE DRAWINGS

Exemplary features of the present disclosure, its nature and various advantages will be apparent from the accompanying drawings and the following detailed description of various embodiments. Non-limiting and non-exhaustive embodiments are described with reference to the accompanying drawings, wherein like labels or reference numbers refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which:

FIGS. 7A-7C show ELISA and Western blot data for IL-15 expression following hVG161 infection of cells.

FIGS. 9A-9C are (A) a schematic of an exemplary construct in which bi-CMV promoter drives expression of the Sushi domain of IL-15Rα and IL-15, and (B-C) a DNA sequence and schematic (SEQ ID No: 557).

FIGS. 10A-10C are (A) a schematic of an exemplary construct in which bi-CMV promoter drives expression of IL-15 and IL-15Rα variant 4, and (B-C) a DNA sequence and schematic (SEQ ID No: 558).

FIGS. 11A-11C are (A) a schematic of an exemplary construct in which bi-CMV promoter drives expression of IL-15-K5 and IL-15Rα Sushi domain-E5, and (B-C) a DNA sequence and schematic (SEQ ID No: 559).

FIGS. 12A-12D are (A) a schematic of an exemplary construct in which bi-CMV promoter drives expression of IL-15-K5 and IL-15Rα variant 4-E5, and (B-D) a DNA sequence and schematic (SEQ ID No: 560).

FIGS. 13A-13D are (A) a schematic of an exemplary construct in which the EF1α promoter controls expression of IL-15-IRES-IL-15Rα Sushi domain, and (B-D) a DNA sequence and schematic (SEQ ID No: 561).

FIGS. 14A-14D are (A) a schematic of an exemplary construct in which the EF1α promoter controls expression of IL-15-IRES-IL-15Rα variant 4, and (B-D) a DNA sequence and schematic (SEQ ID No: 562).

FIGS. 15A-15D are (A) a schematic of an exemplary construct in which the EF1α promoter controls expression of IL-15K5-IRES-IL-15Rα Sushi domainE5, and (B-D) a DNA sequence and schematic (SEQ ID No: 563.

FIGS. 16A-16D are (A) a schematic of an exemplary construct in which the EF1α promoter controls expression of IL-15K5-IRES-IL-15Rα variant 4E5, and (B-D) a DNA sequence and schematic (SEQ ID No: 564).

FIGS. 17A-17E are (A) a schematic of an exemplary construct in which the CMV promoter controls expression of IL-12-p2A-IL-15-p2A-IL-15Rα Sushi domain, and (B-E) a DNA sequence and schematic (SEQ ID No: 565).

FIGS. 18A-18E are (A) a schematic of an exemplary construct in which the CMV promoter controls expression of IL-12-p2A-IL-15-p2A-IL-15Rα variant 1, and (B-E) a DNA sequence and schematic (SEQ ID No: 566).

FIGS. 19A-19D are (A) a schematic of an exemplary construct in which the CMV promoter controls expression of IL-12-p2A-IL-15K5-p2A-IL-15Rα Sushi domainE5, and (B-D) a DNA sequence and schematic (SEQ ID No: 567).

FIGS. 20A-20D are (A) a schematic of an exemplary construct in which the CMV promoter controls expression of IL-12-p2A-IL-15K5-p2A-IL-15Rα variant 1-E5, and (B-D) a DNA sequence and schematic (SEQ ID No: 568).

FIGS. 24A and 24B show the effects of IL-12 and IL-15Rα on cytotoxicity of U87 and MDA-MB-231 tumor cells by peripheral blood mononuclear cells.

FIGS. 25A-25E show results of cell infection with VG161-PLBh and VG161-15 h.

FIG. 15A-15B show results of cell transfection with IL-TF-Fc plasmid carrying IL-12, IL-15, and PD-L1 blocker. FIGS. 15C-15D show results of cell infection with a variety of mutant viruses including hVG161.

FIGS. 27A-27E show results of cell viability assays for hVG161 and HSV-345 on human tumor cell lines and Vero cell line.

FIGS. 28A-28J show results of in vitro assays for various constructs. FIGS. 28A-28E show results of cell viability assays for mVG161 and HSV-345 on mouse tumor cell lines and Vero cell line; FIGS. 28F-28J show the characterization of transgene expression following mVG161 or VG001 infection of CT26 mouse tumor cells.

FIGS. 29A-29E show results of in vitro characterization of transgene expression following hVG161 or VG001 infection of various cell lines.

FIGS. 30A-30G show results of assays to evaluate the ability of hVG161 to kill a variety of human cancer cells in vitro.

DETAILED DESCRIPTION OF THE INVENTION

Figure 1A:
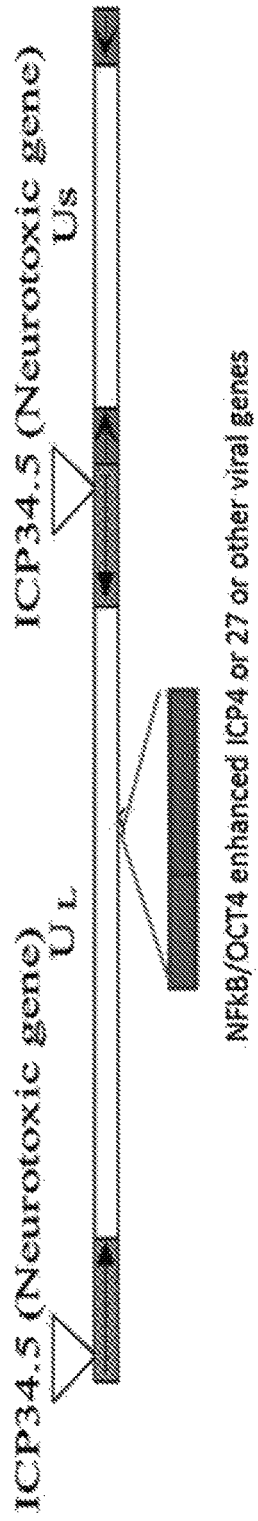
FIGS. 1A and 1B are schematics of exemplary oHSV vectors.

The present disclosure may be understood more readily by reference to the following detailed description of preferred embodiments of the invention and the Examples included herein.

Overview of Disclosure

The present invention may be understood more readily by reference to the following detailed description of preferred embodiments of the invention and the Examples included herein. Briefly stated, the present disclosure provides oncolytic herpes simplex virus type 1 or 2 vectors which express immune stimulator molecules. Representative vectors comprise an expression cassette encoding one or more of IL-12, IL-15 and IL-15Rα. Certain vectors encode murine or human IL-12, murine or human IL-15, and murine or human IL-15Rα. Within certain embodiments the vectors encode murine or human IL-12, hIL15, and hIL15Receptor alpha subunit. Within other embodiments the vectors encode hIL-12, HIL15 and HIL15 Receptor alpha subunit. The three proteins may be expressed on one, two, or three transcripts.

When expressed on the same transcript, post-transcriptional processing ensues to result in expression of the individual proteins. In such case, the coding regions are separated by IRES sequences or sequences that encode self-cleaving 2A peptides. The coding regions may be expressed by a bidirectional promoter. The HSV vector optionally expresses one or more PD-L1 peptides that can be secreted.

A. oHSV Vector

An oncolytic virus is a virus that will lyse cancer cells (oncolysis), preferably in a selective manner. Viruses that selectively replicate in dividing cells over non-dividing cells are often oncolytic. Oncolytic viruses suitable for use herein include Herpes Simplex Viruses 1 and 2.

Herpes Simplex Virus (HSV) 1 and 2 are members of the Herpesviridae family, which infects humans. The HSV genome contains two unique regions, which are designated unique long ($U_L$) and unique short ($U_S$) region. Each of these regions is flanked by a pair of inverted terminal repeat sequences. There are about 75 known open reading frames. The viral genome has been engineered to develop oncolytic viruses for use in e.g. cancer therapy. Tumor-selective replication of HSV may be conferred by mutation of the HSV ICP34.5 (also called γ34.5) gene. HSV contains two copies of ICP34.5. Mutants inactivating one or both copies of the ICP34.5 gene are known to lack neurovirulence, i.e. be avirulent/non-neurovirulent and be oncolytic.

Suitable oncolytic HSV may be derived from either HSV-1 or HSV-2, including any laboratory strain or clinical isolate. In some embodiments, the oHSV may be or may be derived from one of laboratory strains HSV-1 strain 17, HSV-1 strain F, or HSV-2 strain HG52. In other embodiments, it may be of or derived from non-laboratory strain JS-1. Other suitable HSV-1 viruses include HrrR3 (Goldsten and Weller, *J. Virol.* 62, 196-205, 1988), G207 (Mineta et al. *Nature Medicine.* 1(9):938-943, 1995; Kooby et al. *The FASEB Journal*, 13(11):1325-1334, 1999); G47Delta (Todo et al. *Proceedings of the National Academy of Sciences.* 2001; 98(11):6396-6401); HSV 1716 (Mace et al. *Head & Neck*, 2008; 30(8):1045-1051; Harrow et al. *Gene Therapy.* 2004; 11(22):1648-1658); HF10 (Nakao et al. *Cancer Gene Therapy.* 2011; 18(3):167-175); NV1020 (Fong et al. *Molecular Therapy*, 2009; 17(2):389-394); T-VEC (Andtbacka et al. *Journal of Clinical Oncology*, 2015: 33(25): 2780-8); J100 (Gaston et al. *PloS one*, 2013; 8(11):e81768); M002 (Parker et al. *Proceedings of the National Academy of Sciences*, 2000; 97(5):2208-2213); NV1042(Passer et al. *Cancer Gene Therapy.* 2013; 20(1):17-24); G207-IL2 (Carew et al. *Molecular Therapy*, 2001; 4(3):250-256); rQNestin34.5 (Kambara et al. *Cancer Research*, 2005; 65(7):2832-2839); G47Δ-mIL-18 (Fukuhara et al. *Cancer Research*, 2005; 65(23):10663-10668); and those vectors which are disclosed in PCT applications PCT/US2017/030308 entitled "HSV Vectors with Enhanced Replication in Cancer Cells", and PCT/US2017/018539 entitled "Compositions and Methods of Using Stat1/3 Inhibitors with Oncolytic Herpes Virus", all of the above of which are incorporated by reference in their entirety.

The oHSV vector may have modifications, mutations, or deletion of at least one γ34.5 gene. The vector lacks intact γ34.5 genes. In some embodiments, both genes are deleted, mutated or modified. In other embodiments, one is deleted and the other is mutated or modified. Either native γ34.5 gene can be deleted. In one embodiment, the terminal repeat, which comprises γ34.5 gene and ICP4 gene, is deleted. Mutations, such as nucleotide alterations, insertions and deletions render the gene inexpressible or the product inactive. The γ34.5 gene may be modified with miRNA target sequences in its 3' UTR. The target sequences bind miRNAs that are expressed at lower levels in tumor cells than in their normal counterparts. In some embodiments, the modified or mutated γ34.5 gene(s) are constructed in vitro and inserted into the oHSV vector as replacements for the viral gene(s). When the modified or mutated γ34.5 gene is a replacement of only one γ34.5 gene, the other γ34.5 is deleted. The γ34.5 gene may comprise additional changes, such as having an exogenous promoter.

The oHSV may have additional mutations, which may include disabling mutations e.g., deletions, substitutions, insertions), which may affect the virulence of the virus or its ability to replicate. For example, mutations may be made in any one or more of ICP6, ICP0, ICP4, ICP27, ICP47, ICP 24, ICP56. Preferably, a mutation in one of these genes (optionally in both copies of the gene where appropriate) leads to an inability (or reduction of the ability) of the HSV to express the corresponding functional polypeptide. In some embodiments, the promoter of a viral gene may be substituted with a promoter that is selectively active in target cells or inducible upon delivery of an inducer or inducible upon a cellular event or particular environment. In particular embodiments, a tumor-specific promoter drives expression of viral genes essential for replication of HSV. In certain embodiments the expression of ICP4 or ICP27 or both is controlled by an exogenous promoter, e.g., a tumor-specific promoter. Exemplary tumor-specific promoters include survivin or telomerase; other suitable tumor-specific promoters may be specific to a single tumor type and are known in the art. Other elements may be present. In some cases, an enhancer such as NF-kB/OCT4/SOX2 enhancer is present, for example in the regulatory regions of ICP4 or ICP27 or both. As well, the 5'UTR may be exogenous, such as a 5'UTR from growth factor genes such as FGF.

The oHSV may also have genes and nucleotide sequences that are non-HSV in origin. For example, a sequence that encodes a prodrug, a sequence that encodes a cytokine or other immune stimulating factor, a tumor-specific promoter, an inducible promoter, an enhancer, a sequence homologous to a host cell, among others may be in the oHSV genome. Exemplary sequences encode IL12, IL15, OX40L, PD-L1 blocker or a PD-1 blocker. For sequences that encode a product, they are operatively linked to a promoter sequence and other regulatory sequences (e.g., enhancer, polyadenylation signal sequence) necessary or desirable for expression.

The regulatory region of viral genes may be modified to comprise response elements that affect expression. Exemplary response elements include response elements for NF-κB, Oct-3/4-SOX2, enhancers, silencers, cAMP response elements, CAAT enhancer binding sequences, and insulators. Other response elements may also be included. A viral promoter may be replaced with a different promoter. The choice of the promoter will depend upon a number of factors, such as the proposed use of the HSV vector, treatment of the patient, disease state or condition, and ease of applying an inducer (for an inducible promoter). For treatment of cancer, generally when a promoter is replaced it will be with a cell-specific or tissue-specific or tumor-specific promoter. Tumor-specific, cell-specific and tissue-specific promoters are known in the art. Other gene elements may be modified as well. For example, the 5' UTR of the viral gene may be replaced with an exogenous UTR.

B. Immune Stimulatory Molecules

The oHSV vector comprises nucleic acid sequences that encode one or more immune stimulatory molecules (e.g., IL-12, IL-15, and IL-15Rα). The amino acid sequences of exemplary IL-12, IL-15 and IL-15Rα are presented in the Sequence Listing (SEQ ID NOs: 1-6). Any DNA sequence that encodes the amino acid sequence is suitable, although generally codons will be chosen for preferential expression in the subject species slated to receive the oHSV.

1. IL-12

Interleukin 12 (IL-12) is mainly produced by dendritic cells, macrophages, and monocytes in response to bacteria (e.g., lipopolysaccharides), pathogens or activated T cells. IL-12 can induce IFN gamma production, cell proliferation, and activate natural killer cells and T cells. It is also critical for differentiation of T cells to Th1 cells. IL-12 can also suppress tumor growth. Murine IL-12 is equally active to both murine and human cells, and either is suitable for use in the oHSV vector.

Biologically active IL-12 is a heterodimeric molecule composed of a 35 kDa (p35) and a 40 kDa (p40) subunit that are covalently linked by a disulfide bridge. Simultaneous expression of the two subunits is necessary to produce the heterodimer. In the oHSV vector, IL-12 expression may be achieved in a variety of ways. The two subunits can be expressed in separate constructs, each with a promoter, or expressed in one construct from a bidirectional promoter, or expressed from one construct with elements such as IRES or self-cleaving peptides between the coding regions. Alternatively, the subunits can be expressed as a single chain. For example, a functional single chain IL-12 fusion protein can be produced by linking the coding regions for p40 and p35 with linkers, usually composed of Ser or Gly or a combination of Ser and Gly, such as $Ser_5$, $(Gly_4Ser)_3$ or $Gly_6Ser$ (e.g. Lieschke et al. Nature Biotechnology 15:35, 1997; Lode et al. PNAS 95:2475, 1998; see also WO 2015/095249 for an alternative fusion construct). The sequence and length of the linkers is generally chosen to allow for maximal flexibility of the domains (Chen et al., Adv Drug Deliv Rev. 65: 1357, 2013). A computer program can be used to choose the linker sequence. One such program is called LINKER (Crasto and Feng, Protein Eng Design &Selection 13:309). An exemplary single-chain IL-12 has the amino acid sequence of SEQ ID NO: 1. Amino acid substitutions, insertions and deletions may be made as long as the IL-12 retains function.

2. IL-15

IL-15 is a cytokine that regulates natural killer cell and T cell activation and proliferation and may have other biological activities. There are at least two isoforms, which differ in the sequence of the signal peptide and have identical mature protein sequences. The sequence of the isoform with the longer signal peptide (sometimes called LSP-IL15) has GenBank (NCBI) accession no. NP 000576, and the one with the shorter signal peptide (sometimes called SSP-IL15) has Accession No. NP 751915. Either isoform is suitable for use in the oHSV vector. Amino acid insertions, deletions and substitutions, such as are found in polymorphisms, may be present as long as the protein binds IL-15.

In some embodiments, IL-15 and IL-15Rα each have a C-terminal peptide are coiled coils that will selectively dimerize. A number of suitable peptides have been taught (see, e. g., Tripet et al. Protein Engineering 9:1029, 1996; Aronsson et al., Sci Rep 5:14063, 2015). Typically, the amino acid sequence of coiled coils have a heptad repetition of hydrophobic (h) and polar (p) residues in a hpphppp pattern. Two exemplary coiled coils are the K coil (KVSALKE, SEQ ID No. 7) and the E coil (EVSALEK, SEQ ID NO. 8). Generally, from 3-6 tandem copies are used.

In some embodiments herein, 5 tandem copies of each are used. K5 (KVSALKEKVSALKEKVSALKEKVSALKEKVSALKE, SEQ ID NO. 9) and E5 (EVSALEKEVSALEKEVSALEKEVSALEKEVSALEK, SEQ ID NO. 10). The K coil and the E coil were designed to be oppositely charged, so IL-15 is fused with one coiled coil and IL-15Rα is fused to an oppositely charged coiled coil. An exemplary Sushi domain fused to E5 is shown in SEQ ID NO: 12, an exemplary IL-15Rα variant 4 fused to E5 is shown in SEQ ID NO: 13, an exemplary IL-15Rα variant 1 fused to E5 is shown in SEQ ID NO: 14, and an exemplary IL-15 fused to K5 is shown in SEQ ID NO: 15.

3. IL-15Rα Subunit

Interleukin-15 Receptor alpha subunit (IL-15Rα) is one of three subunits of the complex that binds IL-15. The alpha subunit binds IL-15 with high affinity and can bind to it independently of the other subunits. There are at least four variants (isoforms), herein called variant 1 (NP 002180.1) (SEQ ID NO: 3); variant 2 (NP 751950.2) (SEQ ID NO: 4); variant 3 (NP 001230468.1) (SEQ ID NO: 5); and variant 4 (NP_001243694) (SEQ ID NO: 6). The alpha subunit contains a Sushi domain (aka complement control protein (CCP), short consensus repeats (SCRs) or SUSHI repeats) that is the shortest region retaining IL-15 binding activity. A typical Sushi domain is about 60-70 aa containing four cysteines forming two disulfide bonds and is a common motif in protein-protein interactions. The Sushi domain of IL-15Rα encompasses residue 31 to about 95 (in reference to variant 1) (SEQ ID NO: 11). The location of the Sushi domain in the other variants is known. Amino acid substitution of any of the cysteines in sIL-15Rα abolishes its ability to inhibit acute inflammation and T cell response to allogenic antigens in vivo (Wei et al. J Immunol. 167:277, 2001).

The oHSV vector comprises nucleic acid sequence encoding IL-15Rα, a variant of IL-15Rα, or a Sushi domain. Generally, the protein is expressed with a leader peptide, and in some embodiments, the leader peptide is from IL-15Rα. Other leader peptides are known in the art. Amino acid substitutions may be present as long as the protein binds IL-15. Natural substitutions, polymorphisms, are known.

4. PD-L1 Blocking Peptide

Programmed death-ligand 1 (PD-L1) plays a role in suppressing the immune system, probably as an effect of binding the PD-1 receptor. Blocking the protein-protein interaction has been shown to improve cancer therapy.

The oHSV vector may express PD-L1 blocking peptides. Suitable peptides include TAHPSPSPRSAGQF (SEQ ID NO: 16), EYRMSPSNQT (SEQ ID NO: 17), YYRMSPSNQT (SEQ ID NO: 18), TRYPSPSPKPEGRF (SEQ ID NO: 19), and WNRLSPSNQT (SEQ ID NO: 20). Other suitable peptides include those in Table 4 (SEQ ID NOs: 21-500). Generally, the blocking peptides are expressed with a leader sequence. Leader sequences are well known in the art. They include the immunoglobulin kappa chain leader sequence (METDTLLLWVLLLWVPGSTG; SEQ ID NO: 501) and the IL-2 leader sequence (MYRMQLLSCIALSLALVTNS; SEQ ID NO: 502). When more than one blocking peptide is present, typically the peptides will be separated by a linker peptide that confers flexibility. The linkers are usually Gly or Ser or Gly/Ser rich. Examples of suitable linkers are shown in (SEQ ID NOs: 503-519) (see also, Chichili et al. Protein Science 22: 153, 2013). There may be one copy of a peptide or two copies or three copies or more. Multiple copies are usually in tandem and may have a linker between the copies. The blocking peptide constructs may also comprise an Fc sequence at the C-terminus of the peptide, or an immunoglobulin Fc sequence with or without the hinge region. While any of the Fc regions are suitable, in general, the Fc will be from one of the IgG subclasses, e.g., human IgG1, human IgG2, human IgG3, and human IgG4 or their murine counterparts.

C. Organization of Elements

The molecules IL-12, IL-15 and IL-15Rα can be in a variety of different configurations in the oHSV vector. For example, each of the molecules may be individually expressed from a separate promoter/regulatory region or co-expressed from one or two separate promoters/regulatory regions.

In certain embodiments, two or three of the molecules are expressed in a single transcript from one promoter and their coding sequences are separated by IRES (internal ribosome entry site) sequences. IRES regions attract a eukaryotic ribosomal translation initiation complex and thus allow translation initiation in the middle of an mRNA and independently of the commonly utilized 5'-terminal cap structure. Suitable IRES sequences are well known and many may be found in IRESite's database of experimentally verified IRES sequences (see, e.g., http://iresite.org/IRESite_web.php?page=browse_plasmids; accessed 26 May 2016).

In various embodiments, the three genes are present in any order and separated by one or more IRES sequences. The IRES sequences may be identical or not. Additional sequences may be present at the gene/IRES junction or an IRES/IRES junction.

In certain embodiments, two or three of the molecules are expressed in a single transcript from one promoter and their coding sequences are separated by one or more self-cleaving 2A peptides. These peptides are short (about 18-22 amino acids) and are inserted in-frame between coding sequences. During translation, ribosomes skip the synthesis of the glycyl-prolyl peptide bond at the C-terminus of a 2A peptide, leading to the cleavage between a 2A peptide and its immediate downstream protein. As a result, they produce equimolar levels of multiple gene products from the same mRNA. The "cleavage" occurs between the gly-pro residues at the C-terminus, meaning the upstream cistron will have additional residues added to its C-terminus, while the downstream cistron will begin with a proline. Exemplary p2A peptide sequences are shown in SEQ ID NOs: 520-535.

Another means to effect co-expression of the molecules is to use a bidirectional promoter. Bidirectional promoters are a common feature of the human genome (Trinklein et al. Genome Res 14:62, 2004). A bidirectional promoter initiates transcription in both directions and typically contains shared elements that regulate both genes. In addition to natural bidirectional promoters, promoters have been synthesized to be bidirectional. One such promoter is bi-CMV. pBI-CMV1 is a mammalian bidirectional expression vector that allows the constitutive expression of two proteins of interest. Protein expression is driven by one of two constitutively active, minimal human cytomegalovirus promoters, PminCMV1 and PminCMV2 in opposite orientations. An exemplary DNA sequence of a bidirectional CMV promoter is SEQ ID NO. 536.

The bidirectional promoter (e.g., bi-CMV promoter) is mainly used to achieve co-expression of hIL15 and IL-15Rα (or the Sushi domain). When two molecules are co-expressed using IRES or p2A sequences, generally it will be hIL15 and IL-15Rα (or the Sushi domain). In these cases, IL-12 and PD-L1 blocking peptides may be co-expressed using a bidirectional promoter or as a multicistronic transcript with IRES or p2A sequences, or they may be individually expressed from their own promoters/regulatory regions.

Other promoters may be used. Cellular promoters, viral promoters and the like are suitable. The promoters may be constitutive or inducible or cell/tissue-specific. Many promoters are well known. One particular promoter that may be useful is the constitutive EF-la promoter.

The sequences are assembled in one or more expression cassettes. The Examples provide exemplary versions of some expression cassettes. The expression cassette may be inserted into the HSV genome in any location that does not disrupt critical functions (e.g., replication). In certain embodiments, the cassette is inserted in internal or in terminal repeat region after first deleting the repeat. Other suitable areas for insertion include between viral genes, such as, for example, the UL3 and UL4 viral genes, the UL50 and UL51 genes, and between US1 and US2.

In certain embodiments, a cassette expressing PD-L1 blocking peptides in inserted in between viral genes (e.g., UL3 and UL4, UL50 and UL51 and/or US1 and US2). In other embodiments, a cassette expressing IL-12, IL-15 and IL-15Rα is inserted in place of the terminal repeat region and a cassette expressing PD-L1 peptides is inserted in between UL3 and UL4 genes.

D. Therapeutic Compositions

Therapeutic compositions are provided that may be used to prevent, treat, or ameliorate the effects of a disease, such as, for example, cancer. More particularly, therapeutic compositions are provided comprising at least one oncolytic virus as described herein. Representative examples include an oHSV that has an expression cassette for one or more of IL12, IL15 and/or ILReceptor 15 alpha subunit. Within one embodiment, the expression cassette expresses all of IL12, IL15 and the IL Receptor 15 alpha subunit. Within preferred embodiments, the expression cassette comprises murine or human IL12, hIL15, and hIL15Receptor alpha subunit.

In certain embodiments, the compositions will further comprise a pharmaceutically acceptable carrier. The phrase "pharmaceutically acceptable carrier" is meant to encompass any carrier, diluent or excipient that does not interfere with the effectiveness of the biological activity of the oncolytic virus and that is not toxic to the subject to whom it is administered (see generally Remington: The Science and Practice of Pharmacy, Lippincott Williams & Wilkins; 21st ed. (May 1, 2005 and in The United States PharmacopE1A: The National Formulary (USP 40-NF 35 and Supplements).

In the case of an oncolytic virus as described herein, non-limiting examples of suitable pharmaceutical carriers include phosphate buffered saline solutions, water, emulsions (such as oil/water emulsions), various types of wetting agents, sterile solutions, and others. Additional pharmaceutically acceptable carriers include gels, bioadsorbable matrix materials, implantation elements containing the oncolytic virus, or any other suitable vehicle, delivery or dispensing means or material(s). Such carriers can be formulated by conventional methods and can be administered to the subject at an effective dose. Additional pharmaceutically acceptable excipients include, but are not limited to, water, saline, polyethyleneglycol, hyaluronic acid and ethanol. Pharmaceutically acceptable salts can also be included therein, e.g., mineral acid salts (such as hydrochlorides, hydrobromides, phosphates, sulfates, and the like) and the salts of organic acids (such as acetates, propionates, malonates, benzoates, and the like). Such pharmaceutically acceptable (pharmaceutical-grade) carriers, diluents and excipients that may be used to deliver the oHSV to a target cancer cell will preferably not induce an immune response in the individual (subject) receiving the composition (and will preferably be administered without undue toxicity).

The compositions provided herein can be provided at a variety of concentrations. For example, dosages of oncolytic virus can be provided which ranges from about $10^6$ to about $10^9$ pfu. Within further embodiments, the dosage form can range from about $10^6$ to about $10^8$ pfu/ml, with up to 4 mls being injected into a patient with large lesions (e.g., >5 cm) and smaller amounts (e.g., up to 0.1 mls) in patients with small lesions (e.g., <0.5 cm) every 2-3 weeks, of treatment.

Within certain embodiments of the invention, lower dosages than standard may be utilized. Hence, within certain embodiments less than about $10^6$ pfu/ml (with up to 4 mis being injected into a patient every 2-3 weeks) can be administered to a patient.

The compositions may be stored at a temperature conducive to stable shelf-life, and includes room temperature (about 20° C.), 4° C., −20° C., −80° C., and in liquid N2. Because compositions intended for use in vivo generally don't have preservatives, storage will generally be at colder temperatures. Compositions may be stored dry (e.g., lyophilized) or in liquid form.

E. Administration

In addition to the compositions described herein, various methods of using such compositions to treat or ameliorate cancer are provided, comprising the step of administering an effective dose or amount of a HSV vector as described herein to a subject.

The terms "effective dose" and "effective amount" refers to amounts of the oncolytic virus that is sufficient to effect treatment of a targeted cancer, e.g., amounts that are effective to reduce a targeted tumor size or load, or otherwise hinder the growth rate of targeted tumor cells. More particularly, such terms refer to amounts of oncolytic virus that is effective, at the necessary dosages and periods of treatment, to achieve a desired result. For example, in the context of treating a cancer, an effective amount of the compositions described herein is an amount that induces remission, reduces tumor burden, and/or prevents tumor spread or growth of the cancer. Effective amounts may vary according to factors such as the subject's disease state, age, gender, and weight, as well as the pharmaceutical formulation, the route of administration, and the like, but can nevertheless be routinely determined by one skilled in the art.

The therapeutic compositions are administered to a subject diagnosed with cancer or is suspected of having a cancer. Subjects may be human or non-human animals.

The compositions are used to treat cancer. The terms "treat" or "treating" or "treatment," as used herein, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. The terms "treating" and "treatment" can also mean prolonging survival as compared to expected survival if not receiving treatment.

Representative forms of cancer include carcinomas, leukemia's, lymphomas, myelomas and sarcomas. Further examples include, but are not limited to cancer of the bile duct cancer, brain (e.g., glioblastoma), breast, cervix, colorectal, CNS (e.g., acoustic neuroma, astrocytoma, craniopharyogioma, ependymoma, glioblastoma, hemangioblastoma, medulloblastoma, menangioma, neuroblastoma, oligodendroglioma, pinealoma and retinoblastoma), endometrial lining, hematopoietic cells (e.g., leukemia's and lymphomas), kidney, larynx, lung, liver, oral cavity, ovaries, pancreas, prostate, skin (e.g., melanoma and squamous cell carcinoma) and thyroid. Cancers can comprise solid tumors (e.g., sarcomas such as fibrosarcoma, myxosarcoma, liposarcoma, chondrosarcoma and osteogenic sarcoma), be diffuse (e.g., leukemia's), or some combination of these (e.g., a metastatic cancer having both solid tumors and disseminated or diffuse cancer cells). Cancers can also be resistant to conventional treatment (e.g. conventional chemotherapy and/or radiation therapy).

Benign tumors and other conditions of unwanted cell proliferation may also be treated.

The oHSV as described herein may be given by a route that is e.g. oral, topical, parenteral, systemic, intravenous, intramuscular, intraocular, intrathecal, intratumor, subcutaneous, or transdermal. Within certain embodiments the oncolytic virus may be delivered by a cannula, by a catheter, or by direct injection. The site of administration may be intra-tumor or at a site distant from the tumor. The route of administration will often depend on the type of cancer being targeted.

The optimal or appropriate dosage regimen of the oncolytic virus is readily determinable within the skill of the art, by the attending physician based on patient data, patient observations, and various clinical factors, including for example a subject's size, body surface area, age, gender, and the particular oncolytic virus being administered, the time and route of administration, the type of cancer being treated, the general health of the patient, and other drug therapies to which the patient is being subjected. According to certain embodiments, treatment of a subject using the oncolytic virus described herein may be combined with additional types of therapy, such as chemotherapy using, e.g., a chemotherapeutic agent such as etoposide, ifosfamide, adriamycin, vincristin, doxicyclin, and others.

oHSV may be formulated as medicaments and pharmaceutical compositions for clinical use and may be combined with a pharmaceutically acceptable carrier, diluent, excipient or adjuvant. The formulation will depend, at least in part, on the route of administration. Suitable formulations may comprise the virus and inhibitor in a sterile medium. The formulations can be fluid, gel, paste or solid forms. Formulations may be provided to a subject or medical professional A therapeutically effective amount is preferably administered. This is an amount that is sufficient to show benefit to the subject. The actual amount administered and time-course of administration will depend at least in part on the nature of the cancer, the condition of the subject, site of delivery, and other factors.

Within yet other embodiments of the invention the oncolytic virus can be administered intratumorally, or, after surgical resection of a tumor.

The following examples are offered by way of illustration, and not by way of limitation.

EXAMPLES

All constructs are generated using standard recombinant techniques, including chemical synthesis.

Example 1

Schematic of Exemplary oHSV Vectors

Figure 1B:
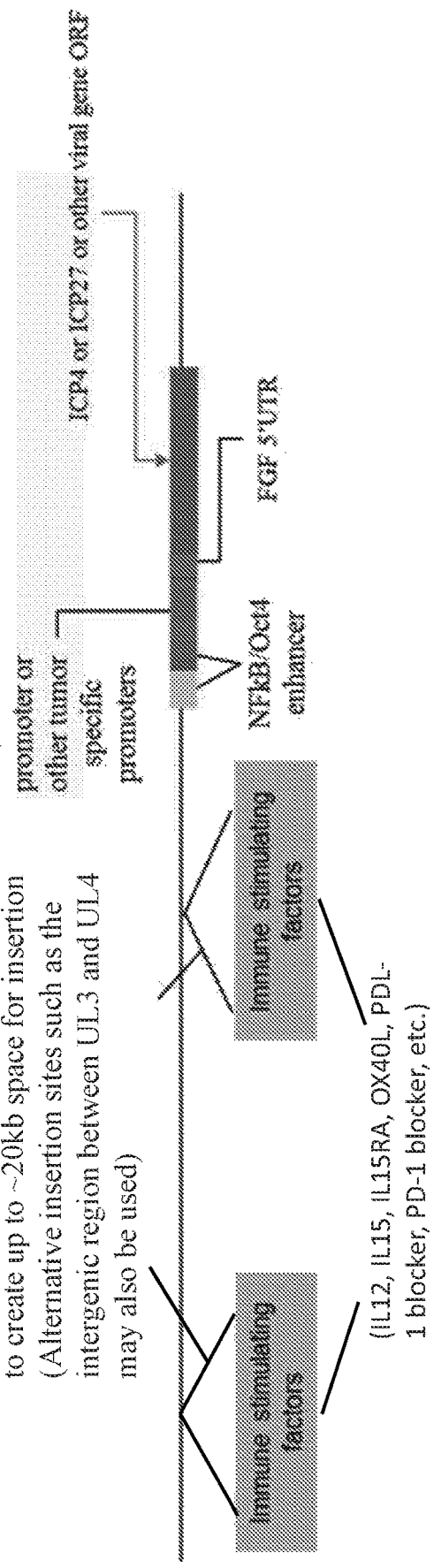

FIGS. 1A and 1B provide and exemplary schematic of representative oHSV vectors.

Example 2

Exemplary Constructs

Figure 2:
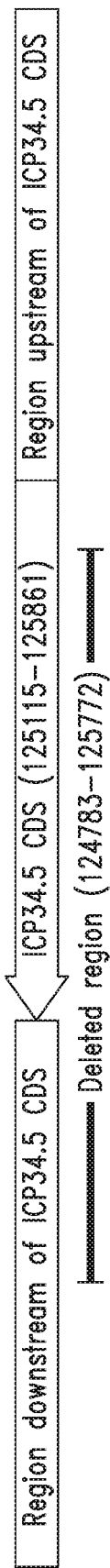
FIG. 2 shows a schematic of the modified ICP34.5 region (SEQ ID NO: 572) for virus hVG161.
Figure 3:
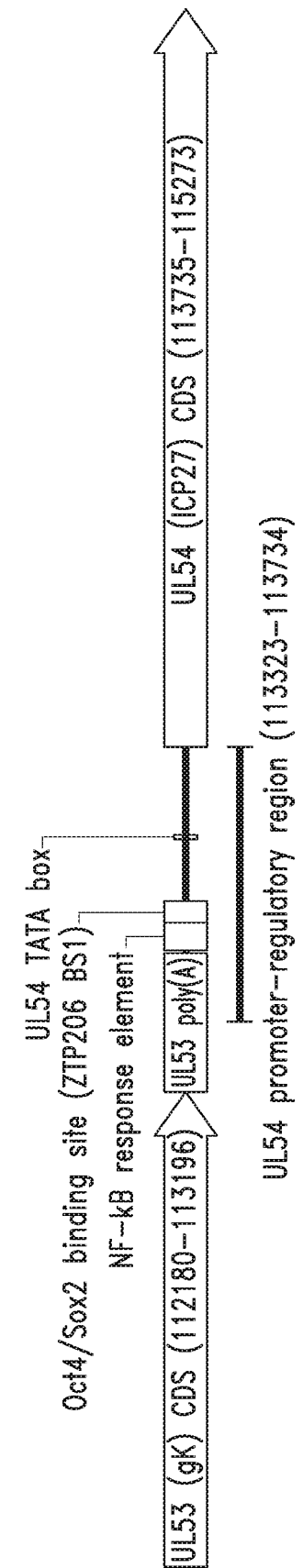
FIG. 3 shows a schematic of a modified UL54 promoter region (SEQ ID NO: 573) for virus hVG161.
Figure 4:
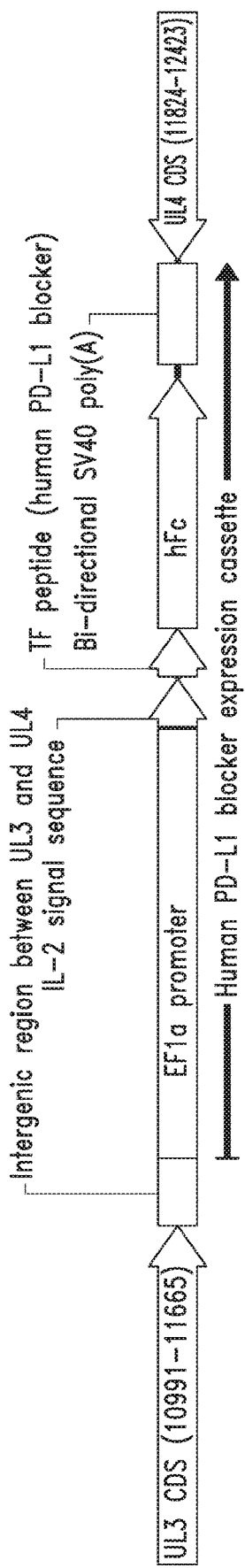
FIG. 4 shows a schematic of hVG161.viral genome with an insertion of a PD-L1 blocker (SEQ ID NO: 574).
Figure 5:
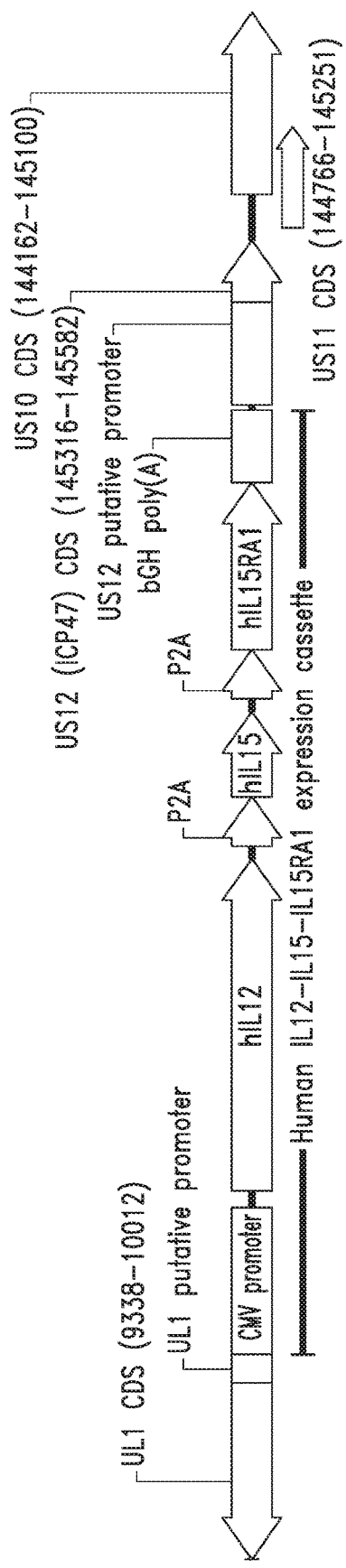
FIG. 5 shows a schematic of hVG161 modified TR region (SEQ ID NO: 575).

In this example, various constructs and their sequences are presented.

hVG161 comprises a modified ICP34.5 region (FIG. 2; SEQ ID NO. 572), a modified UL54 promoter-regulatory region (FIG. 3; SEQ ID NO. 573), an insertion of a PD-L1 blocker within the intergenic region between UL3 and UL4 (FIG. 4; SEQ ID No. 574), and a modified terminal repeat (TR) region carrying an expression cassette encoding IL-12, IL-15, and IL-15 receptor alpha subunit (FIG. 5; SEQ ID NO. 575). These four viruses also have a modified and partially deleted ICP 34.5 region.

mVG161 is a functionally identical mouse version of hVG161 except that that mVG161 carries a mouse version of IL-12 and a mouse PD-L1 blocker in the same location on the viral genome where hVG161 carries a human IL-12 and a human PD-L1 blocker.

Example 3

Abbreviations Used in Subsequent Examples

TF-Fc: PD-L1 blocking peptide (TF) fused to Fc and used for construction of VG161.

IL-TF-Fc: plasmid carrying IL-12, IL-15, and PD-L1 blocker.

HSV-345: ICP34.5-deleted virus.

OS-ICP27 2-11: ICP34.5-deleted virus with Oct4/Sox2 binding site and surviving promoter (OS) inserted within the promoter-regulatory region of ICP27 (OS-ICP27) that was not used for construction of VG161.

OS-ICP27 5-7: ICP34.5-deleted virus with OS-ICP27 mutation that was not used for construction of VG161.

NO-ICP27 1-4-4 (also known as NO-ICP27-145): ICP34.5-deleted virus with NF-kB response element and Oct4/Sox2 binding site (NO) inserted within the promoter-regulatory region of ICP27 (NO-ICP27) at a location 145 bp upstream of the transcription start site of ICP27 and that was used for construction of VG161.

NO-ICP27 5-2-2 (also known as NO-ICP27-99): ICP34.5-deleted virus with NF-kB response element and Oct4/Sox2 binding site (NO) inserted within the promoter-regulatory region of ICP27 (NO-ICP27) at a location 99 bp upstream of the transcription start site of ICP27 and that was not used for construction of VG161.

VG001 (also known as VG160): backbone virus that was used for construction of VG161 (NO-ICP27 1-4-4 mutant carrying an exogenous promoter and poly(A) flanking an empty MCS within deleted terminal repeat region of the viral genome that is subsequently used for insertion of the IL-12/IL-15 expression cassette).

VG001-15h (also known as VG161-15h): VG001 carrying human IL-15.

VG001-1215h (also known as VG161-1215h): VG001 carrying human IL-12 and human IL-15.

VG001-PLBh (also known as VG161-PLBh): VG001 carrying human PD-L1 blocker inserted within intergenic region between UL3 and UL4.

8-8-15RA1-PDL1b: VG001 carrying human IL-15 and human PD-L1 blocker.

VG161-1215PLBm (also known as mVG161): VG001 carrying mouse IL-12, human IL-15, and mouse PD-L1 blocker.

VG161-1215PLBh (also known as hVG161 or VG161): VG001 carrying human IL-12, human IL-15, and human PD-L1 blocker.

Example 4

Expression of IL-12 Following Infection of Cells by hVG161

In this Example, Western blot and ELISA data of II-12 expression is shown.

Figures 6A, 6B, 6C:
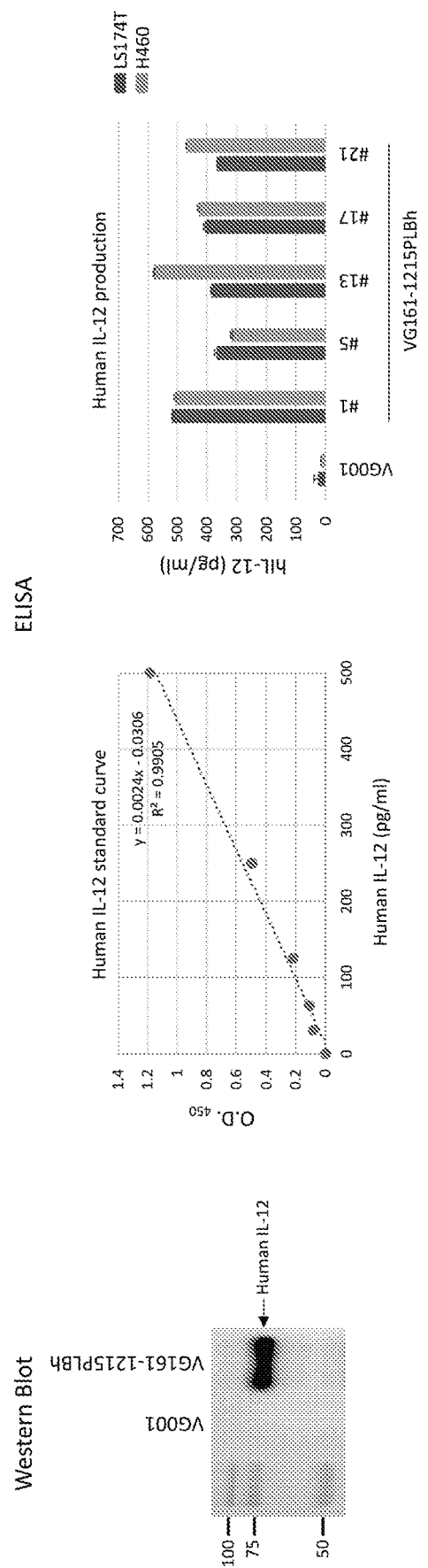
FIGS. 6A-6C show ELISA and Western blot data for IL-12 expression following hVG161 infection of cells.

FIG. 6A shows Western Blot results after VG161-1215PLBh virus infection. H460 tumour cells were infected with VG161-1215PLB or VG001 virus (MOI=1) for 24 hours. Cell lysates were prepared, ran on 12% SDS-PAGE gel, and transferred to PVDF membrane. The membrane was blotted with anti-human IL-12 antibody followed by HRP-conjugated anti-mouse IgG secondary antibody and the mage was detected and analyzed using Bio-Rad ImageLab system.

FIGS. 6B-6C shows that production of human IL-12 is upregulated after VG161-1215PLBh virus infection. LS174T or H460 tumour cells were infected with VG161-1215PLB or VG001 virus (MOI=1) for 48 hours. Infected cell supernatants were harvested and bound to anti-human IL-12 capture antibody coated 96-well Immuno Maxisorp flat bottom plate. Binding was detected via a biotinylated anti-human IL-12 antibody, avidin-horseradish peroxidase (HRP), and 3,3',5,5'-Tetramethylbenzidine (TMB) substrate. Absorbance measurements were collected at 450 nm via a plate reader. The concentration of human IL-12 in cultured supernatants was calculated based on human IL-12 standard curve.

Example 5

Expression of IL-15 Following Infection of Cells by hVG161

In this Example, Western blot and ELISA data of IL-15 expression is shown.

FIG. 7A shows Western Blot results after VG161-1215PLBh virus infection. H460 tumour cells were infected with VG161-1215PLB or VG001 virus (MOI=1) for 24 hours. Cell lysates were prepared, ran on 12% SDS-PAGE gel, and transferred to PVDF membrane. The membrane was blotted with anti-human IL-15 antibody followed by HRP-conjugated anti-mouse IgG secondary antibody and the image was detected and analyzed using Bio-Rad ImageLab system.

FIGS. 7B-7C shows that production of human IL-15 is upregulated after VG161-1215PLBh virus infection. LS174T or H460 tumour cells were infected with VG161-1215PLB or VG001 virus (MOI=1) for 48 hours. Infected cell supernatants were harvested and bound to anti-human IL-15 capture antibody coated 96-well Immuno Maxisorp flat bottom plate. Binding was detected via a biotinylated anti-human IL-15 antibody, avidin-horseradish peroxidase (HRP), and 3,3',5,5'-Tetramethylbenzidine (TMB) substrate. Absorbance measurements were collected at 450 nm via a plate reader. The concentration of human IL-15 in cultured supernatants was calculated based on human IL-15 standard curve.

Example 6

Expression of IgG4 Following Infection of Cells by hVG161

In this Example, Western blot and ELISA data of IgG4 expression is shown.

Figures 8A, 8B, 8C:
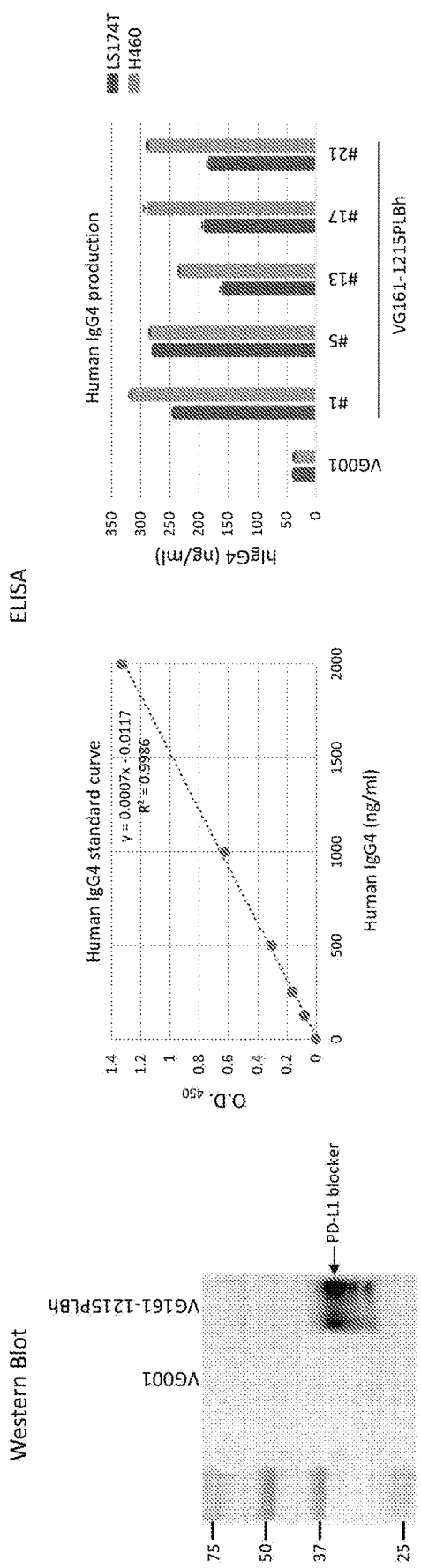
FIGS. 8A-8C show ELISA and Western blot data for IgG4 expression following hVG161 infection of cells.

FIG. 8A shows Western Blot results after VG161-1215PLBh virus infection. H460 tumour cells were infected with VG161-1215PLB or VG001 virus (MOI=1) for 24 hours. Cell lysates were prepared, ran on 12% SDS-PAGE gel, and transferred to PVDF membrane. The membrane was blotted with HRP-conjugated anti-human IgG antibody and the image was detected and analyzed using Bio-Rad Image-Lab system.

FIGS. 8B-8C shows that production of human PD-L1 blocker (fused to human Fc domain) is upregulated after VG161-1215PLBh virus infection. LS174T or H460 tumour cells were infected with VG161-1215PLB or VG001 virus (MOI=1) for 48 hours. Infected cell supernatants were harvested and bound to anti-human IgG4 capture antibody coated 96-well Immuno Maxisorp flat bottom plate. Binding was detected via a biotinylated anti-human IgG4 antibody, avidin-horseradish peroxidase (HRP), and 3,3',5,5'-Tetramethylbenzidine (TMB) substrate. Absorbance measurements were collected at 450 nm via a plate reader. The concentration of human IgG4 in cultured supernatants was calculated based on human IgG4 standard curve.

Example 7

Constructs Comprising PD-L1 Blocking Peptides

PD-L1 blocking peptides are generated with an Ig κ chain leader sequence (SEQ ID NO: 501). When two or more blocking peptides are in the same construct, they are linked with a Gly-Ser rich sequence (Gly$_4$Ser)$_3$ (SEQ ID NO: 503). The following constructs are made.

TF alone:
(SEQ ID NO: 537)
METDTLLLWVLLLWVPGSTGTAHPSPSPRSAGQF;

ET + TF:
(SEQ ID NO: 538)
METDTLLLWVLLLWVPGSTGEYRMSPSNQTGGGGSGGGGSGGGGSTAHPS
PSPRSAGQF;

YT + TF:
(SEQ ID NO: 539)
METDTLLLWVLLLWVPGSTGYYRMSPSNQTGGGGSGGGGSGGGGSTAHPS
PSPRSAGQF;

Mouse TF:
(SEQ ID NO: 540)
METDTLLLWVLLLWVPGSTGTRYPSPSPKPEGRF;

Mouse WT + TF:
(SEQ ID NO: 541)
METDTLLLWVLLLWVPGSTGWNRLSPSNQTGGGGSGGGGSGGGGSTRYPS
PSPKPEGRF.

Triple TF + ET:
(SEQ ID NO: 542)
METDTLLLWVLLLWVPGSTGTAHPSPSPRSAGQFTAHPSPSPRSAGQFTA
HPSPSPRSAGQFGGGGSGGGGSGGGGSEYRMSPSNQTEYRMSPSNQTEYR
MSPSNQT (SEQ ID NO: 543)
METDTLLLWVLLLWVPGSTGEYRMSPSNQTEYRMSPSNQTEYRMSPSNQT
GGGGSGGGGSGGGGSTAHPSPSPRSAGQFTAHPSPSPRSAGQFTAHPSPS
PRSAGQF.

TF alone:
(SEQ ID NO: 546)
MYRMQLLSCIALSLALVTNSTAHPSPSPRSAGQFISAMVRSPPCPSCPAP

EFLGGPSVFLFPPKPKDTLMISRTPEVTCVVVDVSQEDPEVQFNWYVDGV

EVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEAL

HNHYTQKSLSLSPGK

ET + TF:
(SEQ ID NO: 547)
MYRMQLLSCIALSLALVTNSEYRMSPSNQTGGGGSGGGGSGGGGSTAHPS

PSPRSAGQFISAMVRSPPCPSCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSPGK

YT + TF:
(SEQ ID NO: 548)
MYRMQLLSCIALSLALVTNSYYRMSPSNQTGGGGSGGGGSGGGGSTAHPS

PSPRSAGQFISAMVRSPPCPSCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSPGK

Mouse TF:
(SEQ ID NO: 549)
MYRMQLLSCIALSLALVTNSTRYPSPSPKPEGRFISAMVRSGCKPCICTV

PEVSSVFIFPPKPKDVLTITLTPKVTCVVVDISKDDPEVQFSWFVDDVEV

HTAQTQPREEQFNSTFRSVSELPIMHQDWLNGKEFKCRVNSAAFPAPIEK

TISKTKGRPKAPQVYTIPPPKEQMAKDKVSLTCMITDFFPEDITVEWQWN

GQPAENYKNTQPIMDTDGSYFVYSKLNVQKSNWEAGNTFTCSVLHEGLHN

HHTEKSLSHSPGK

Mouse WT + TF:
(SEQ ID NO: 550)
MYRMQLLSCIALSLALVTNSWNRLSPSNQTGGGGSGGGGSGGGGSTRYPS

PSPKPEGRFISAMVRSGCKPCICTVPEVSSVFIFPPKPKDVLTITLTPKV

TCVVVDISKDDPEVQFSWFVDDVEVHTAQTQPREEQFNSTFRSVSELPIM

HQDWLNGKEFKCRVNSAAFPAPIEKTISKTKGRPKAPQVYTIPPPKEQMA

-continued

KDKVSLTCMITDFFPEDITVEWQWNGQPAENYKNTQPIMDTDGSYFVYSK

LNVQKSNWEAGNTFTCSVLHEGLHNHHTEKSLSHSPGK.

Other constructs are made using an IL-2 signal sequence (MYRMQLLSCIALSLALVTNS (SEQ ID NO: 502), and the human IgG4 Fc region (with hinge region) (SEQ ID NO: 544) or the murine IgG1 Fc region (with hinge region)(SEQ ID NO: 545). The constructs are:

Example 8

Constructs Comprising IL-15 and IL-15Rα Under Control of a Bidirectional CMV Promoter In this example, a variety of constructs are generated to co-express IL-15 and IL-15Rα under control of a bidirectional CMV promoter.

Figure 9C:
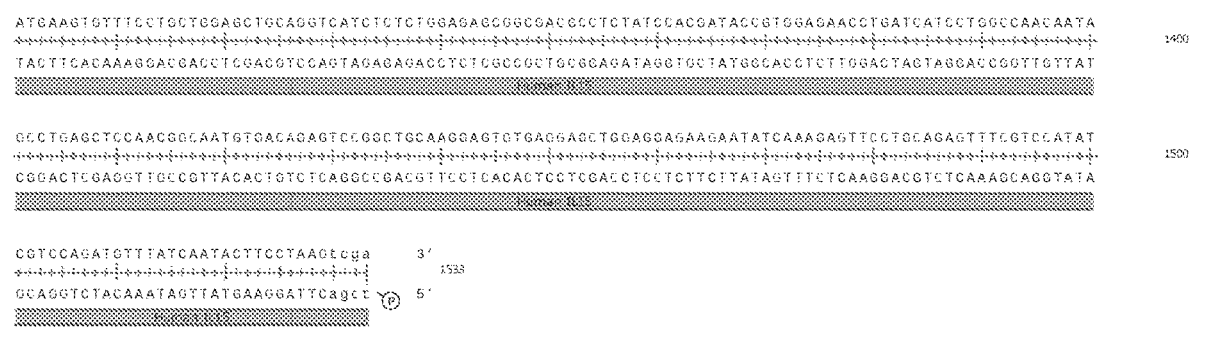

In construct 1, bi-CMV promoter drives expression of the Sushi domain of IL-15Rα and IL-15 (FIG. 9, SEQ ID No. 557).

Figure 10C:
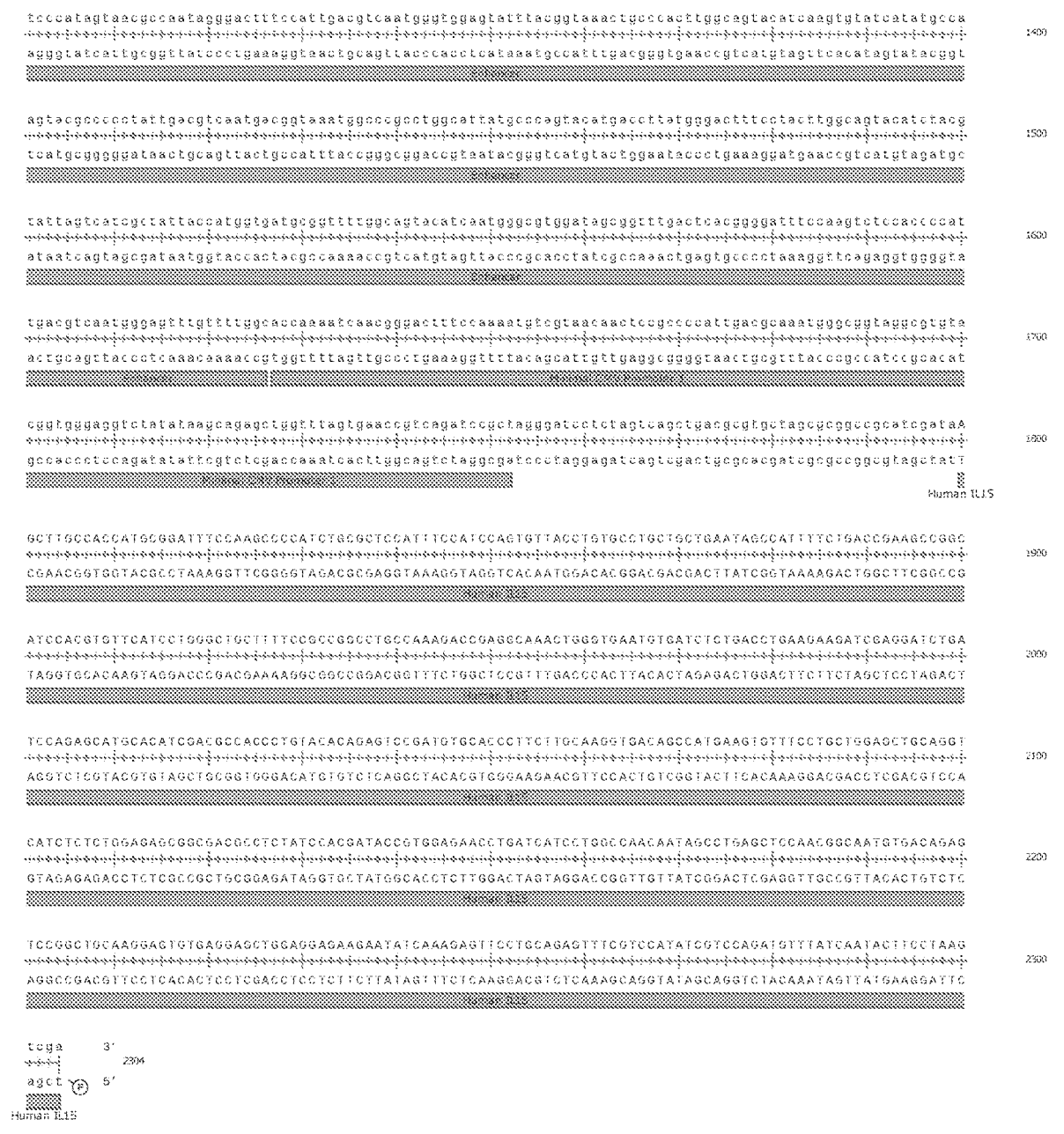

In construct 2, bi-CMV promoter drives expression of IL-15 and IL-15Rα variant 4 (FIG. 10, SEQ ID No. 558).

Figure 11A:
Figure 11C:
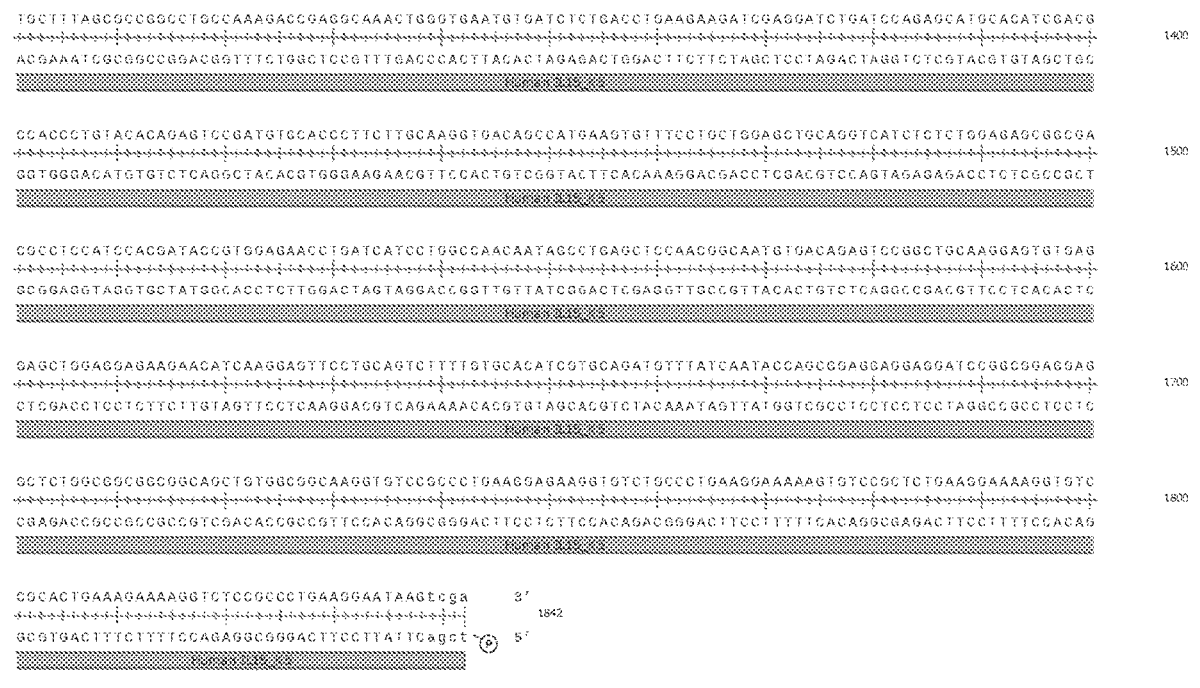

In construct 3, bi-CMV promoter drives expression of IL-15-K5 and IL-15Rα Sushi domain-E5. (FIG. 11, SEQ ID No. 559).

Figure 12A:
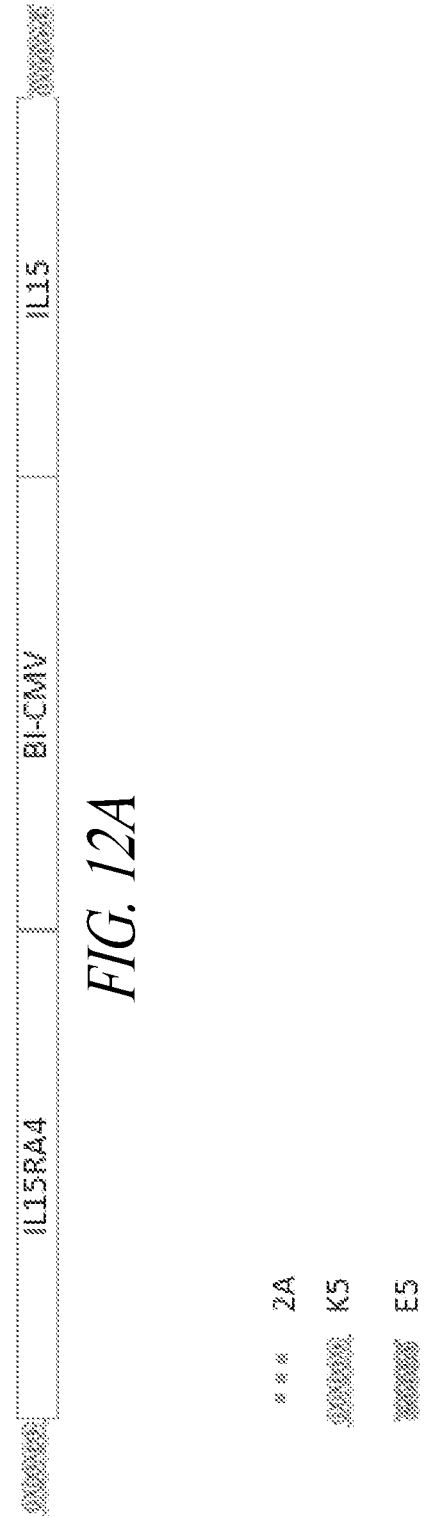
Figures 12C, 12D:
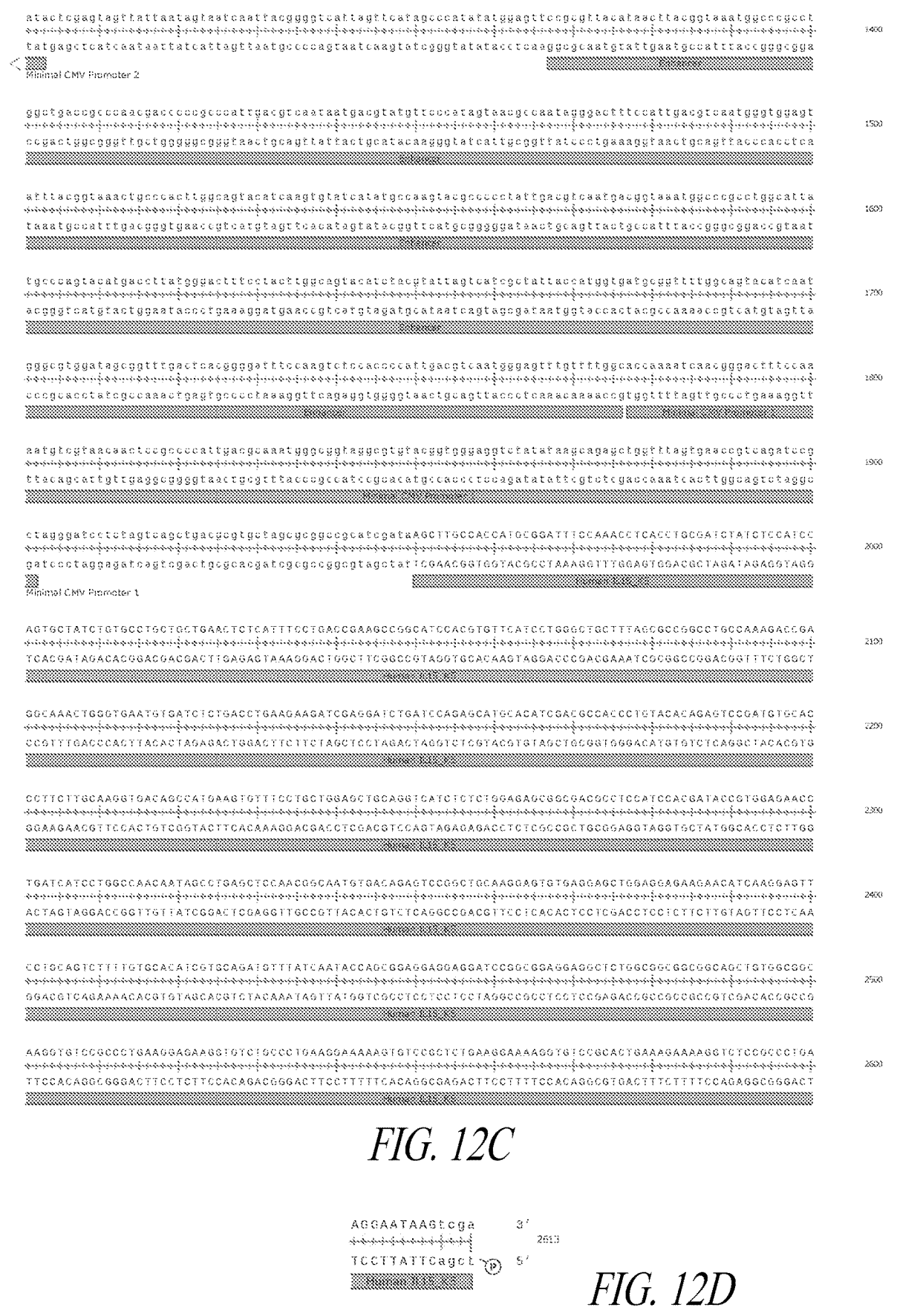

In construct 4, bi-CMV promoter drives expression of IL-15-K5 and IL-15Rα variant 4-E5 (FIG. 12, SEQ ID No. 560).

Example 9

Constructs Comprising IL-15 and IL-15Rα Genes Under Control of an EF1α Promoter In this example, a variety of constructs are generated to express IL-15 and IL-15Rα in a multi-cistronic transcript under control of an EF1α promoter (SEQ ID NO: 551). IL-15 and IL-15Rα are linked by an exemplary IRES sequence (SEQ ID NO: 552).

Figure 13D:
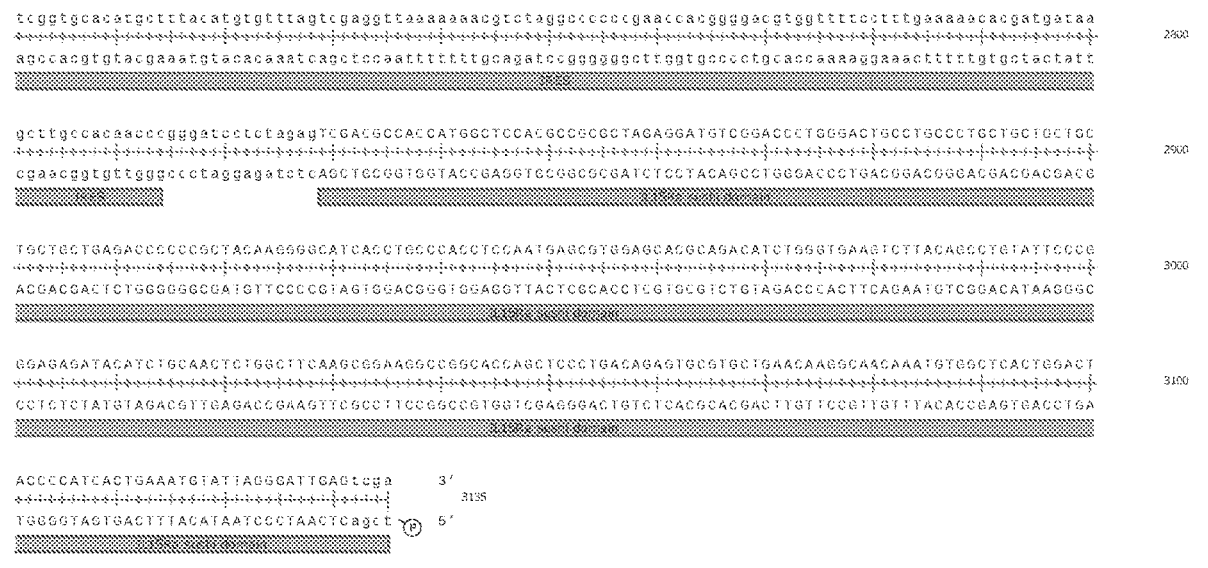

In construct 1, the EF1α promoter controls expression of IL-15-IRES-IL-15Rα Sushi domain. (FIG. 13, SEQ ID No. 561.)

Figure 14A:
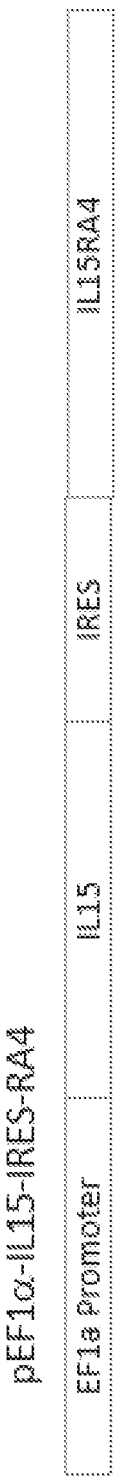
Figure 14D:
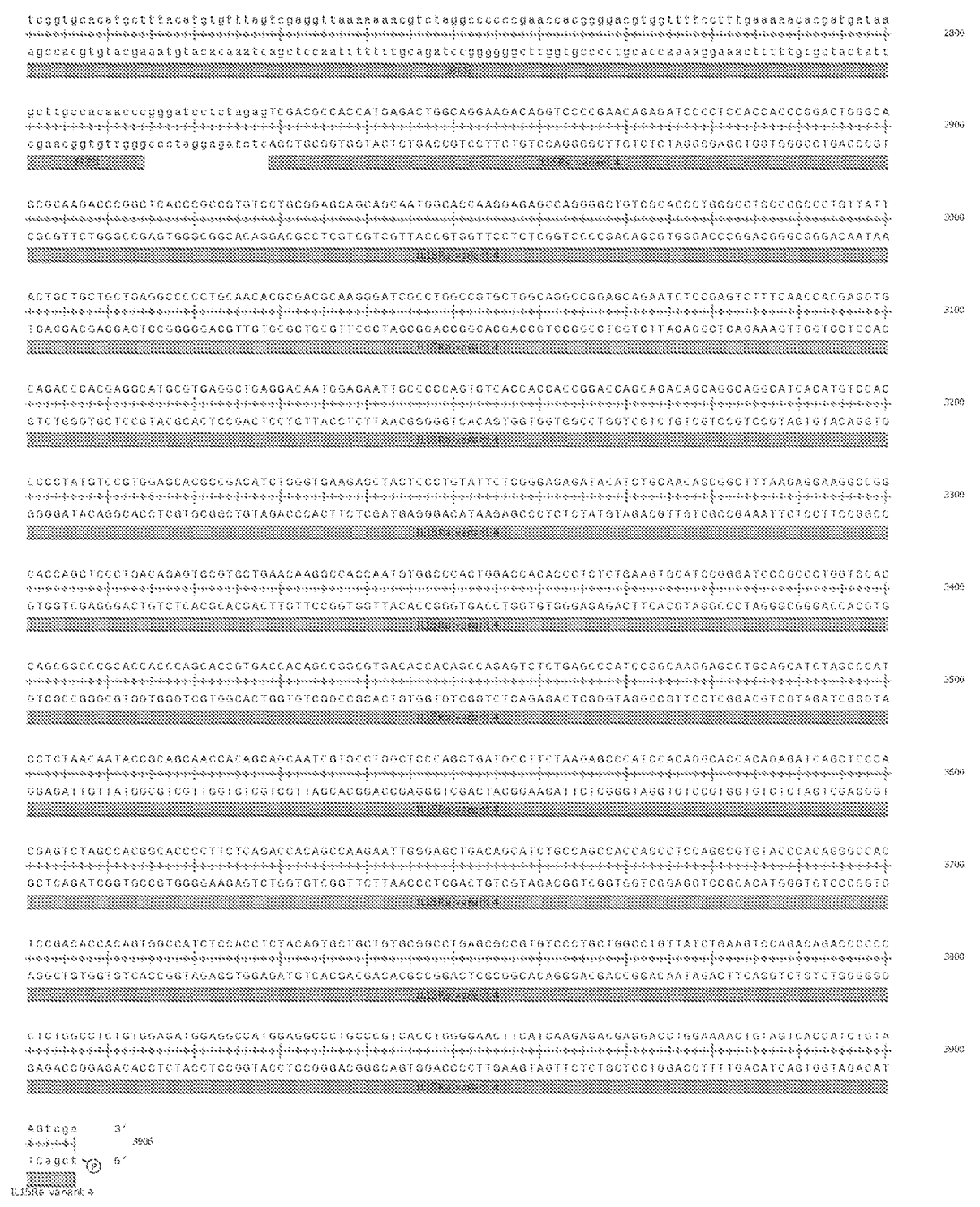

In construct 2, the EF1α promoter controls expression of IL-15-IRES-IL-15Rα variant 4 (FIG. 14, SEQ ID No. 562.)

Figure 15A:
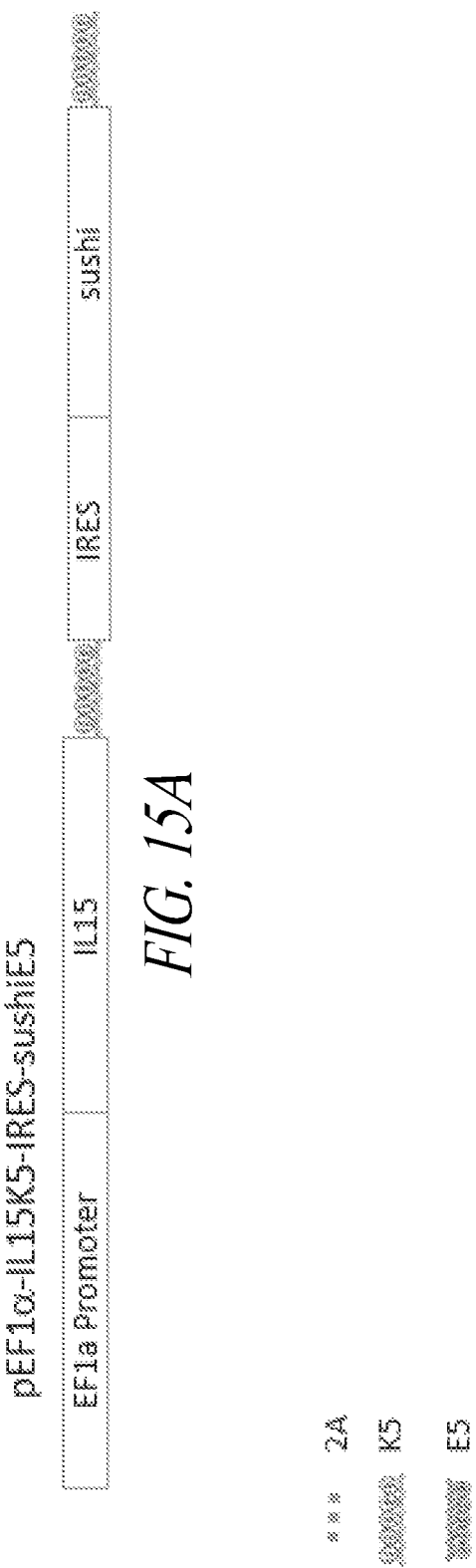
Figure 15D:
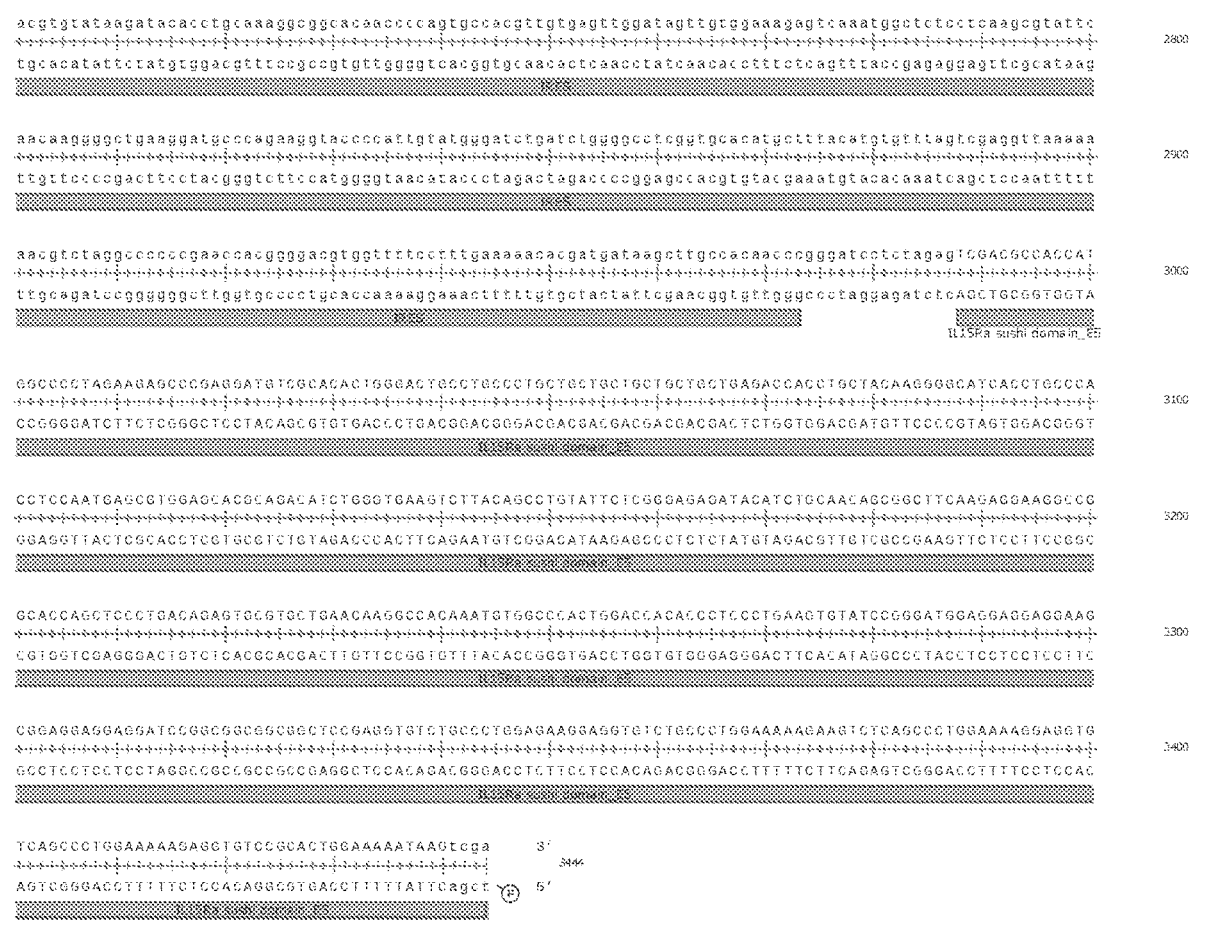

In construct 3, the EF1α promoter controls expression of IL-15K5-IRES-IL-15Rα Sushi domainE5. (FIG. 15, SEQ ID No. 563.)

Figure 16A:
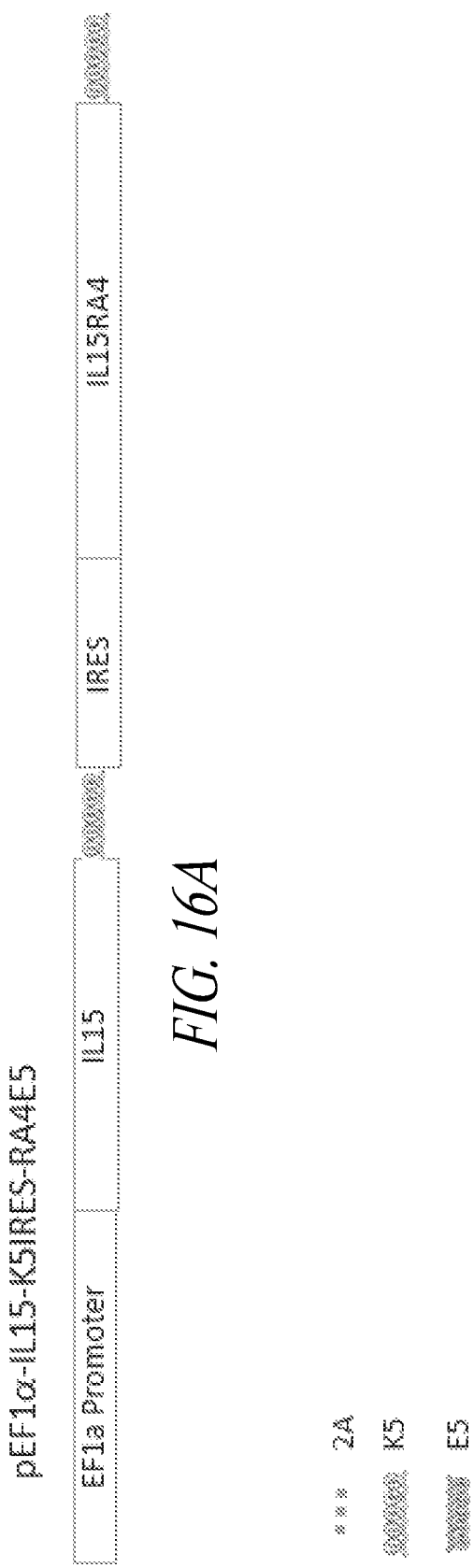
Figure 16C:
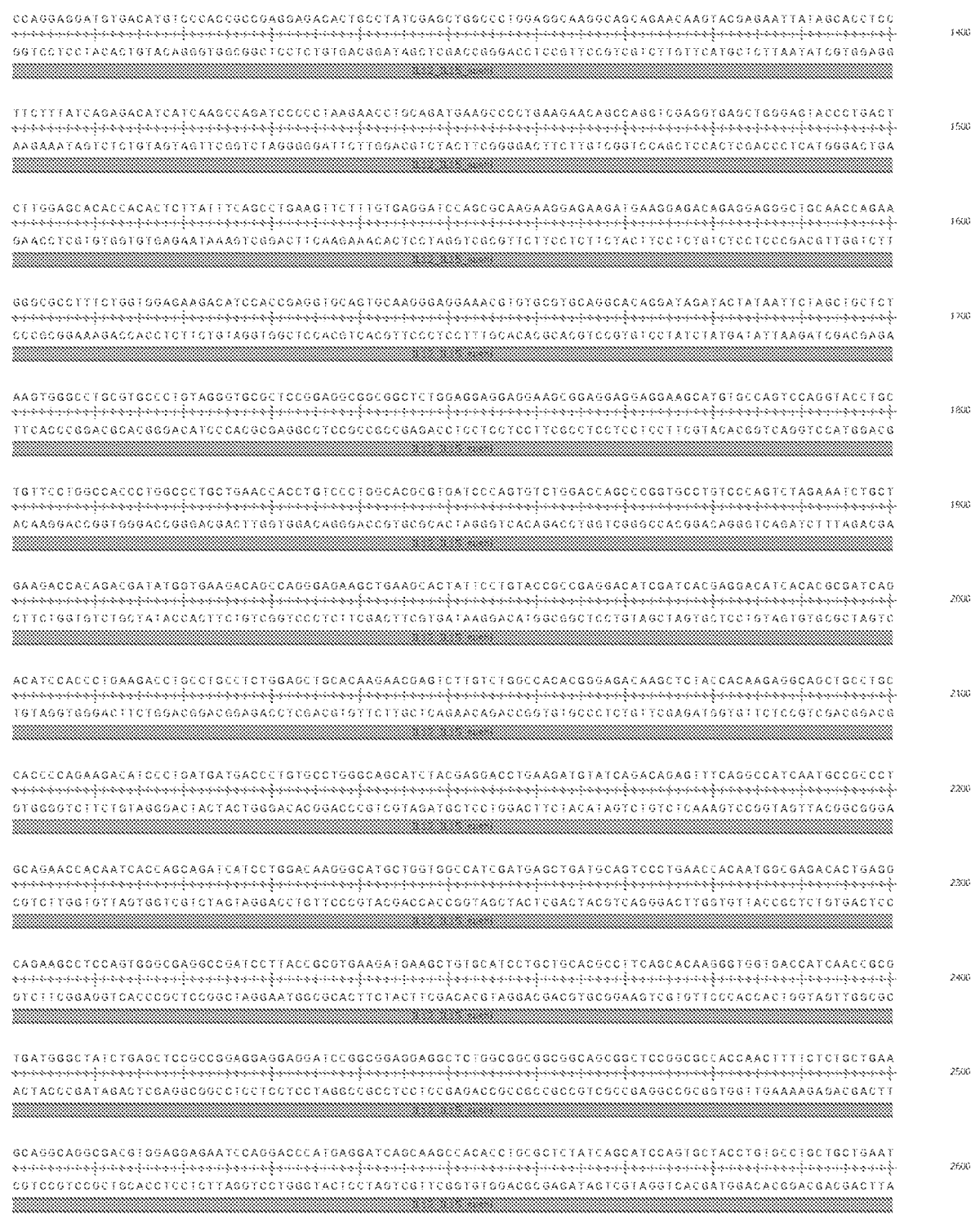

In construct 4, the EF1α promoter controls expression of IL-15K5-IRES-IL-15Rα variant 4E5. (FIG. 16, SEQ ID No. 564.)

Example 10

Constructs Comprising IL-12, IL-15 and IL-15Rα Genes Under Control of a CMV Promoter In this example, a variety of constructs are generated to express IL-12, IL-15 and IL-15Rα in a multi-cistronic transcript under control of a CMV promoter. IL-12, IL-15 and IL-15Rα are linked by an exemplary p2A sequence (SEQ ID NO: 554).

Figure 17A:
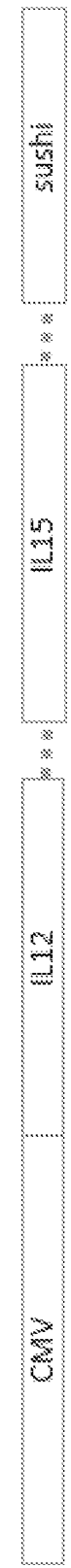
Figure 17E:
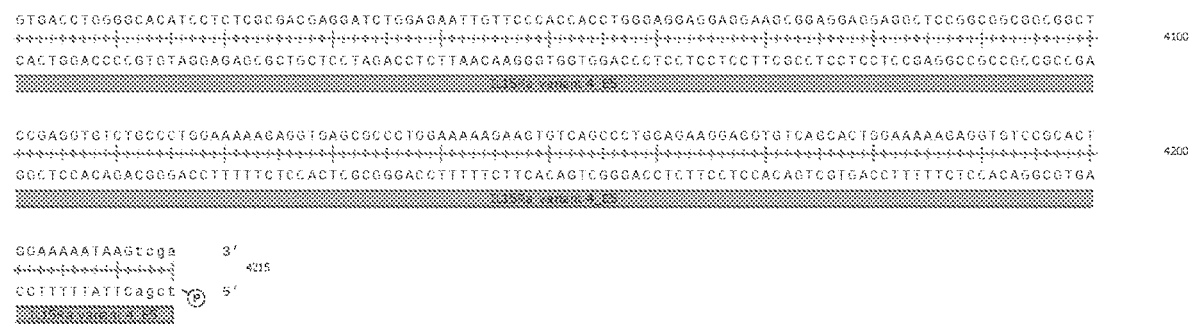

In construct 1, the CMV promoter (SEQ ID NO: 553) controls expression of IL-12-p2A-IL-15-p2A-IL-15Rα Sushi domain. (FIG. 17, SEQ ID Nos. 565, 569.)

Figure 18A:
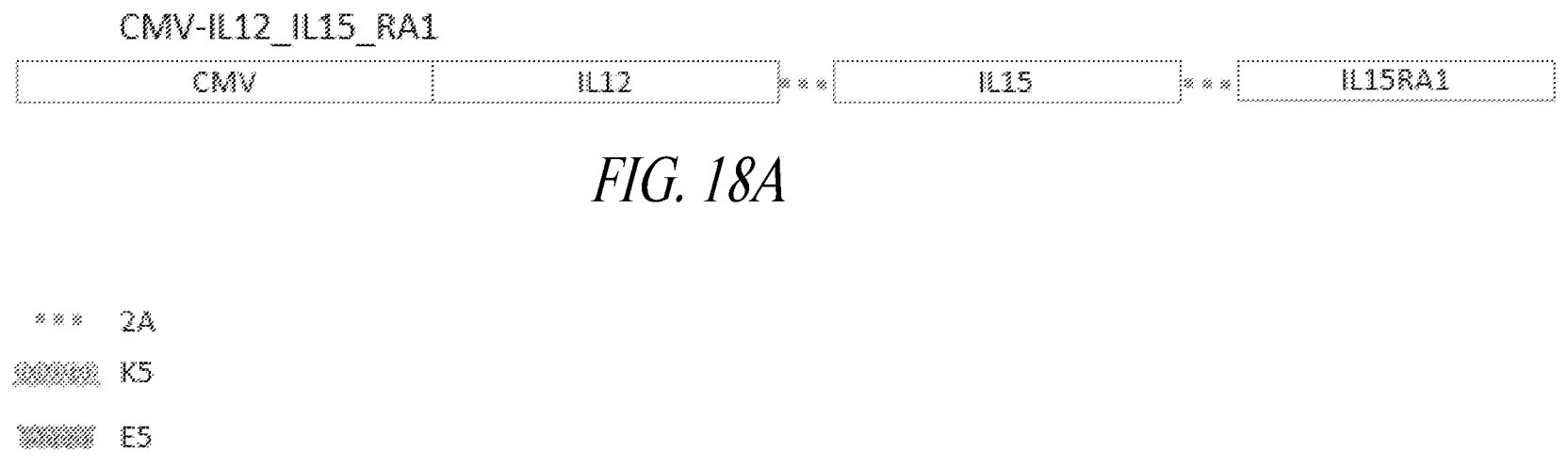
Figure 18B:
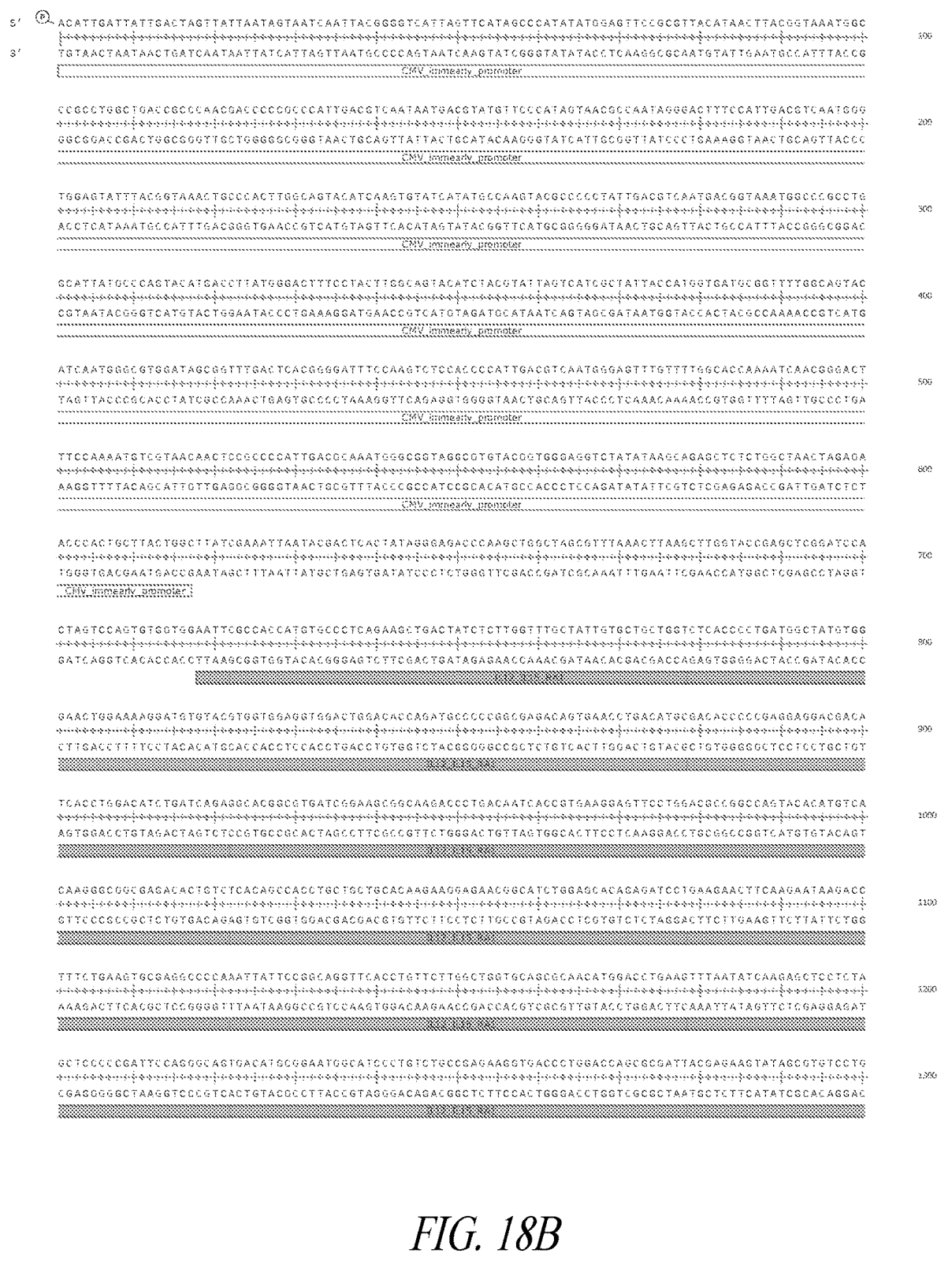
Figure 18D:

In construct 2, the CMV promoter controls expression of IL-12-p2A-IL-15-p2A-IL-15Rα variant 1 (FIG. 18O, SEQ ID Nos. 566, 570.)

Figure 19A:
Figure 19B:
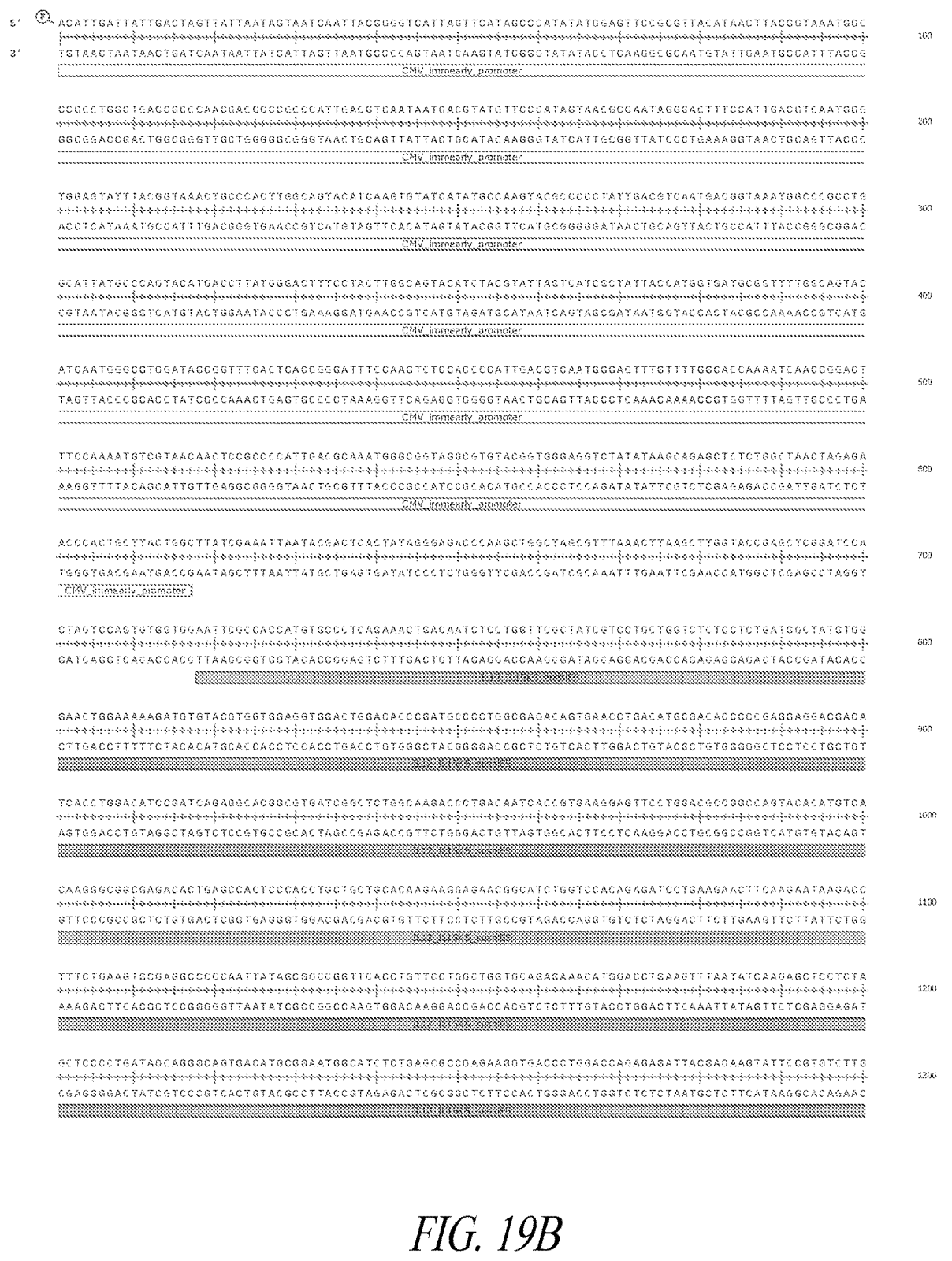
Figure 19C:
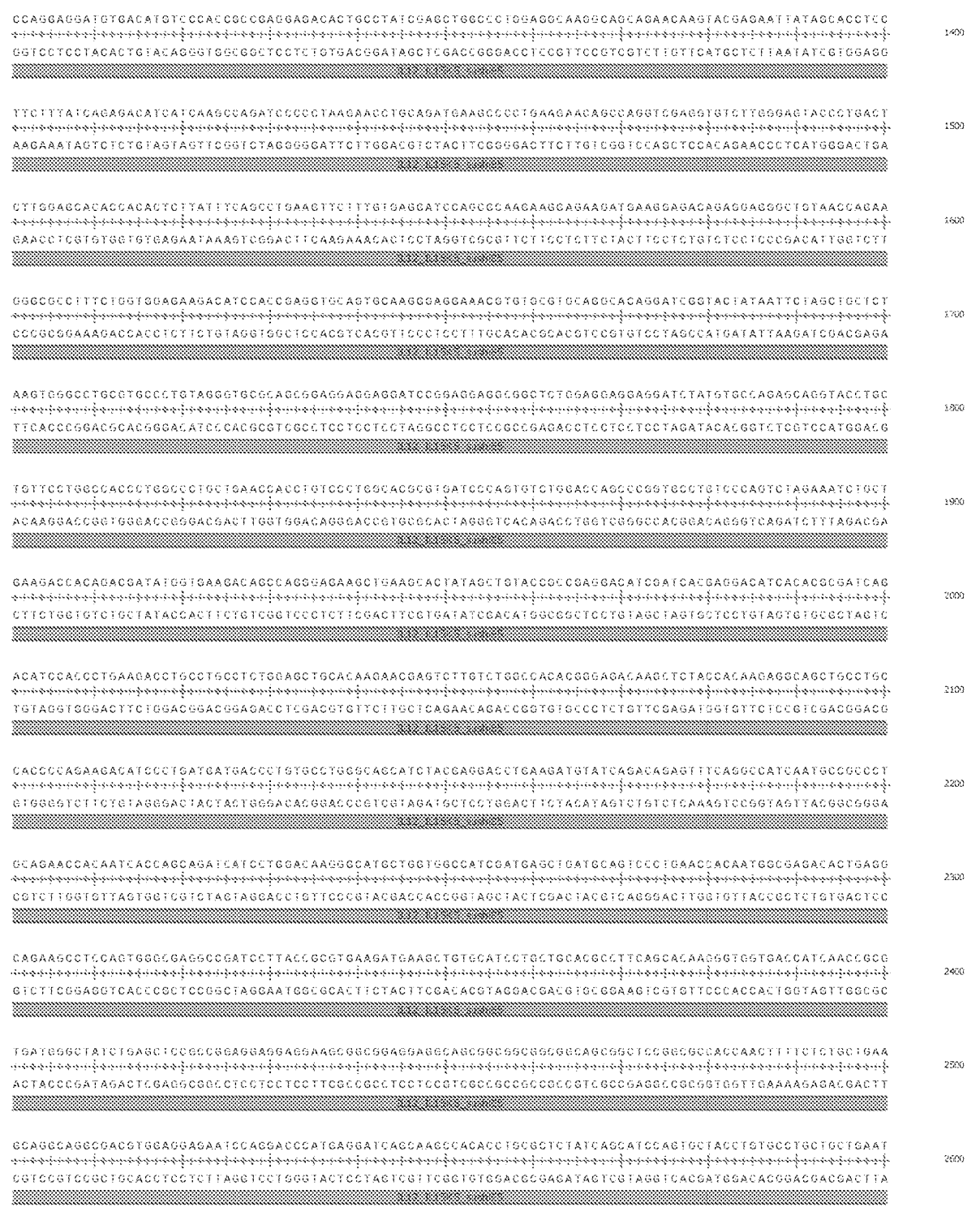

In construct 3, the CMV promoter controls expression of IL-12-p2A-IL-15K5-p2A-IL-15Rα Sushi domainE5. (FIG. 19, SEQ ID Nos. 567, 571.)

Figure 20A:
Figure 20C:
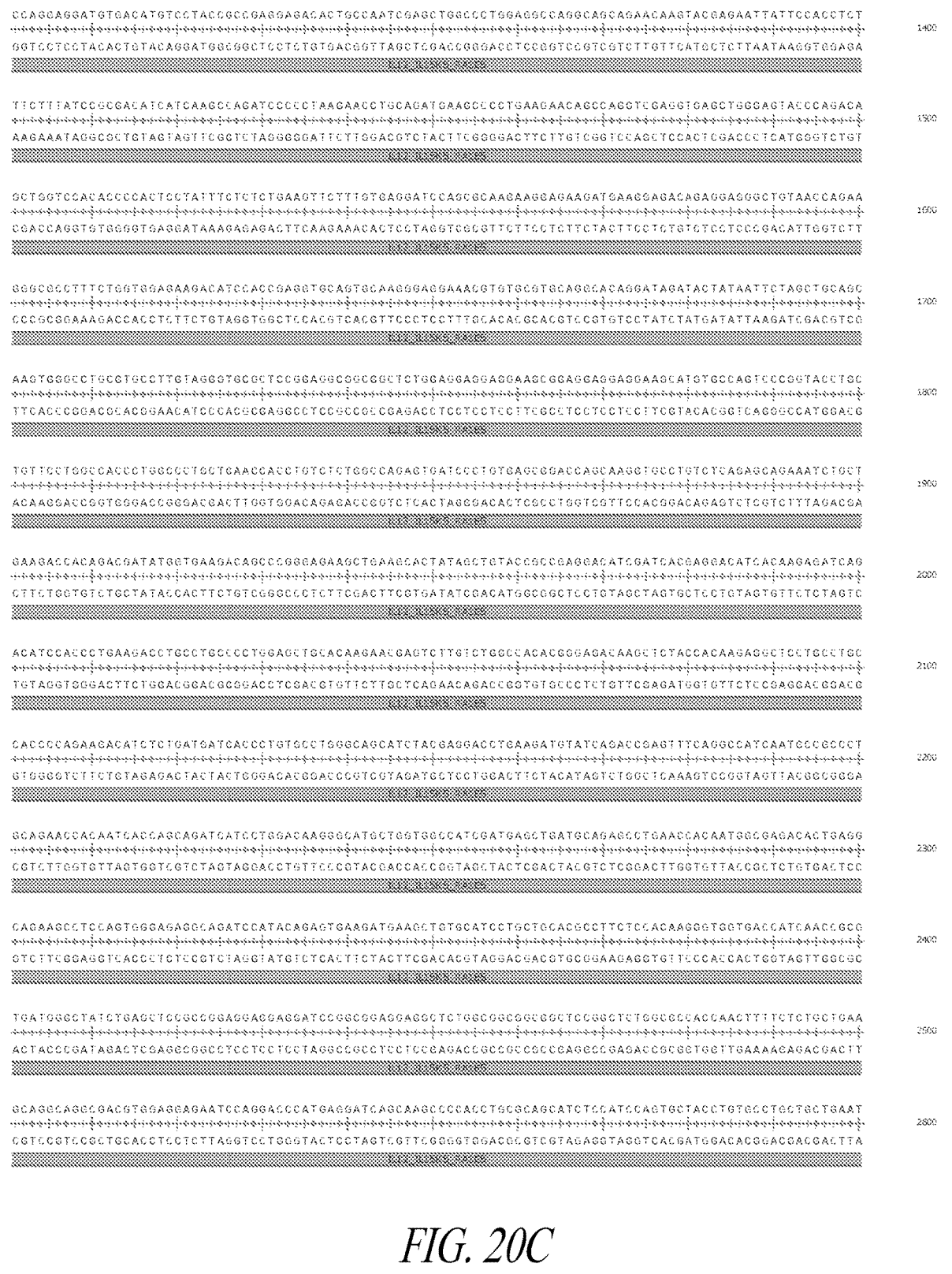
Figure 20D:
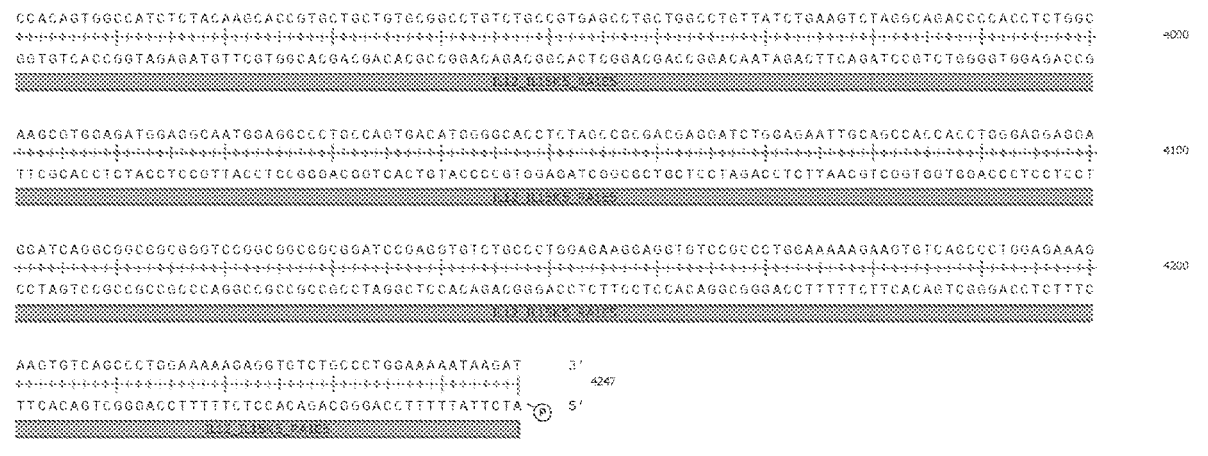

In construct 4, the CMV promoter controls expression of IL-12-p2A-IL-15K5-IRES-IL-15Rα variant 1E5. (FIG. 20, SEQ ID Nos. 568, 572.)

Example 11

Constructs Comprising PD-L1 Blocker Inserted Between UL3 and UL4

In this example, a construct is generated to express PD-L1 blocking peptide within the intergenic region between UL3 and UL4 between bases 829 and 830. In SEQ ID NO: 556, bases 1-675: UL3 coding sequence; bases 676-829: region between UL3 and UL4 and upstream of the PD-L1 blocker cassette; bases 830-833: region between UL3 and UL4 and downstream of the PD-L1 blocker cassette; bases 834-1433: UL4 coding sequence.

Example 12

Inhibition of Human PD-L1 Binding to PD-1 by Blocking Peptides

Figure 21:
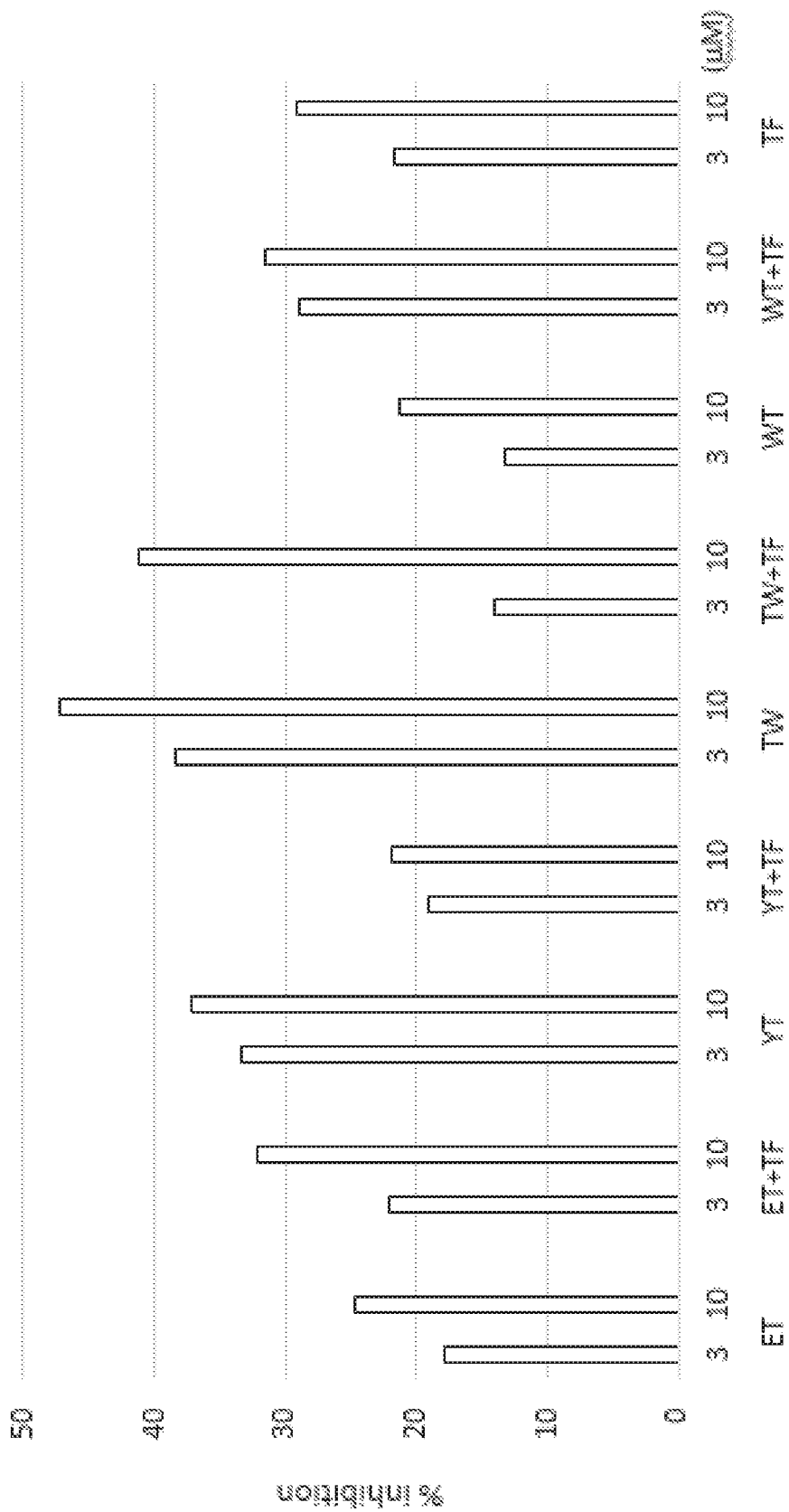
FIG. 21 is a chart showing percentage inhibition of PD-L1 binding to PD-1 by blocking peptides.
Figure 22B:
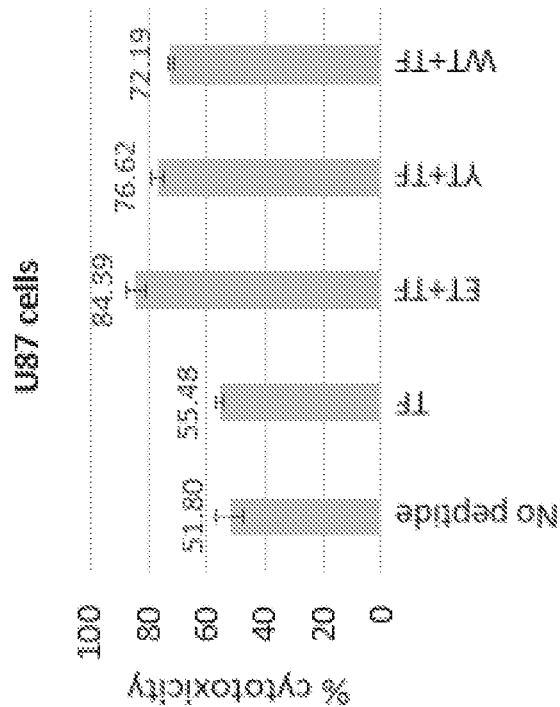
FIGS. 22A-22D show the effect of PD-L1 inhibiting peptides on cytotoxicity of target cells by anti-CD 3 stimulated human peripheral blood mononuclear cells.
Figure 22A:
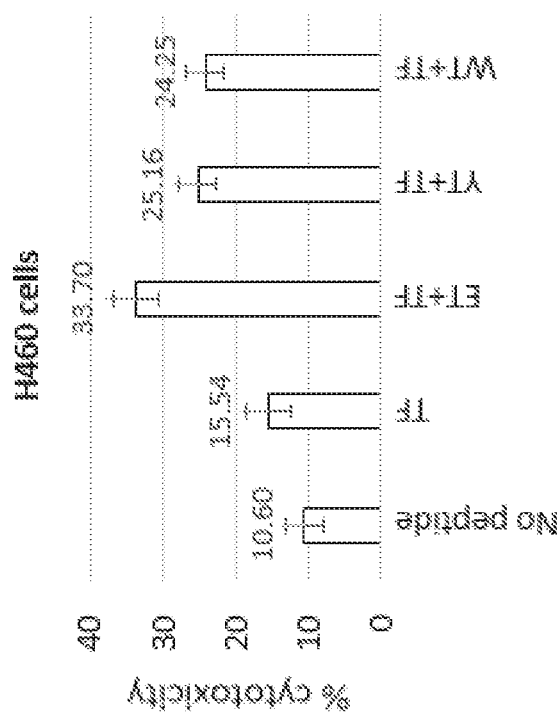
Figure 22D:
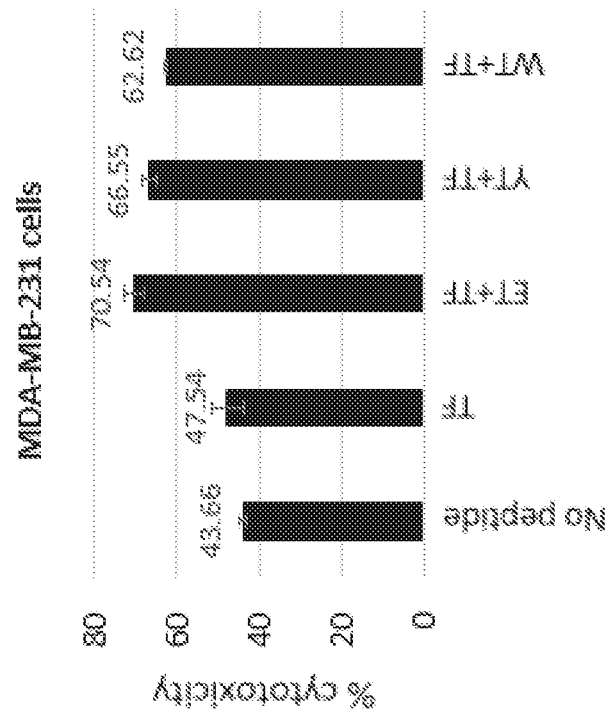
Figure 22C:
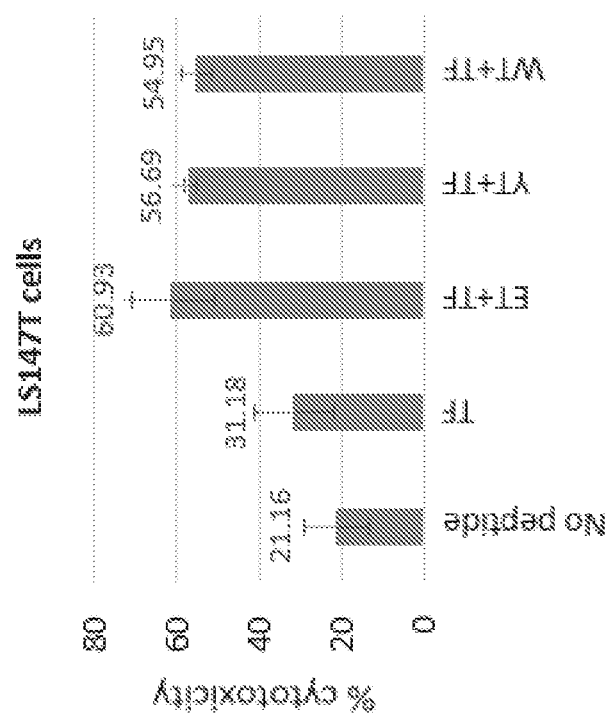

Recombinant human PD-L1 Fc protein was coated to the bottom of 96-well flat-bottom plate at 4° C. for overnight. After overnight plate coating, different PD-L1 blockers were added into each well of plate and incubated at room temperature for 2 hours before addition of recombinant human PD-1 Fc protein. Biotinylated anti-human IgG antibody and Streptavidin-HRP were subsequently added into each well, and the binding of human PD-1 to PD-L1 was detected by adding TMB substrate. Color development was measured by microplate reader at 450 nm wavelength. Percentage of inhibition was calculated by comparing to no synthesized peptide control. FIG. 21 shows the percentage inhibition by peptides ET, ET+TF, YT, YT+TF, TW, TW+TF, WT, WT+TF and TF at two different concentrations (3 and 10 µM). At 10 µM, inhibition ranged from about 22% to about 48%.

Example 13

Blocking PD-L1 Binding by Blocking Peptides Enhances Cytotoxicity Against Tumour Cells Human peripheral blood mononuclear cells (PBMCs) were stimulated with anti-CD3 antibody plus human IL-2 for 24 hours and were subsequently incubated with different synthesized PD-L1 blockers and calcein-AM labelled target cells for 4 hours. Cell cultured supernatants were harvested after 4-hour incubation and released calcein-AM fluorescence was measured by microplate reader. Percentage of cytotoxicity was calculated based on the following formula: [(sample reading−minimum release)/(Maximum release−minimum release)]×100.

FIGS. 22A-22D shows results for four different tumour cells: H460, U87, LS147T and MDA-MB-231 cells. Increase of cytotoxicity was statistically significant for all peptides except for TF on some tumour cells.

19

Example 14

Synergistic Effect of IL-12 and IL-15 on Cytokine Production

Human PBMCs were incubated with medium control, IL-12 alone, IL-15RA alone, or combined IL-12, IL-15, and IL-15Rα 1 plus neutralizing anti-IL-12 or anti-IL-15 antibody for 48 hours. Cell cultured supernatants were harvested to measure the production of human IFNγ and TNFα by ELISA.

Figure 23B:
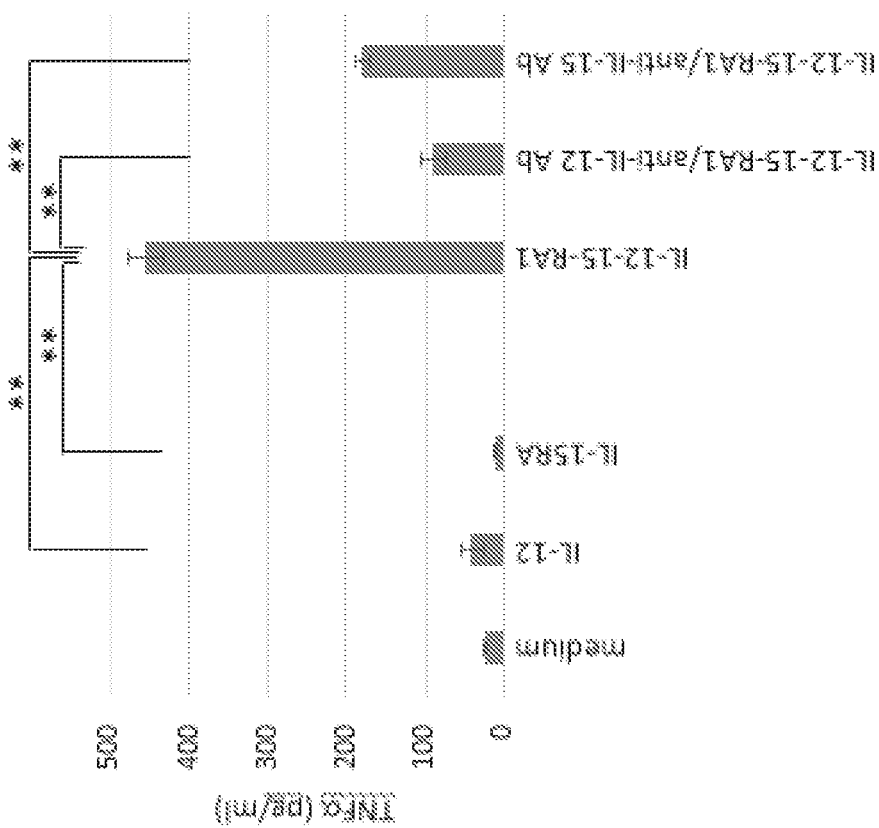
FIGS. 23A and 24B show the effects IL-12 alone, IL-15Rα alone, and IL-12 and 1L-15Rα together on production of IFNγ and TNFα in human peripheral blood mononuclear cells.
Figure 23A:
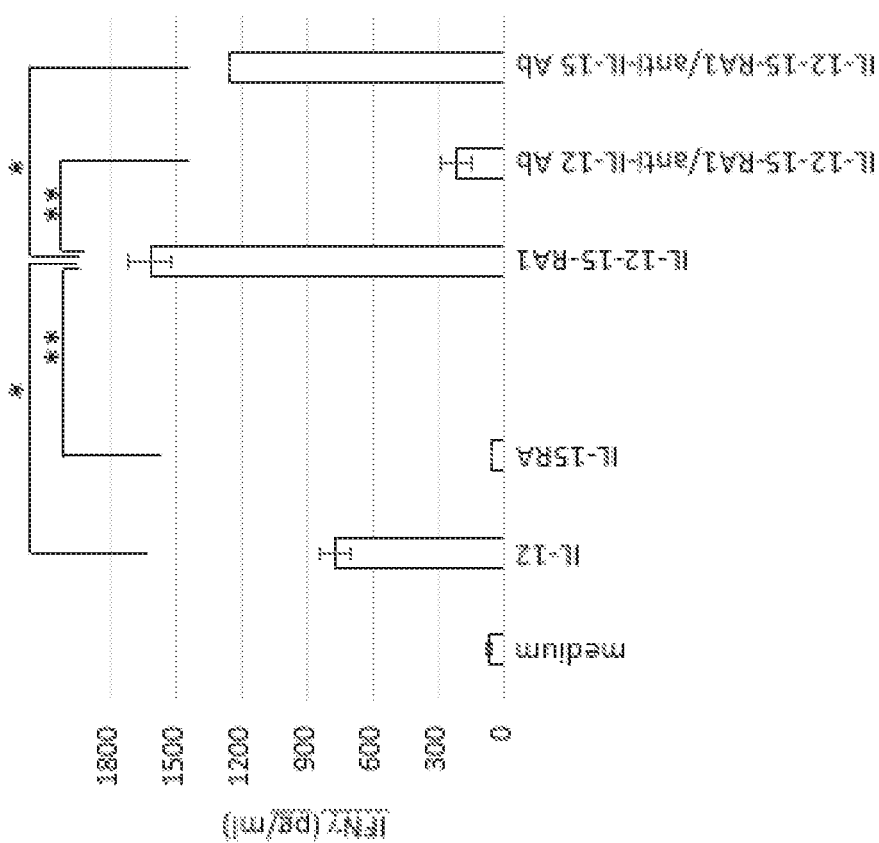

FIGS. 23A and 23B shows results of cytokine production. The combination of IL-12 and IL-15Rα 1 caused a statistically significant increase of cytokines human IFNγ and TNFα. Production was inhibited with anti-IL-12 antibody.

Example 15

Synergistic Effect of IL-12 and IL-15 on Cytotoxicity Against Tumour Cells

Human PBMCs were co-incubated with tumour target cells and medium control, IL-12 alone, IL-15RA alone, or combined IL-12, IL-15, and IL-15RA1 plus neutralizing anti-IL-12 or anti-IL-15 antibody for 24 hours. Cell cultured supernatants were harvested to measure cytotoxicity by LDH assay. Percentage of cytotoxicity was calculated based on the following formula: [(sample reading−minimum release)/(Maximum release−minimum release)]×100.

Figure 24B:
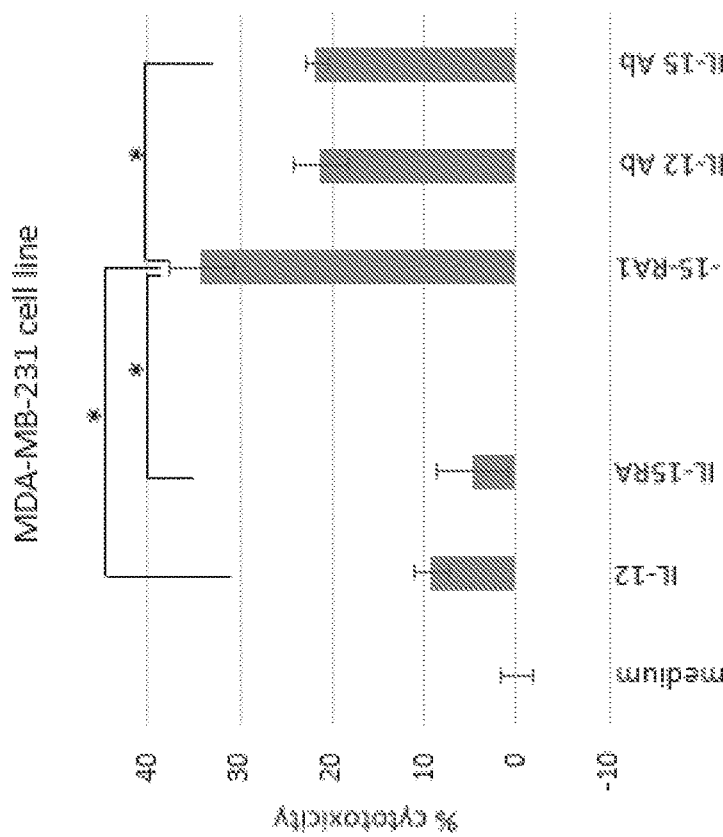
Figure 24A:
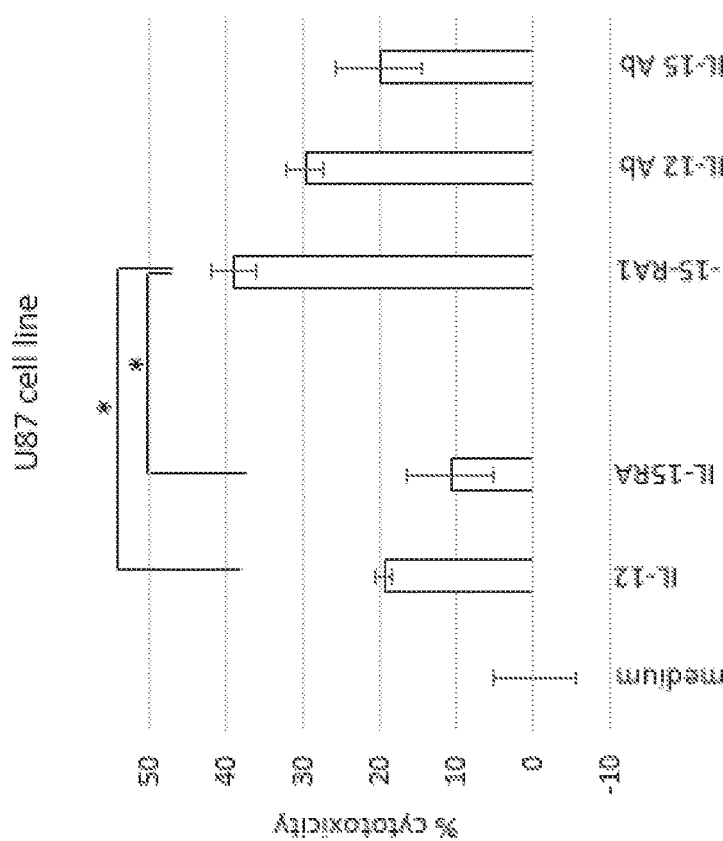

FIGS. 24A and 24B shows that IL-12 and IL-15 together increased cytotoxicity in a statistically significant manner. On the MDA-MB-231 cell line, the addition of anti-IL-12 or IL-15 antibody significantly reduced the effect.

Example 16

In Vitro Efficacy of Viruses VG161-pLBh and VG161-15h

In this example, $3 \times 10^4$ H460 or LS174T tumour cells were seeded into each well of 96-well plate and cultured at 37° C. for overnight. Next day, seeded cells were infected with VG001 backbone, VG161-PLBh, or VG161-15h virus (MOI=1) for 24 hours and the productions of human IL-12, human IL-15, and human IgG4 were assessed (FIG. 25A-C). $3 \times 10^5$ human PBMCs were subsequently added into the culture and co-incubated for 24 hour to assess cytotoxicity by LDH assay (FIG. 25D) or 48 hours for human IFNg production by ELISA (FIG. 25E). For the cytotoxicity assay, percentage of cytotoxicity was calculated based on the following formula: [(actual reading−minimum release)/(Maximum release−minimum release)]×100%. Supernatant harvested from tumour cells incubated with medium only was used as minimum release, and supernatant harvested from tumour cells incubated with lysis buffer was used as maximum release.

Example 17

In Vitro Efficacy of Various Constructs

FIGS. 26A-26D show results of in vitro assays for various constructs.

Figure 26B:
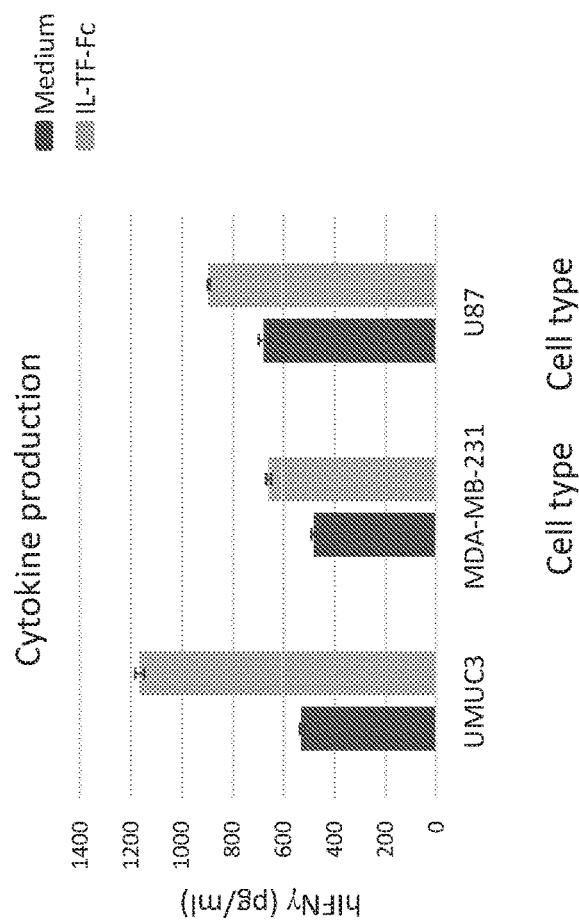
FIGS. 26A-26D show results of in vitro assays for various constructs.
Figure 26A:
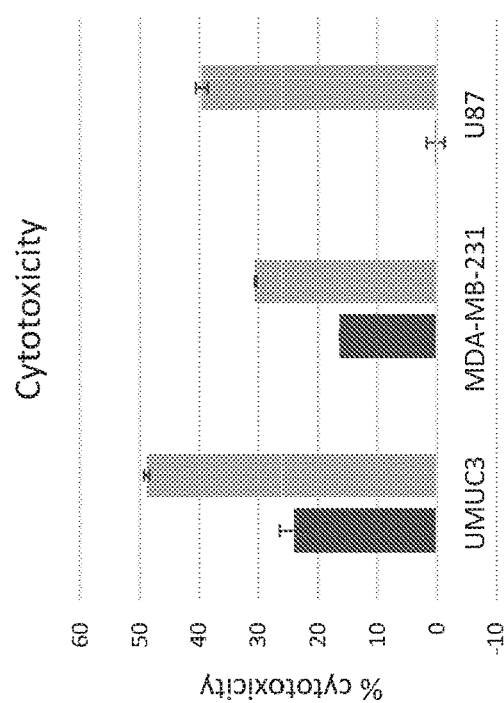

FIGS. 26A-26B show results of cell transfection with IL-TF-Fc plasmid carrying IL-12, IL-15, and PD-L1 blocker. In FIGS. 26A-26B, different tumour cell lines were transfected with IL-TF-Fc plasmid DNA for 24 hours, and human PBMCs were subsequently added into the culture. Cell supernatants were harvested after 24 hours for quantification of cytotoxicity by LDH assay (FIG. 26A), and after 48 hours for detection of human IFNg production by ELISA assay (FIG. 26B).

Figure 26D:
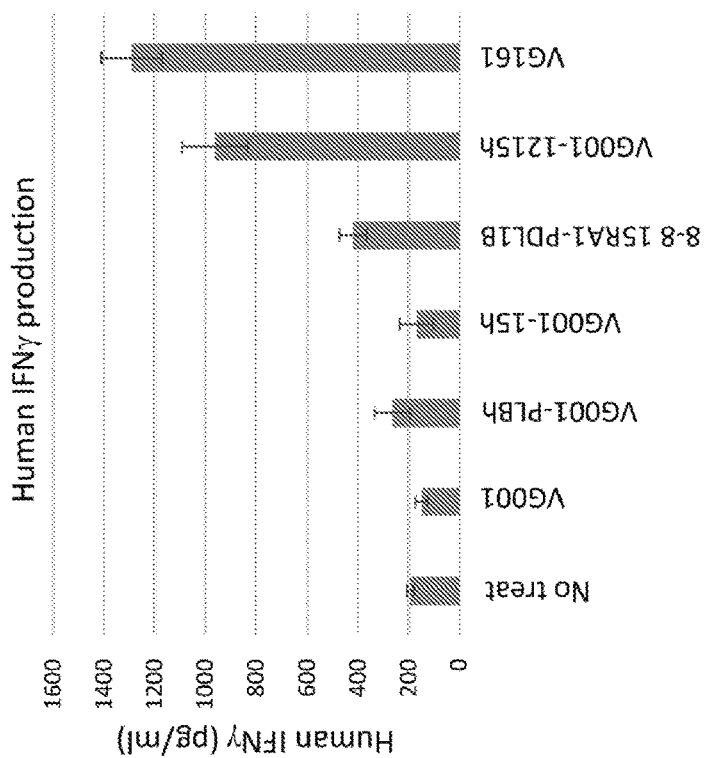
Figure 26C:
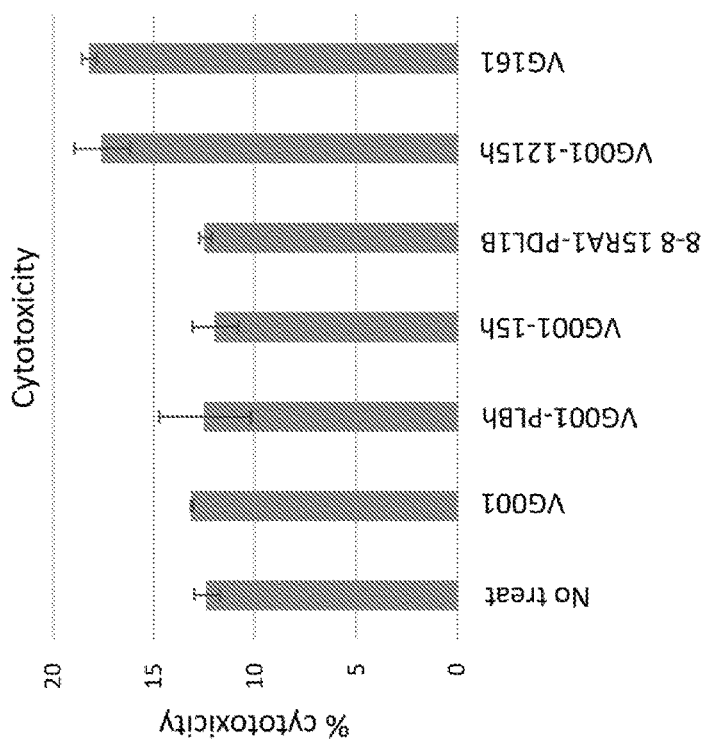
Figure 30F:
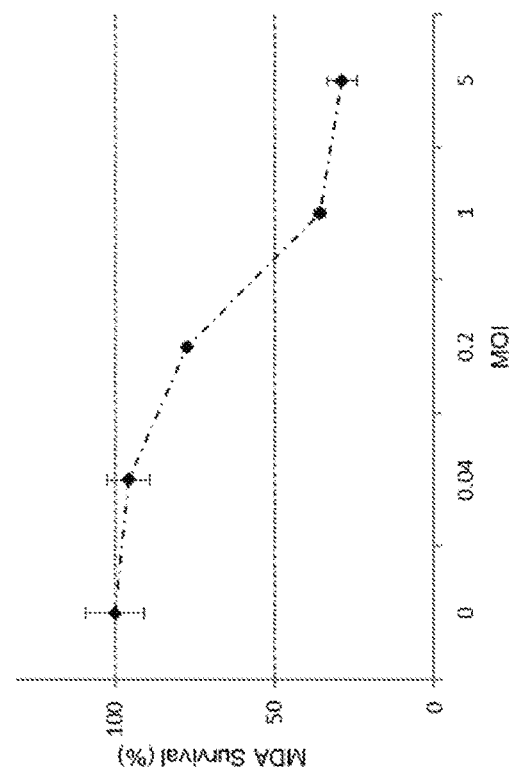
Figure 30E:
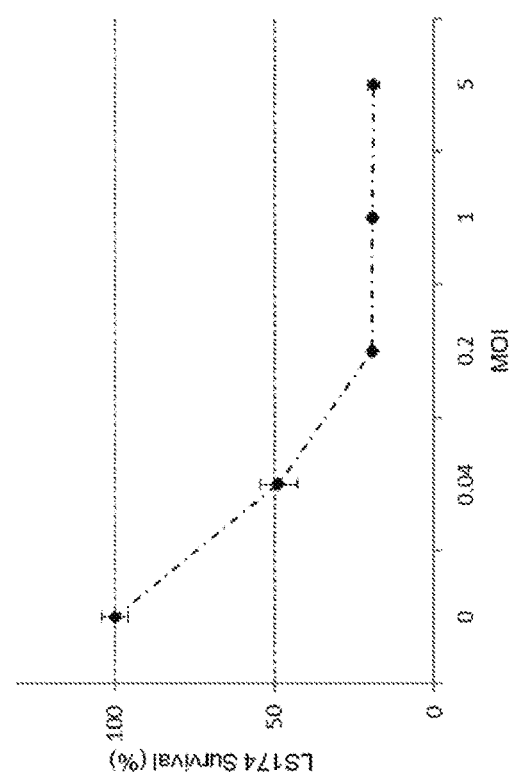
Figure 30G:
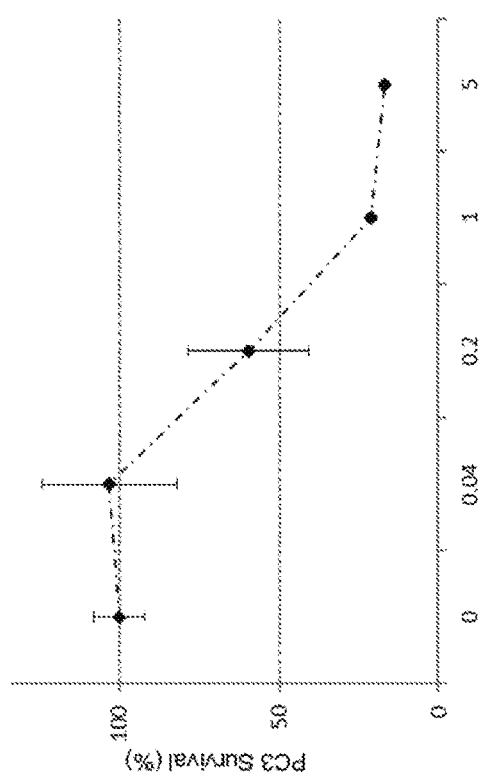

FIGS. 26C-26D show results of cell infection with a variety of mutant viruses including hVG161. Virally encoded IL12, IL15, and PD-L1 blocker synergistically enhance IFNg production and cytotoxicity. H460 tumour cells were seeded into each well of a 96-well plate and cultured at 37° C. for overnight. Next day, seeded cells were infected with the indicated viruses at MOI=1 for 24 hours. Human PBMCs were subsequently added into the culture and co-incubated for 24 hour to assess cytotoxicity by LDH assay (FIG. 26C) or 48 hours for human IFNg production by ELISA (FIG. 26D). For cytotoxicity assay, the percentage of cytotoxicity was calculated based on the following formula: [(actual reading−minimum release)/(Maximum release−minimum release)]×100%. Supernatant harvested from tumour cells incubated with medium only was used as minimum release, and supernatant harvested from tumour cells incubated with lysis buffer was used as Maximum release.

In FIGS. 27A-27E, a panel of 9 different human tumor cell lines (plus Vero cells) was infected with VG161-1212PLBh (VG161h) and HSV-345 viruses at MOI 0, 0.04, 0.2, 1, and 5. Cell viability was quantified using MTT assay at 48 hours post infection.

FIGS. 28A-28J show results of in vitro assays for various constructs. FIGS. 28A-28E show results of cell viability assays for mVG161 and HSV-345 on mouse tumor cell lines and Vero cell line; FIGS. 28F-28J show the characterization of transgene expression following mVG161 or VG001 infection of CT26 mouse tumor cells.

In FIGS. 28A-28E, a panel of 6 different mouse tumor cell lines (plus Vero cells) was infected with VG161m and HSV-345 viruses at MOI 0, 0.04, 0.2, 1, and 5. Cell viability was quantified using MTT assay at 48 hours post infection.

In FIGS. 28F-28J, $3 \times 10^4$ CT26 tumour cells were seeded into each well of 96-well plate and cultured at 37° C. for overnight. Next day, seeded cells were infected with VG001 backbone or VG161-1215PLBm virus (MOI=1) for 24 hours and the production of mouse IL-12, human IL-15, and mouse IgG was assessed. $3 \times 10^5$ splenocytes from Balb/c mouse were subsequently added into the culture and co-incubated for 24 hour to assess cytotoxicity by LDH assay or 48 hours for mouse IFNg production by ELISA. For the cytotoxicity assay, percentage of cytotoxicity was calculated based on the following formula: [(actual reading−minimum release)/(Maximum release−minimum release)]×100%. Supernatant harvested from tumour cells incubated with medium only was used as minimum release, and supernatant harvested from tumour cells incubated with lysis buffer was used as maximum release.

In FIGS. 29A-29E, $3 \times 10^4$ H460, LS174T, or UMUC3 tumor cells were seeded into each well of 96-well plate and cultured at 37° C. for overnight. Next day, seeded cells were infected with VG001 backbone and VG161-1215h virus (MOI=1) for 24 hours and the productions of human IL-12, human IL-15, and human IgG4 were assessed (18R). $3 \times 10^5$ human PBMCs were subsequently added into the culture and co-incubated for 24 hour to assess cytotoxicity by LDH assay (18S) or 48 hours for human IFNγ production by ELISA (18T). For the cytotoxicity assay, percentage of cytotoxicity was calculated based on the following formula: [(actual reading−minimum release)/(Maximum release−minimum release)]×100%. Supernatant harvested from tumor cells incubated with medium only was used as minimum release, and supernatant harvested from tumor cells incubated with lysis buffer was used as maximum release.

In FIGS. 30A-30G, the antitumor effect of VG161-1215PLBh (hVG161) virus was evaluated in a variety human cancer cells including U87, MCF7, H460, LNCaP, LS174T, MDA, and PC3 at 72h post infection and MOIs ranging from 0 to 5. Cell survival percentage was quantified by MTT assay. The VG161-1215PLBh virus exhibits robust cell killing ability in all of the tested human tumor cell lines.

Example 18

In Vivo Efficacy of VG161 Viral Constructs

Figure 31A:
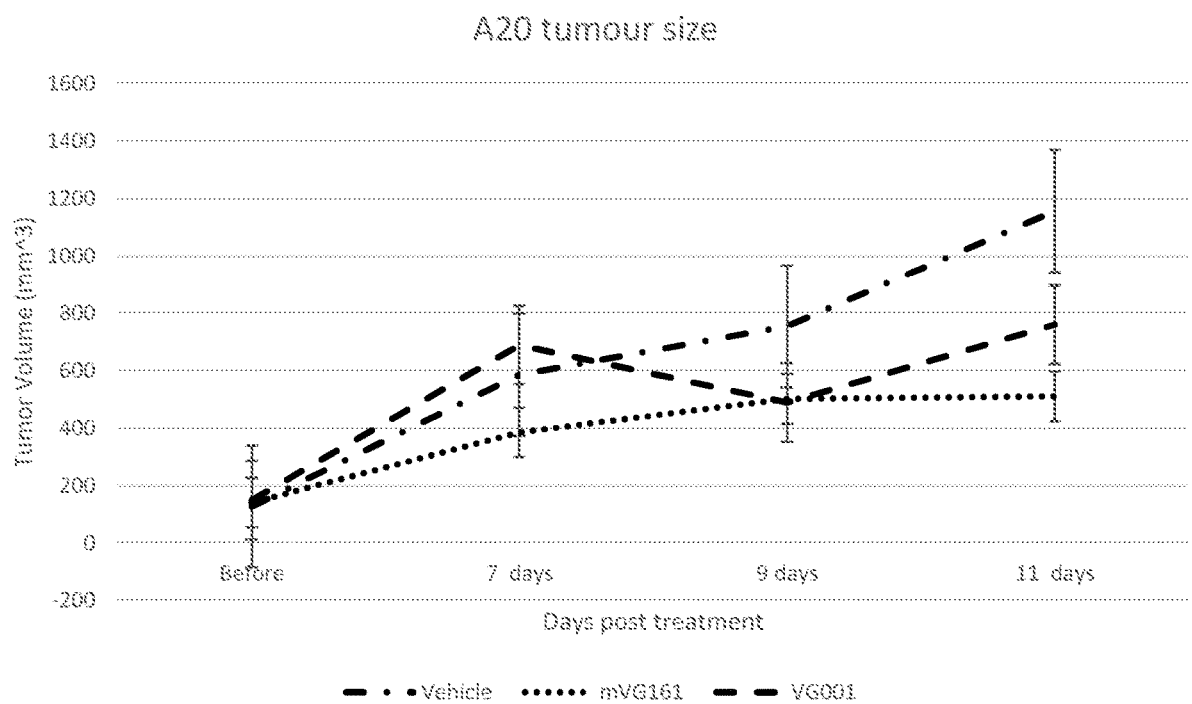
FIGS. 31A-31G show results of in vivo assays for mVG161 and hVG161 constructs.
Figure 31B:
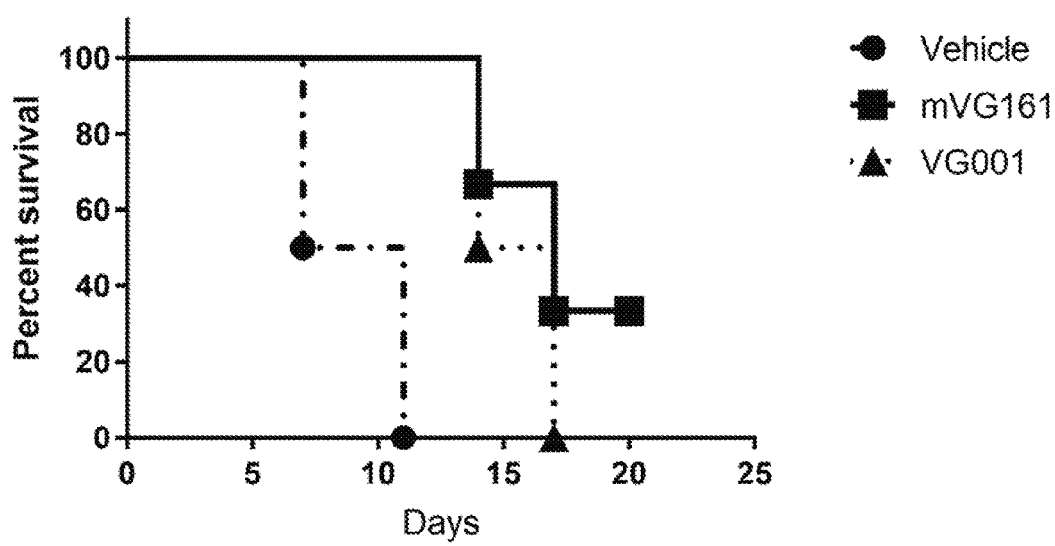

In FIGS. 31A-31B, BALB/c mice bearing A20 murine B-cell lymphoma tumors were injected 5 times intratumorally with a total of $1\times10^7$ PFU/mouse of either VG161-1215PLBm (mVG161) virus or VG001 backbone virus or with PBS (vehicle control). Tumor size measurements were performed at the indicated times post injection. Mice treated with VG161-1215PLBm exhibited a significant (P<0.05) reduction in tumor volume compared to mice treated with PBS.

Figure 31C:
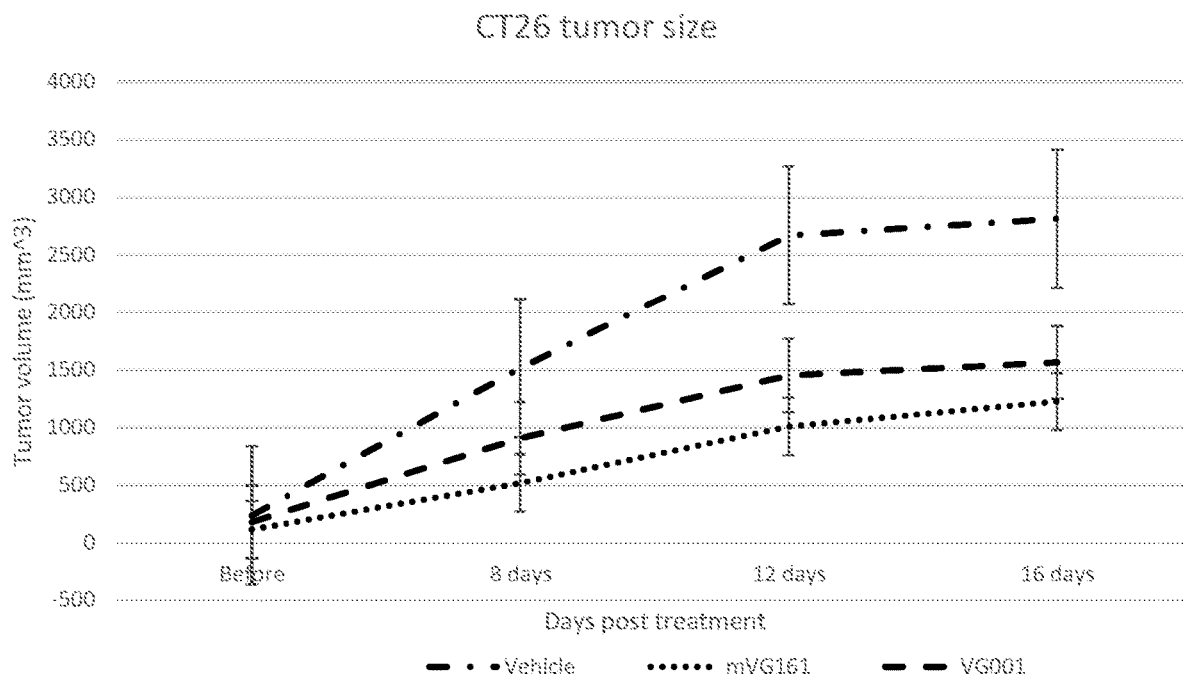
Figure 31D:
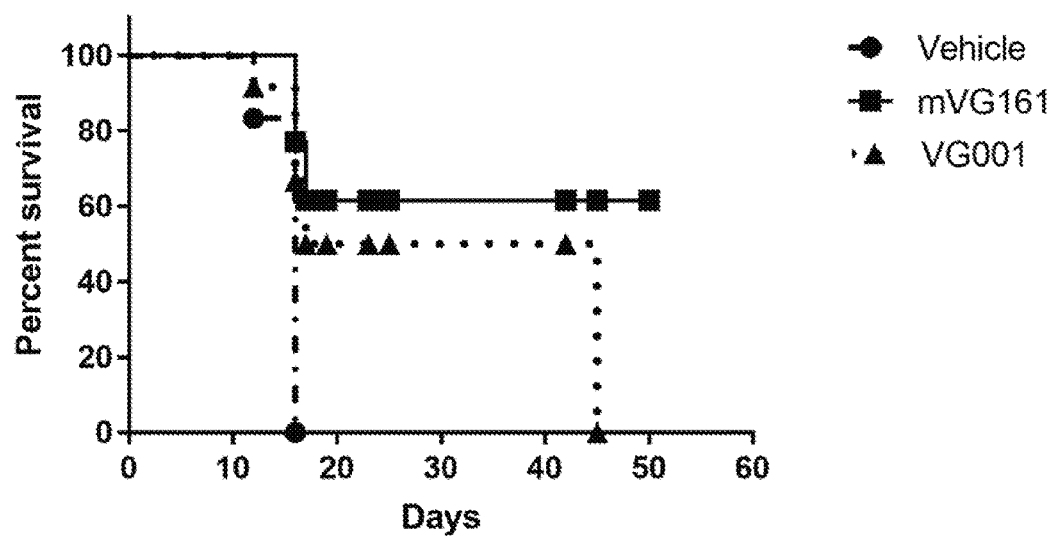

In FIGS. 31C-31D, BALB/c mice bearing CT26 murine colon carcinoma tumors were injected 5 times intratumorally with a total of $5\times10^6$ PFU/mouse of either VG161-1215PLBm (mVG161) virus or VG001 backbone virus or with PBS (vehicle control). Tumor size measurements were performed at the indicated times post injection. Mice treated with VG161-1215PLBm exhibited a significant (P<0.05) reduction in tumor volume compared to mice treated with PBS.

Figure 31E:
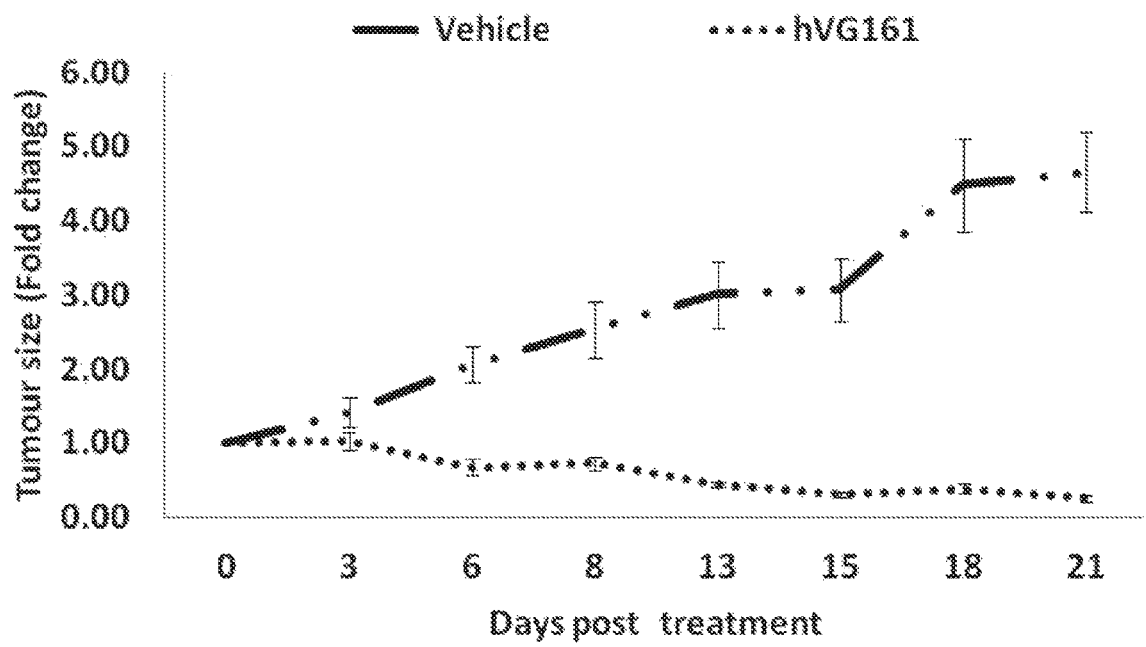
Figure 31F:
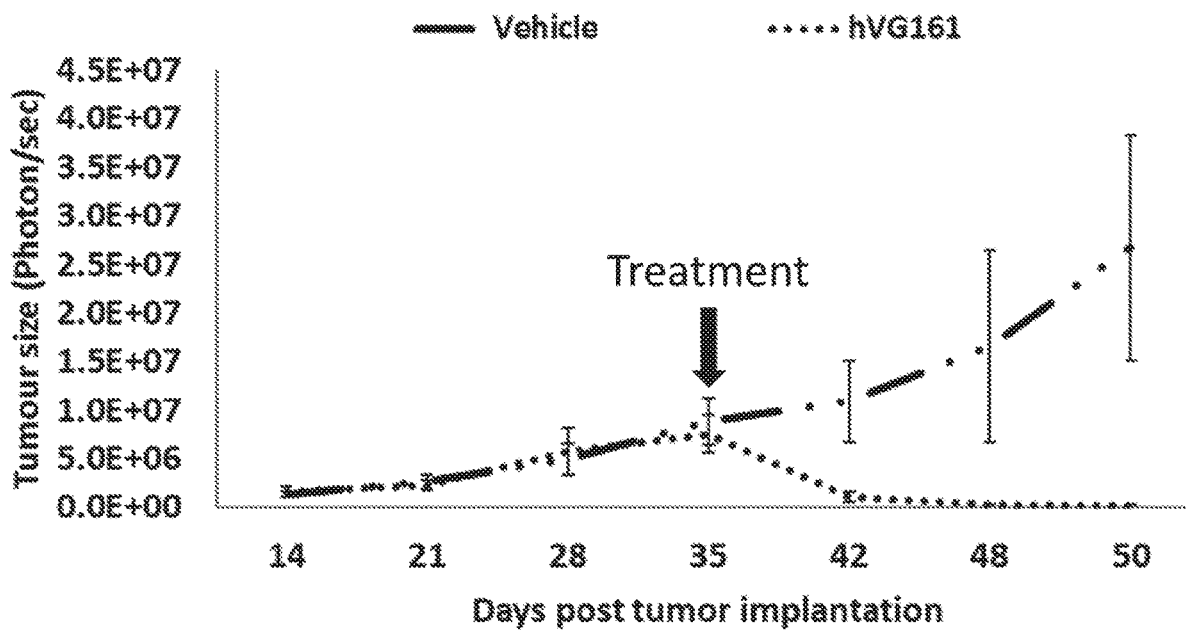
Figure 31G:
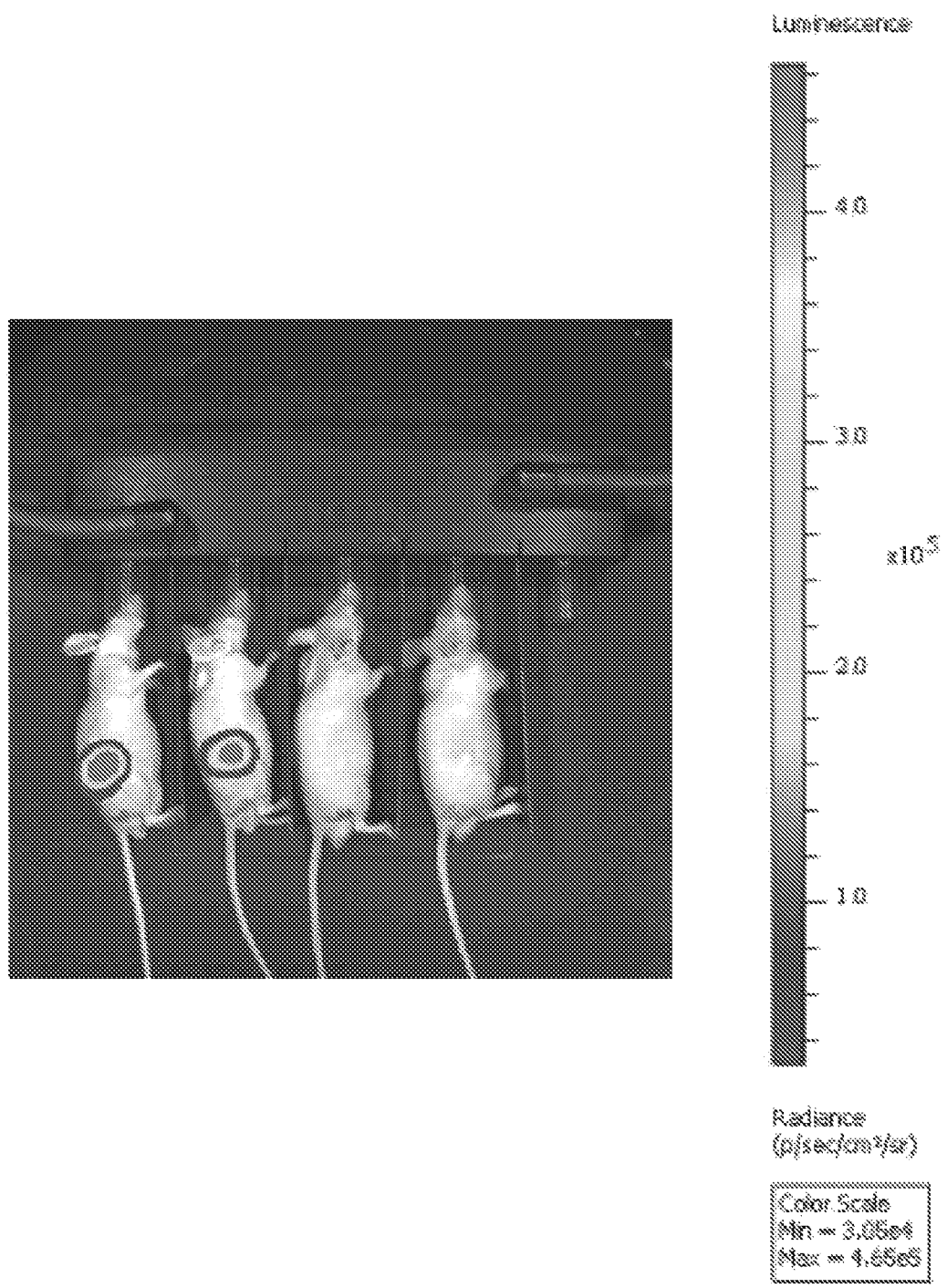
Figure 32A:
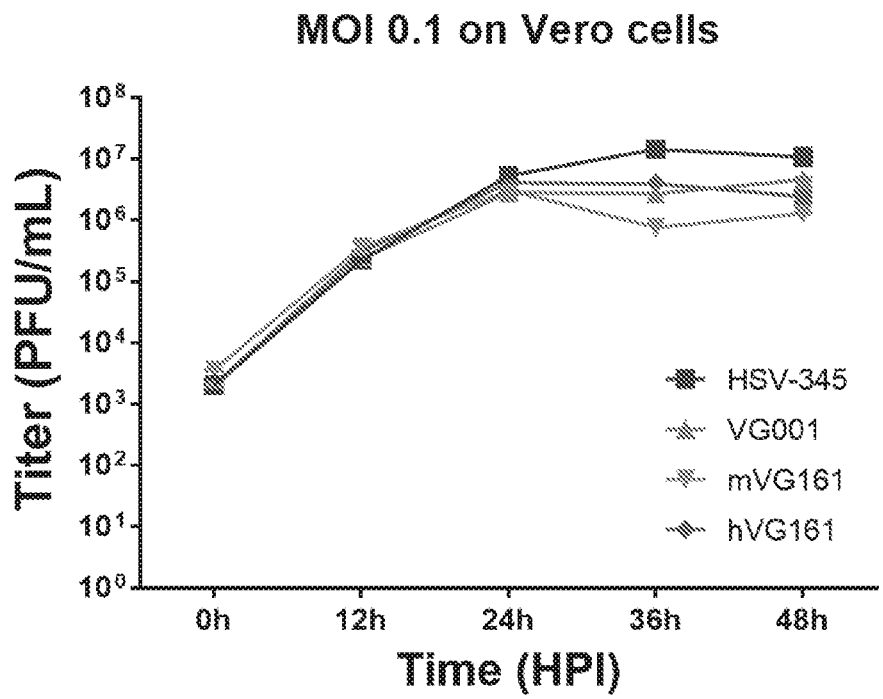
FIGS. 32A-32C show growth curves for different viruses on three different human cell lines.
Figure 32B:
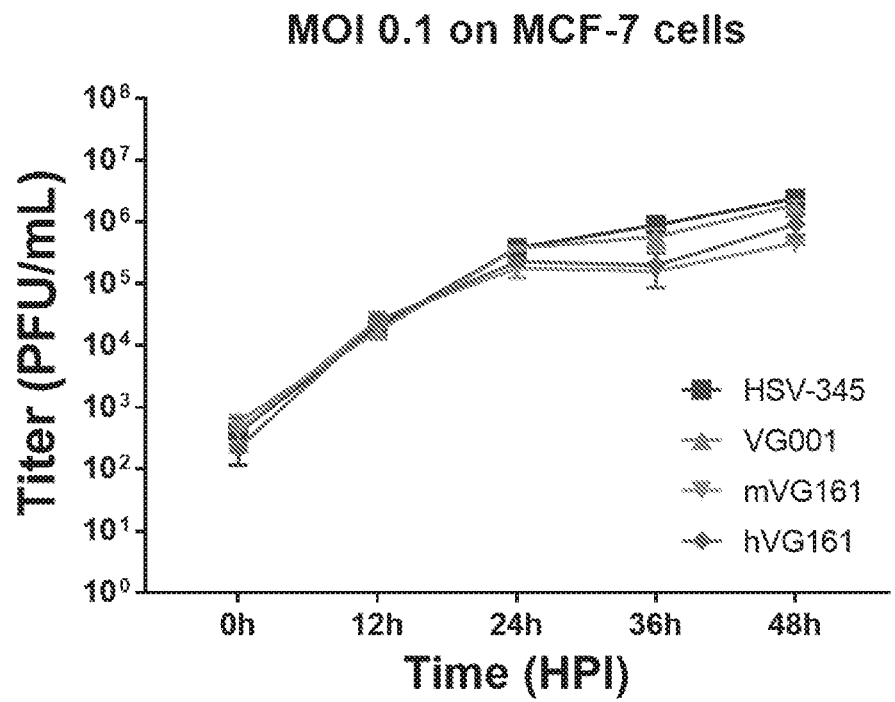
Figure 32C:
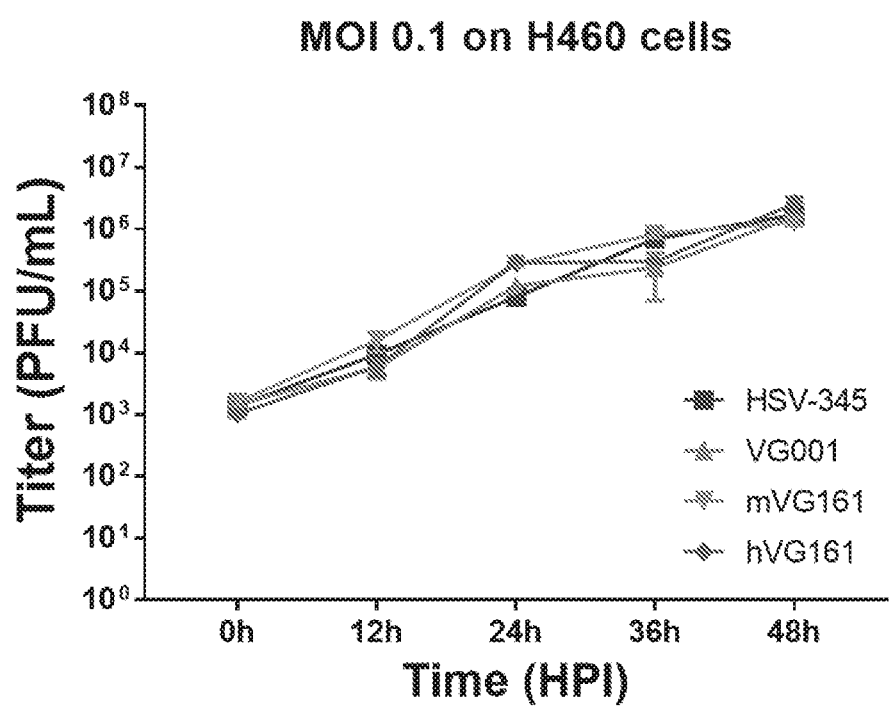
Figure 33B:
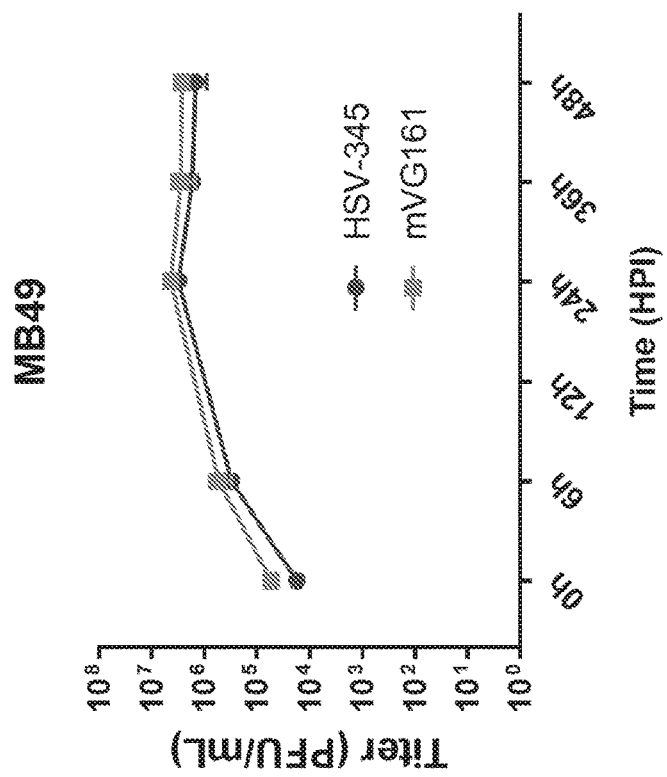
FIGS. 33A-33D show growth curves of mVG161 and HSV-345 on mouse tumor cell lines and Vero cell line.
Figure 33A:
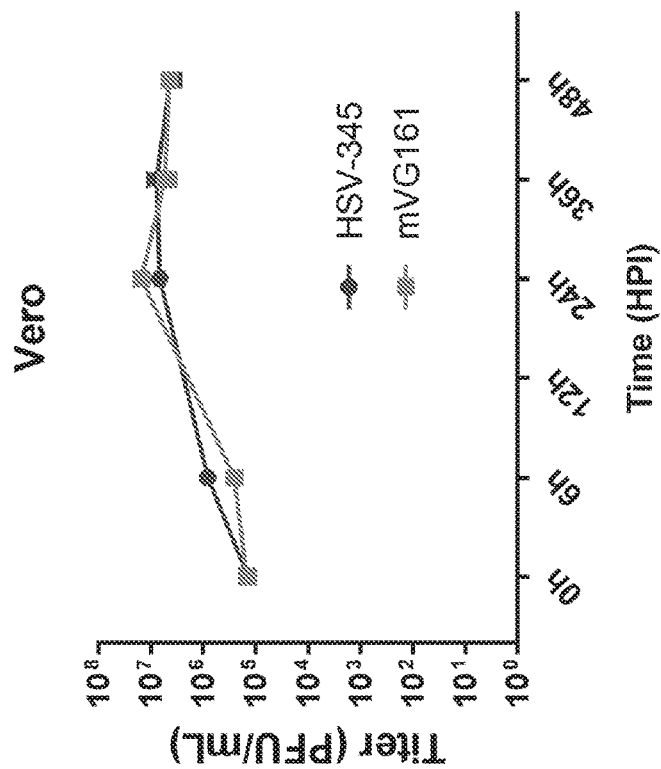
Figure 33D:
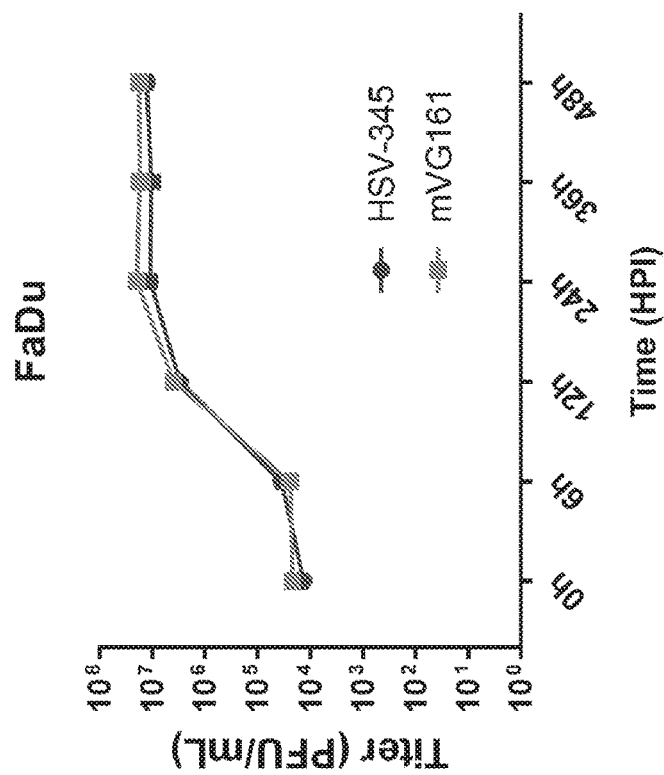
Figure 33C:
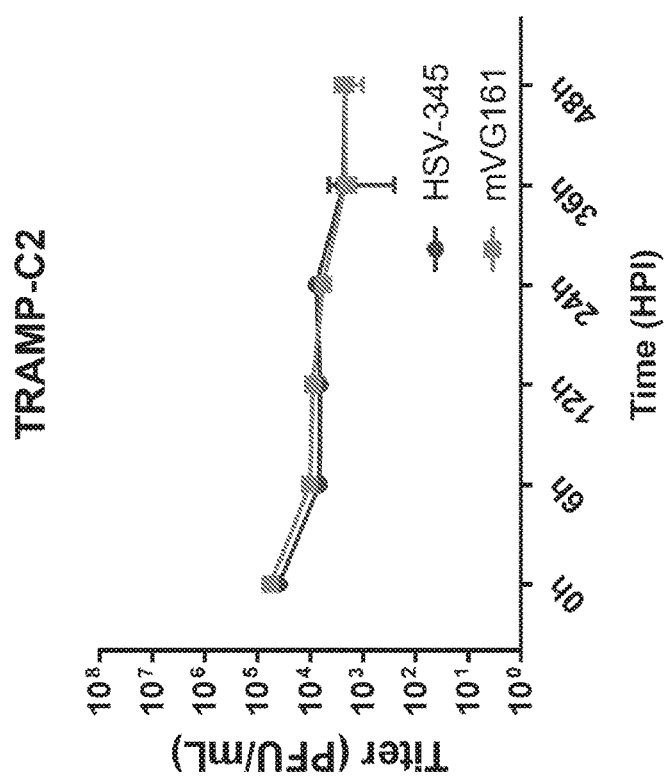
Figure 34A:
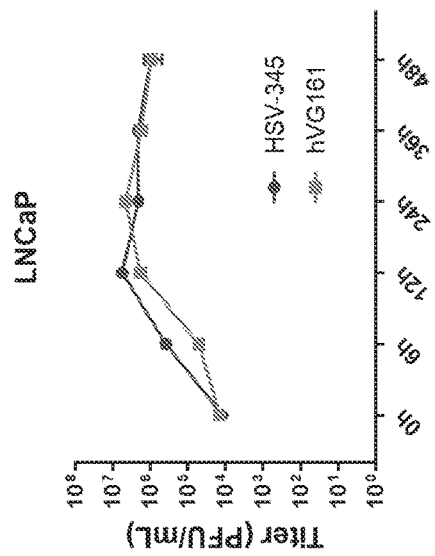
FIGS. 34A-34E show growth curves of hVG161 and HSV-345 on human tumor cell lines and Vero cell line.
Figure 34B:
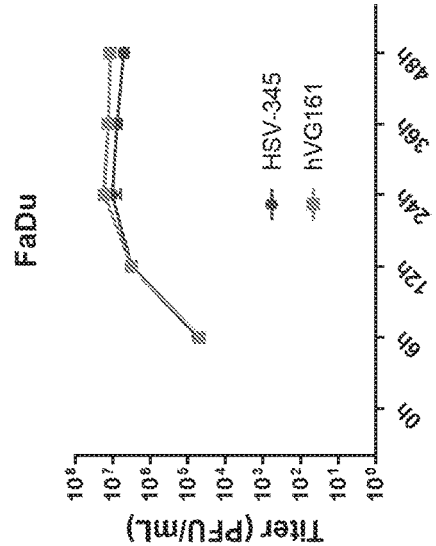
Figure 34D:
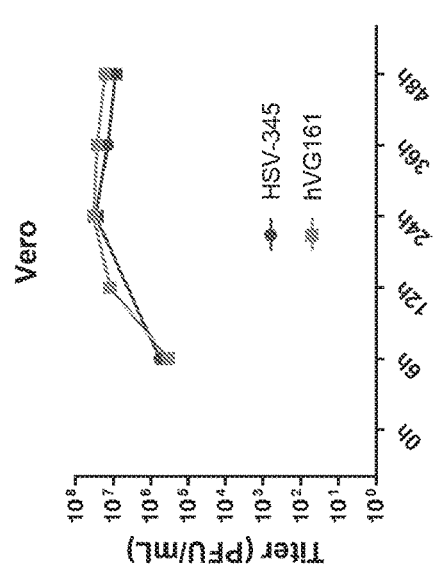
Figure 34C:
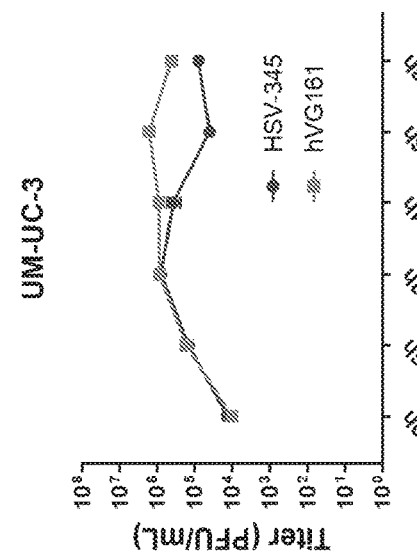
Figure 34E:
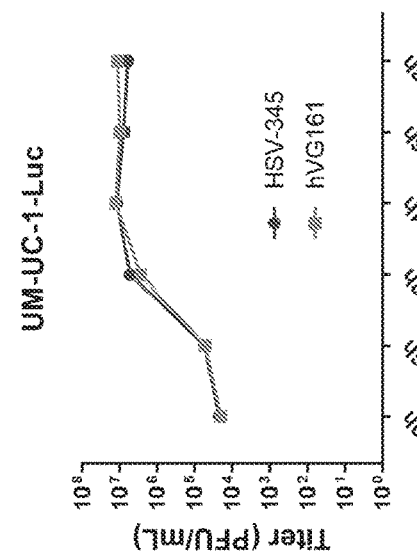
Figure 35A:
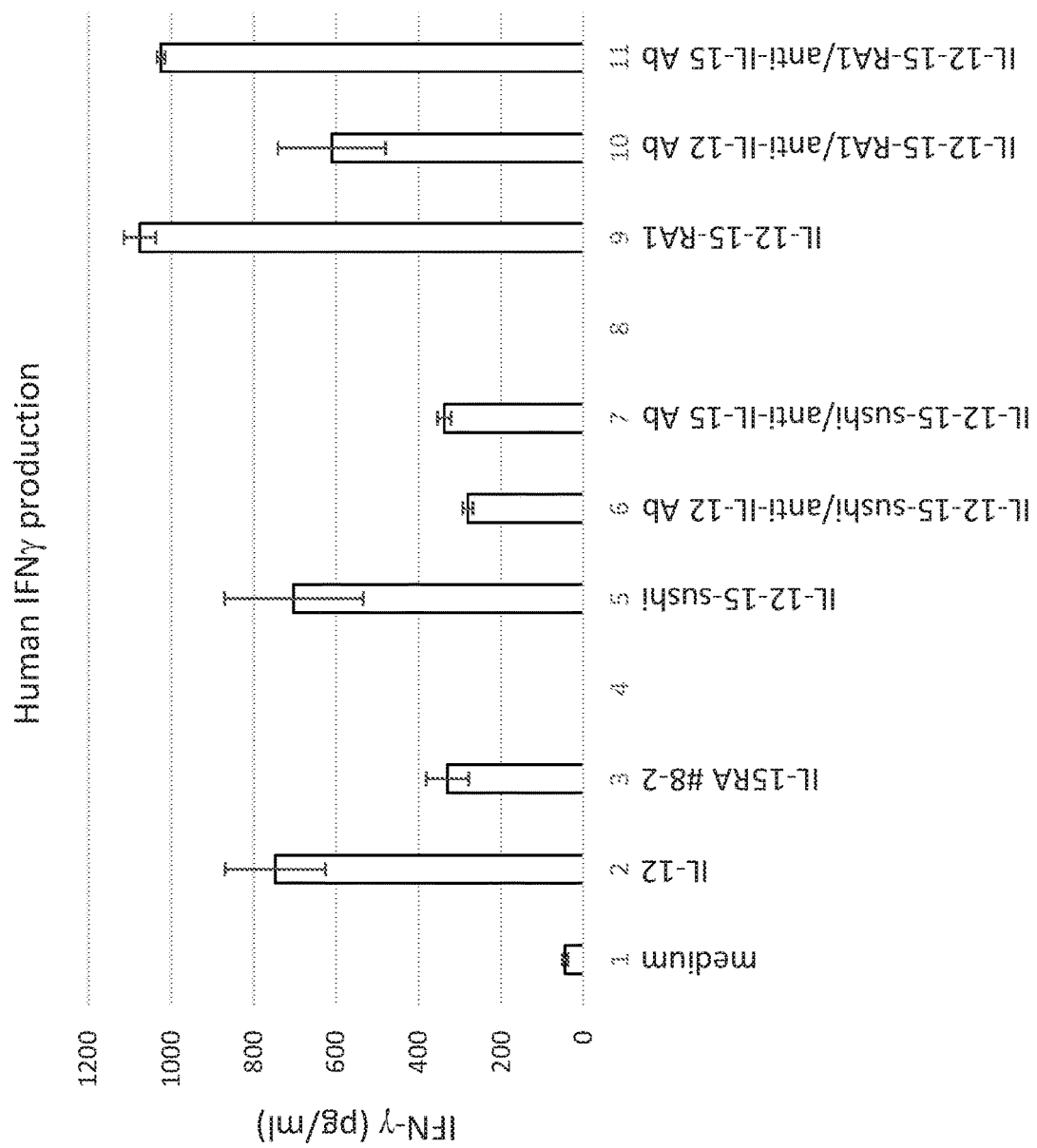
FIGS. 35A-35D show the effects of virus modifications.
Figure 35B:
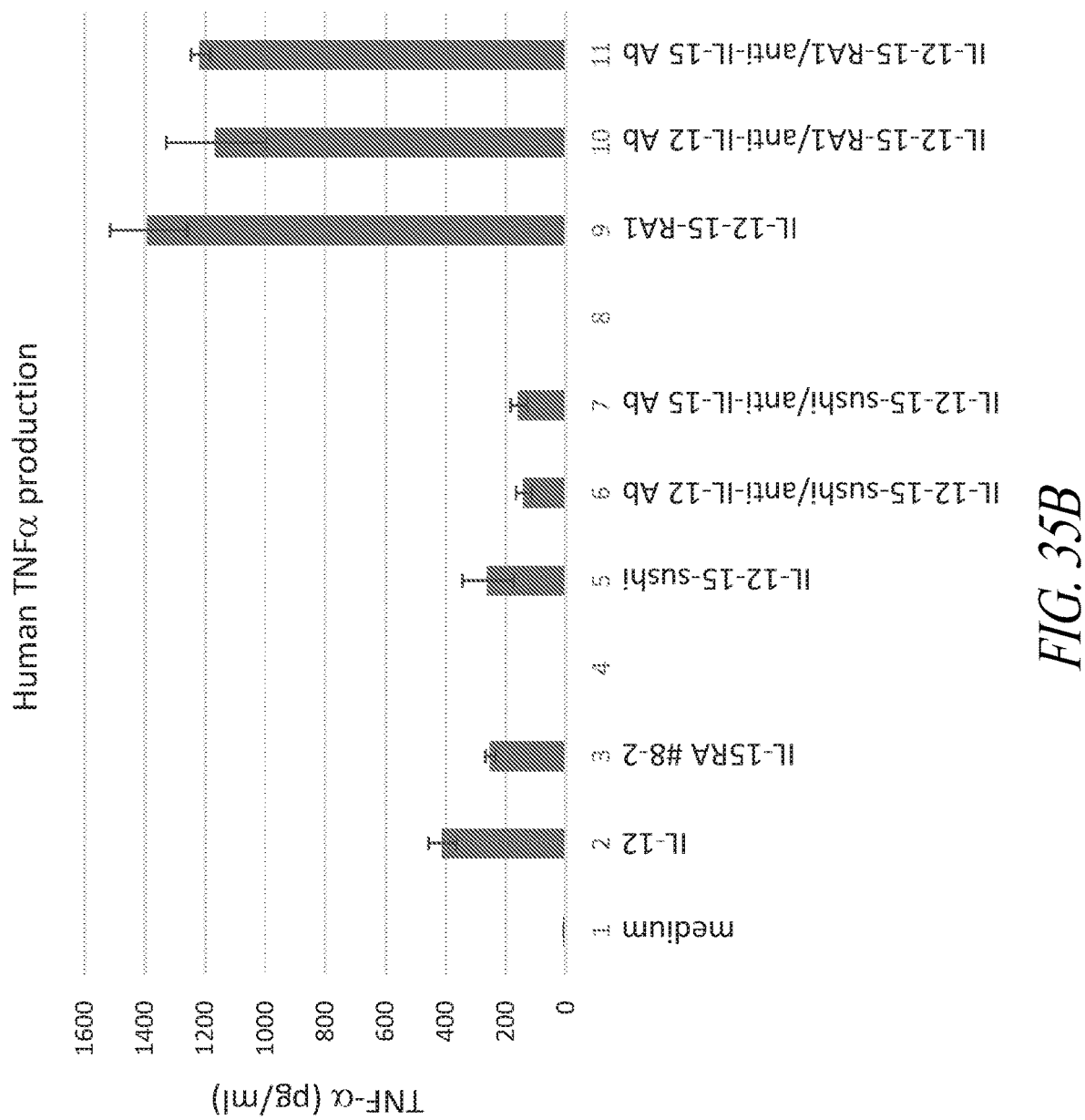
Figure 35C:
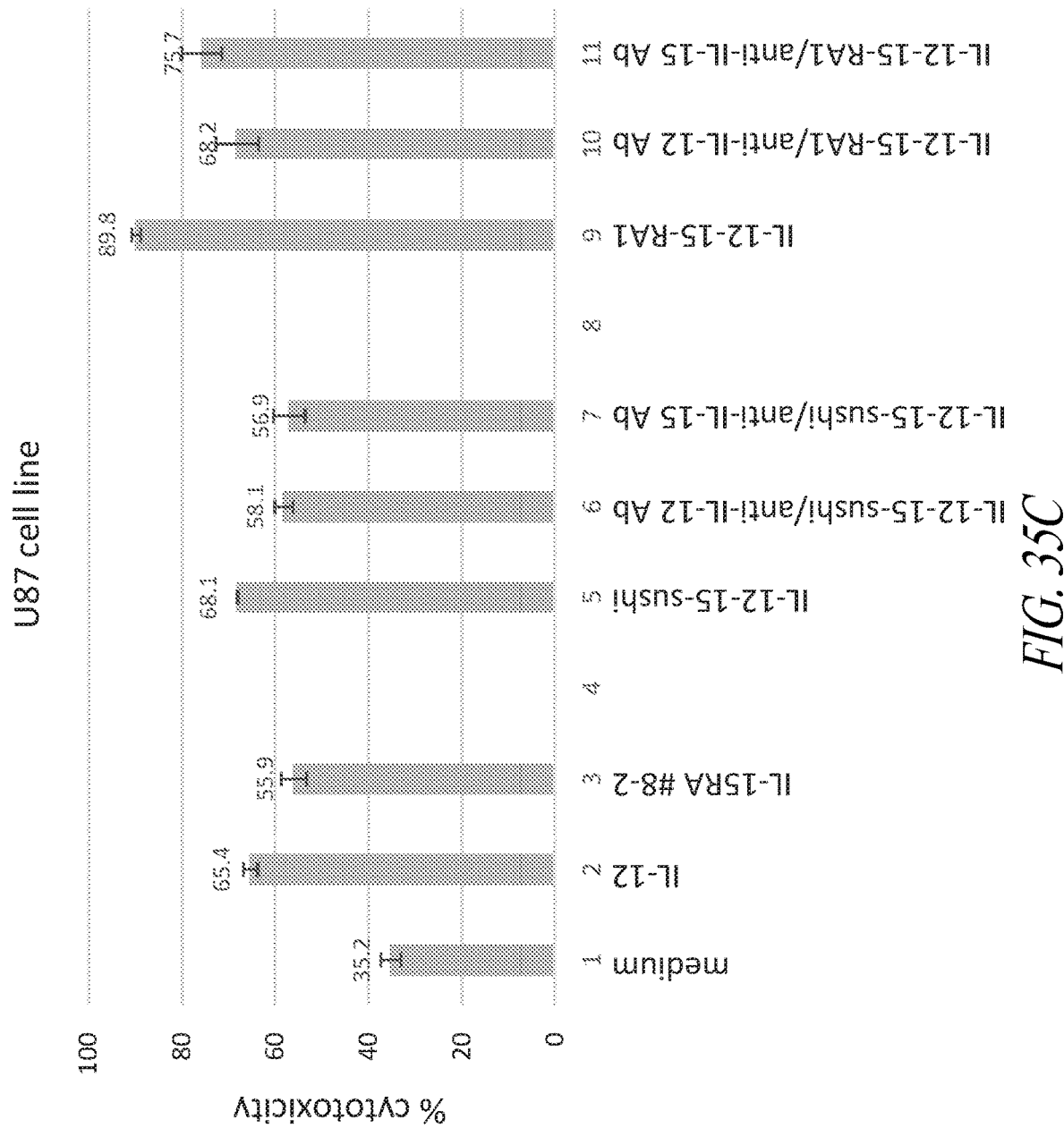
Figure 35D:
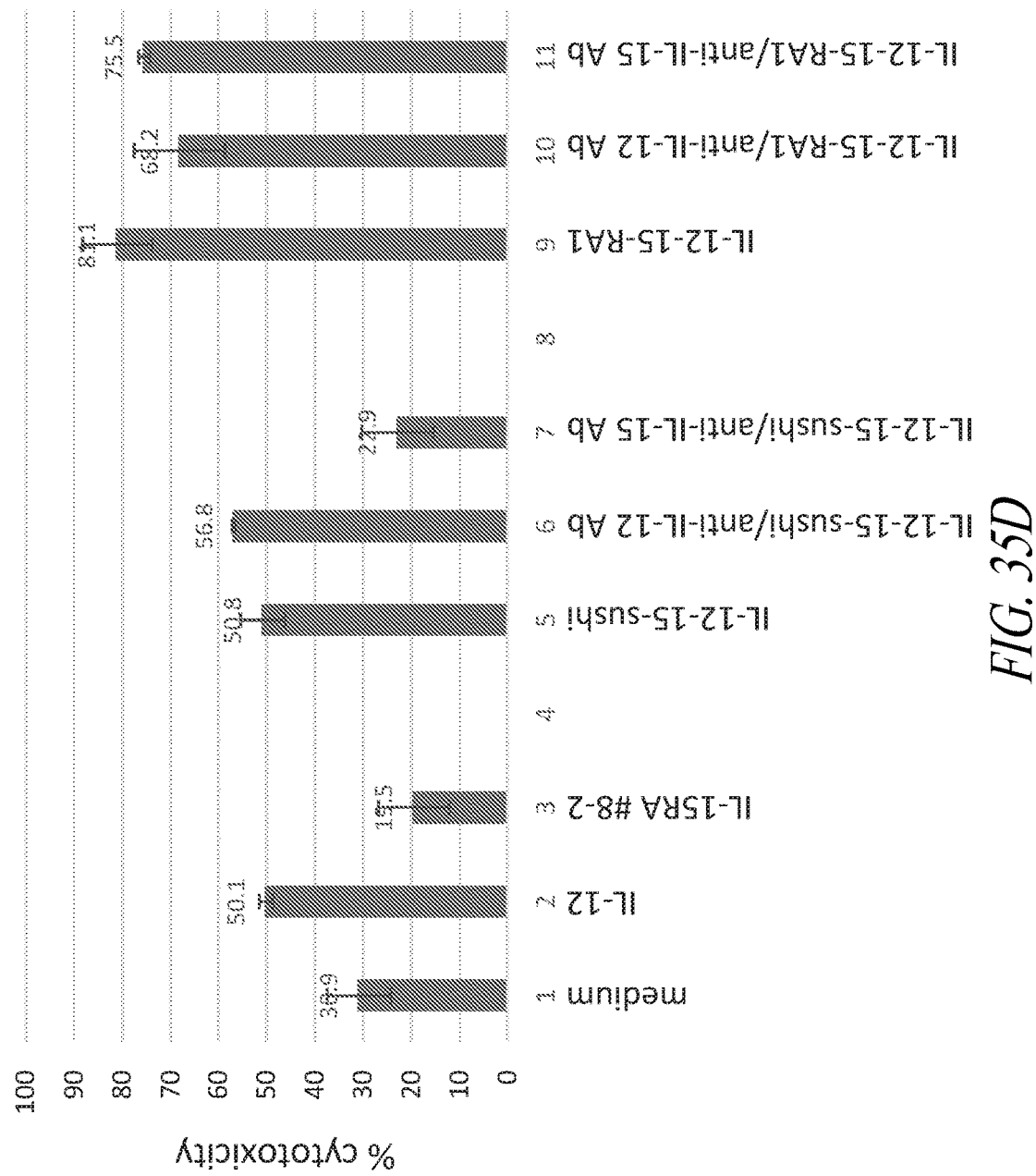

In FIGS. 31E-31G, oHSV treatment of xenograft human prostate tumors in mice was assessed. Twelve mice were implanted with LNCaP human prostate tumor cells in the right lower flank. At 35 days post implantation, a randomly selected group of 6 animals was injected twice intratumorally with a total of $5\times10^7$ PFU/mouse of VG161-1215PLBh (hVG161) virus, while the remaining 6 animals served as a vehicle control and were injected twice with an equivalent volume of PBS. Tumor size measurements were performed using two different methods. Caliper measurements are expressed as fold change in tumor volume at a given time point compared to the tumor volume at the time of virus or PBS injection (FIG. 31E). Tumor-bearing mice treated with VG161-1215PLBh virus exhibited robust tumor shrinkage during the course of the study with over 50% reduction in tumor size at the end of 15 days, while vehicle-treated mice showed approximately 3-fold increases in tumor volume during the same time span. Tumor growth was also monitored using a whole animal bioluminescent imaging system (IVIS Imaging System; Xenogen, Mountain View, CA). Signal intensities were quantified as the sum of all detected photons per second (FIG. 31F). Quantitative imaging of tumor growth using the IVIS system shows an even more dramatic reduction in tumor size in oHSV-treated animals compared to PBS-treated controls, with fluorescence dropping to undetectable levels by 50 days post tumor implantation (FIG. 32G; two vehicle controls on left and two oHSV-treated mice on right).

Example 19

Replication of hVG161 in Cell Lines

The growth curve and cytotoxicity data in FIGS. 32A-C, FIGS. 33A-D and FIGS. 34A-E show that hVG161 viruses replicate as well as the parental HSV-345 virus. These data also show that the viruses do not grow as well in mouse tumor cell lines compared to human cell lines, but HSV-1 is known to grow poorly in mouse cells.

Example 20

Evaluation of Virus Modifications

Human PBMCs were stimulated with medium alone, recombinant IL-12 alone, recombinant IL-15 alone, or IL-12 plus different forms of IL-15/IL-15RA1 complex with or without anti-IL-12 (6 mg/ml) or anti-IL-15 (0.5 mg/ml) neutralizing antibody for 48 hours. Cultured supernatants were subsequently harvested for human IFNg and human TNFα production using ELISA assays as shown in FIGS. 35 A and 35 B.

To assess cytotoxicity against tumour cells, calcein-AM-labelled tumour cells were co-incubated with stimulated human PBMCs for 24 hours. Supernatants were harvested for measurement of released fluorescence. Supernatant harvested from calcein-labelled tumour cells incubated with medium only was used as minimum release, and supernatant harvested from calcein-labelled tumour cells incubated with lysis buffer was used as Maximum release. The percentage of cytotoxicity was calculated based on the formula: [(actual reading−minimum release)/(Maximum release−minimum release)]×100%. Cytotoxicity result for U87 tumour cells is shown as FIG. 35C and MDA-MB-231 tumour cells is shown as FIG. 35D.

Example 21

In Vitro Efficacy Data

Figure 36A:
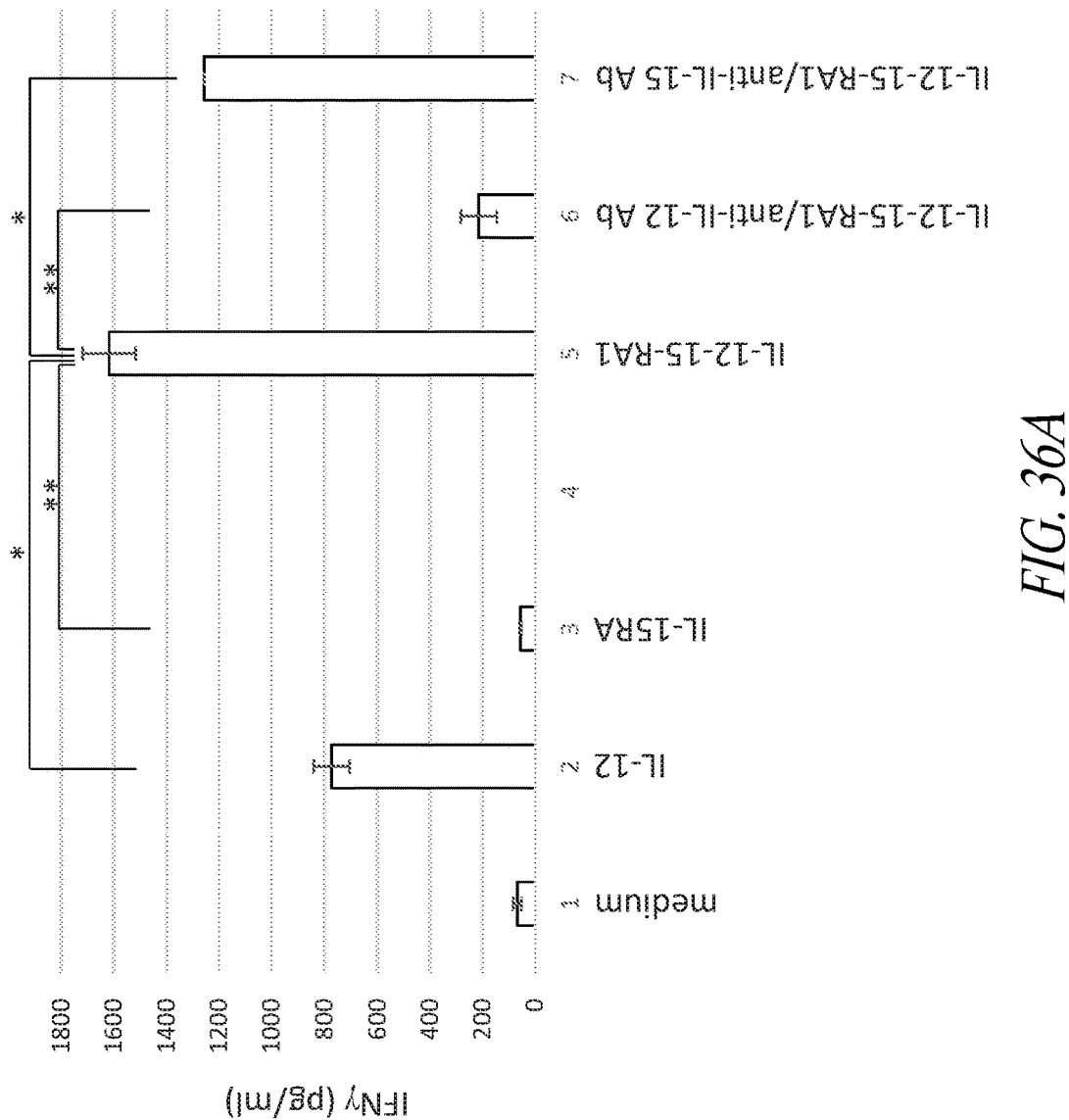
FIGS. 36A-36D provide in vitro efficacy data.
Figure 36B:
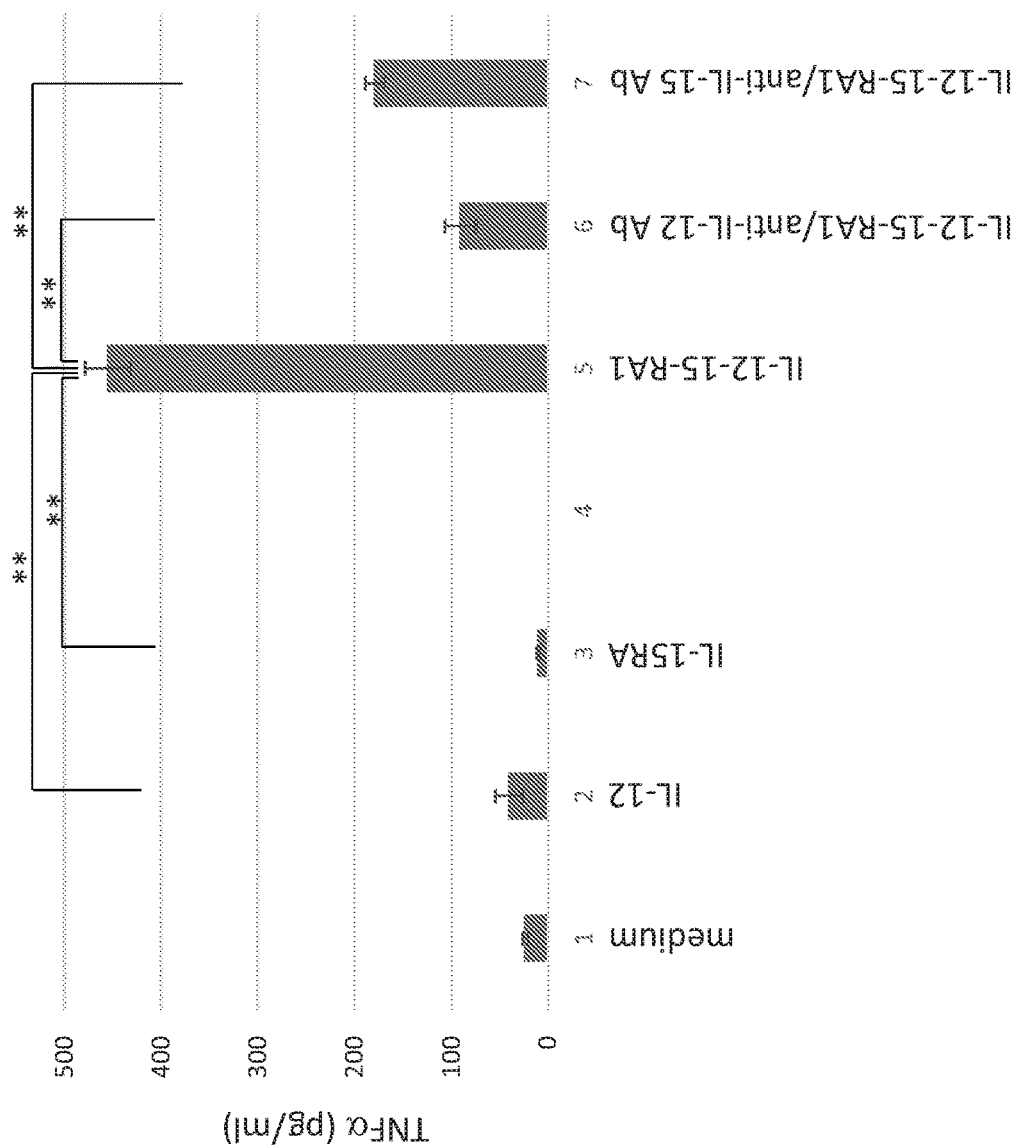

Human peripheral blood mononuclear cells (PBMCs) were stimulated with medium alone, recombinant IL-12 alone, recombinant IL-15 alone, or IL-12 plus IL-15/IL-15RA1 complex with or without anti-IL-12 (6 mg/ml) or anti-IL-15 (0.5 mg/ml) neutralizing antibody for 48 hours. Cultured supernatants were subsequently harvested for human IFNg and human TNFα production using ELISA assays as shown in FIGS. 36A and B.

Figure 36C:
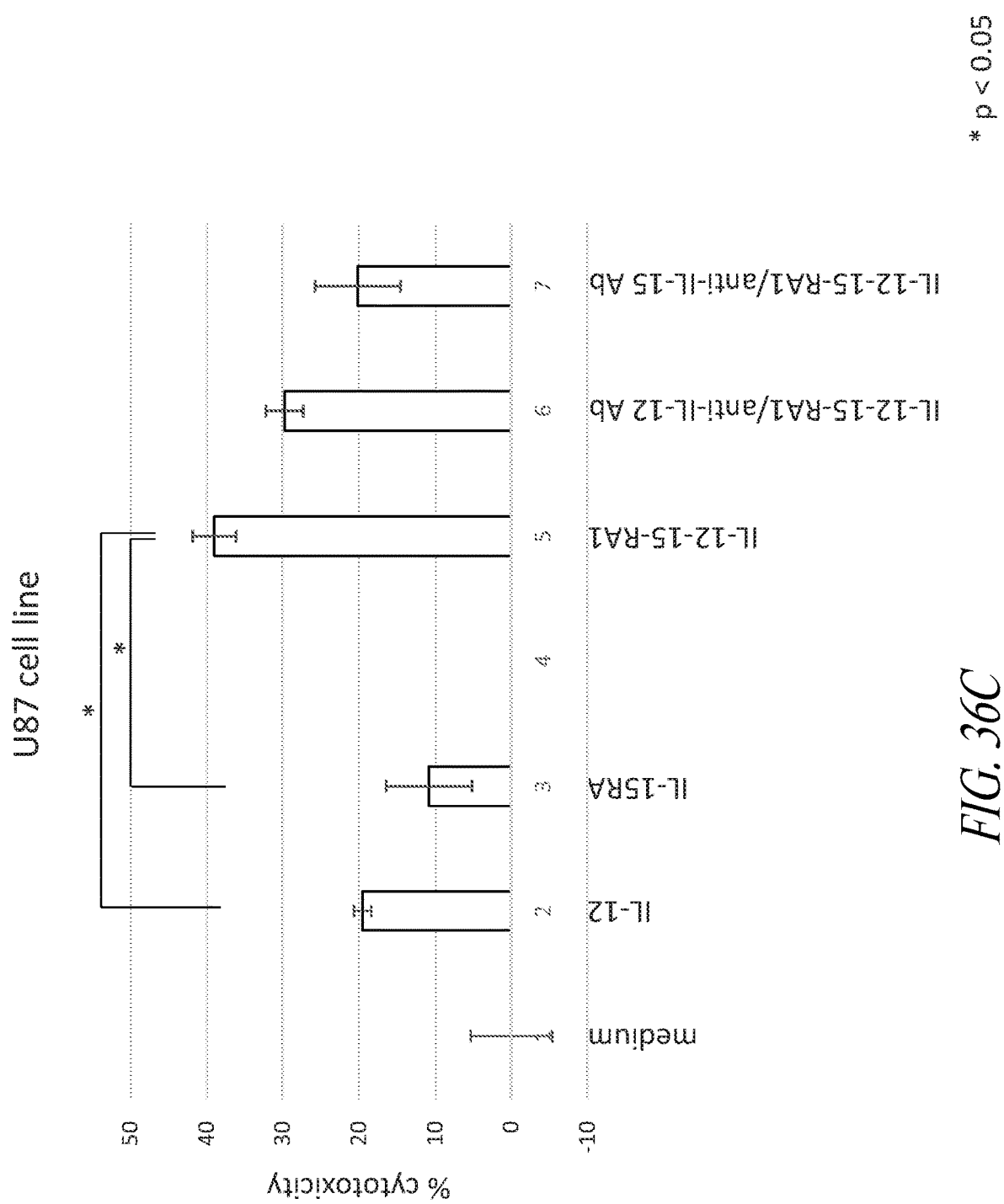
Figure 36D:
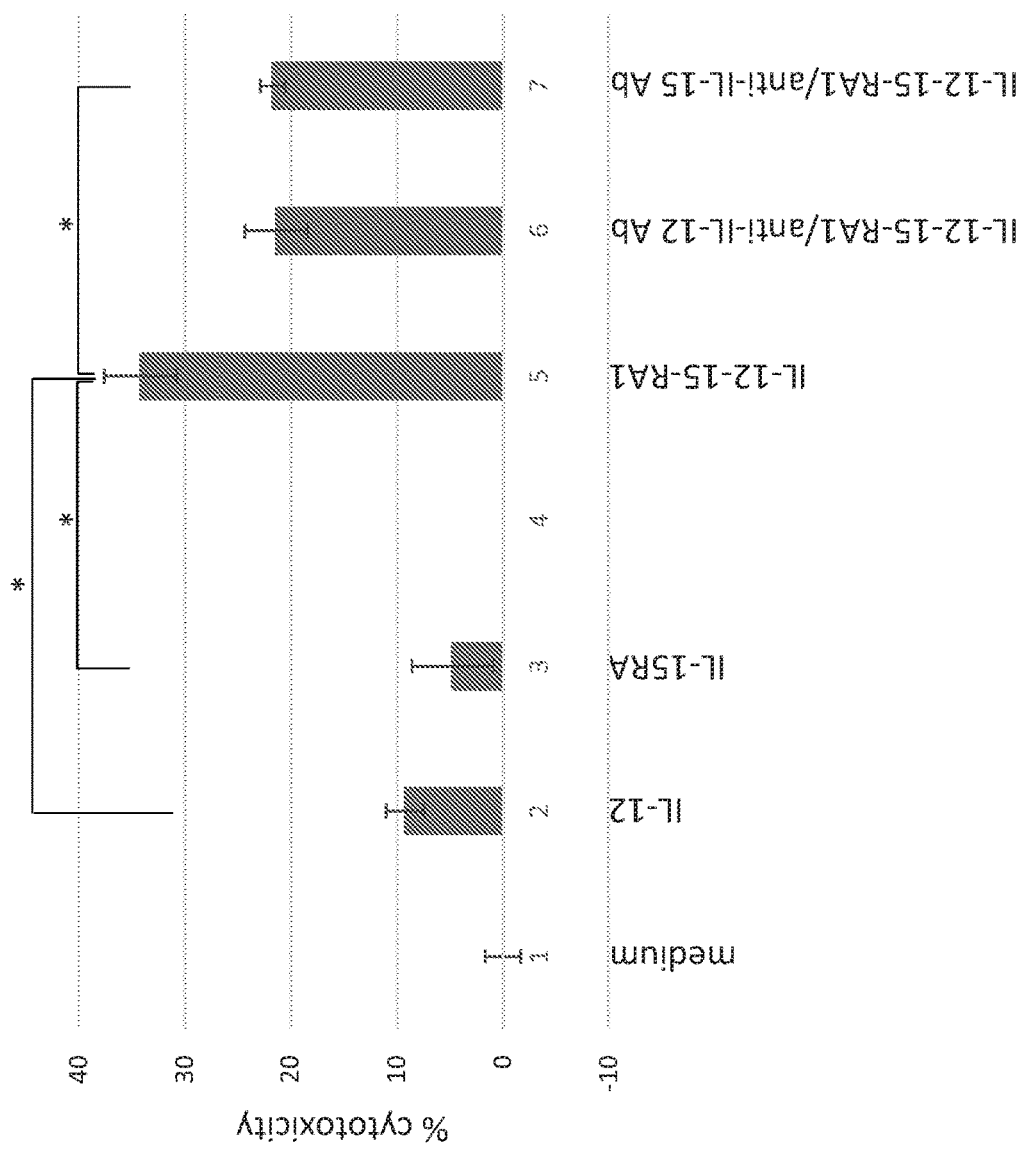

To assess cytotoxicity against tumour cells, $1\times10^4$ calcein-AM-labelled tumour cells were co-incubated with $1\times10^5$ stimulated human PBMCs for 24 hours. Supernatants were harvested for measurement of released fluorescence. Supernatant harvested from calcein-labelled tumour cells incubated with medium only was used as minimum release, and supernatant harvested from calcein-labelled tumour cells incubated with lysis buffer was used as Maximum release. The percentage of cytotoxicity was calculated based on the formula: [(actual reading−minimum release)/(Maximum release−minimum release)]×100%. Cytotoxicity results for U87 tumour cells are shown as FIG. 36C and results for MDA-MB-231 tumour cells are shown as FIG. 36D.

Example 22

VG161h Infected Tumour Cells Produce Human IL-12, Human IL-15/IL15Rα, and Human IgG4

Briefly, LNCaP cells were implanted in nude mice and received injection of vehicle, ICP27-, or VG161h virus. Serum and tumour samples were harvested 120 hours after injection and the productions of human IL-12, human IL-15/

Figure 37A:
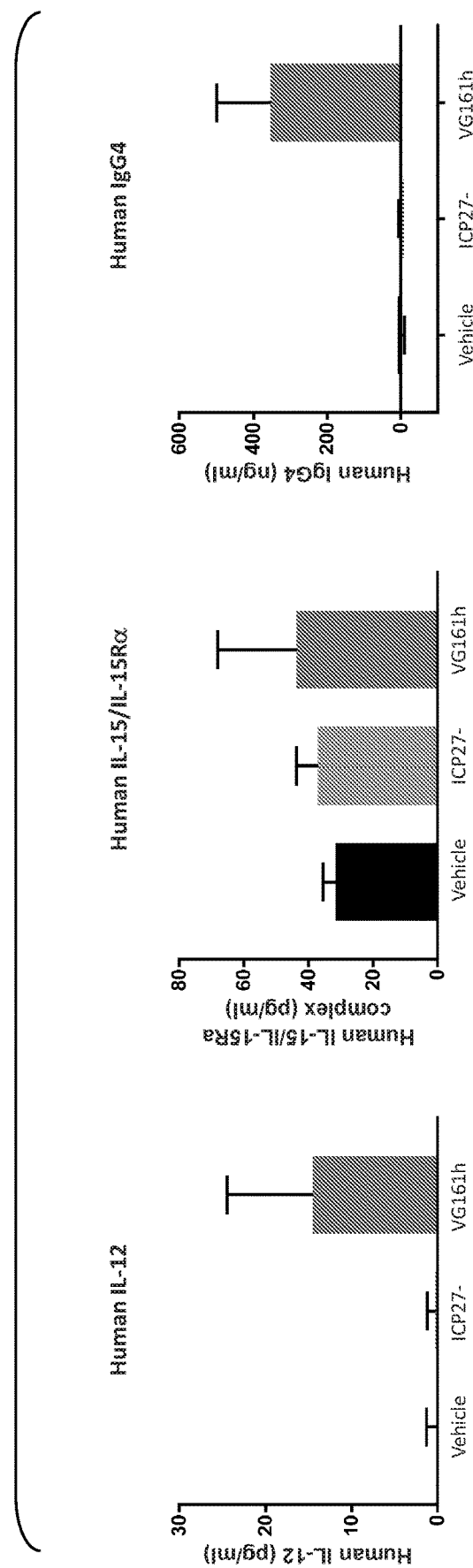
FIGS. 37A and 37B provide in vivo data.
Figure 37B:
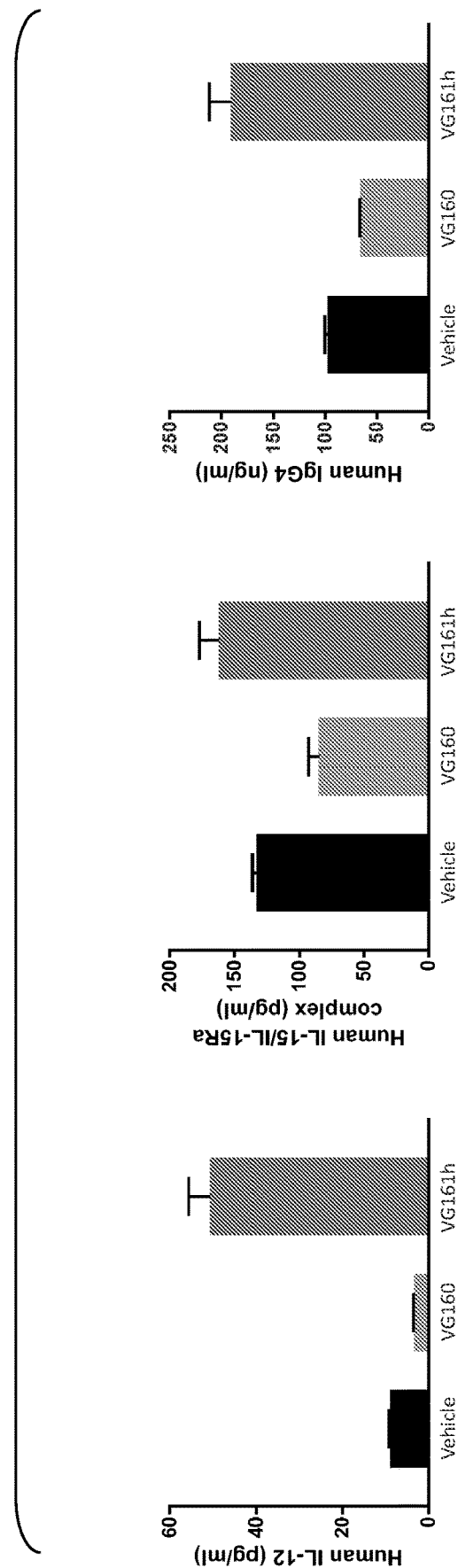

IL-15Rα, and human IgG4 were assessed by ELISA. The results are shown in FIG. 37A Fadu cells were implanted in nude mice and received injection of vehicle, VG160, or VG161h virus. Tumour samples were harvested 24 hours after injection and the productions of human IL-12, human IL-15/IL-15Rα, and human IgG4 were assessed by ELISA. The results are shown in FIG. 37B.

Example 23

Effect of VG161m in Immune Response

Figure 38A:
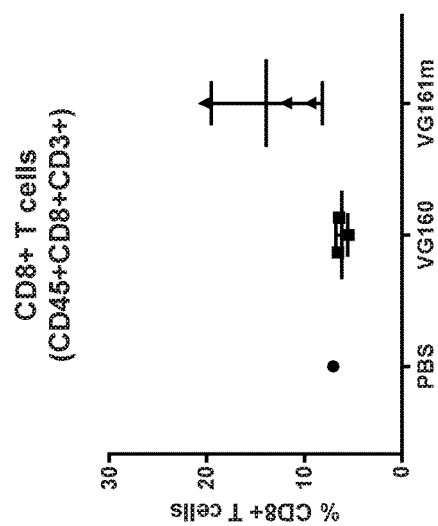
FIGS. 38A-38C provide data on the effect of VG161m in immune response.
Figure 38B:
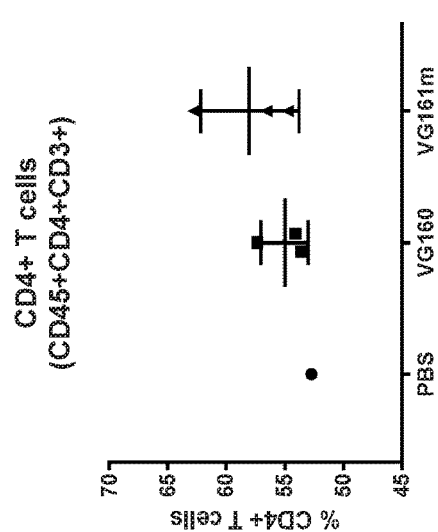
Figure 38C:
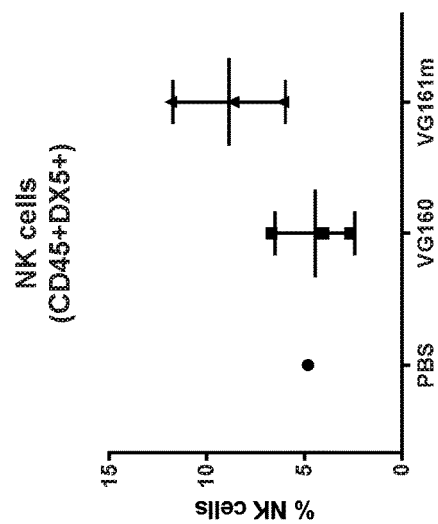

CT26 colon cancer cells were implanted in balb/c mice and received injection of PBS, VG160, or VG161m virus. Tumour samples were harvested 24 hours after injection and the percentage of CD8+ T cells, CD4+ T cells, or NK cells was assessed by flow cytometry. The results are shown in FIGS. 38A-C.

The following are additional exemplary embodiments of the present disclosure:

1) An HSV vector which expresses one or more of IL12, IL15 and/or an ILReceptor 15 alpha subunit. Within one embodiment, the HSV vector comprises an expression cassette which expresses IL12, IL15 and the IL Receptor 15 alpha subunit. Within various embodiments the IL12, IL15 and IL15 Receptor alpha subunit sequences which are expressed are of mammalian origin (e.g., of murine or human origin). Within preferred embodiments the expression cassette expresses murine or human IL12, murine or human IL15, and murine or human IL15Receptor alpha subunit. Within yet other embodiments the expression cassette expresses either murine or human IL12, hIL15, and murine and h15Receptor alpha subunit.

2) The HSV vector of embodiment 1, wherein nucleic acid sequence encoding a self-cleaving 2A peptide is located in-frame between coding sequences for IL12, IL15, and IL15Receptor alpha subunit. Within preferred embodiments, IL12 is a murine or human sequence, IL15 is human sequence, and IL15 Receptor alpha subunit is a human sequence.

3) The HSV vector of embodiment 2, wherein the nucleic acid sequence encodes a self-cleaving 2A peptide selected from the group consisting of VKQTLNFDLLKLAGD-VESNPGP (SEQ ID NO: 520), QCTNYALLKLAGD-VESNPGP (SEQ ID NO: 521), ATNF-SLLKOAGDVEEN-PGP (SEQ ID NO: 522), HYAGYFADLLIHDIETNPGP (SEQ ID NO: 523), GIFN-AHYAGYFADLLIHDIETNPGP (SEQ ID NO: 524), KAVRGYHADYYKQRLIHD-VEMNPGP (SEQ ID NO: 525), GATNF-SLLKLAGD-VELNPGP (SEQ ID NO: 526), EGRGSLLTCGDVEEN-PGP (SEQ ID NO: 527),-AARQMLLLLSGDVETNPGP (SEQ ID NO: 528), FLRKRTQLLMSGDVESNPGP (SEQ ID NO: 529), GSWTDILLLLSGDVETNPGP (SEQ ID NO: 530), TRAEUEDELIRAGIESNPGP (SEQ ID NO: 531), AKFQIDKILISGDVELNPGP (SEQ ID NO: 532), SKFQIDKILISGDIELNPGP (SEQ ID NO: 533), SSIIRTKMLVSGDVEENPGP (SEQ ID NO: 534) and CDAQRQKLLLSGDIEQNPGP (SEQ ID NO: 535).

4) The HSV vector of any one of embodiments 1 to 3, wherein one or more IRES sequences is located between the coding sequences for IL12, IL15, and IL15Receptor alpha subunit. Within preferred embodiments, IL12 is a murine or human sequence, IL15 is human sequence, and IL15 Receptor alpha subunit is a human sequence.

5) The HSV vector of any one of embodiments 1 to 4, where the IL15 and IL15Receptor alpha subunit are co-expressed using a IRES sequence. Within preferred embodiments, IL12 is a murine or human sequence, IL15 is human sequence, and IL15 Receptor alpha subunit is a human sequence.

6) The HSV vector of any one of embodiments 1 to 5, where the IL15 and IL15Receptor alpha subunit are expressed by a bi-directional promoter. Within preferred embodiments, IL12 is a murine or human sequence, IL15 is human sequence, and IL15 Receptor alpha subunit is a human sequence.

7) The HSV vector of embodiment 6, wherein the bi-directional promoter is bi-CMV.

8) The HSV vector of any one of embodiments 1 to 7, wherein each of the IL15 and IL15Receptor alpha subunit is followed by a nucleic acid sequence encoding Lys5 or Glu5. Within preferred embodiments, IL12 is a murine or human sequence, IL15 is human sequence, and IL15 Receptor alpha subunit is a human sequence.

9) The HSV vector of any one of embodiments 1 to 8, wherein the hIL15Receptor alpha subunit is selected from the group consisting of variant 1, variant 2, variant 3 and variant 4.

10) The HSV vector of any one of embodiments 1 to 9, further comprising an expression cassette for one or more PD-L1 blocking peptides, or, wherein said expression cassette expresses one or more PD-L1 blocking peptides.

11) The HSV vector of any one of embodiments 1 to 10, further comprising sequence encoding a peptide linker between multiple PD-L1 blocking peptides.

12) The HSV vector of any one of embodiments 1 to 11, further comprising one or more IRES sequences between multiple PD-L1 blocking peptides.

13) The HSV vector of any one of embodiments 1 to 12, further comprising sequence encoding an Fc domain linked to the 3'-end of the PD-L1 blocking peptide.

14) The HSV vector of any one of embodiments 1 to 13, where the expression cassette is inserted in the either an internal repeat region or the terminal repeat region of HSV genome.

15) The HSV vector of embodiment 10, wherein the sequence encoding a PD-L1 blocking peptide is inserted in between viral genes, such as, for example, the UL3 and UL4 viral genes, the UL50 and UL51 genes, and/or between US1 and US2.

16) The HSV vector of any one of embodiments 1-15, further comprising an NFKB and an OCT4/SOX2 enhancing element in ICP4 or ICP27 regulatory regions.

17) The HSV vector of any one of embodiments 1-16, wherein the ICP34.5 genes are deleted.

18) The HSV vector of any one of embodiments 1 to 17, wherein the expression cassette comprises at least one bidirectional CMV promoter.

19) The HSV vector of any one of embodiments 1 to 18, wherein the expression cassette comprises at least one cellular promoter.

20) The HSV vector of any one of embodiments 1 to 19, the expression cassette for IL12/IL15/IL15Receptor alpha subunit is inserted into either an internal repeat region or the terminal repeat region where the original viral sequence is replaced by the cassette 21) The HSV vector of any of embodiments 1-20, wherein the HSV is either HSV-1 or HSV-2.

22) The HSV vector of any one of embodiments 1 to 21, wherein the ICP34.5 gene is regulated by a 3'UTR containing target sequences of miRNAs that are under-expressed in tumor cells.

23) A pharmaceutical composition, comprising a HSV vector according to any one of embodiments 1 to 22, and a pharmaceutically acceptable carrier.

24) A method of treating cancer, comprising administering to a patient a HSV vector according to any one of embodiments 1 to 22, or a pharmaceutical composition according to embodiment 23.

25) The method according to embodiment 24 wherein said cancer is selected from the group consisting of carcinomas, leukemia's, lymphomas, myelomas and sarcomas.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred nonlimiting embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in nonlimiting embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various nonlimiting embodiments and/or preferred nonlimiting embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and applicants reserve the right to revise the application or claims to refer specifically to any individual member or any subgroup of members of the Markush group.

Other nonlimiting embodiments are within the following claims. The patent may not be interpreted to be limited to the specific examples or nonlimiting embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. An HSV vector comprising an expression cassette for IL12, IL15, and IL15Receptor alpha subunit.

2. The HSV vector of claim 1, wherein nucleic acid sequence encoding a self-cleaving 2A peptide is located in-frame between coding sequences for IL12, IL15, and/or an IL15Receptor alpha subunit.

3. The HSV vector of claim 2, wherein the nucleic acid sequence encodes a self-cleaving 2A peptide selected from the group consisting of VKQTLNFDLLKLAGDVESNPGP (SEQ ID NO: 520), QCTNYALLKLAGDVESNPGP (SEQ ID NO: 521), ATNF-SLLKQAGDVEENPGP (SEQ ID NO: 522), HYAGYFADLLIHDIETNPGP (SEQ ID NO: 523), GIFN-AHYAGYFADLLIHDIETNPGP (SEQ ID NO: 524), KAVRGYHADYYKQRLIHDVEMNPGP (SEQ ID NO: 525), GATNF-SLLKLAGDVELNPGP (SEQ ID NO: 526), EGRGSLLTCGDVEENPGP (SEQ ID NO: 527), AAR-QMLLLLSGDVETNPGP (SEQ ID NO: 528), FLRKRTQLLMSGDVESNPGP (SEQ ID NO: 529}, GSWTDILLLLSGDVETNPGP (SEQ ID NO: 530), TRA-EUEDELIRAGIESNPGP (SEQ ID NO: 531), AKFQID-KILISGDVELNPGP (SEQ ID NO: 532), SKFQIDKILIS-GDIELNPGP (SEQ ID NO: 533), SSIIRTKMLVSGDVEENPGP (SEQ ID NO: 534) and CDAQRQKLLLSGDIEQNPGP (SEQ ID NO: 535).

4. The HSV vector of claim 1, wherein one or more IRES sequences is located between the coding sequences for IL12, IL15, and/or an IL15Receptor alpha subunit.

5. The HSV vector of claim 1, wherein one or more of IL12, IL15 and an IL15Receptor alpha subunit are expressed by a bi-directional promoter.

6. The HSV vector of claim 1, wherein the hIL15Receptor alpha subunit is selected from the group consisting of variant 1, variant 2, variant 3 and variant 4.

7. The HSV vector of claim 1, which expresses IL-12, IL-15 and a PD-L1 blocking peptide.

8. The HSV vector of claim 7, further comprising sequence encoding a peptide linker between multiple PD-L1 blocking peptides.

9. The HSV vector of claim 7, further comprising sequence encoding an Fc domain linked to the 3'-end of the PD-L1 blocking peptide.

10. The HSV vector of claim 1, where an expression cassette is inserted either in an internal repeat region, a terminal repeat region, between the US1 and US2 genes, the UL3 and UL4 viral genes, or the UL50 and UL51 genes.

11. The HSV vector of claim 1, further comprising an NFkB and an OCT4/SOX2 enhancing element in ICP4 or ICP27 regulatory regions.

12. The HSV vector of claim 1, wherein the ICP34.5 genes are deleted.

13. The HSV vector of claim 1, wherein the expression cassette comprises a CMV promoter or an EF-1alpha promoter.

14. The HSV vector of claim 1, wherein the HSV is either HSV-1 or HSV-2.

15. The HSV vector of claim 1, wherein the ICP34.5 gene is regulated by a 3'UTR containing target sequences of miRNAs that are under-expressed in tumor cells.

16. A pharmaceutical composition, comprising a HSV vector according to claim 1, and a pharmaceutically acceptable carrier.

17. A method of enhancing the efficacy of an immune response, comprising administering the HSV vector according to claim 1, or a pharmaceutical composition according to claim 16 to a patient having cancer.

18. The method according to claim 17 wherein said cancer is selected from the group consisting of carcinomas, leukemia's, lymphomas, myelomas and sarcomas.

* * * * *